United States Patent
Ramirez-Fort et al.

(10) Patent No.: US 11,707,223 B2
(45) Date of Patent: Jul. 25, 2023

(54) ULTRAVIOLET RADIATION TREATMENTS

(71) Applicants: Marigdalia Kaleth Ramirez-Fort, Guaynabo, PR (US); Migdalia Fort, Guaynabo, PR (US)

(72) Inventors: Marigdalia Kaleth Ramirez-Fort, Guaynabo, PR (US); Migdalia Fort, Guaynabo, PR (US)

( * ) Notice: Subject to any disclaimer, the term of this patent is extended or adjusted under 35 U.S.C. 154(b) by 0 days.

(21) Appl. No.: 17/914,403

(22) PCT Filed: Mar. 26, 2021

(86) PCT No.: PCT/US2021/024520
§ 371 (c)(1),
(2) Date: Sep. 26, 2022

(87) PCT Pub. No.: WO2021/195586
PCT Pub. Date: Sep. 30, 2021

(65) Prior Publication Data
US 2023/0107906 A1    Apr. 6, 2023

Related U.S. Application Data

(60) Provisional application No. 63/161,161, filed on Mar. 15, 2021, provisional application No. 63/040,134, filed on Jun. 17, 2020, provisional application No. 63/000,302, filed on Mar. 26, 2020.

(51) Int. Cl.
*A61B 5/00* (2006.01)
*A61N 2/00* (2006.01)
*A61N 5/06* (2006.01)

(52) U.S. Cl.
CPC ............ *A61B 5/4836* (2013.01); *A61N 2/004* (2013.01); *A61N 5/0603* (2013.01); *A61N 2005/0626* (2013.01)

(58) Field of Classification Search
CPC .... A61B 5/4836; A61N 2/004; A61N 5/0603; A61N 2005/0626
See application file for complete search history.

(56) References Cited

U.S. PATENT DOCUMENTS

| | | |
|---|---|---|
| 10,779,875 B2 | 9/2020 | Palti et al. |
| 10,918,886 B2 | 2/2021 | Smith et al. |
| 2004/0120958 A1 | 6/2004 | Bander et al. |
| 2013/0060185 A1 | 3/2013 | Lee |
| 2013/0090549 A1 | 4/2013 | Meltsner et al. |
| 2014/0044640 A1 | 2/2014 | Govindan et al. |
| 2014/0140959 A1 | 5/2014 | Szalay et al. |

(Continued)

FOREIGN PATENT DOCUMENTS

| | | |
|---|---|---|
| WO | 2013/102051 A1 | 7/2013 |
| WO | 2019/194862 A2 | 10/2019 |
| WO | 2020/028324 A1 | 2/2020 |

OTHER PUBLICATIONS

Wakim LM, Jones CM, Gebhardt T, Preston CM, Carbone FR. CD8(+) T-cell attenuation of cutaneous herpes simplex virus infection reduces the average viral copy number of the ensuing latent infection. Immunology and cell biology. 2008;86(8):666-675.

(Continued)

*Primary Examiner* — Jonathan T Kuo
(74) *Attorney, Agent, or Firm* — Van Court & Aldridge LLP

(57) ABSTRACT

Systems, methods, and computer-readable media for enabling ultraviolet radiation treatments are provided.

20 Claims, 36 Drawing Sheets

(56) References Cited

U.S. PATENT DOCUMENTS

| | | | |
|---|---|---|---|
| 2016/0346385 | A1 | 12/2016 | Krensky et al. |
| 2017/0119915 | A1 | 5/2017 | Lin et al. |
| 2018/0088120 | A1 | 3/2018 | Bander |
| 2018/0154178 | A1 | 6/2018 | Oldham et al. |
| 2018/0296675 | A1 | 10/2018 | Coleman et al. |
| 2019/0300622 | A1 | 10/2019 | Ho et al. |

OTHER PUBLICATIONS

Koelle DM, Chen HB, Gavin MA, Wald A, Kwok WW, Corey L. CD8 CTL from genital herpes simplex lesions: recognition of viral tegument and immediate early proteins and lysis of infected cutaneous cells. Journal of immunology. 2001;166(6):4049-4058.

Koelle DM, Posavad CM, Barnum GR, Johnson ML, Frank JM, Corey L. Clearance of HSV-2 from recurrent genital lesions correlates with infiltration of HSV-specific cytotoxic T lymphocytes. The Journal of clinical investigation. 1998;101(7):1500-1508.

Cadnum JL, Jencson AL, Gestrich SA, et al. A comparison of the efficacy of multiple ultraviolet light room decontamination devices in a radiology procedure room. Infect Control Hosp Epidemiol. 2019;40(2):158-163.

Fisher EM, Shaffer RE. A method to determine the available UV-C dose for the decontamination of filtering facepiece respirators. J Appl Microbiol. 2011;110(1):287-295.

Lindblad M, Tano E, Lindahl C, Huss F. Ultraviolet-C decontamination of a hospital room: Amount of UV light needed. Burns. 2019.

Mbonimpa EG, Blatchley ER, 3rd, Applegate B, Harper WF, Jr. Ultraviolet A and B wavelength-dependent inactivation of viruses and bacteria in the water. J Water Health. 2018;16(5):796-806.

Nakashima H, Koyanagi Y, Harada S, Yamamoto N. Quantitative evaluations of the effect of UV irradiation on the infectivity of HTLV-III (AIDS virus) with HTLV-I-carrying cell line, MT-4. J Invest Dermatol. 1986;87(2):239-243.

Pichon M, Lebail-Carval K, Billaud G, Lina B, Gaucherand P, Mekki Y. Decontamination of Intravaginal Probes Infected by Human Papillomavirus (HPV) Using UV-C Decontamination System. J Clin Med. 2019;8(11).

Sagripanti JL, Lytle CD. Inactivation of influenza virus by solar radiation. Photochem Photobiol. 2007;83(5):1278-1282.

Silva AA. The Shadow Rule, the UV Index, and the 5S Steps in the Tropics. Health Phys. 2020.

Song L, Li W, He J, et al. Development of a Pulsed Xenon Ultraviolet Disinfection Device for Real-Time Air Disinfection in Ambulances. J Healthc Eng. 2020;2020:6053065.

Urban M, Motteram J, Jing HC, et al. Inactivation of plant infecting fungal and viral pathogens to achieve biological containment in drainage water using UV treatment. J Appl Microbiol. 2011;110(3):675-687.

Jacobson CC, Kumar S, Kimball AB. Latitude and psoriasis prevalence. J Am Acad Dermatol. 2011;65(4):870-873.

Schweitzer AD, Howell RC, Jiang Z, et al. Physico-chemical evaluation of rationally designed melanins as novel nature-inspired radioprotectors. PloS One. 2009;4(9):e7229.

Ramirez-Fort MK, Gottlieb AB, Au SC, Lebwohl MG. A cross-sectional study of Fitzpatrick's skin type and psoriasis in Puerto Rico. Journal of the American Academy of Dermatology, May 2014; 70(5); suppl 1; p. AB79; Abstract.

Chauhan PS, Kaur I, Dogra S, De D, Kanwar AJ. Narrowband ultraviolet B versus psoralen plus ultraviolet A therapy for severe plaque psoriasis: an Indian perspective. Clin Exp Dermatol. 2011;36(2):169-173.

Kwon IH, Woo SM, Choi JW, Youn JI. A retrospective review of 20% vs. 10% incremental narrowband UVB regimens to treat psoriasis in skin phototypes III-V Koreans. Photodermatol Photoimmunol Photomed. 2009;25(3):124-127.

Sugiyama H, Misumi M, Kishikawa M, et al. Skin cancer incidence among atomic bomb survivors from 1958 to 1996. Radiat Res. 2014;181(5):531-539.

Ramirez-Fort MK, Kauffman JA, Khan F, Nguyen H, Rapini RP, Rady P, Tyring SK. [Observation]: A case of Merkel cell carcinoma infected by Merkel cell polyomavirus DNA. Journal of the American Academy of Dermatology. Apr. 2013; 68(4): suppl 1; p. AB131; Abstract.

Ramirez-Fort MK, Meier B, Lachance KS, Chruch CD, Lange CS, French LE, Nghiem P, Bander NH. (Sep. 2017). Folate hydrolase-1 is a novel target for J591-brachytherapy in Merkel cell carcinoma. Poster presented at: European Society for Dermatological Research; Salzburg, Austria.

Ramirez-Fort MK, Navarro V, Meier B, Liu H, Levesque M, Paulitschke V, Vissicchio JR, Moy J, Contassot E, Kim S, Robinson B, Christos P, Tagawa ST, Bander NH, French LE, Lange CS. (Apr. 2017). Possible cancer stem cells: Folate hydrolase-1 is expressed in a subset of Oct4-positive melanoma cells. Poster presented at: American Association for Cancer Research; Washington, DC.

Ramirez-Fort MK, Meier B, Vissicchio JR, Moy J, Liu H, Contassot E, Robinson BD, Navarro V, Kim S, Leconet W, Nguyen D, Nwokedi EC, Lange CS, Tagawa ST, Bander NH, French LE. Melanoma induces endothelial folate hydrolase-1 (FOLH1) expression and facilitated internalization of immunotheragnostic agent, J591. Int J Radiat Oncol Biol Phys. Oct. 1, 2016;96(2S): E703-E704. PubMed PMID: 27675409.

Feily, A., et al., Follicular Transplantation, Microneedling, and Adjuvant Narrow-band Ultraviolet-B Irradiation as Cost-Effective Regimens for Palmar-Plantar Vitiligo: A Pilot Study. Cureus, 2020. 12(4): p. e7878.

Feily, A., V. Seifi, and M.K. Ramirez-Fort, Fractional CO2 Laser Pretreatment to Autologous Hair Transplantation and Phototherapy Improves Perifollicular Repigmentation in Refractory Vitiligo: A Randomized, Prospective, Half-Lesion, Comparative Study. Dermatol Surg, 2016. 42(9): p. 1082-8.

Takada, A., et al., Bactericidal effects of 310 nm ultraviolet light-emitting diode irradiation on oral bacteria. BMC Oral Health, 2017. 17(1): p. 96.

Miwa, S., et al., Imaging UVC-induced DNA damage response in models of minimal cancer. J Cell Biochem, 2013. 114(11): p. 2493-9. PMID: 23744630.

Al-Aidaroos, A.M., et al., High mortality of Red Sea zooplankton under ambient solar radiation. PloS One, 2014. 9(10): p. e108778.

Lu H, Stratton CW, Tang YW. Outbreak of pneumonia of unknown etiology in Wuhan, China: The mystery and the miracle. J Med Virol. 2020;92(4):401-402.

Lytle CD, Sagripanti JL. Predicted inactivation of viruses of relevance to biodefense by solar radiation. J Virol. 2005;79(22):14244-14252.

Sagripanti JL, Lytle CD. Estimated Inactivation of Coronaviruses by Solar Radiation With Special Reference to COVID-19. Photochem Photobiol. 2020.

Lange CS, Gilbert CW. Studies on the cellular basis of radiation lethality. 3. The measurement of stem-cell repopulation probability. Int J Radiat Biol Relat Stud Phys Chem Med. 1968;14(4):373-388; Abstract.

Kogelnik HD. [100 years radiotherapy. On the birth of a new specialty]. Wien Klin Wochenschr. 1998;110(9):313-320; Abstract.

Jarrett P, Scragg R. A short history of phototherapy, vitamin D and skin disease. Photochem Photobiol Sci. 2017;16(3):283-290; Abstract.

Ramirez-Fort MK, Mahase SS, Osborne JR, Lange CS. Theragnostic Target, Prostate-Specific Membrane Antigen—Also Specific for Nonprostatic Malignancies. Int J Radiat Oncol Biol Phys 2018;101(3):646-649.

Niaz MJ, Batra JS, Walsh RD, et al. Pilot Study of Hyperfractionated Dosing of Lutetium-177-Labeled Antiprostate-Specific Membrane Antigen Monoclonal Antibody J591 ((177) Lu-J591) for Metastatic Castration-Resistant Prostate Cancer. Oncologist. 2020.

Niaz MO, Sun M, Ramirez-Fort MK, Niaz MJ. Review of Lutetium-177-labeled Anti-prostate-specific Membrane Antigen Monoclonal Antibody J591 for the Treatment of Metastatic Castration-resistant Prostate Cancer. Cureus. 2020;12(2):e7107.

Singers, Berneburg M. Phototherapy. J Dtsch Dermatol Ges. 2018;16(9):1120-1129.

(56) References Cited

OTHER PUBLICATIONS

Welch D, Buonanno M, Grilj V, et al. Far-UVC light: A new tool to control the spread of airborne-mediated microbial diseases. Sci Rep. 2018;8(1):2752.
Ramirez-Fort MK, Rogers MJ, Santiago R, et al. Prostatic irradiation-induced sexual dysfunction: a review and multidisciplinary guide to management in the radical radiotherapy era (Part I defining the organ at risk for sexual toxicities). Rep Pract Oncol Radiother. 2020;25(3):367-375.
Ramirez-Fort MK, Zeng J, Feily A, et al. Radiotherapy-induced reactivation of neurotrophic human herpes viruses: Overview and management. J Clin Virol. 2018;98:18-27.
"Introduction to health physics." Cember, Herman, Johnson TE, and Alaei P eds. Medical Physics 35.12 (2008): 5959.
Miwa S, Yano S, Hiroshima Y, et al. Imaging UVC-induced DNA damage response in models of minimal cancer. J Cell Biochem. 2013;114(11):2493-2499.
Al-Aidaroos AM, El-Sherbiny MM, Satheesh S, et al. High mortality of Red Sea zooplankton under ambient solar radiation. PloS One. 2014;9(10):e108778.
Takeda K, Fujisawa K, Nojima H, Kato R, Ueki R, Sakugawa H. Hydroxyl radical generation with a high power ultraviolet light emitting diode (UV-LED) and application for determination of hydroxyl radical reaction rate constants. J Photochem. 2017;340:8-14.
Rastogi RP, Richa, Kumar A, Tyagi MB, Sinha RP. Molecular mechanisms of ultraviolet radiation-induced DNA damage and repair. J Nucleic Acids. 2010;2010:592980.
McGuigan KG, Joyce TM, Conroy RM, Gillespie JB, Elmore-Meegan M. Solar disinfection of drinking water contained in transparent plastic bottles: characterizing the bacterial inactivation process. J Appl Microbiol. 1998;84(6):1138-1148.
Dessie A, Alemayehu E, Mekonen S, Legesse W, Kloos H, Ambelu A. Solar disinfection: an approach for low-cost household water treatment technology in Southwestern Ethiopia. J Environ Health Sci Eng. 2014;12(1):25.
Amichai B, Grunwald MH, Davidovici B, Shemer A. "Sunlight is said to be the best of disinfectants"*: the efficacy of sun exposure for reducing fungal contamination in used clothes. Isr Med Assoc J. 2014;16(7):431-433.
Tseng CC, Li CS. Inactivation of viruses on surfaces by ultraviolet germicidal irradiation. J Occup Environ Hyg. 2007;4(6):400-405.
Sagripanti JL, Lytle CD. Sensitivity to ultraviolet radiation of Lassa, vaccinia, and Ebola viruses dried on surfaces. Arch Virol. 2011;156(3):489-494.
Sagripanti JL, Voss L, Marschall HJ, Lytle CD. Inactivation of vaccinia virus by natural sunlight and by artificial UVB radiation. Photochem Photobiol. 2013;89(1):132-138.
Ianevski A, Zusinaite E, Shtaida N, et al. Low Temperature and Low UV Indexes Correlated with Peaks of Influenza Virus Activity in Northern Europe during 2010(-)2018. Viruses 2019; 11(3).
Trauer JM, Denholm JT, McBryde ES. Construction of a mathematical model for tuberculosis transmission in highly endemic regions of the Asia-Pacific. J Theor Biol. 2014;358:74-84.
Liu Y, Ning Z, Chen Y, et al. Aerodynamic analysis of SARS-CoV-2 in two Wuhan hospitals. Nature. 2020.
Interrante JD, Haddad MB, Kim L, Gandhi NR. Exogenous Reinfection as a Cause of Late Recurrent Tuberculosis in the United States. Ann Am Thorac Soc. 2015;12(11):1619-1626.
Schiroli C, Carugati M, Zanini F, et al. Exogenous reinfection of tuberculosis in a low-burden area. Infection. 2015;43(6):647-653.
Shen X, Yang C, Wu J, et al. Recurrent tuberculosis in an urban area in China: Relapse or exogenous reinfection? Tuberculosis (Edinb). 2017;103:97-104.
Smith J. South Korea reports more recovered coronavirus patients testing positive again. https://www.reuters.com/article/us-health-coronavirus-southkorea/south-korea-reports-more-recovered-coronavirus-patients-testing-positive-again-idUSKCN21V0JQ (Apr. 13, 2020).
Ye G, Pan Z, Pan Y, et al. Clinical characteristics of severe acute respiratory syndrome coronavirus 2 reactivation. J Infect. 2020;80(5):e14-e17.
Gordon CJ, Tchesnokov EP, Woolner E, et al. Remdesivir is a direct-acting antiviral that inhibits RNA-dependent RNA polymerase from severe acute respiratory syndrome coronavirus 2 with high potency. J Biol Chem. 2020.
Ledford H. Hopes rise for coronavirus drug remdesivir. Nature. 2020.
Maverakis E, Miyamura Y, Bowen MP, Correa G, Ono Y, Goodarzi H. Light, including ultraviolet. J Autoimmun. 2010;34(3):J247-257.
Carratala A, Dionisio Calado A, Mattle MJ, Meierhofer R, Luzi S, Kohn T. Solar Disinfection of Viruses in Polyethylene Terephthalate Bottles. Appl Environ Microbiol. 2016;82(1):279-288.
Bichai F, Polo-Lopez MI, Fernandez Ibanez P. Solar disinfection of wastewater to reduce contamination of lettuce crops by *Escherichia coli* in reclaimed water irrigation. Water Res. 2012;46(18):6040-6050.
Casini B, Tuvo B, Cristina ML, et al. Evaluation of an Ultraviolet C (UVC) Light-Emitting Device for Disinfection of High Touch Surfaces in Hospital Critical Areas. Int J Environ Res Public Health. 2019;16(19).
Nerandzic MM, Thota P, Sankar CT, et al. Evaluation of a pulsed xenon ultraviolet disinfection system for reduction of healthcare-associated pathogens in hospital rooms. Infect Control Hosp Epidemiol. 2015;36(2):192-197.
Beck SE, Ryu H, Boczek LA, et al. Evaluating UV-C LED disinfection performance and investigating potential dual-wavelength synergy. Water Res. 2017;109:207-216.
Lowe J.J., Paladino, K.D., Farke, J.D., et al. N95 Filtering Facepiece Respirator Ultraviolet Germicidal Irradiation (UVGI) Process for Decontamination and Reuse 2020; https://www.nebraskamed.com/sites/default/files/documents/covid-19/n-95-decon- process.pdf. Accessed Mar. 16, 2020.
Chang, Kenneth. "Scientists Consider Indoor Ultraviolet Light to Zap Coronavirus in the Air". The New York Times. May 9, 2020 (accessed May 25, 2020).
Takada A, Matsushita K, Horioka S, Furuichi Y, Sumi Y. Bactericidal effects of 310 nm ultraviolet light-emitting diode irradiation on oral bacteria. BMC Oral Health. 2017;17(1):96.
Perez-Laguna V, Gilaberte Y, Millan-Lou MI, et al. A combination of photodynamic therapy and antimicrobial compounds to treat skin and mucosal infections: a systematic review. Photochem Photobiol Sci. 2019;18(5):1020-1029.
Perez-Laguna V, Garcia-Malinis AJ, Aspiroz C, Rezusta A, Gilaberte Y. Antimicrobial effects of photodynamic therapy. G Ital Dermatol Venereol. 2018;153(6):833-846; Abstract.
Schreiner M, Baumler W, Eckl DB, Spath A, Konig B, Eichner A. Photodynamic inactivation of bacteria to decolonize ethicillin-resistant *Staphylococcus aureus* from human skin. Br J Dermatol. 2018;179(6):1358-1367.
Khaskhely NM, Maruno M, Uezato H, et al. Low-dose UVB contributes to host resistance against Leishmania amazonensis infection in mice through induction of gamma interferon and tumor necrosis factor alpha cytokines. Clin Diagn Lab Immunol. 2002;9(3):677-686.
Mashayekhi Goyonlo V, Karrabi M, Kiafar B. Efficacy of erbium glass laser in the treatment of Old World cutaneous leishmaniasis: A case series. Australas J Dermatol. 2019;60(1):e29-e32.
Balevi A, Ustuner P, Kaksi SA, Ozdemir M. Narrow-band UV-B phototherapy: an effective and reliable treatment alternative for extensive and recurrent pityriasis versicolor. J Dermatolog Treat. 2018;29(3):252-255; Abstract.
Rassai S, Rafeie E, Ramirez-Fort MK, Feily A. Adjuvant Narrow Band UVB Improves the Efficacy of Oral Azithromycin for the Treatment of Moderate to Severe Inflammatory Facial Acne Vulgaris. J Cutan Aesthet Surg. 2014;7(3):151-154.
Nguyen HP, Ramirez-Fort MK, Rady PL. The biology of human papillomaviruses. Curr Probl Dermatol. 2014;45:19-32.
Zhang K, Ren J, Ren JX, Liu C, Sun L. Successful treatment of verruca plana with NB-UVB: A case report. Dermatol Ther. 2020;33(2):e13207.

(56) References Cited

OTHER PUBLICATIONS

Cantero-Munoz P, Urien MA, Ruano-Ravina A. Efficacy and safety of intraoperative radiotherapy in colorectal cancer: a systematic review. Cancer Lett. 2011;306(2):121-133.
Ruano-Ravina A, Cantero-Munoz P, Eraso Urien A. Efficacy and safety of intraoperative radiotherapy in breast cancer: a systematic review. Cancer Lett. 2011;313(1):15-25.
Nishioka A, Ogawa Y, Miyatake K, et al. Safety and efficacy of image-guided enzyme-targeting radiosensitization and intraoperative radiotherapy for locally advanced unresectable pancreatic cancer. Oncol Lett. 2014;8(1):404-408.
Treister N, Li S, Lerman MA, Lee S, Soiffer R. Narrow-band UVB phototherapy for management of oral chronic graft-versus-host disease. Photodermatol Photoimmunol Photomed. 2015;31(2):75-82.
Morita A, Weiss M, Maeda A. Recent developments in phototherapy: treatment methods and devices. Recent Pat Inflamm Allergy Drug Discov. 2008;2(2):105-108.
Koreck AI, Csoma Z, Bodai L, et al. Rhinophototherapy: a new therapeutic tool for the management of allergic rhinitis. J Allergy Clin Immunol. 2005;115(3):541-547.
Kemeny L, Koreck A. Ultraviolet light phototherapy for allergic rhinitis. J Photochem Photobiol B. 2007;87(1):58-65.
Csoma Z, Ignacz F, Bor Z, et al. Intranasal irradiation with the xenon chloride ultraviolet B laser improves allergic rhinitis. J Photochem Photobiol B. 2004;75(3):137-144.
Kovalenko EL. [The results of treating periapical periodontitis with ultraviolet irradiation of the root canal and the use of gentamycin]. Lik Sprava. 1998(5):136-139.
Alyasin S, Nabavizadeh SH, Houshmand H, Esmaeilzadeh H, Jelodar S, Amin R. Short Time Efficiency of Rhinophototherapy in Management of Patients with Allergic Rhinitis Resistant to Medical Therapy. Iran J Allergy Asthma Immunol. 2016;15(4):317-327.
Koreck A, Szechenyi A, Morocz M, et al. Effects of intranasal phototherapy on nasal mucosa in patients with allergic rhinitis. J Photochem Photobiol B. 2007;89(2-3):163-169.
Wolfel R, Corman VM, Guggemos W, et al. Virological assessment of hospitalized patients with COVID-2019. Nature. 2020.
Gera R, Chehade H, Wazir U, Tayeh S, Kasem A, Mokbel K. Locoregional therapy of the primary tumour in de novo stage IV breast cancer in 216 066 patients: A meta-analysis. Sci Rep. 2020;10(1):2952.
Barr ML, Meiser BM, Eisen HJ, et al. Photopheresis for the prevention of rejection in cardiac transplantation. Photopheresis Transplantation Study Group. N Engl J Med. 1998;339(24):1744-1751.
Edelson R, Berger C, Gasparro F, et al. Treatment of cutaneous T-cell lymphoma by extracorporeal photochemotherapy. Preliminary results. N Engl J Med. 1987;316(6):297-303.
McKenna KE, Whittaker S, Rhodes LE, et al. Evidence-based practice of photopheresis 1987-2001: a report of a workshop of the British Photodermatology Group and the U.K. Skin Lymphoma Group. Br J Dermatol. 2006;154(1):7-20.
Marshall SR. Technology insight: ECP for the treatment of GvHD—can we offer selective immune control without generalized immunosuppression? Nat Clin Pract Oncol. 2006;3(6):302-314.
Hivelin M, Siemionow M, Grimbert P, Lantieri L. Extracorporeal photopheresis: from solid organs to face transplantation. Transpl Immunol. 2009;21(3):117-128.
Kaufman HL, Russell J, Hamid O, Bhatia S, Terheyden P, D'Angelo SP, et al. Avelumab in patients with chemotherapy-refractory metastatic Merkel cell carcinoma: a multicentre, single-group, open-label, phase 2 trial. Lancet Oncol. 2016; 17(10):1374-85.
Kaufman HL, Russell JS, Hamid O, Bhatia S, Terheyden P, D'Angelo SP, et al. Updated efficacy of avelumab in patients with previously treated metastatic Merkel cell carcinoma after >/=1 year of follow-up: JAVELIN Merkel 200, a phase 2 clinical trial. J Immunother Cancer. 2018;6(1):7.
Gunaratne DA, Howle JR, Veness MJ. Definitive radiotherapy for Merkel cell carcinoma confers clinically meaningful in-field locoregional control: A review and analysis of the literature. J Am Acad Dermatol. 2017;77(1):142-8 e1.
Balakrishnan V, Berry S, Stew B, Sizeland A. Benefits of combined modality treatment of Merkel cell carcinoma of the head and neck: single institution experience. The Journal of laryngology and otology. 2013;127(9):908-16; Abstract.
Bichakjian CK, Olencki T, Alam M, Andersen JS, Berg D, Bowen GM, et al. Merkel cell carcinoma, version 1.2014. Journal of the National Comprehensive Cancer Network: JNCCN. 2014;12(3):410-24.
Kang SH, Haydu LE, Goh RY, Fogarty GB. Radiotherapy is associated with significant improvement in local and regional control in Merkel cell carcinoma. Radiation oncology. 2012;7:171.
Sexton KW, Poteet SP, Hill JB, Schmidt A, Patel A, Del Corral GA, et al. Adjuvant radiation therapy increases disease-free survival in stage IB Merkel cell carcinoma. Annals of plastic surgery. 2014;73(5):531-4.
Network NCC. NCCN Clinical Practice Guidelines in Oncology. Merkel Cell Carcinoma (Version 1.2018). 2018 (accessed Jun. 2018).
Ramirez-Fort MK, Mahase SS, Osborne JR, Lange CS. Theragnostic Target, Prostate-Specific Membrane Antigen—Also Specific for Nonprostatic Malignancies. Int J Radiat Oncol Biol Phys. 2018;101(3):646-9.
Tagawa ST, Vallabhajosula S, Christos PJ, Jhanwar YS, Batra JS, Lam L, et al. Phase 1/2 study of fractionated dose lutetium-177-labeled anti-prostate-specific membrane antigen monoclonal antibody J591 ((177) Lu-J591) for metastatic castration-resistant prostate cancer. Cancer. 2019;125(15):2561-9.
Niaz MJ, Batra JS, Walsh RD, Ramirez-Fort MK, Vallabhajosula S, Jhanwar YS, et al. Pilot Study of Hyperfractionated Dosing of Lutetium-177-Labeled Antiprostate-Specific Membrane Antigen Monoclonal Antibody J591 ((177) Lu-J591) for Metastatic Castration-Resistant Prostate Cancer. Oncologist. 2020;25(6):477-e895.
Batra JS, Niaz MJ, Whang YE, Sheikh A, Thomas C, Christos P, et al. Phase I trial of docetaxel plus lutetium-177-labeled anti-prostate-specific membrane antigen monoclonal antibody J591 ((177)Lu-J591) for metastatic castration-resistant prostate cancer. Urol Oncol. 2020.
Nguyen DP, Xiong PL, Liu H, Pan S, Leconet W, Navarro V, et al. Induction of PSMA and Internalization of an Anti-PSMA mAb in the Vascular Compartment. Mol Cancer Res. 2016;14(11):1045-53.
Tagawa ST, Akhtar NH, Nikolopoulou A, Kaur G, Robinson B, Kahn R, et al. Bone marrow recovery and subsequent chemotherapy following radiolabeled anti-prostate-specific membrane antigen monoclonal antibody j591 in men with metastatic castration-resistant prostate cancer. Front Oncol. 2013;3:214.
Tagawa ST, Milowsky MI, Morris M, Vallabhajosula S, Christos P, Akhtar NH, et al. Phase II study of Lutetium-177-labeled anti-prostate-specific membrane antigen monoclonal antibody J591 for metastatic castration-resistant prostate cancer. Clin Cancer Res. 2013;19(18):5182-91.
O'Donoghue JA, Bardies M, Wheldon TE. Relationships between tumor size and curability for uniformly targeted therapy with beta-emitting radionuclides. J Nucl Med. 1995;36(10):1902-9.
Milowsky MI, Nanus DM, Kostakoglu L, Vallabhajosula S, Goldsmith SJ, Bander NH. Phase I trial of yttrium-90-labeled anti-prostate-specific membrane antigen monoclonal antibody J591 for androgen-independent prostate cancer. J Clin Oncol. 2004;22(13):2522-31.
Kratochwil C, Bruchertseifer F, Rathke H, Hohenfellner M, Giesel FL, Haberkorn U, et al. Targeted alpha-Therapy of Metastatic Castration-Resistant Prostate Cancer with (225)Ac-PSMA-617: Swimmer-Plot Analysis Suggests Efficacy Regarding Duration of Tumor Control. J Nucl Med. 2018;59(5):795-802.
Niaz MO, Sun M, Ramirez-Fort MK, Niaz MJ. Prostate-specific Membrane Antigen Based Antibody-drug Conjugates for Metastatic Castration-resistance Prostate Cancer. Cureus. 2020;12(2):e7147.
Ramirez-Fort MK, Meier B, Liu H, et al. Possible cancer stem cells: Folate hydrolase-1 is expressed in a subset of Oct4-positive mela-

(56) References Cited

OTHER PUBLICATIONS noma cells. Poster presented at: American Association for Cancer Research; Apr. 1-5, 2017; Washington, DC.
Ma D, Hopf CE, Malewicz AD, Donovan GP, Senter PD, Goeckeler WF, et al. Potent antitumor activity of an auristatin-conjugated, fully human monoclonal antibody to prostate-specific membrane antigen. Clin Cancer Res. 2006;12(8):2591-6.
Morris MJ, Pandit-Taskar N, Divgi CR, Bender S, O'Donoghue JA, Nacca A, et al. Phase I evaluation of J591 as a vascular targeting agent in progressive solid tumors. Clin Cancer Res. 2007;13(9):2707-13.
National Nuclear Data Center ENSDF Decay Data in the MIRD (Medical Internal Radiation Dose). Format for 177Lu. 2012.
Kim SH, Park WS, Park EY, Park B, Joo J, Joung JY, et al. The prognostic value of BAP1, PBRM1, pS6, PTEN, Tgase2, PD-L1, CA9, PSMA, and Ki-67 tissue markers in localized renal cell carcinoma: A retrospective study of tissue microarrays using immunohistochemistry. PloS One. 2017;12(6):e0179610.
Haffner MC, Laimer J, Chaux A, Schafer G, Obrist P, Brunner A, et al. High expression of prostate-specific membrane antigen in the tumor-associated neo-vasculature is associated with worse prognosis in squamous cell carcinoma of the oral cavity. Mod Pathol. 2012;25(8):1079-85.
Mhawech-Fauceglia P, Smiraglia DJ, Bshara W, Andrews C, Schwaller J, South S, et al. Prostate-specific membrane antigen expression is a potential prognostic marker in endometrial adenocarcinoma. Cancer Epidemiol Biomarkers Prev. 2008;17(3):571-7.
Zeng C, Ke ZF, Yang Z, Wang Z, Yang SC, Luo CQ, et al. Prostate-specific membrane antigen: a new potential prognostic marker of osteosarcoma. Med Oncol. 2012;29(3):2234-9.
Perner S, Hofer MD, Kim R, Shah RB, Li H, Moller P, et al. Prostate-specific membrane antigen expression as a predictor of prostate cancer progression. Hum Pathol. 2007;38(5):696-701.
Cronin KA, Harlan LC, Dodd KW, Abrams JS, Ballard-Barbash R. Population-based estimate of the prevalence of HER-2 positive breast cancer tumors for early stage patients in the US. Cancer Invest. 2010;28(9):963-8.
Donepudi S, DeConti RC, Samlowski WE. Recent advances in the understanding of the genetics, etiology, and treatment of Merkel cell carcinoma. Semin Oncol. 2012;39(2):163-72.
Fernandez-Cobo M, Jobes DV, Yanagihara R, et al. Reconstructing population history using JC virus: Amerinds, Spanish, and Africans in the ancestry of modern Puerto Ricans. Hum Biol. 2001;73(3):385-402; Abstract.
Gravel S, Zakharia F, Moreno-Estrada A, et al. Reconstructing Native American migrations from whole-genome and whole-exome data. PloS Genet. 2013;9(12):e1004023.
Edmondson DA, Nordness ME, Zacharisen MC, Kurup VP, Fink JN. Allergy and "toxic mold syndrome". Ann Allergy Asthma Immunol. 2005;94(2):234-239.
Ahmed Adam MA, Tabana YM, Musa KB, Sandai DA. Effects of different mycotoxins on humans, cell genome and their involvement in cancer (Review). Oncol Rep. 2017;37(3):1321-1336.
Zhang X, Norback D, Fan Q, et al. Dampness and mold in homes across China: Associations with rhinitis, ocular, throat and dermal symptoms, headache and fatigue among adults. Indoor Air. 2019;29(1):30-42.
Furman D, Campisi J, Verdin E, et al. Chronic inflammation in the etiology of disease across the life span. Nat Med. 2019;25(12):1822-1832.
McClelland S, 3rd, Xanthopoulos EP, Mitin T. The Sin of Exclusion: Applicability of Trials Encouraging Omission of Radiation Therapy to Nonwhite Patients With Breast Cancer. J Oncol Pract. 2018;14(11):635-638.
https://gis.cdc.gov/Cancer/USCS/DataViz.html (obtained Sep. 29, 2018).
Teloken C. Management of erectile dysfunction secondary to treatment for localized prostate cancer. Cancer Control. 2001;8(6):540-545; Abstract.
Mantz CA, Nautiyal J, Awan A, et al. Potency preservation following conformal radiotherapy for localized prostate cancer: impact of neoadjuvant androgen blockade, treatment technique, and patient-related factors. The cancer journal from Scientific American. 1999;5(4):230-236; Abstract.
Donovan JL, Hamdy FC, Lane JA, et al. Patient-Reported Outcomes after Monitoring, Surgery, or Radiotherapy for Prostate Cancer. N Engl J Med. 2016;375(15):1425-1437.
Ramirez-Fort MK, Suarez P, Carrion M, et al. Prostatic irradiation-induced sexual dysfunction: A review and multidisciplinary guide to management in the radical radiotherapy era (Part III on Psycho-sexual Therapy and the Masculine Self-Esteem). Rep Pract Oncol Radiother. 2020;25(4):625-631.
Rogers MJ, Ramirez-Fort MK, Kashanian JA, et al. Prostatic irradiation-induced sexual dysfunction: A review and multidisciplinary guide to management in the radical radiotherapy era (Part II on Urological Management). Rep Pract Oncol Radiother. 2020;25(4):619-624.
Forbat L, White I, Marshall-Lucette S, Kelly D. Discussing the sexual consequences of treatment in radiotherapy and urology consultations with couples affected by prostate cancer. BJU Int. 2012;109(1):98-103.
Korfage IJ, Hak T, de Koning HJ, Essink-Bot ML. Patients' perceptions of the side-effects of prostate cancer treatment—a qualitative interview study. Soc Sci Med. 2006;63(4):911-919; Abstract.
O'Brien R, Rose P, Campbell C, et al. "I wish I'd told them": a qualitative study examining the unmet psychosexual needs of prostate cancer patients during follow-up after treatment. Patient Educ Couns. 2011;84(2):200-207.
Singer PA, Tasch ES, Stocking C, Rubin S, Siegler M, Weichselbaum R. Sex or survival: trade-offs between quality and quantity of life. Journal of clinical oncology : official journal of the American Society of Clinical Oncology. 1991;9(2):328-334.
McMahon CG. Nonsurgical treatment of cavernosal venous leakage. Urology. 1997;49(1):97-100.
Hellstrom WJ, Montague DK, Moncada I, et al. Implants, mechanical devices, and vascular surgery for erectile dysfunction. J Sex Med. 2010;7(1 Pt 2):501-523; Abstract.
Porst H, Burnett A, Brock G, et al. SOP conservative (medical and mechanical) treatment of erectile dysfunction. J Sex Med. 2013;10(1):130-171; Abstract.
Brison D, Seftel A, Sadeghi-Nejad H. The resurgence of the vacuum erection device (VED) for treatment of erectile dysfunction. J Sex Med. 2013;10(4):1124-1135; Abstract.
Kimura M, Caso JR, Banez LL, et al. Predicting participation in and successful outcome of a penile rehabilitation programme using a phosphodiesterase type 5 inhibitor with a vacuum erection device after radical prostatectomy. BJU Int. 2012;110(11 Pt C):E931-938.
Bergman J, Gore JL, Penson DF, Kwan L, Litwin MS. Erectile aid use by men treated for localized prostate cancer. J Urol. 2009;182(2):649-654.
Liu C, Lopez DS, Chen M, Wang R. Penile Rehabilitation Therapy Following Radical Prostatectomy: A Meta-Analysis. J Sex Med. 2017;14(12):1496-1503; Abstract.
Nolan MW, Marolf AJ, Ehrhart EJ, et al. Pudendal nerve and internal pudendal artery damage may contribute to radiation-induced erectile dysfunction. Int J Radiat Oncol Biol Phys. 2015;91(4):796-806.
Mahmood J, Connors CQ, Alexander AA, et al. Cavernous Nerve Injury by Radiation Therapy May Potentiate Erectile Dysfunction in Rats. Int J Radiat Oncol Biol Phys. 2017;99(3):680-688.
Lange CS, Liberman DF, Clark RW, Ferguson P. The organization and repair of DNA in the mammalian chromosome. I. Calibration procedures and errors in the determination of the molecular weight of native DNA. Biopolymers. 1977;16(5):1063-1081; Abstract.
Lange CS, Liberman DF, Clark RW, Ferguson P, Sheck LE. The organization and repair of DNA in the mammalian chromosome. III. Determination of the molecular weight of a mammalian native DNA. Biopolymers. 1977;16(5):1093-1014; Abstract.
Siegel RL, Miller KD, Jemal A. Cancer statistics, 2016. CA Cancer J Clin. 2016;66(1):7-30.

(56) References Cited

OTHER PUBLICATIONS

Silver DA, Pellicer I, Fair WR, Heston WD, Cordon-Cardo C. Prostate-specific membrane antigen expression in normal and malignant human tissues. Clinical cancer research : an official journal of the American Association for Cancer Research. 1997;3(1):81-5.
Troyer JK, Beckett ML, Wright GL, Jr. Detection and characterization of the prostate-specific membrane antigen (PSMA) in tissue extracts and body fluids. Int J Cancer. 1995;62(5):552-8.
Wright GL, Jr., Grob BM, Haley C, Grossman K, Newhall K, Petrylak D, et al. Upregulation of prostate-specific membrane antigen after androgen-deprivation therapy. Urology. 1996;48(2):326-34.
Wright GL, Jr., Haley C, Beckett ML, Schellhammer PF. Expression of prostate-specific membrane antigen in normal, benign, and malignant prostate tissues. Urol Oncol. 1995;1(1):18-28.
Liu H, Rajasekaran AK, Moy P, Xia Y, Kim S, Navarro V, et al. Constitutive and antibody-induced internalization of prostate-specific membrane antigen. Cancer research. 1998;58(18):4055-60.
Rajasekaran SA, Anilkumar G, Oshima E, Bowie JU, Liu H, Heston W, et al. A novel cytoplasmic tail MXXXL motif mediates the internalization of prostate-specific membrane antigen. Mol Biol Cell. 2003;14(12):4835-45.
Furchgott RF. The 1996 Albert Lasker Medical Research Awards. The discovery of endothelium-derived relaxing factor and its importance in the identification of nitric oxide. JAMA. 1996;276(14):1186-8.
Hemmens B, Mayer B. Enzymology of nitric oxide synthases. Methods Mol Biol. 1998;100:1-32; Abstract.
Kraehling JR, Sessa WC. Contemporary Approaches to Modulating the Nitric Oxide-cGMP Pathway in Cardiovascular Disease. Circ Res. 2017;120(7):1174-82.
Gratton JP, Lin MI, Yu J, Weiss ED, Jiang ZL, Fairchild TA, et al. Selective inhibition of tumor microvascular permeability by cavtratin blocks tumor progression in mice. Cancer Cell. 2003;4(1):31-9.
Lin MI, Yu J, Murata T, Sessa WC. Caveolin-1-deficient mice have increased tumor microvascular permeability, angiogenesis, and growth. Cancer Res. 2007;67(6):2849-56.
Kosuri S, Akhtar NH, Smith M, Osborne JR, Tagawa ST. Review of salvage therapy for biochemically recurrent prostate cancer: the role of imaging and rationale for systemic salvage targeted anti-prostate-specific membrane antigen radioimmunotherapy. Adv Urol. 2012;2012:921674.
Tercel M, Lee HH, Yang S, Liyanage HD, Mehta SY, Boyd PD, et al. Preparation and antitumour properties of the enantiomers of a hypoxia-selective nitro analogue of the duocarmycins. ChemMedChem. 2011;6(10):1860-71; Abstract.
Tagawa ST, Milowsky MI, Morris M, Vallabhajosula S, Christos P, Akhtar NH, et al. Phase II study of Lutetium-177-labeled anti-prostate-specific membrane antigen monoclonal antibody J591 for metastatic castration-resistant prostate cancer. Clinical cancer research : an official journal of the American Association for Cancer Research. 2013;19(18):5182-91.
Bander NH, Milowsky MI, Nanus DM, Kostakoglu L, Vallabhajosula S, Goldsmith SJ. Phase I trial of 177lutetium-labeled J591, a monoclonal antibody to prostate-specific membrane antigen, in patients with androgen-independent prostate cancer. Journal of clinical oncology : official journal of the American Society of Clinical Oncology. 2005;23(21):4591-601.
Milowsky MI, Nanus DM, Kostakoglu L, Vallabhajosula S, Goldsmith SJ, Bander NH. Phase I trial of yttrium-90-labeled anti-prostate-specific membrane antigen monoclonal antibody J591 for androgen-independent prostate cancer. Journal of clinical oncology : official journal of the American Society of Clinical Oncology. 2004;22(13):2522-31.
Tagawa ST, Vallabhajosula S, Osborne J, Goldsmith SJ, Petrillo K, Tyrell L, Dhillon GS, Beltran H, Bander NH, Nanus DM. Phase I trial of fractionated-dose 177lutetium radiolabeled anti-prostate-specific membrane antigen (PSMA) monoclonal antibody J591 (177Lu-J591) in patients (pts) with metastatic castration-resistant prostate cancer (metCRPC). J Clin Oncol 28:7s, 2010 (suppl; abstr 4667).
Horoszewicz JS, Leong SS, Kawinski E, Karr JP, Rosenthal H, Chu TM, Mirand EA, Murphy GP 1983. LNCaP model of human prostatic carcinoma. Cancer Res. 43 (4): 1809-18. PMID 6831420.
Ramirez-Fort MK, Rogers MJ, Santiago R, Mahase SS, Mendez M, Zheng Y, Kong X, Kashanian JA, Niaz MJ, McClelland S 3rd, Wu X, Bander NH, Schlegel P, Mulhall JP, Lange CS. Prostatic irradiation-induced sexual dysfunction: a review and multidisciplinary guide to management in the radical radiotherapy era (Part I defining the organ at risk for sexual toxicities). Rep Pract Oncol Radiother. May-Jun. 2020;25(3):367-375. Doi: 10.1016/j.rpor.2020.03.007. Epub Mar. 19, 2020. PMID: 32322175; PMCID: PMC7163290.
Rogers MJ, Ramirez-Fort MK, Kashanian J, Broster SA, Matta J, Mahase SS, Fort DV, Niaz MJ, McClelland S 3rd, Bander NH, Fort, M, Lange CS, Schlegel P, Mulhall J. Prostatic irradiation-induced sexual dysfunction: A review and nultidisciplinary guide to management in the ablative RT era (Part II: On Uriological Management). Rep Pract Oncol and Radiother. May-Jun. 2020;25(5):619-624. Doi: 10.1016/j.rpor.2020.03.0011. Epub May 6, 2020.
Ramirez-Fort MK, Suarez P, Carrion M, Postle C, Weiner J, Lange CS, Arribas R, Fort M. Prostatic irradiation-induced sexual dysfunction: A review and multidisciplinary guide to management in the ablative RT era (Part III: Psychosexual Therapy). Rep Pract Oncol and Radiother. May-Jun. 2020;25(5):625-631. Doi: 10.1016/j.rpor.2020.03.0014. Epub Apr. 30, 2020.
Ramirez-Fort MK, Meier-Schiesser B, Niaz MJ, Niaz MO, Feily A, Fort M, Lange CS, Caba D. Dermatofibrosarcoma Protuberans: The Current State of Multidisciplinary Management. Skinmed. Oct. 1, 2020;18(5):288-293. PMID: 33160438. https://pubmed.ncbi.nlm.nih.gov/33160438/.
Ramirez-Fort MK, Meier-Schiesser B, Lachance K, Mahase SS, Church CD, Niaz MJ, Liu H, Navarro V, Nikolopoulou A, Kazakov DV, Contassot E, Nguyen DP, Sach J, Hadravsky L, Sheng Y, Tagawa ST, Wu X, Lange CS, French LE, Nghiem PT, Bander NH. Folate hydrolase-1 (FOLH1) is a novel target for antibody-based brachytherapy in Merkel cell carcinoma. Skin Health Dis. 2020;e9. https://doi.org/10.1002/ski2.9.
Niaz MO, Sun M, Ramirez-Fort MK, Niaz MJ. Prostate-specific Membrane Antigen Based Antibody-drug Conjugates for Metastatic Castration-resistance Prostate Cancer. Cureus. Feb. 29, 2020;12(2):e7147. Doi: 10.7759/cureus.7147. Review. PubMed PMID: 32257692; PubMed Central PMCID: PMC7105266.
Niaz MO, Sun M, Ramirez-Fort MK, Niaz MJ. Review of Lutetium-177-labeled Anti-prostate-specific Membrane Antigen Monoclonal Antibody J591 for the Treatment of Metastatic Castration-resistant Prostate Cancer. Cureus. Feb. 26, 2020;12(2):e7107. Doi:10.7759/cureus.7107. Review. PubMed PMID: 32257655; PubMed Central PMCID: PMC7100619.
Feily A, Feily A, Alexander JS, Niaz MJ, Gianfaldoni S, Lotti T, Ramirez-Fort MK*. Pseudo-dense Hair Transplantation: Strategy of "Less Inside, More Outside" and Central Bulking with Curled Chest Hairs as Treatment for Scalp Scars. J Cutan Aesthet Surg. Jul.-Sep. 2020;13(3):226-228. Doi: 10.4103/JCAS.JCAS_104_19. PMID: 33209000; PMCID: PMC7646433.
Feily A, Firoozifard A, Sokhandani T, Elosegui-Rodriguez P, Perez-Rivera E, Lange CS, Hosseinpoor M, Ramirez-Fort MK*. Follicular Transplantation, Microneedling, and Adjuvant Narrow-band Ultraviolet-B Irradiation as Cost-Effective Regimen for Palmar-Plantar Vitiligo: A Pilot Study. Cureus. Apr. 28, 2020;12(4):e7878. Doi: 10.7759/cureus. 7878. PMID: 32489732; PMCID: PMC7255558.
T.P. Coohill, and F. Ghetti. 2012. Action Spectroscopy: Ultraviolet Radiation. CRC Handbook of Organic Photochemistry and Photobiology. 3rd edition, vol. 2. pp. 1093-1103, eds.
Ash C, Dubec M, Donne K, Bashford T. Effect of wavelength and beam width on penetration in light-tissue interaction using computational methods. Lasers Med Sci. Nov. 2017;32(8):1909-1918. Doi: 10.1007/s10103-017-2317-4. Epub Sep. 12, 2017. PMID: 28900751; PMCID: PMC5653719.
Haensch S, Bianucci R, Signoli M, Rajerison M, Schultz M, Kacki S, Vermunt M, Weston DA, Hurst D, Achtman M, Carniel E, Bramanti B. Distinct clones of Yersinia pestis caused the black

(56) References Cited

OTHER PUBLICATIONS death. PloS Pathog. Oct. 7, 2010;6(10):e1001134. Doi: 10.1371/journal.ppat.1001134. PMID: 20949072; PMCID: PMC2951374.
Fajuyigbe D, Young AR. The impact of skin colour on human photobiological responses. Pigment Cell Melanoma Res. Nov. 2016;29(6):607-618. Doi: 10.1111/pcmr.12511. Epub Aug. 16, 2016. PMID: 27454804; PMCID: PMC5132026.
Burrell LM, Risvanis J, Kubota E, Dean RG, MacDonald PS, Lu S, Tikellis C, Grant SL, Lew RA, Smith AI, Cooper ME, Johnston CI. Myocardial infarction increases ACE2 expression in rat and humans. Eur Heart J. Feb. 2005;26(4):369-75; discussion 322-4. Doi: 10.1093/eurheartj/ehi114. Epub Jan. 25, 2005. PMID: 15671045.
Raj Verma T, Kumar Painuly N, Prasad Mishra S, Yoganathan SA, Singh N, Bhatt MLB, Jamal N. Evaluation of Lung Density and Its Dosimetric Impact on Lung Cancer Radiotherapy: A Simulation Study. J Biomed Phys Eng. Feb. 1, 2019;9(1):17-28. PMID: 30881931; PMCID: PMC6409377.
Folate Hydrolase-1 is a novel target for J591-brachytherapy in Merkel cell carcinoma, Barbara Meier, Marigdalia K. Ramirez-Fort et al. (2017).
External beam irradiation may increase the therapeutic index of J591-brachytherapy, M.K. Ramirez-Fort et al. (2017).
Park S, Ang RR, Duffy SP, Bazov J, Chi KN, Black PC, Ma H. Morphological differences between circulating tumor cells from prostate cancer patients and cultured prostate cancer cells. PloS One. Jan. 8, 2014;9(1):e85264. Doi: 10.1371/journal.pone.0085264. PMID: 24416373; PMCID: PMC3885705.
177Lu Radiolabeled Monoclonal Antibody HuJ591-GS (177Lu-J591) in Patients With Nonprostate Metastatic Solid Tumors: A Pilot Study; ClinicalTrials.gov Identifier: NCT00967577; Aug. 28, 2009.
RK Riegelman & RP Hirsch, Studying a Study and Testing a Test, Little Brown & Co.,1996.
177Lu Radiolabeled Monoclonal Antibody HuJ591 (177Lu-J591) and Ketoconazole in Patients With Prostate Cancer; ClinicalTrials.gov Identifier: NCT00859781; Mar. 11, 2009.
LinkedIn post by Ramirez-Fort MK on Mar. 16, 2020 at https://www.linkedin.com/in/marigdalia/detail/recent-activity/ at https://www.linkedin.com/posts/marigdalia_study-covid-19-is-also-spread-by-fecal-oral-activity-6645189377850949632-VCcp/?utm_source=share&utm_medium=member_desktop.
Lea DE., Actions of Radiations on Livings Cells, 1st ed. 402 pp. Macmillan, New York, 1947.
El Ghissassi, Fatiha, Robert Baan, Kurt Straif, Yann Grosse, Béatrice Secretan, Véronique Bouvard, Lamia Benbrahim-Tallaa, Neela Guha, Crystal Freeman, Laurent Galichet, and Vincent Cogliano. 'A review of human carcinogens 2014;Part D: radiation', The Lancet Oncology, 10: 751-52.
Halsted, C.H., Jejunal brush-border folate hydrolase. A novel enzyme. West J Med, 1991. 155(6): p. 605-9.
Lavoie, A., E. Tripp, and A.V. Hoffbrand, Sephadex-gel filtration and heat stability of human jejunal and serum pteroylpolyglutamate hydrolase (folate conjugase). Evidence for two different forms. Biochem Med, 1975. 13(1): p. 1-6; Abstract.
Blakely, R.D., et al., Hydrolysis of the brain dipeptide N-acetyl-L-aspartyl-L-glutamate: subcellular and regional distribution, ontogeny, and the effect of lesions on N-acetylated-alpha-linked acidic dipeptidase activity. J Neurochem, 1988. 50(4): p. 1200-9.
Robinson, M.B., et al., Hydrolysis of the brain dipeptide N-acetyl-L-aspartyl-L-glutamate. Identification and characterization of a novel N-acetylated alpha-linked acidic dipeptidase activity from rat brain. J Biol Chem, 1987. 262(30): p. 14498-506.
Silink, M. and P.B. Rowe, The localization of glutamate carboxypeptidase in rat liver lysosomes. Biochim Biophys Acta, 1975. 381(1): p. 28-36.
Israeli, R.S., et al., Expression of the prostate-specific membrane antigen. Cancer Res, 1994. 54(7): p. 1807-11.
Israeli, R.S., et al., Molecular cloning of a complementary DNA encoding a prostate-specific membrane antigen. Cancer Res, 1993. 53(2): p. 227-30.
Liu, H., et al., Monoclonal antibodies to the extracellular domain of prostate-specific membrane antigen also react with tumor vascular endothelium. Cancer Res, 1997. 57(17): p. 3629-34.
O'Keefe, D.S., et al., Mapping, genomic organization and promoter analysis of the human prostate-specific membrane antigen gene. Biochim Biophys Acta, 1998. 1443(1-2): p. 113-27.
Ramirez-Fort MK, Navarro V, Liu H, Meier B, Levesque M, Vissicchio JR, Moy J, Contassot E, Christos P, Tagawa ST, Bander NH, Lange CS, French LE. Possible cancer stem cells: Folate hydrolase-1 is expressed in a subset of Oct4-positive melanoma cells. 2017 Proceedings of the AACR Cancer Research. Apr. 2017; abstr 1905.
Ramirez-Fort, M.K., et al., Folate hydrolase-1 (FOLH1) is a novel target for antibody-based brachytherapy in Merkel cell carcinoma. Skin Health Dis, 2021. 1(1).
Ramirez-Fort MK, Meier B, Feily A, Cooper SL, Lange CS. Adjuvant irradiation to prevent keloidal fibroproliferative growth should be standard of care. Br J Dermatol. 2017;177(6):e327-e328.
Niaz MJ, Batra JS, Walsh RD, et al. Pilot Study of Hyperfractionated Dosing of Lutetium-177-Labeled Antiprostate-Specific Membrane Antigen Monoclonal Antibody J591 ((177) Lu-J591) for Metastatic Castration-Resistant Prostate Cancer. Oncologist. Jan. 30, 2020. Doi:10.1634/theoncologist.2020-0028. [Epub ahead of print] PubMed PMID: 31999003.
Feily A, Seifi V, Ramirez-Fort MK. Fractional CO2 Laser Pretreatment to Autologous Hair Transplantation and Phototherapy Improves Perifollicular Repigmentation in Refractory Vitiligo: A Randomized, Prospective, Half-Lesion, Comparative Study. Dermatol Surg. 2016;42(9):1082-1088.
Au SC, Ramirez-Fort MK, Gottlieb AB. Analysis of trial data for infliximab and golimumab: baseline C-reactive protein level and prediction of therapeutic response in patients with psoriatic arthritis. Arthritis Care Res (Hoboken). 2014;66(7):1114-1118.
Doan HQ, Ung B, Ramirez-Fort MK, Khan F, Tyring SK. Zostavax : a subcutaneous vaccine for the prevention of herpes zoster. Expert Opin Biol Ther. 2013;13(10):1467-1477.
Feily A, Lotti T, Lange CS, Gianfaldoni S, Ramirez-Fort MK. Is HPV vaccination of pregnant women really safe? Dermatol Ther. 2018;31(3):e12593.
Kim SR, Khan F, Ramirez-Fort MK, Downing C, Tyring SK. Varicella zoster: an update on current treatment options and future perspectives. Expert Opin Pharmacother. 2014;15(1):61-71.
Mays R, Curry J, Kim K, et al. Eruptive squamous cell carcinomas after vemurafenib therapy. J Cutan Med Surg. 2013;17(6):419-422.
Nguyen DP, Xiong PL, Liu H, et al. Induction of PSMA and Internalization of an Anti-PSMA mAb in the Vascular Compartment. Mol Cancer Res. 2016;14(11):1045-1053.
Ramirez-Fort MK, Au SC, Javed SA, Loo DS. Management of cutaneous human papillomavirus infection: pharmacotherapies. Curr Probl Dermatol. 2014;45:175-185.
Ramirez-Fort MK, Case EC, Rosen AC, Cerci FB, Wu S, Lacouture ME. Rash to the mTOR inhibitor everolimus: systematic review and meta-analysis. Am J Clin Oncol. 2014;37(3):266-271.
Ramirez-Fort MK, Levin AA, Au SC, Gottlieb AB. Continuous versus intermittent therapy for moderate-to-severe psoriasis. Clin Exp Rheumatol. 2013;31(4 Suppl 78):S63-70.
Schlichte MJ, Downing CP, Ramirez-Fort M, Gordon R, Tyring S. Bloodroot associated eschar. Dermatol Online J. 2014;20(7).
Shelton M, Ramirez-Fort MK, Lee KC, Ladizinski B. Krokodil: from Russia with love. JAMA Dermatol. 2015;151(1):32.
Rasaii S, Sohrabian N, Gianfaldoni S, et al. Intralesional triamcinolone alone or in combination with botulinium toxin A is ineffective for the treatment of formed keloid scar: A double blind controlled pilot study. Dermatol Ther. 2019;32(2):e12781.
Varada S, Ramirez-Fort MK, Argobi Y, Simkin AD. Remission of refractory benign familial chronic pemphigus (hailey-hailey disease) with the addition of systemic cyclosporine. J Cutan Med Surg. 2015;19(2):163-166.
Ladizinski B, Ramirez-Fort MK, Cohen YK, Rosendahl C, Elpem DJ. Pseudofolliculitis barbae: a dermatoscopic correlate. Dermatol Pract Concept. 2013;3(2):53-54.
Ladizinski B, Ramirez-Forte MK, Elpern DJ. Dermoscopy: What is your diagnosis? Dermatol Pract Concept. 2013;3(3):23.

(56) References Cited

OTHER PUBLICATIONS

Ramirez-Fort MK. Human papillomavirus-induced periungual pigmented Bowen's disease. Dermatol Pract Concept. 2012;2(1):57-59.

Ramirez-Fort MK, Al Jalbout S, Kittler H, Pellacani G. Lichenoid keratosis: non-invasive imaging in the setting of diagnostic uncertainty. Dermatol Pract Concept. 2013;3(2):63-65.

Javed S, Khan F, Ramirez-Fort M, Tyring SK. Bites and mites: prevention and protection of vector-borne disease. Curr Opin Pediatr. 2013;25(4):488-491.

Doan HQ, Ramirez-Fort MK, Rady PL. Viral oncogenesis. Curr Probl Dermatol. 2014;45:33-46.

Ramirez-Fort MK, Downing C, Doan HQ, et al. Coxsackievirus A6 associated hand, foot and mouth disease in adults: clinical presentation and review of the literature. J Clin Virol. 2014;60(4):381-386.

Ramirez-Fort MK, Sam H, Manders EK. Management of cutaneous human papillomavirus infection: surgery. Curr Probl Dermatol. 2014;45:186-196.

Varada S, Posnick M, Alessa D, Ramirez-Fort MK. Management of cutaneous human papillomavirus infection in immunocompromised patients. Curr Probl Dermatol. 2014;45:197-215.

Kleker BM, Ramirez-Fort MK, Puchalsky D, Longley BJ, Swanson A, Zone J. A generalized annular eruption with occasional vesicles. Arch Dermatol. 2012;148(4):531-536.

Khan F, Ramirez-Fort MK, Chan CS, Rosen T. Hyperkeratotic necrobiosis lipoidica. Dermatol Pract Concept. 2013;3(1):13-15.

McClelland S, 3rd, Brown SA, Ramirez-Fort MK, Jaboin JJ, Zellars RC. The surgical nature of radiation oncology should be better reflected in pre-residency training. Rep Pract Oncol Radiother. 2019;24(5):507-508.

Bicknell LM, Ladizinski B, Tintle SJ, Ramirez-Fort MK. Lips as red as blood: areca nut lip staining. JAMA Dermatol. 2013;149(11):1288.

Ramirez-Fort MK, Doan HQ, Nguyen HP, Khan F, Kauffman J, Campbell LS. Chronic unilateral eruption of painful, erythematous papules and nodules. Piloleiomyoma. JAMA Dermatol. 2013;149(7):865-866.

Ramirez-Fort MK, Khan F, Rosendahl CO, Mercer SE, Shim-Chang H, Levitt JO. Acquired perforating dermatosis: a clinical and dermatoscopic correlation. Dermatol Online J. 2013;19(7):18958.

Ramirez-Fort MK, Lastra-Vicente R, Levitt JO, Sanchez JL, Reizner GT. Organizing a dermatology service mission. Int J Dermatol. 2013;52(3):342-349.

Schmidtberger L, Ladizinski B, Ramirez-Fort MK. Wax on, wax off: pubic hair grooming and potential complications. JAMA Dermatol. 2014;150(2):122.

Feily A, Hosseinpoor M, Bakhti A, et al. Digit-Length Ratios (2D:4D) as a Phenotypic Indicator of in Utero Androgen Exposure is Not Prognostic for Androgenic Alopecia: a Descriptive-Analytic Study of 1200 Iranian Men. Dermatol Reports. 2016;8(1):6386.

Mohebipour A, Gianfaldoni S, Lotti T, et al. Recycling of Previously Transplanted Hair: A Novel Indication for Follicular Unit Extraction. Open Access Maced J Med Sci. 2018;6(6):1095-1097.

Xu X, Chen P, Wang J, et al. Evolution of the novel coronavirus from the ongoing Wuhan outbreak and modeling of its spike protein for risk of human transmission. Sci China Life Sci. 2020;63(3):457-460.

Yan R, Zhang Y, Li Y, Xia L, Guo Y, Zhou Q. Structural basis for the recognition of the SARS-CoV-2 by full-length human ACE2. Science. 2020.

Rice GI, Jones AL, Grant PJ, Carter AM, Turner AJ, Hooper NM. Circulating activities of angiotensin-converting enzyme, its homolog, angiotensin-converting enzyme 2, and neprilysin in a family study. Hypertension. 2006;48(5):914-920.

Lai CC, Shih TP, Ko WC, Tang HJ, Hsueh PR. Severe acute respiratory syndrome coronavirus 2 (SARS-CoV-2) and coronavirus disease-2019 (COVID-19): The epidemic and the challenges. Int J Antimicrob Agents. 2020;55(3):105924.

Paules CI, Marston HD, Fauci AS. Coronavirus Infections—More Than Just the Common Cold. JAMA. 2020.

Chan JF, Yuan S, Kok KH, et al. A familial cluster of pneumonia associated with the 2019 novel coronavirus indicating person-to-person transmission: a study of a family cluster. Lancet. 2020;395(10223):514-523.

Ong SWX, Tan YK, Chia PY, et al. Air, Surface Environmental, and Personal Protective Equipment Contamination by Severe Acute Respiratory Syndrome Coronavirus 2 (SARS-CoV-2) From a Symptomatic Patient. JAMA. 2020.

Szeto W, Yam WC, Huang H, Leung DYC. The efficacy of vacuum-ultraviolet light disinfection of some common environmental pathogens. BMC Infect Dis. 2020;20(1):127.

Bedell K, Buchaklian AH, Perlman S. Efficacy of an Automated Multiple Emitter Whole-Room Ultraviolet-C Disinfection System Against Coronaviruses MHV and MERS-CoV. Infect Control Hosp Epidemiol. 2016;37(5):598-599.

Hoshino Y, Dalai SK, Wang K, et al. Comparative efficacy and immunogenicity of replication-defective, recombinant glycoprotein, and DNA vaccines for herpes simplex virus 2 infections in mice and guinea pigs. Journal of virology. 2005;79(1):410-418.

Cho A, Jantschitsch C, Knobler R. Extracorporeal Photopheresis—An Overview. Front Med (Lausanne). 2018;5:236.

Rajagopal K, Keller SP, Akkanti B, et al. Advanced Pulmonary and Cardiac Support of COVID-19 Patients: Emerging Recommendations From ASAIO—a Living Working Document. Circ Heart Fail. 2020;13(5):e007175.

Li JJ. Mitigating Coronavirus-Induced Acute Respiratory Distress Syndrome by Radiotherapy. iScience. 2020;23(6):101215.

Kefayat A, Ghahremani F. Low dose radiation therapy for COVID-19 pneumonia: a double-edged sword. Radiother Oncol. 2020.

Kirkby C, Mackenzie M. Is low dose radiation therapy a potential treatment for COVID-19 pneumonia? Radiother Oncol. 2020.

Shimizuguchi T, Sekiya N, Hara K, et al. Radiation therapy and the risk of herpes zoster in patients with cancer. Cancer. 2020.

Lai YL, Su YC, Kao CH, Liang JA. Increased risk of varicella-zoster virus infection in patients with breast cancer after adjuvant radiotherapy: A population-based cohort study. PLoS One. 2019;14(1):e0209365.

Fujii T, Kitamura Y, Mizuguchi H, et al. Effects of irradiation with narrowband-ultraviolet B on up-regulation of histamine H1 receptor mRNA and induction of apoptosis in HeLa cells and nasal mucosa of rats. J Pharmacol Sci. 2018;138(1):54-62.

Preston DL, Ron E, Tokuoka S, et al. Solid cancer incidence in atomic bomb survivors: 1958-1998. Radiat Res. 2007;168(1):1-64.

Dennis LK, Vanbeek MJ, Beane Freeman LE, Smith BJ, Dawson DV, Coughlin JA. Sunburns and risk of cutaneous melanoma: does age matter? A comprehensive meta-analysis. Ann Epidemiol. 2008;18(8):614-627.

Amano S. Characterization and mechanisms of photoageing-related changes in skin. Damages of basement membrane and dermal structures. Exp Dermatol. 2016;25 Suppl 3:14-19.

Rivas M, Rojas E, Araya MC, Calaf GM. Ultraviolet light exposure, skin cancer risk and vitamin D production. Oncol Lett. 2015;10(4):2259-2264.

Armstrong BK, Kricker A, English DR. Sun exposure and skin cancer. Australas J Dermatol. 1997;38 Suppl 1:S1-6.

Hasche D, Stephan S, Braspenning-Wesch I, et al. The interplay of UV and cutaneous papillomavirus infection in skin cancer development. PLoS Pathog. 2017; 13(11):e1006723.

UV Penetration depths in skin Meinhardt, Merve, et al. "Wavelength-dependent penetration depths of ultraviolet radiation in human skin." Journal of biomedical optics 13.4 (2008): 044030.

Kirz, Janos, Chris Jacobsen, and Malcolm Howells. "Soft X-ray microscopes and their biological applications." Quarterly reviews of biophysics 28.1 (1995): 33-130; Abstract.

Bander, N.H., et al., Phase I trial of 177lutetium-labeled J591, a monoclonal antibody to prostate-specific membrane antigen, in patients with androgen-independent prostate cancer. J Clin Oncol, 2005. 23(21): p. 4591-601.

Milowsky, M.I., et al., Phase 1/2 multiple ascending dose trial of the prostate-specific membrane antigen-targeted antibody drug conjugate MLN2704 in metastatic castration-resistant prostate cancer. Urol Oncol, 2016. 34(12): p. 530 e15-530 e21.

(56) References Cited

OTHER PUBLICATIONS

Tagawa, S.T., et al., Phase II study of Lutetium-177-labeled antiprostate-specific membrane antigen monoclonal antibody J591 for metastatic castration-resistant prostate cancer. Clin Cancer Res, 2013. 19(18): p. 5182-91.
Holland, J.P., et al., 89Zr-DFO-J591 for immunoPET of prostate-specific membrane antigen expression in vivo. J Nucl Med, 2010. 51(8): p. 1293-300.
Osborne, J.R., et al., A prospective pilot study of (89)Zr-J591/prostate specific membrane antigen positron emission tomography in men with localized prostate cancer undergoing radical prostatectomy. J Urol, 2014. 191(5): p. 1439-45.
Pandit-Taskar, N., et al., (8)(9)Zr-huJ591 immuno-PET imaging in patients with advanced metastatic prostate cancer. Eur J Nucl Med Mol Imaging, 2014. 41(11): p. 2093-105.
Pandit-Taskar, N., et al., Indium 111-labeled J591 anti-PSMA antibody for vascular targeted imaging in progressive solid tumors. EJNMMI Res, 2015. 5: p. 28.
Vallabhajosula, S., et al., Radioimmunotherapy of Metastatic Prostate Cancer with (1)(7)(7)Lu-DOTAhuJ591 Anti Prostate Specific Membrane Antigen Specific Monoclonal Antibody. Curr Radiopharm, 2016. 9(1): p. 44-53.
Ramirez-Fort, M.K., et al., Theragnostic Target, Prostate-Specific Membrane Antigen—Also Specific for Nonprostatic Malignancies. Int J Radiat Oncol Biol Phys, 2018. 101(3): p. 646-649.
Niaz, M.J., et al., Pilot Study of Hyperfractionated Dosing of Lutetium-177-Labeled Antiprostate-Specific Membrane Antigen Monoclonal Antibody J591 ((177) Lu-J591) for Metastatic Castration-Resistant Prostate Cancer. Oncologist, 2020.
Niaz, M.O., et al., Review of Lutetium-177-labeled Anti-prostate-specific Membrane Antigen Monoclonal Antibody J591 for the Treatment of Metastatic Castration-resistant Prostate Cancer. Cureus, 2020. 12(2): p. e7107.
Liu, H., et al., Constitutive and antibody-induced internalization of prostate-specific membrane antigen. Cancer Res, 1998. 58(18): p. 4055-60.
Rajasekaran, S.A., et al., A novel cytoplasmic tail MXXXL motif mediates the internalization of prostate-specific membrane antigen. Mol Biol Cell, 2003. 14(12): p. 4835-45.
Ma, D., et al., Potent antitumor activity of an auristatin-conjugated, fully human monoclonal antibody to prostate-specific membrane antigen. Clin Cancer Res, 2006. 12(8): p. 2591-6.
Wu, G., et al., Site-specific conjugation of boron-containing dendrimers to anti-EGF receptor monoclonal antibody cetuximab (IMC-C225) and its evaluation as a potential delivery agent for neutron capture therapy. Bioconjug Chem, 2004. 15(1): p. 185-94; Abstract.
Wu, G., et al., Boron containing macromolecules and nanovehicles as delivery agents for neutron capture therapy. Anticancer Agents Med Chern, 2006. 6(2): p. 167-84; Abstract.
Barth, R.F., et al., Design, synthesis, and evaluation of cisplatin-containing EGFR targeting bioconjugates as potential therapeutic agents for brain tumors. Onco Targets Ther, 2016. 9: p. 2769-81.
Hodgson NC. Merkel cell carcinoma: changing incidence trends. Journal of surgical oncology. 2005;89(1):1-4.
Lemos B, Nghiem P. Merkel cell carcinoma: more deaths but still no pathway to blame. The Journal of investigative dermatology. 2007;127(9):2100-3.
Paulson KG, Park SY, Vandeven NA, Lachance K, Thomas H, Chapuis AG, et al. Merkel cell carcinoma: Current US incidence and projected increases based on changing demographics. J Am Acad Dermatol. 2018;78(3):457-63 e2.
Allen PJ, Bowne WB, Jaques DP, Brennan MF, Busam K, Coit DG. Merkel cell carcinoma: prognosis and treatment of patients from a single institution. J Clin Oncol. 2005;23(10):2300-9.
Tothill R, Estall V, Rischin D. Merkel cell carcinoma: emerging biology, current approaches, and future directions. American Society of Clinical Oncology educational book / ASCO American Society of Clinical Oncology Meeting. 2015;35:e519-26.
Tai PT, Yu E, Tonita J, Gilchrist J. Merkel cell carcinoma of the skin. Journal of cutaneous medicine and surgery. 2000;4(4):186-95.
Garneski KM, Nghiem P. Merkel cell carcinoma adjuvant therapy: current data support radiation but not chemotherapy. Journal of the American Academy of Dermatology. 2007;57(1):166-9.
Poulsen M, Rischin D, Walpole E, Harvey J, Mackintosh J, Ainslie J, et al. High-risk Merkel cell carcinoma of the skin treated with synchronous carboplatin/etoposide and radiation: a Trans-Tasman Radiation Oncology Group Study—TROG 96:07. Journal of clinical oncology : official journal of the American Society of Clinical Oncology. 2003;21(23):4371-6.
Poulsen MG, Rischin D, Porter I, Walpole E, Harvey J, Hamilton C, et al. Does chemotherapy improve survival in high-risk stage I and II Merkel cell carcinoma of the skin? International journal of radiation oncology, biology, physics. 2006;64(1):114-9; Abstract.
Sharma D, Flora G, Grunberg SM. Chemotherapy of metastatic Merkel cell carcinoma: case report and review of the literature. American journal of clinical oncology. 1991;14(2):166-9; Abstract.
Afanasiev OK, Yelistratova L, Miller N, Nagase K, Paulson K, Iyer JG, et al. Merkel polyomavirus-specific T cells fluctuate with merkel cell carcinoma burden and express therapeutically targetable PD-1 and Tim-3 exhaustion markers. Clin Cancer Res. 2013;19(19):5351-60.
Lipson EJ, Vincent JG, Loyo M, Kagohara LT, Luber BS, Wang H, et al. PD-L1 expression in the Merkel cell carcinoma microenvironment: association with inflammation, Merkel cell polyomavirus and overall survival. Cancer Immunol Res. 2013;1(1):54-63.

300 ⤸

Percent Transmission to the Center of Selected
Cells and Viruses in the UV

| Biological Sample | Diameter (μm) | Wavelength (nm) | | | |
|---|---|---|---|---|---|
| | | 200 | 250 | 300 | 350 |
| Bacteriophage (T2) | 0.1 | 74 | 86 | 100 | 100 |
| Herpes Simplex Virus | 0.15 | 66 | 80 | 100 | 100 |
| Bacterial Cell | 1 | 33 | 78 | 98 | 100 |
| Yeast Cell | 5 | 1.6 | 69 | 97 | 100 |
| Mammalian Cell (Spherical) | 20 | 10[a] | 20 | 91 | 96 |
| Mammalian Tissue (100 μm Thick) | — | — | — | 10[b] | 39 | 66 |

*Note:* All Values are Approximate. Values at λ Above 300nm can Vary Widely Due to the Presence of Endogenous Chromophores

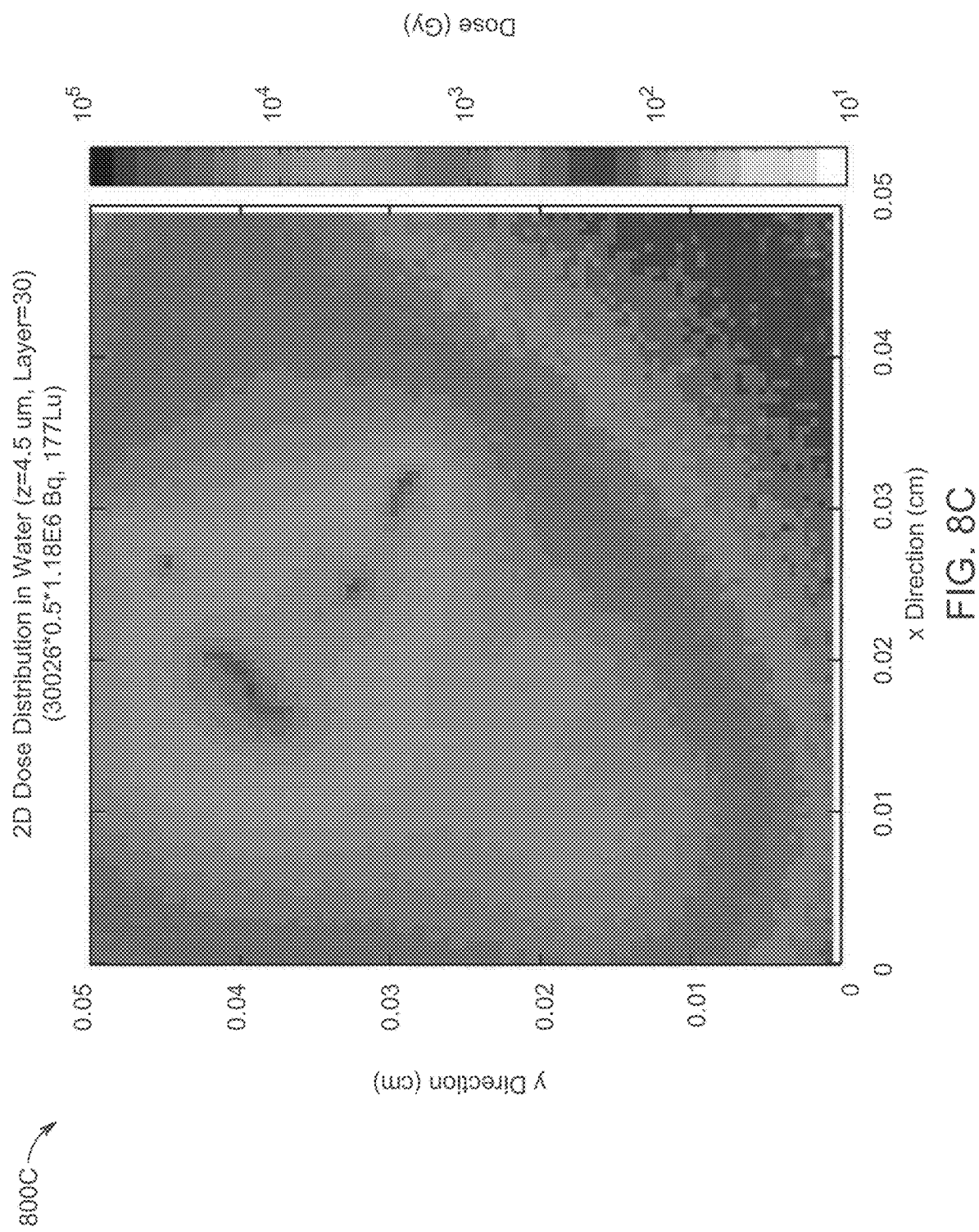

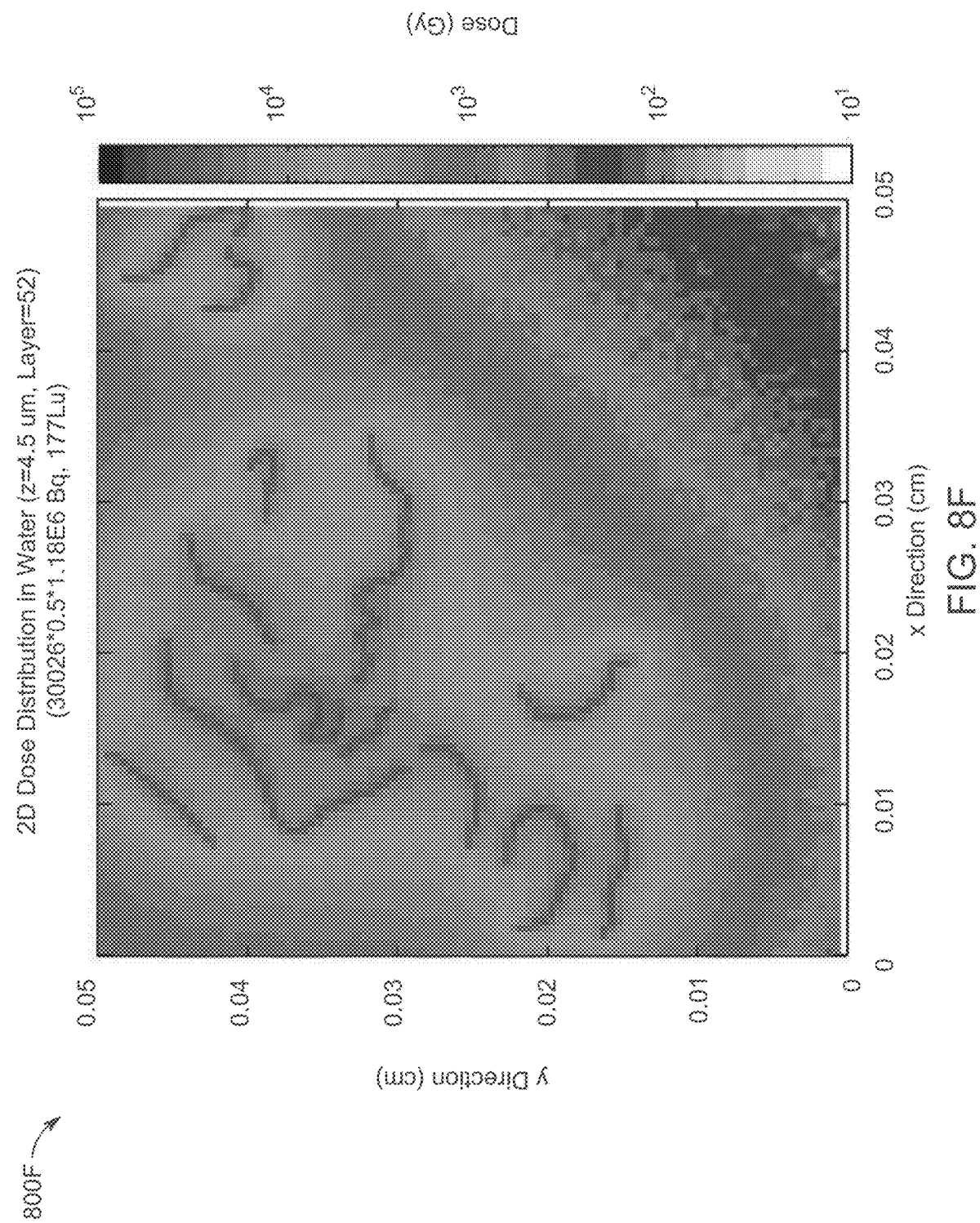

TABLE 1 Patient Demographics

| Characteristic | FOLH1 Negative (n = 6) | FOLH1 Positive (n = 29) | Total Cohort (n = 35) p |
|---|---|---|---|
| Sex | | | |
| Male (n = 21) | 3 | 18 | 0.664 |
| Female (n = 14) | 3 | 11 | - |
| Age at Diagnosis | | | |
| ≥65 (n = 26) | 3 | 23 | 0.162 |
| <65 (n = 9) | 3 | 6 | - |
| Immunosuppressed | | | |
| Yes (n = 5) | 0 | 5 | 0.539 |
| No (n = 18) | 4 | 14 | - |
| Received RT to Primary Site | | | |
| Yes (n = 17) | 4 | 13 | 1 |
| No (n = 3) | 0 | 3 | - |
| Stage Number | | | |
| IA (n = 1) | 1 | 0 | 0.317 |
| IB (n = 2) | 0 | 3 | - |
| IIA (n = 3) | 0 | 2 | - |
| IIB (n = 2) | 0 | 2 | - |
| IIIA (n = 7) | 2 | 5 | - |
| IIIB (n = 5) | 0 | 5 | - |
| IV (n = 3) | 1 | 2 | - |
| Sentinel Lymph Node Biopsy Performed? | | | |
| Yes (n = 13) | 3 | 8 | 0.616 |
| No (n = 9) | 1 | 8 | - |

| Characteristic | FOLH1 Negative (n = 6) | FOLH1 Positive (n = 29) | Total Cohort (n = 35) p |
|---|---|---|---|
| Site | | | 0.605 |
| Head & Neck (n = 14) | 4 | 10 | - |
| Trunk (n = 2) | 0 | 2 | - |
| Upper Limb (n = 7) | 0 | 7 | - |
| Lower Limb (n = 9) | 2 | 7 | - |
| Unknown Primary (n = 1) | 0 | 1 | - |
| Received Chemotherapy | | | 0.549 |
| Yes (n = 6) | 2 | 4 | - |
| No (n = 14) | 2 | 12 | - |
| Local/Regional Recurrence | | | 1 |
| Yes (n = 8) | 1 | 7 | - |
| No (n = 14) | 3 | 11 | - |
| Draining LN Recurrence | | | 1 |
| Yes (n = 11) | 1 | 10 | - |
| No (n = 9) | 2 | 7 | - |
| Distant Metastatic Recurrence | | | 0.587 |
| Yes (n = 13) | 2 | 11 | - |
| MCC Cells | | | 0.587 |
| No (n = 7) | 2 | 5 | - |
| 50%-75% (n = 7) | 2 | 5 | - |
| 76%-100% (n = 13) | 2 | 11 | - |

Abbreviations: FOLH1, Folate Hydrolase-1; LN, Lymph Node; MCC, Merkel Cell Carcinoma; RT, Radiotherapy.

FIG. 13 (Continued)

ULTRAVIOLET RADIATION TREATMENTS

CROSS-REFERENCE TO RELATED APPLICATION(S)

This application is a National Phase entry of International Patent Application No. PCT/US2021/024520, filed Mar. 26, 2021, which claims the benefit of prior filed U.S. Provisional Patent Application No. 63/000,302, filed Mar. 26, 2020, prior filed U.S. Provisional Patent Application No. 63/040,134, filed Jun. 17, 2020, and prior filed U.S. Provisional Patent Application No. 63/161,161, filed Mar. 15, 2021, each of which is hereby incorporated by reference herein in its entirety.

COPYRIGHT NOTICE

At least a portion of the disclosure of this patent document contains material that is subject to copyright protection. The copyright owner may have no objection to the facsimile reproduction by anyone of the patent document or patent disclosure as it appears in the Patent and Trademark Office patent file or records, but otherwise reserves all copyright rights whatsoever.

FIELD

This generally relates to enabling energy-based treatments (e.g., ultraviolet radiation, ionizing radiation, infrared radiation, magnetic radiation, etc.), as well as to systems, methods, and computer readable media for use thereof.

BACKGROUND

Ultraviolet ("UV") light has been used for irradiation of air and external surface targets. However, treatment of targets internal to a host with UV light has heretofore not been done, and deemed ineffective and/or unsafe.

SUMMARY

Systems, methods, and computer-readable media for enabling energy-based treatments are provided.

As an example, a method for determining an amount of energy to be delivered to cause an end effect on a target invasive entity of a target in a host is provided that may include determining the type of the target invasive entity, estimating the sensitivity of the determined target invasive entity to a particular energy-based therapy, estimating, based on the estimated sensitivity, a waveband-specific dose required to result in 10% remaining target invasive entity that is a 1-log reduction as a $D_{10}$ value, defining the treatment volume of the target, determining the maximal multiple of the estimated $D_{10}$ value of the target invasive entity that overlaps within the shoulder of the cellular survival curve pertaining to the treatment volume of the target, determining a permissible dose per fraction based on the determined maximal multiple when administered is to result in no more than a cellular $D_{90}$ to result in a 10% reduction of cells, determining a percent depth-dose or depth dose characterizations to identify the isodose distribution of the particular energy-based therapy in a particular treatment volume density, optimizing the volume of the defined treatment volume of the target to receive 100% of the maximal permissible dose per fraction, and prescribing a dose based on the determining the maximal multiple, the determining the permissible dose, the determining the percent depth-dose, and the optimizing.

As another example, a method for providing therapy to a target using a smart device is provided that may include determining, using the smart device, an amount of UV exposed to the target, for an invasive entity, determining, using the smart device, a dose-for-sterilization calculation for a particular type of exposure at the target based on a particular quantity of the target, and presenting, using the smart device, a length of time for exposing the target to the amount of UV based on the determined dose-for-sterilization calculation.

As yet another example, a method for monitoring a patient exposed to a known carcinogen at an exposing event is provided that may include, a period of time after the exposing event, performing a FOLH1 PET/CT on the patient to detect any FOLH1-avid tissue, and performing a diagnostic or confirmatory biopsy of the detected FOLH1-avid tissue to determine if the FOLH1-avid tissue is a cancer.

As yet another example, a method for adaptively treating a volume of cells with electromagnetic irradiation is provided that may include conjugating a chemical nuclei to an agent with FOLH1 binding capacity, administering the nuclei-agent construct into a body of cells for exposing a volume of cells of the body of cells to the nuclei-agent construct, waiting for a period of time after the administering to allow binding to occur, and exposing the volume of cells to electromagnetic irradiation for modifying the chemical nuclei within the volume of cells.

As yet another example, a method for measuring the absorbed dose of energy delivered via a target within a volume of cells is provided that may include measuring a specific activity and initial activity of a chemical nuclei that is attached to an agent with target binding capacity, quantifying target molecule(s) (FOLH1) for the volume of cells, and inputting the measured value and the quantified value into a mathematical simulation to estimate the possible outcomes of an uncertain event.

As yet another example, a method for enabling FOLH1 target upregulation is provided that may include applying energy to a volume of cells, waiting for a period of time after the energy application for an FOLH1 target to upregulate or to appear de novo, and, after the waiting, exposing the volume of cells to an embodiment with target binding capacity.

As yet another example, a method for optimizing the absorbed dose of electromagnetic irradiation delivered via a target within in a volume of cells is provided that may include identifying the initial activity of a chemical nuclei that is attached to an agent with target binding capacity, identifying a dose rate or absorption rate of the chemical nuclei or into cells within the volume, identifying the absorbed dose, identifying the time required for target replenishment after complete or partial target depletion, identifying the time required for target replenishment so that 50-100% of the initial dose of chemical nuclei can be absorbed as a subsequent dose, and waiting for a period of time between doses.

As yet another example, a therapy system for a patient appendage is provided that may include a hollow body including an interior surface defining at least a portion of a hollow space that is operative to receive at least a portion of the patient appendage, a plurality of suction passageway openings provided through the interior surface, a plurality of light passageway openings provided through the interior surface, and a plurality of magnetic energy passageway openings provided through the interior surface, a light apparatus operative to provide light through the plurality of light passageway openings, a suction apparatus operative to suck fluid from the hollow space through the plurality of suction passageway openings, and a magnet apparatus operative to provide magnetic energy through the plurality of magnetic energy passageway openings.

As yet another example, a therapy system for a patient cavity is provided that may include a body including an exterior surface that is operative to be inserted into at least a portion of the patient cavity, a plurality of suction passageway openings provided through the exterior surface, a plurality of light passageway openings provided through the exterior surface, and a plurality of magnetic energy passageway openings provided through the exterior surface, a light apparatus operative to provide light through the plurality of light passageway openings, a suction apparatus operative to suck fluid from an environment through the plurality of suction passageway openings, and a magnet apparatus operative to provide magnetic energy through the plurality of magnetic energy passageway openings.

This Summary is provided only to summarize some example embodiments, so as to provide a basic understanding of some aspects of the subject matter described in this document. Accordingly, it will be appreciated that the features described in this Summary are only examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

BRIEF DESCRIPTION OF THE DRAWINGS

The discussion below makes reference to the following drawings, in which like reference characters refer to like parts throughout, and in which:

FIG. 3 is a table listing depth dose data;
FIGS. 8A-8F are graphs of dose distribution in various layers;
FIG. 13 is a table listing patient demographic data.

DETAILED DESCRIPTION

Figure 1:
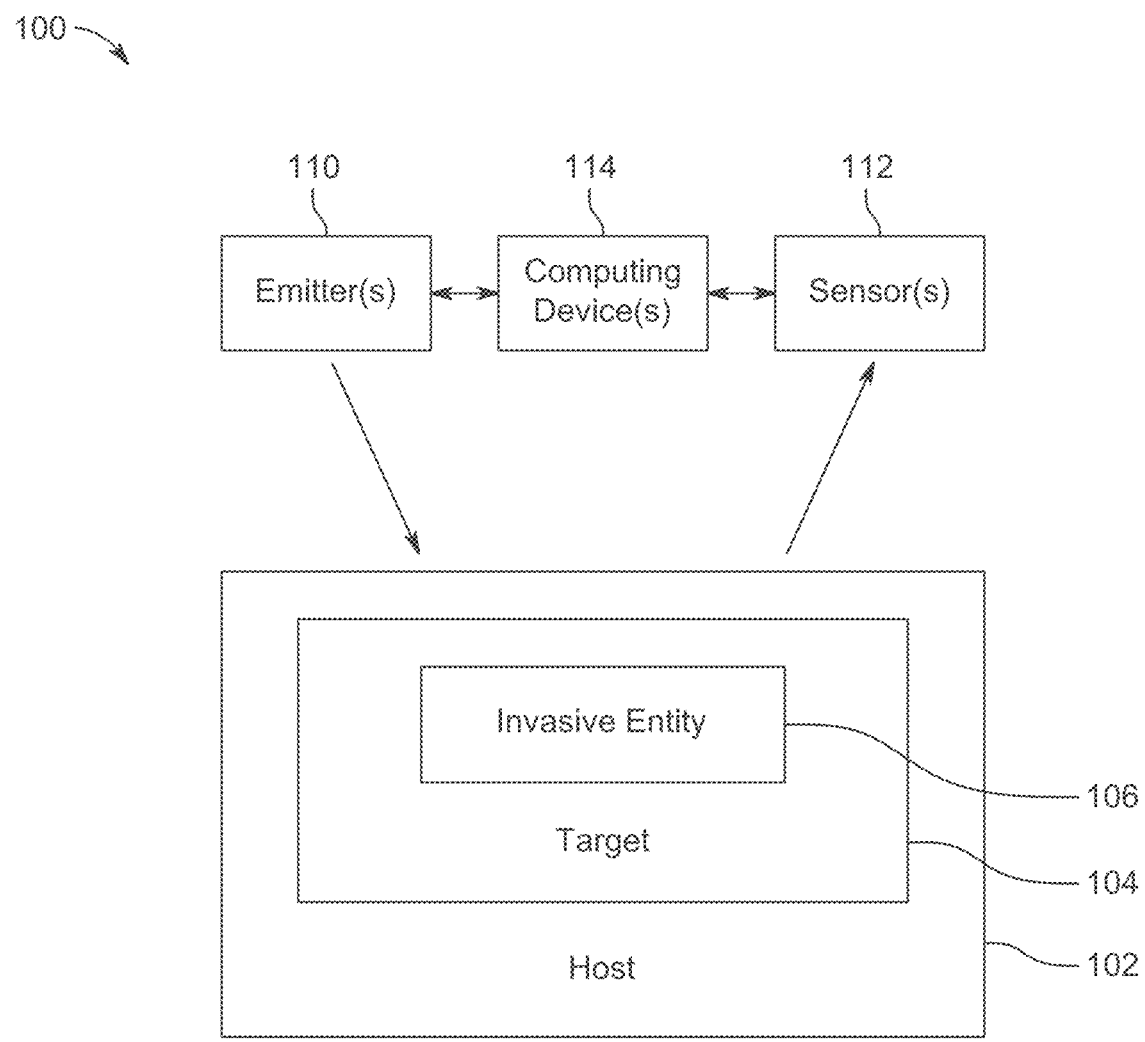
FIG. 1 is a schematic view of an illustrative system.

In the following detailed description, for purposes of explanation, numerous specific details are set forth to provide a thorough understanding of the various embodiments described herein. Those of ordinary skill in the art will realize that these various embodiments are illustrative only and are not intended to be limiting in any way. Other embodiments will readily suggest themselves to such skilled persons having the benefit of this disclosure.

In addition, for clarity purposes, not all of the routine features of the embodiments described herein are shown or described. One of ordinary skill in the art will readily appreciate that in the development of any such actual embodiment, numerous embodiment-specific decisions may be required to achieve specific design objectives. These design objectives will vary from one embodiment to another and from one developer to another. Moreover, it will be appreciated that such a development effort might be complex and time-consuming, but would nevertheless be a routine engineering undertaking for those of ordinary skill in the art having the benefit of this disclosure.

The present disclosure relates to enabling ultraviolet radiation treatments.

Systems, methods, and computer-readable media for enabling ultraviolet radiation treatments are provided and described with reference to FIGS. 1-25.

One or some components of a methodology of this disclosure may be developed within the context of one or more distinct disciplines in science (e.g., radiobiology, photobiology (see, e.g., references REF001-REF006, REF015, REF285-REF289, and REF292-REF294 of the list of references provided hereinbelow), pharmacology (see, e.g., references REF002, REF004, and REF006-REF019 of the list of references provided hereinbelow), biophysics (see, e.g., references REF001-REF006 and REF020-REF023 of the list of references provided hereinbelow), virology (see, e.g., references REF002, REF008-REF010, REF013, REF022, and REF024-REF029 of the list of references provided hereinbelow), immunology/inflammation (see, e.g., references REF002, REF003, REF005-REF010, REF013-REF016, REF018, REF019, REF023, REF024, and REF028-REF031 of the list of references provided hereinbelow), etc.) and/or in medicine (e.g., radiation oncology (see, e.g., references REF001-REF006, REF011, REF012, REF022, REF025, REF032, REF285-REF289, and REF291 of the list of references provided hereinbelow), dermatology (see, e.g., references REF001-REF003, REF005-REF009, REF011-REF024, REF027-REF031, REF033-REF039, REF286, REF288, and REF289 of the list of references provided hereinbelow), infectious diseases (see, e.g., references REF002, REF006, REF008-REF010, REF013, REF017, REF022, REF024-REF029, REF036, and REF037 of the list of references provided hereinbelow), surgery (see, e.g., references REF003, REF005, REF018, REF028, REF032, REF036, REF039, REF0285, REF286, and REF288 of the list of references provided hereinbelow), invasive and/or non-invasive imaging (see, e.g., references REF001, REF004, REF023, REF035, REF286, and REF287), etc.). Training in a combination of the aforementioned disciplines is rare in any individual.

The aim of a novel treatment and/or therapy platform of this disclosure, which may hereinafter be referred to as BIOFORT Regimen Platform or related to the field of "BioDefense", is to develop and manage the novel and non-obvious paradigm(s), protocol(s), method(s), organization(s), structure(s), design(s), pattern(s), formula(s), educational curriculum(s), license(s), certification(s), nomenclature(s), dosimetry(s), technology(s), device(s), and/or software mechanisms developed for and/or required/recommended to conduct safe and optimal environmental and human/animal energy-based therapy (e.g., ultraviolet radiation ("UVR") waveband therapy, infrared waveband therapy, magnetic field therapy, etc.) and/or global viral load reduction ("GVLR"), which may include, but are not limited to, air exposure ("AE"), surface exposure ("SE"), volume exposure ("VE"), external exposure ("EE"), intracavitary exposure, and/or interstitial exposure, and which may be used alone or in combination with other mechanisms towards the management of (1) invasive diseases afflicting members of the Animal Kingdom (e.g., human and/or other animal host) and Plant Kingdom, (2) invasive disease outbreaks, (3) invasive disease epidemics, and/or (4) invasive disease pandemics. Invasive disease may include all infiltrative and infectious disease entities (e.g., viruses, bacteria, fungi, cancer, etc.). In the context of non-viral invasive disease, the therapy platform and/or regimen may be termed in accordance to the targeted agent (e.g., global bacterial load reduction, global mycotic load reduction, global cancer load reduction, etc.). This therapy platform may be applied to the management of other invasive and/or non-invasive Animal and/or Plant disease etiologies not described herein, or that have not yet been discovered. BIOFORT's platform intends to commercialize the therapy platform, provide sustainable, cost-effective, and accessible health solutions to members of the Animal and Plant Kingdoms, optimize safe and equal access to the energy-based therapy(s) described herein (e.g., UVR therapy), and to develop educational curriculums/materials (e.g., patient education) for the public. BIOFORT's platform completely supports safe and equal opportunity to energy-based therapy, clean drinking water, clean air, healthcare, learning, and life-saving knowledge for all (in accordance to the Civil Rights Act of 1964, as amended).

Severe Acute Respiratory Syndrome Coronavirus-2 ("SARS-CoV-2"), most commonly known as Coronavirus Disease 2019 ("COVID-19") is thought to have originated from a mutated zoonotic (i.e., animal) virus in Wuhan, Hubei Province, China during December 2019 (see, e.g., reference REF040 of the list of references provided hereinbelow). COVID-19 quickly propagated through vulnerable human hosts (e.g., those who produce relatively lower levels of angiotensin converting enzyme-2 ("ACE2"), such as the elderly and Chinese population). COVID-19 caused/causes a clinical picture of a respiratory tract infection (e.g., fever, sore throat, cough, shortness of breath, etc.) with exaggerated "ACE-inhibitor-like pharmacotoxicity" (e.g., lung inflammation with severe cough, diarrhea, etc.). By mid-March 2020, COVID-19 became a pandemic, with a force that overwhelmed country-specific and global infectious disease protocols. COVID-19 stumped innumerable physicians, scientists, and academic medical centers around the world. COVID-19 has thrown the world into the United Darwinistic Crisis (i.e., the choice of succumbing to death in the face of the threat versus adapting to survive the threat) that we face today. A Darwinistic crisis often involves a forced natural selection process, where only the fittest should survive. As King David demonstrated with Goliath, "fitness to survive" is achieved by "outsmarting" the threat.

Scientific hypotheses and data support that coronavirus surface spike (S) protein mediated ACE2 receptor recognition, fusion and receptor-mediated cell endocytosis or internalization is a central mechanism of infection in SARS-CoV-2 disease, leading to the present COVID-19 pandemic (see, e.g., references REF041 and REF042 of the list of references provided hereinbelow). The ACE2 viral target is largely expressed in the human small intestine, lungs (i.e., alveolar epithelial cells), heart, gallbladder, kidneys, testis, and/or the like (see, e.g., references REF041 and REF043 of the list of references provided hereinbelow). Once COVID-19 enters (e.g., endocytoses, internalizes) into the ACE2-expressing cells of the aforementioned organs, the virus replicates within the cytoplasm (i.e., fluid region inside the cell) during a reported incubation period of approximately 2-11 days (see, e.g., references REF044 and REF045 of the list of references provided hereinbelow). Cytoplasmic viral replication presumably results in cell death, release of a massive viral load (i.e., quantity of infectious COVID-19 virions) into fluids surrounding the cells of ACE2-expressing organs. This process may be known as viral shedding and is the point at which the human (or other animal host) is most infectious to others. Once the virus sheds into the surrounding fluids, the human (or other animal host) can expel the virus from the body in such a way that the virus will be airborne (e.g., having similar trajectory characteristics such as "dust") and/or contaminate surfaces that have come in contact with the infected host body fluid(s).

Viral shedding presumably occurs in ACE2-rich tissues/organs, such as the nasopharynx, oropharynx, lungs and gastrointestinal tract, and, therefore, secretions (e.g., fluids, semi-solids or aerosolized particles) from these tissues are or could be infectious if the virus genetic material remains intact (see, e.g., references REF046, REF047, and REF305 of the list of references provided hereinbelow). COVID-19 virions spread to the environment within material (e.g., aerosols, respiratory droplets, feces, etc.) that is released by the infected host. Whether or not COVID-19 is transmissible by vector (e.g., mosquito, fly, flea, tick, etc.) is unclear, yet is possible.

COVID-19 virions may have multiple mechanisms for prolonged existence in the environment that need to be elucidated with targeted research. Until more information is available, shadow reduction, isolation, precautions against body aerosols, bodily fluid, and/or surface tactile contamination are advisable (e.g., optimizing personal hygiene, use of sterile drinking water, sterilization of surfaces that could be or have been exposed to virions, avoidance of positioning oneself downwind from an infected person, quarantines/isolation, not eating fresh animal products that could reasonably contain COVID-19 virions, etc.). The SARS-CoV-2 virus may exist in host or non-host fluid volumes, host or non-host surfaces, and host or non-host air (enclosed or not enclosed by a cavity).

Energy-based therapy within the ultraviolet (UV) and ionizing radiation wavebands results in the inactivation of viruses and viral-induced inflammatory responses, respectively. In 1903, the Nobel Prize in Medicine was awarded to Niels Finsen for demonstrating the successful treatment of skin *Mycobacterium tuberculosis* ("TB") with electromagnetic radiation ("EMR") in the ultraviolet waveband (see, e.g., reference REF084 of the list of references provided hereinbelow). Subsequent to this demonstration, external exposure to solar and EMR-emitting devices became the standard of care for TB until the invent of systemic antibiotics. The therapeutic utility of UV radiation was developed through the field of Photobiology within the medical discipline of Dermatology. A few years earlier, in 1896, Leopold Freund demonstrated the successful treatment of a tumor (i.e., hairy nevus) with x-rays; such demonstration marked the birth of Therapeutic Radiology that is now known as Radiation Oncology (see, e.g., reference REF083 of the list of references provided hereinbelow). Since the turn of the $20^{th}$ century, the therapeutic utility of electro-magnetic irradiation in the x-ray and gamma-ray wavebands for solid tumors was developed through Radiobiology within the medical discipline of Radiation Oncology. Bridging knowledge and applicability of Photobiology and Radiobiology may be required in order to implement a concerted effort towards GVLR.

For context, light can be visualized as an electro-magnetic wave corresponding to perpendicular oscillations of electric and magnetic fields. A wavelength ($\lambda$) is the distance between two successive points of the same phase along the wave. A wavelength is the distance per cycle of the wave. Light can also behave like a moving particle (analogous to a water molecule in an ocean wave) with each particle being quantized into discrete units or packets of energy, termed photons. The light energy ($E_\lambda$) contained in a photon is defined as: $E_\lambda = h\nu = hc/\lambda$, where h is termed the Planck's constant. A photon of light has an energy that is directly proportional to its frequency, and inversely proportional to its wavelength in a vacuum (i.e., ideal transmittance environment).

UV EMR may be emitted by the Sun and UV emitters. Ionizing EMR may be similarly emitted by radioactive substances (e.g., Radium-226, Cobalt-60, Iodine-125, Iridium-192, Gold-198, Lutetium-177) and ionizing radiation emitters (e.g., superficial radiation devices, orthovoltage machines, linear accelerators, Gamma Knife). External exposures of phototherapy (e.g., UV EMR) or external beam radiotherapy (e.g., ionizing EMR), may utilize EMR-emitters to transfer energy from the patient exterior to the patient surface and/or interior, where this energy is deposited in tissue as dose. Whereas brachytherapy may involve EMR of short penetration distance (e.g., intracavitary, interstitial, catheter-based, antibody-mediated, etc.) (see, e.g., references REF085, REF086, and REF087 of the list of references provided hereinbelow), using emitters that are placed within the body and/or near to the intended target. Ionizing radiation may be delivered with megavoltage (MeV) electrons, photons, or brachytherapy. The tissue penetration of electrons may be limited (e.g., at a rate of about 2 MeV/cm), so that for a 6 MeV electron beam, 80-100% of the dose may be deposited within about 1.8 cm from the exposed surface. Unlike electron beams, the surface dose for a photon beam may be approximately 10-25% of the total delivered dose, indicating a lower skin dose and greater penetration. The depth region between the surface and the depth of maximum dose deposition is termed the "buildup region". During keloidal irradiation, a bolus with material that is similar in density to tissue, may be typically used to increase the skin's surface dose of photons by proximal initiation of dose deposition. The effect of ionizing irradiation may be a result of direct and indirect particle actions. Direct action may be the interaction of radiation with molecules resulting in damage to the molecules. Indirect action may be the reaction between solute molecules and "activated" water molecules or free radical production in aqueous solution that subsequently result in molecular damage (see, e.g., reference REF306 of the list of references provided hereinbelow). Specifically, the direct action of electrons may result in double-strand breaks in DNA that when un-repaired may cause mitotic (e.g., reproductive) death of cells within the treatment tissue volume. The effect of ionizing irradiation may be the reproductive death of cells within the treatment tissue volume. The inflammatory infiltrate similar to that seen during an infectious process or during wound healing may be radiosensitive and may be largely eliminated via interphase death (e.g., apoptosis) after approximately 2 Gy (see, e.g., reference REF003 of the list of references provided hereinbelow). While UV is capable of resulting in direct damage (e.g., particularly in the UV-C waveband), the effect of UV results via indirect damage.

UVR within the UVC and UVB wavebands may inactivate pathogens by disrupting the genetic materials (see, e.g., reference REF048 of the list of references provided hereinbelow). UVR emitter therapy may be the best or optimized or most efficacious therapeutic modality known to result in coronavirus inactivation (e.g., 90-99% coronavirus inactivation after 5-20 minutes of exposure), such as via lethal genetic damage (see, e.g., references REF049 and REF081 of the list of references provided hereinbelow). However, sustainable radiotherapy protocols (e.g., GVLR) to treat the environment and infected host(s) have heretofore not been proposed or implemented.

COVID-19 hosts can be inoculated from the environment and/or by an infected host. In the context of human herpes virus ("HHV") infection, a large viral load at inoculation is associated with heightened clinical severity (i.e., more severe symptomatology) (see, e.g., references REF002 and REF050-REF053 of the list of references provided hereinbelow). As is seen clinically with cancer management, the cornerstone to reducing viral symptomatology and improving the overall survival of hosts may be to reduce the viral load in the environment (i.e., exposure viral load) and/or within infected hosts (or as news media is calling and has called, the "viral curve"). In the circumstances of a pandemic, Global Viral Load Reduction ("GVLR") with UVR therapy may be the anlagen to contain COVID-19 and/or other viral or invasive threats. To optimize the efficacy of UVR therapy, a concerted global effort must be made towards shadow reduction (i.e., exposing the dark to the light). Therefore, the basis for reducing viral inoculation load, reducing COVID-19 symptomatology, and improving the overall survival of infected hosts, is to implement a GVLR regimen (i.e., "flatten the viral curve"). Notably, although global efforts have been undertaken via vaccination methods, vaccination does not inactivate the virus, does not prevent infection of host by the virus, and does not prevent infectivity of the virus-infected host.

Historical pandemic pattern analysis suggests that if an attempt to globally sterilize the COVID-19 (e.g., GVLR protocol) is not implemented, the pandemic might survive via seasonal oscillation between hemispheres. COVID-19 may also mutate to survive by gaining the capacity to infect hosts of non-human species (and/or perhaps plants), as has been seen already. Examples of major pandemics and their duration include, but are not limited to, Peste Antonina (165-180 AD; 2,000 deaths/day), Praga Cipriano (240-270 AD; 5,000 deaths/day), Praga Justiniano (Bubonic Plague) (541-544 AD; ~100 million deaths total), Black Death (recurring every ~10 years between 1347 and 1666 AD; ~70-200 million deaths in the first 4 years (1347-1351)) (see, e.g., reference REF297 of the list of references provided hereinbelow), each with a variable duration of 4-319 years. After over a year of the COVID-19 pandemic, we face a similar socio-political and economic crisis that also occurred in association to the aforementioned historical pandemics.

BIOFORT recommends a concerted global effort towards the development and immediate implementation of a sustainable GVLR protocol based on and/or including the development of UVR therapy. The protocol(s) may include, but is not limited to, use of (1) anti-viral and/or viral sensitizing pharmacotherapy, (2) UVR therapy to viral load "hot spots", (3) optimization of protective environmental factors (e.g., solar UVR therapy and reflective capacity ("RC") of water), and/or (4) mitigation of human behavioral patterns that potentiate viral infectivity and spread.

BIOFORT proposes as a treatment the implementation of a GVLR protocol that may include environmental and human/animal UVR therapy (e.g., including, but not limited to, AE, SE, VE, EE, intracavitary exposure, interstitial exposure, and/or the like).

Viruses (e.g., similar to cancer cells) may be highly mutable entities (see, e.g., references REF002, REF008, REF009, and REF025-REF027 of the list of references provided hereinbelow). Therefore, the development of effective targeted therapies is fastidious. Such is exemplified by experience with human immunodeficiency virus ("HIV") and cancer (e.g., both disease entities frequently require the use of multiple concomitant agents (pharmacotherapies), multidisciplinary teams, and there are no reliable vaccines available).

It has been reported that 10 minutes of whole-room UVR with commercially available multiple emitter lamps results in 99.9% coronavirus sterilization, in vitro (see, e.g., reference REF049 of the list of references provided hereinbelow). Effective coronavirus disinfection is an anticipated finding, given that UVR is already used to sterilize/disinfect agents (e.g., viruses, bacteria, fungi) that invade air, surfaces, water, hospital rooms, devices, personal protective equipment, plants, and foods (see, e.g., references REF048, REF049, and REF054-REF063 of the list of references provided hereinbelow).

Interestingly, epidemiological studies show that respiratory viral pandemics (e.g., Spanish Influenza, SARS-CoV) demonstrate seasonal and/or latitude "viral sparing" in regions of optimized solar UVR (e.g., natural shadow reduction) (see, e.g., reference REF060 of the list of references provided hereinbelow). Solar UVR may be defined as the electromagnetic energy waveband ranging from ~100-400 nm. Solar UVR may generally be divided into four characteristic sub-bands: UVA1 (340-400 nm); UVA2 (320-340 nm); UVB (295-320 nm), and UVC (100-280 nm). Solar UVC wavelengths may be mostly shielded by the earth's atmosphere, but given global pollution/ozone depletion, regions of the globe are likely to have a greater proportion of UVC penetrance. A concerted effort to quantify UVC penetrance by globe latitude and longitude may be needed in order to elucidate the full therapeutic potential of solar UVR (e.g., potential for solar disinfection systems within the GVLR protocol) and/or to define solar UVR dosimetry. Solar UVR dosimetry may be developed in mirror to the dosimetry for gamma-irradiation sources (i.e., naturally occurring radiation sources) like Cobalt-60. Optimizing both environmental and human/animal solar UVR therapy (e.g., within sun toxicity guidelines that may already be set forth by dermatologic societies) can be implemented immediately. An example of immediate implementation of solar UVR therapy, GVLR, and shadow reduction may be instructions to the public not to stay indoors for the entire day, in the shadows, where the shadows may serve as foci for viral "hot spots". As another example of shadow reduction and maintaining quality of life, local governments can support grouped festive activities (e.g., New York City's New Year's Eve Ball drop) to occur outside in the sun at solar noon versus midnight. Depending on latitude (i.e., distance from the equator), ~10-300 minutes of solar UVR (e.g., sun exposure) may significantly reduce COVID-19 viral load to exposed materials. The duration of UVR therapy may vary (e.g., by latitude and/or altitude and/or cloud coverage and/or the like) to completely sterilize a certain quantity of COVID-19 virions and may be clearly defined for the broad implemented use of solar UVR.

Solar UVR and UVR emitters may be the backbone to the treatment of psoriasis (see, e.g., reference REF015 of the list of references provided hereinbelow). Interestingly, at the population level, psoriasis may demonstrate seasonal and/or latitude "symptom sparing" in regions of optimized solar UVR (i.e., natural shadow reduction) (see, e.g., references REF061 and REF064 of the list of references provided hereinbelow). Skin color might be the important modifier for risk of psoriasis symptom/manifestation because melanosomes attenuate (absorb) non-ionizing energies of UVR wavelengths and high-energy recoil electrons of ionizing radiation (IR) wavelengths (see, e.g., reference REF065 of the list of references provided hereinbelow). As such, a significant expression of psoriatic symptomatology has been identified in people with darker skin types (e.g., 3.9% in types I-III versus 7.9% in types IV-VI, $p=0.046$) in Puerto Rico (latitude 18.41°)(see, e.g., reference REF066 of the list of references provided hereinbelow). These findings suggest that darker skin may serve as a natural radioprotector (e.g., survival advantage) during GVLR efforts (see, e.g., reference REF065 of the list of references provided hereinbelow). In actuality, it is likely the skin melanosome and/or chromophore density (not the skin color) that may provide the survival advantage (see, e.g., reference REF298 of the list of references provided hereinbelow).

The radiobiology and physics of UVR emitters may need further development (see, e.g., references REF058 and REF298 of the list of references provided hereinbelow). Current UVR emitter dosimetry may be sub-optimal and in consideration of current time-constraints, may be developed in mirror of ionizing radiation ("IR") dosimetry. In general, UVR may be readily blocked (+/−reflected) by any object that interrupts the path between the UVR source and target. Organic materials will absorb UVR; there is no associated reflection. The use of UVR mirrors and reflective materials (e.g., roof sealants with UV reflection capacity) may be developed towards therapeutically optimizing scatter UVR (particularly UVA/B) into the "shadows" (e.g., shadow reduction). Filters may be developed to modulate, calibrate, and/or adjust UVR exposure wavelengths (e.g., allow narrow band UVB or blue light, but block UVA and UVC). Blue light has shown significant bactericidal properties. Cloud-induced UV scatter may need to be accounted for in UV Index values (see, e.g., reference REF061 of the list of references provided hereinbelow). Attenuation and shielding coefficients for environmental treatment fields may need to be defined (see, e.g., reference REF056 of the list of references provided hereinbelow). The therapeutic ratio of solar UVR and UVR emitters may be further elucidated before used to treat humans/animals externally and/or internally (e.g., clinical trials may follow FDA guidelines during the COVID-19 pandemic).

In addition to psoriasis, UVR therapy with UVA/B wavelengths may also be a standard of practice for treating inflammatory and or pigmentary diseases, such as acne and/or vitiligo (see, e.g., references REF015, REF067, and REF068 of the list of references provided hereinbelow). Therefore, these clinical entities may serve as a source of abundant clinical safety data for UVR therapy. The normal tissue dose response to UVR therapy of non-cutaneous epithelium may theoretically mimic that of Fitzpatrick skin type I. Further, it has been reported that UVR data could be further extrapolated towards therapeutic purposes, whereby the viral inactivation curve may be log-linear (i.e., "no shoulder") and biphasic in the 254-320 nm wavelength range, with an expected inverse relationship between viral inactivation UVR wavelength (see, e.g., reference REF057 of the list of references provided hereinbelow). Importantly, the bacteria dose-response curve may be sigmoidal (e.g., similar to mammalian cells), having a shoulder that may account for DNA repair after UVR exposure. Reversible bacterial DNA damage has been identified between the 297-320 nm wavelength range (e.g., UVB range) (see, e.g., reference REF057 of the list of references provided hereinbelow). Mammalian cell DNA repair capacity may be stronger (e.g., fitter to survive) compared to bacterial repair capacities, which suggests that intracavitary/interstitial UVA/B may be as safe (e.g., with respect to therapeutic window for viral inactivation) as EE UVA/B already is in current dermatological practice. UVC may have the highest disinfectant capacity of the UVR waveband, with peak efficacy at 265 nm (see, e.g., references REF048, REF049, and REF058 of the list of references provided hereinbelow). The wave characteristics of the UVC waveband may cusp those of higher energy waves in the IR waveband (e.g., dose may be a measure of intensity and duration of exposure; inverse square law may be applicable (see, e.g., reference REF056 of the list of references provided hereinbelow), more difficult to reflect, etc.). However, it should be noted that UVC has a greater risk of toxicity and mutagenesis, when compared to other UV wavebands and may be limited to environmental treatment. Data from atomic bomb survivors showed a significant excess relative risk ("ERR") of 0.74 (95% CI: 0.26, 1.6) at 1 Gy exposure for basal cell carcinoma ("BCC") (i.e., a 74% increased risk above background). The ERR was highest for those exposed at 0-9 years (15, 95% CI: 4.2, 43), decreasing with age at exposure to 1.3 (95% CI: 0.35, 2.9) for those 20-39 years old, and becoming nonsignificant for those over age 40. Age at exposure was the most significant modifier, with a coefficient estimate of −0.11 (95% CI: −0.17, −0.07) (i.e., ERR decreased 11% (95% CI: 6.7%, 15%, $P<0.001$) with each one year increase in age at exposure) (see, e.g., reference REF069 of the list of references provided hereinbelow). However, these ERR values are almost 10 times greater than those reported for medical radiation exposures (see, e.g., reference REF069 of the list of references provided hereinbelow). Ultraviolet irradiation results in pyrimidine-pyrimidine dimers, which if unrepaired or misrepaired can lead to non-lethal mutations, resulting in the increased risk of squamous cell carcinoma ("SCC"), which are more locally invasive and morbid compared to the BCCs associated with radiotherapy (see, e.g., reference REF307 of the list of references provided hereinbelow).

It is hereby recommended to redirect resources towards expanding the UVR therapeutic action spectra. Optimizing both environmental and human/animal therapeutic solar UVR therapy (e.g., within sun toxicity guidelines already set forth by dermatologic societies) can be implemented immediately. An example of immediate implementation of solar UVR therapy, GVLR, and shadow reduction may be instructions to the public not to stay indoors for the entire day, in the shadows—the shadows serve as foci for viral replication or viral "hot spots".

Commercially available UVR emitters, such as those used for hospital room sterilization or sterilization of cell culture hoods, commonly emit UVC wavelengths (100-280 nm). While UVC has demonstrated in vitro efficacy to sterilize coronaviruses, the safety of therapeutic UVC use in humans, animals, and/or plants has been unclear (see, e.g., reference REF049 of the list of references provided hereinbelow). However, UVC emitters (e.g., +/−Vacuum-ultraviolet light) can be immediately implemented into GVLR methods. Examples of immediate implementation of UVC therapy and GVLR may include, but are not limited to, sterilization of air vents (see, e.g., references REF048 and REF062 of the list of references provided hereinbelow), rotational sterilization of hospital rooms, wings, stations, equipment, and/or protection gear (see, e.g., references REF054, REF055, and REF059 of the list of references provided hereinbelow), sterilization of city and rural water sources (see, e.g., reference REF057 of the list of references provided hereinbelow), sterilization of meat and plant-derived food products (see, e.g., reference REF063 of the list of references provided hereinbelow), and/or sterilization of personal items that are high risk for contamination (e.g., per CDC guidelines). As an example, academic hospitals may mandate that all non-essential personnel stay home, including scientists. Therefore, the UVR lights standardly installed in cell culture hoods can be configured to sterilize equipment in limited supply, such as face masks. Additionally, far UVC emitters may be installed into streetlamps of high pedestrian walkways (e.g., for use after dark in low latitude regions, all day in higher latitude regions). A home may also include one or more storage areas that may be equipped with UVR emitter(s) (e.g., closets with UVR emitters operative to inactivate virus or mold that may have landed on clothing and shoes, kitchen cabinets with UVR emitters operative to inactivate virus or mold that may have landed on fresh produce (e.g., by creating a designative UVR box in the kitchen), etc.). UVC can be used for these purposes, although lock mechanisms and/or timers should be provided so that people aren't exposed in an unwanted fashion (e.g., in accordance to standard radiation safety measures).

Various types of UVR sources may be utilized by the therapy platform of this disclosure, including, but not limited to, solar UVR (e.g., dose calculations for volumes may be analogous to gamma-radiation (e.g., a naturally occurring Cobalt-60 source as used for GammaKnife) and build upon the later described Sagripanti and Lytle model to estimate therapeutic dose prescriptions (see, e.g., references REF080, REF081, and REF101 of the list of references provided hereinbelow)), any suitable UVR emitting devices (e.g., dose calculations could be analogous to "X-Ray" radiation (e.g., photons produced by a man-made orthovoltage machine or linear accelerators)), including, but not limited to, UVR emitters modified for external/internal AE, UVR emitters modified for external/internal SE, UVR emitters modified for external/internal VE, UVR emitters modified to fit the nasal cavity, UVR emitters modified to fit the oral cavity, UVR emitters modified to fit the ear canal, UVR emitters modified as a bronchoscope, UVR emitters modified as an endoscope, UVR emitters modified for other intracavitary procedures, UVR emitters modified for vaginal brachytherapy (see, e.g., reference REF059 of the list of references provided hereinbelow), UVR emitters modified for anal brachytherapy, UVR emitters modified for catheter-based brachytherapy, UVR emitters modified for interstitial brachytherapy, UVR emitters modified for antibody-based brachytherapy (see, e.g., reference REF001 of the list of references provided hereinbelow), and/or the like (see, e.g., system 1700 of FIG. 17, system 1800 of FIG. 18, and/or the like (e.g., catheters, needles, endoscopes, and/or the like that may be configured like these systems or otherwise) that may be provided with surface holes to allow UV, blue light (e.g., for bacteria) or infrared light (e.g., for scar reduction/ inhibition) to pass through and penetrate target tissue, where the holes can be covered with quartz glass or any suitable light transparent material for sterilization ability for subsequent treatment of other patients).

Combination UVR therapy may be provided. UVR therapy can be used sequentially or concomitantly with pharmacological agents that may be independently toxic to the invasive entity. Chemotherapy may be administered during, before, and/or after energy-based therapy, depending on the invasive entity being treated. UVR therapy can be used sequentially or concomitantly with sound wave therapy ("SWT"), other electromagnetic wavelength therapy, hyperbaric oxygen therapy, filtration, steam and/or vapor therapy, acid and/or base therapy, and/or the like.

Prescription dose calculation is critical to environmental and human/animal safety in therapeutic intervention. There are biotechnical dosimeters, spectral and electronic radiometers, and chemical dosimeters for UVR measurements that may be made available to all researchers and hospitals implementing UVR-based therapy for COVID-19 GVLR.

Patient education on disease and management may be critical to environmental and human/animal safety in therapeutic intervention. A photoactive ink has been developed (e.g., by Intellego Technologies AB, (Gothenburg, Sweden)) that changes to certain colors at predetermined UVR therapy exposure energies. Such photoactive ink may be relatively inexpensive compared to biotechnical dosimeters and can be mass produced with greater ease for immediate public use (e.g., similar to the use of UVR reactive bracelet/necklace beads in "Sun Protection Fun" campaigns towards teaching children about UVR and risk for skin cancer). Smart device-compatible radiometry software may facilitate public education on environmental solar UVR therapy and therefore facilitate access to clean air, food products, and drinking water to people in rural to urban locations around the world. Such proposed radiometry software may be configured to have one, some, or each of the following functionalities: (1) UVR wavelength and intensity reading functionality; (2) SE/AE/VE dose-for-sterilization calculation functionality for distinct invasive entities (e.g., viruses, bacteria, fungi, etc.); (3) SE/AE/VE dose-for-sterilization calculation functionality for multiple volume quantities (e.g., 2.5 ml, 5 ml, 10 ml, etc.); and/or (4) user-friendly interface. For example, when a user is concerned about a particular target in its environment (e.g., a water bottle that an unknown person drank from or a sandwich that an unknown person sneezed on, a user's smart device (e.g., an iPhone or any portable media device) may be operative to determine the amount of UV that is being exposed to the target (e.g., surrogate measurement based on detected light by a smart phone or an extrapolated measurement based on visible light detected or weather data that may be accessed) or direct sensor (e.g., dosimeter in smart phone). The smart device may also determine an appropriate SE/AE/VE dose-for-sterilization calculation for any one or more suitable invasive entities that may be pertinent (e.g., COVID if unknown person is suspected or likely to be infected), where this data may be accessed from an app running on the smart device or from some remote server servicing this process. The smart device may then calculate the appropriate SE/AE/VE dose-for-sterilization calculation functionality for multiple volume quantities (e.g., 2.5 ml, 5 ml, 10 ml, etc.) or for a specific quantity of the target that may be provided by user (e.g., 1 liter water bottle). The smart device may then present a user interface or instructions to the user on how long to expose the target to the available UV in order to treat the suspected invasive entity(ies) at the target.

Prolonging the photon distance traveled and time to absorption with use of redirecting material (e.g., minimal absorption capacity/maximal reflective capacity) may increase UVR therapy exposure time and/or reduce the shadows. Therefore, prolonging the photon distance traveled and/or time to absorption may increase UVR dose. A public effort to optimize solar UVR therapy may include, but is not limited to, (1) removing/opening window shades, (2) opening windows with UV protection/filtration in the glass, (3) strategic placement of mirrors and/or reflective materials outside and/or inside of households to redirect and to increase indoor lighting (i.e., shadow reduction) (e.g., as may be quantified with radiometers), (4) safe maximal time in the sun (i.e., solar UVR therapy exposure below the risk of sun burn), (5) safe maximal time in fresh air, and/or (6) seek areas of higher elevation (e.g., mountains) or regions near bodies of water or snow (i.e., reflect the sun). As UVA/B wavebands tend to travel with the visual spectrum, then, as a general rule of thumb, where there is sunlight, there is some potential for solar UVR therapy.

Placing reflective material behind, underneath, and/or next to solar panels can optimize electric current production. Development of double-sided solar panels can optimize electric current production. This enhanced production of electricity from solar UVR therapy can be directed to power several entities and services including, but not limited to, UVR emitters, publicly available radiometers, water pumps, water filtration systems, and/or the like (e.g., directly or via battery). Surplus of sterilized water (e.g., solar UVR sterilized rain water (e.g., also known as "holy water" in biblical times)) has value (perhaps the most value) and can be sold and/or traded for currency and/or other goods.

UVR may be more mutagenic than IR therapy, particularly in cells with low densities of melanosomes (e.g., white skin not including vitiliginous skin) (see, e.g., references REF003, REF065, and REF069 of the list of references provided hereinbelow). Early diagnosis and treatment of cancers make them curable. Therefore, cancer surveillance and management may be critical to the safety of epithelial and interstitial tissues exposed to UVR therapy (e.g., skin cancer screenings, mole photograph monitoring, non-invasive imaging of psoriasis patients that receive UVR therapy, etc.). Based on clinical experience with skin cancers, early diagnosis and treatment can be curative. Another great clinical example is that of human papillomavirus ("HPV") oncogenesis of female cervix cells (i.e., squamous cell carcinoma of the cervix) (see, e.g., references REF025 and REF059 of the list of references provided hereinbelow), which may include (1) early detection and treatment of the invasive entity, which may minimize risk of cancer development, and/or (2) early stage cervical cancer that may be curable without need for expensive chemotherapy or IR therapy. Research towards the development of prophylactic and/or therapeutic use of UVR for HPV invasion of the vaginal cavity (and other cavities predisposed to HPV-induced cancers) is hereby recommended.

For non-cutaneous cancers, theragnostic positron emission tomography—computed tomography ("PET/CT") imaging (e.g., folate hydrolase-1 ("FOLH1"), human epidermal growth factor receptor-2 ("HER-2"), etc.) may have greater specificity and perhaps sensitivity than widely used fluorodeoxyglucose ("FDG") PET/CT imaging. FOLH1

PET/CT may also be the only available non-invasive imaging modality that can specifically visualize growing tissues and cancer. Theragnostic PET/CT (e.g., based on imaging of target molecules expressed by the cancer) may improve diagnostic certainty over FDG PET/CT (e.g., based on whether a cancer is eating more glucose compared to other tissues in the body). Furthermore, the radiotoxicity of positron emitting isotopes conjugated to small molecule peptides or antibody fragments is no greater than FDG PET/CT imaging. The toxicity is not expected to be and has not been shown to be significantly worse than or different from FDG PET/CT (see, e.g., reference REF001 of the list of references provided hereinbelow). There is already sufficient and significant clinical safety data in favor of FDA approval theragnostic PET/CT for FDA review and approval. As such, the FDA approved FOLH1 PET/CT imaging of prostate cancer in the summer of 2020. Theragnostic PET/CT surveillance of exposed tissues may be made available to UVR treated humans/animals. The smallest detection size of non-prostatic cancer with FOLH1 PET/CT imaging may be elucidated. FOLH1 nomenclature should be unified in the scientific literature. As FOLH1 PET/CT is used for prostate imaging, FOLH1 PET/CT imaging should be a standard of care for cancer (e.g., solid tumor) surveillance of individuals that have been exposed to a known carcinogen. For example, after a period of time after atomic bomb exposure, atomic bomb survivors may undergo a FOLH1 PET/CT to determine if they have any FOLH1-avid tissue. Then they may undergo a diagnostic or confirmatory biopsy of that detected FOLH1-avid tissue to determine histopathologically (e.g., by microscopic examination of tissue) if the FOLH1-avid tissue is in fact a cancer. If so, the cancer may then be managed in accordance to standard of care treatment set forth by nation specific or global guidelines (e.g., NCCN guidelines). Theragnostic PET/CT (e.g., folate hydrolase-1 ("FOLH1"), human epidermal growth factor receptor-2 ("HER-2"), etc.) surveillance of exposed tissues may be made available to UVR treated humans/animals. Theragnostic PET/CT surveillance (e.g., using FOLH1 or HER-2) of cell volumes exposed to UVR may be carried out.

In general terms, easily accessible small cancers (e.g., skin cancer) can be treated surgically. Small cancers that are not easily or safely accessible or located in places where tissue sparing is needed (e.g., face) can be treated non-invasively with ionizing radiation therapy or ionizing radiation surgery (e.g., radiosurgery). Larger cancers (e.g., greater disease burden) likely need combination of surgery (e.g., to debulk disease), chemotherapy, immunotherapy, other pharmacotherapy and/or antibody-based brachytherapy (e.g., to reduce burden of disseminated disease), and/or ionizing radiation therapy (e.g., to sterilize primary and/or metastatic tumor sites). Antibody-based brachytherapy targeting FOLH1 may be able to target and sterilize disseminated cancers with ionizing radiation or other agents (see, e.g., references REF001, REF070-REF073, and REF289 of the list of references provided hereinbelow). As described herein, dosimetry (e.g., dose calculation) for FOLH1 targeted antibody-based brachytherapy may be defined (see, e.g., reference REF289 of the list of references provided hereinbelow).

UVR quality, UVR dose, number of dose fractions, exposure time, and/or biologic system or endpoint for UVR therapy may be defined. Invasive entity dose-response behaviors may be determined (e.g., via clinical research and/or via baseline clinical data that may serve as a surrogate understanding of tissue-dose response).

UVR has not yet been therapeutically and clinically optimized to the level seen in clinical ionizing radiation therapy (i.e., clinical radiation oncology). However, the worst expected acute toxicity with UVR therapy is a "sun burn" (i.e., leukocyte infiltration (accentuated inflammatory process) with dermal vasodilatation (opening of skin blood vessels)) on or within any treated epithelial or interstitial area, respectively. However, a "sun burn" is an extreme toxicity that should only occur with excessive or toxic levels of UVR therapy exposure.

Defining UVR quality, UVR dose, number of dose fractions, exposure time, duration of overall treatment, and/or biologic system or endpoint may be done so as to reduce or eliminate risk of developing a "sun burn". For clinical application as intended by the therapy platform, UVR therapy may be asymptomatic (e.g., UVR therapy may not alarm or be detectible by the human/host senses of touch, taste, hearing, smell, etc.). Acceptable short-term treatment changes may include, but are not limited to, hyperpigmentation (e.g., slow tanning), dry skin, epithelium, and/or the like. UVR therapy may result in phototoxicity (e.g., "sun burn") if administered within 30 days of photosensitizing pharmacological agents. Phototoxicity can be mitigated with steroidal agents.

The major late toxicities for UVR therapy may mirror those late toxicities known to occur after a lifetime of sun exposure, which may include both deterministic and stochastic effects. Cataracts are an example of a deterministic effect. Risk of cataract development can be mitigated with the use of polarized or UVR-blocking eyeglasses and/or contact lenses. Developed cataracts may be effectively treated with cataract lens-removal surgery and implantation of biosynthetic lenses.

Secondary cancers are an example of a stochastic effect. Risk of secondary cancer development can be mitigated by optimizing the UVR therapeutic ratio. Cure of secondary cancer can be optimized by surveillance and early diagnosis with theragnostic PET/CT imaging (and reduce healthcare costs). UVR may have poor penetration into tissues and therefore risk of secondary cancers may be limited to the exposed tissue. As mentioned, data from atomic bomb survivors showed a significant excess relative risk ("ERR") of 0.74 (95% CI: 0.26, 1.6) at 1 Gy exposure for basal cell carcinoma ("BCC") (i.e., a 74% increased risk above background). The ERR was highest for those exposed at 0-9 years (15, 95% CI: 4.2, 43), decreasing with age at exposure to 1.3 (95% CI: 0.35, 2.9) for those 20-39 years old, and becoming nonsignificant for those over age 40. Age at exposure was the most significant modifier, with a coefficient estimate of −0.11 (95% CI: −0.17, −0.07) (i.e., ERR decreased 11% (95% CI: 6.7%, 15%, P<0.001) with each one year increase in age at exposure) (see, e.g., reference REF069 of the list of references provided hereinbelow). However, these ERR values are almost 10 times greater than those reported for medical radiation exposures (see, e.g., reference REF069 of the list of references provided hereinbelow). Ultraviolet irradiation results in pyrimidine-pyrimidine dimers, which if unrepaired or misrepaired can lead to non-lethal mutations, resulting in the increased risk of squamous cell carcinoma ("SCC"), which are more locally invasive and morbid compared to the BCCs associated with radiotherapy (see, e.g., reference REF307 of the list of references provided hereinbelow).

A "vaccine" is not equal to a "cure". A vaccine is a substance presented to the host immune system with the purpose of labeling the molecular structures in the substance as a threat to the host that should be eliminated, if encountered. Viral vaccines are typically subdivided into therapeutic (e.g., vaccination of a diseased host for the immune system to remove the threat) and preventive (e.g., vaccination of a non-diseased host for the immune system to surveillance the threat). A major cause of death in COVID-19 is excessive vasoconstriction leading to ischemia and/or infarcted tissue as well as an excessive pro-inflammatory state causing lung tissue damage and fibrosis until the host develops respiratory failure (e.g., unable to breath without help) and death. The inability to breath or exchange blood gases with air gases due to massive scarring of lung tissue is incompatible with mammalian life. Therapeutic vaccines for COVID-19 should be used with caution, particularly in phase ½ of the investigational roll-out. If a COVID-19 infected host receives and is primed by a therapeutic vaccine, the host immune system may be primed to send a larger than usual number of inflammatory cells to the sites of COVID-19 viral shedding, which may lead to greater end organ damage (e.g., dependent on the viscera involved). If SARS-CoV-2 has already infected lung cells at the time of vaccination, there is a theoretical possibility of exacerbating the COVID-19 pro-inflammatory, death of lung cells, scarring of lung tissue, respiratory failure, and/or death of host (e.g., a clinical situation that may be analogous to the rejection of a host with a transplanted lung) (see, e.g., reference REF029 of the list of references provided hereinbelow). Respiratory failure is associated with a high death rate. Death is irreversible. If SARS-CoV-2 has already infected human tissues at the time of vaccination, there is a theoretical possibility of exacerbating the COVID-19 vasoconstriction. Said vasoconstriction may be the cause of early pregnancy loss in female Puerto Rican (e.g., protected underrepresented minority) physicians that were obligated by the Colegio de Medicos Cirujanos de Puerto Rico, Inc., to receive early investigative versions of the COVID-19 vaccine under duress (e.g., the threat of being unable to renew their medical licenses) in the low COVID-19 risk geographical location of Puerto Rico. From a virological standpoint, a safer and likely more effective strategy is to decrease the overall inflammation in the host while the virus is treated (see, e.g., reference REF029 of the list of references provided hereinbelow) Enhancing tolerance to COVID-19 infection with non-steroidal anti-inflammatory drugs ("NSAIDs"), steroids, may also slow down and might prevent the mechanism of death by respiratory failure by allowing time (e.g., an opportunity) for UVR viral load reduction and "slow, survivable" viral elimination by the host immune system. Similarly, vasodilators may be administered to counteract the virus-induced vasoconstriction. Tolerance may improve overall survival. Preventive vaccines should potentially only be administered to COVID-19 negative hosts. The ideal time for preventive vaccination may be before COVID-19 reaches the host's geographical location (e.g., similar to the administration of the influenza vaccine before "flu season"). Preventive vaccination can help to prevent future outbreaks, epidemics, and pandemics, but it may not prevent a pandemic that is already in action.

Optimizing diagnostic sensitivity/specificity of disease may decrease management complexity, could increase efficiency in treatment, could improve patient outcomes, and/or could reduce the overall cost of healthcare (e.g., including cancer and COVID-19). COVID-19 polymerase chain reaction ("PCR") testing may be expensive. Pathological elevations of serum angiotensin-converting enzyme ("ACE")2 may be associated to cytotoxicity of ACE2 expressing cells (e.g., smooth muscle, endothelium, etc.) (see, e.g., reference REF299 of the list of references provided hereinbelow). Therefore, serum ACE2 quantification could serve as a surrogate marker (e.g., cost-effective diagnostic aid) of COVID-19 infection in cases with high clinical suspicion, and/or serum ACE2 quantification could be an aid to monitor patient response to treatment (e.g., to see whether someone is getting better or worse). Combining ACE2 quantification with radiographic diagnostic imaging may increase diagnostic accuracy compared to using each test alone and be of aid during when and if there is a shortage of COVD-19 PCR kits.

Plants and animal-based food products and drinking water are potential reservoirs for COVID-19 virions. Humans express ACE2 (e.g., COVID-19 target) in the oropharynx and gastrointestinal tract, which means that humans can be "inoculated" and become "infected" by the process of eating and/or drinking. A concerted effort towards UVR sterilization of food products and drinking water is recommended herein. Dosimetric data on solar UVR is available, and the solar UVR sterilization dose for COVID-19, and other invasive entities, for surfaces and volumes may be made public (see, e.g., reference REF081 of the list of references provided hereinbelow).

COVID-19 is a zoonotic virus, meaning that it can infect and therefore survive in animals. Based on information and belief, there has been a report of a non-human primate that has already been infected with COVID-19. Veterinary medical practitioners should be informed and be ready to manage COVID-19 infection in the non-human Animal Kingdom population.

UVB appears to be the safest therapeutic candidate waveband for internal UV irradiation. The literature supports the clinical safety of narrow-band ("nb") UVB (~310 nm). It is therefore suggested that the therapeutic profile of nbUVB therapy (see, e.g., references REF074 and REF075 of the list of references provided hereinbelow) be built upon (e.g., by the therapy platform). While external UV electro-magnetic radiation ("EMR") treatment is important to reduce aerosolized and surfaced viral load, internal UV-B EMR may be the safest and most efficient mechanism to inactivate patient or host viral load. It is estimated that just 69 mJ/cm$^2$ UV-B dose (310 nm) is needed to result in 1-log viral reduction of SARS-CoV-2 at a certain cell layer depth. The Lethal Dose, 50% ("$LD_{50}$") or median lethal dose of oral mucosa cells irradiated with 310 nm UVB is 401.8 mJ/cm$^2$ (see, e.g., reference REF076 of the list of references provided hereinbelow). Mucosal cell survival curves for UV-B irradiation are not readily available/accessible, however it has been reported that no acute damage or cytotoxicity to human oral mucosa cells occurred with doses up to 105 mJ/cm$^2$ with UV-B (310 nm) (see, e.g., reference REF076 of the list of references provided hereinbelow). These data indicate that 105 mJ/cm$^2$ falls within the shoulder of the human mucosa cellular survival curve. Fraction sizes of 69-138 mJ/cm$^2$ (e.g., dose within and perhaps on the brink of the exponential linear survival slope) may be ideal to achieve a therapeutic gain of 1-log (90%) to 2-log (99%) viral inactivation to a presumable depth of 50 μm in tissue (e.g., primary inoculation sites). Allowing for a 2-6 hour inter-fraction period may permit redistribution of virus and shielding organic materials within cells and cellular repair of mammalian DNA damage (if any). The former redistribution may reduce the influence of the biphasic viral survival curve, however, further studies may be conducted.

Fractionation of internal nbUVB (or other possible wavelengths (bands)) may follow the general principle of utilizing the dose resulting in maximal log reduction of virus, bacteria, fungi, and/or the like that overlaps within the shoulder (e.g., perhaps down to a cellular $D_{90}$-dose resulting in a 10% reduction of cells) of the cellular survival curve. Fractions may be spaced by 2-6 hours to allow for cellular recovery (e.g., timing may ultimately be determined by the disease being treated). If hyperfactionation is possible (e.g., patient is intubated or has a chest tube), smaller fraction doses (e.g., strictly within the shoulder of the cell survival curve) can be administered every 2 hours.

Depth may be defined for UV-B in tissue (e.g., as it has been done for ionizing wavebands). A few studies report a very wide range of depth dose penetration. For example, induction of UV-induced 53BP1 focus formation occurred at a maximal depth of 40 μm in 3D-culture of MiaPaCa-2 cells (see, e.g., reference REF077 of the list of references provided hereinbelow). Studies on UV-B mortality of zooplankton in turbid creek water (e.g., analogous to cellular cytoplasm) show that inactivating intensities of UV-B can penetrate 2.2 to 13.5 m (see, e.g., reference REF078 of the list of references provided hereinbelow). Depth dose characterizations for energy deposition within the UV EMR waveband has been defined (see, e.g., reference REF295 of the list of references provided hereinbelow). It may be most practical to define UV dose in "Gy" (e.g., as the doses are for ionizing wavebands) but may need an accurately measured volume parameter to convert from $mJ/cm^2$ (e.g., UV dose based on area of tissue) to Gy (e.g., UV dose based on volume of tissue). Initial experiments may be performed in ex-vivo skin and intestinal epithelium as well as in media (as previously described) to determine the depth dose (and, perhaps, dose build-up) for a variety of fraction sizes that might be employed. Multiple studies have already demonstrated the clinical efficacy and safety of UV EMR (e.g., with or without photosensitizers and antimicrobial drugs) in treating a variety of skin and mucosal microbial infections (e.g., bacteria, parasites, fungi, yeast, viruses, etc.) (see, e.g., references REF124-REF129 of the list of references provided hereinbelow). In addition to genome inactivation, UV EMR of skin has been identified to result in activation of human macrophages via toll-like receptors that in turn, upregulate the vitamin D receptor gene resulting in induction of the antimicrobial peptide, cathelicidin (see, e.g., reference REF084 of the list of references provided hereinbelow). A study of narrow band ("NB") UVB irradiation with 1170 $mJ/cm^2$ of inflammatory facial acne vulgaris lesions (i.e., active micro-infection) demonstrated significant therapeutic synergism (P=0.002) with systemic azithromycin (see, e.g., reference REF130 of the list of references provided hereinbelow). A recent case report demonstrated the cure of cutaneous human papillomavirus infection with nbUVB alone.

Once the above data is obtained, a clinical trial targeting the oral cavity, oro-pharynx, and/or naso-pharynx may follow (e.g., trials targeting other anatomical regions can be performed at a later date (e.g., using UVB LED radially lined intubation tubes, chest tubes, pigtails, endoscopes, and/or the like)). Standard of care techniques for brachytherapy and intraoperative radiotherapy (see, e.g., references REF133-REF135 of the list of references provided hereinbelow) may be modified to deliver internal UV EMR waveband photons (see, e.g., references REF136-REF143 of the list of references provided hereinbelow) to directly inactivate replicating and shedding virus that contribute to active infection, increasing viral load, and infectivity to others (see, e.g., reference REF144 of the list of references provided hereinbelow). The analogy of SARS-CoV-2 hotspots in ACE2-rich tissues to bacterial accumulation in abscesses, enables an understanding of the clinical purpose of locoregional therapy. Similarly, there is evidentiary support that the surgical resection or radiotherapy (e.g., loco-regional therapy) of primary tumors in the setting of metastatic disease is associated with overall survival improvements (see, e.g., reference REF145 of the list of references provided hereinbelow). These findings suggest that locoregional EMR therapy of primary sites of infectious virion shedding can also lead to overall survival benefits in patients with systemic COVID-19 disease by reducing the viral load. There is a strong need for identification of any measures that can be used to treat this illness or reduce its transmission from person to person. Ultraviolet irradiation may be the only agent able to result in 1-2 log viral reduction with doses that would be relatively safe for human use. The therapy platform may be configured to provide 4×daily irradiation using a nbUVB emitter prototype designed to optimize irradiation to the desired treatment field that will help to reduce the viral load in the nasopharynx and/or oropharynx and/or other tissue in patients who are SARS-CoV-2+, as well as in the lungs, nostrils, oral cavity, rectal cavity, vaginal cavity, stomach, esophagus, vascular blood volumes, plural space of the lungs, and/or any other suitable internal target of the host patient (e.g., not just the skin or nose or mouth). This may have an impact on disease progression, time to recovery of clinical symptoms, as well as reduce shedding of the virus by infected patients. Multiple studies have already demonstrated the clinical efficacy and safety of UV EMR (e.g., with or without photosensitizers and antimicrobial drugs) in treating a variety of skin and mucosal microbial infections (e.g., bacteria, parasites, fungi, yeast and viruses) (see, e.g., references REF124-REF129 of the list of references provided hereinbelow). In addition to genome inactivation, UV EMR of skin results has been identified in activation of human macrophages via toll-like receptors that in turn, upregulate the vitamin D receptor gene resulting in induction of the antimicrobial peptide, cathelicidin (see, e.g., reference REF084 of the list of references provided hereinbelow). A study of narrow band ("NB") UVB irradiation with 1170 $mJ/cm^2$ of inflammatory facial acne vulgaris lesions (i.e., active micro-infection) demonstrated significant therapeutic synergism (P=0.002) with systemic azithromycin (see, e.g., reference REF130 of the list of references provided hereinbelow) A recent case report demonstrated the cure of cutaneous human papillomavirus infection with nbUVB alone. However, inactivated viral particles may still be oncogenic.

For a study, ~50 patients who have been diagnosed with COVID-19 may be randomly assigned to four study groups: (1) control, (2) ~69-138 $mJ/cm^2$ nbUVB to oral cavity/oropharynx, (3) ~69-138 $mJ/cm^2$ nbUVB to nasopharynx, and (4) ~69-138 $mJ/cm^2$ nbUVB to oral cavity/oropharynx+nasopharynx. Each patient may be asked to apply the nbUVB irradiation to their throat and in their nose four times daily. Patients may then be tested for COVID-19 once daily in the evening for 7 days and viral loads may be measured. The study design may be allocation: randomized, the intervention model may be parallel assignment, the intervention model description may be randomized controlled open label trial, parallel design, the masking may be none (e.g., open label), and/or the primary purpose may be treatment. Primary outcome measures may be viral load (and/or cycle time to PCR as a proxy for quantitative viral load) in the nasopharynx and oropharynx (e.g., time frame: 7 days) nasopharyngeal swab for viral PCR may be taken at the end of each day for 7 days. Secondary outcome measures may be (1) oxygen requirement of the patient (e.g., time frame: 7 days) recorded daily, and/or (2) oxygen saturation of the patient (e.g., time frame: 7 days) recorded daily, and/or the like. Extracorporeal photopheresis (ECP) may be a safe and effective therapeutic regimen to reduce systemic viral load in patients with SARS-CoV-2 infection (see, e.g., reference REF146 of the list of references provided hereinbelow). ECP is a leukapheresis-based therapy that is approved for the treatment of certain subtypes of cutaneous T-cell lymphoma, particularly the erythrodermic and leukemic variant Sézary syndrome for which it has received FDA approval in 1988 (see, e.g., reference REF147 of the list of references provided hereinbelow). Moreover, it is utilized in the context of Graft-versus-Host Disease, and in the context of rejection of solid organ transplantation, and hematopoietic stem cell transplantation (see, e.g., references REF148-REF150 of the list of references provided hereinbelow). During traditional ECP, patient whole blood may be collected, leukocytes may be separated (buffy coat) and then exposed to UV-A in the presence of the photosensitizer 8-methoxypsoralen (see, e.g., reference REF151 of the list of references provided hereinbelow). In the context of SARS-CoV-2-disinfection, UV-B and/or UV-C wavelengths (e.g., without a cellular photosensitizer) may be used on whole blood (e.g., as is) for efficiency; EMR may be incorporated into technologies for extracorporeal membrane oxygenation in order to have the additional effect of blood oxygenation to disinfection (see, e.g., reference REF152 of the list of references provided hereinbelow).

Any suitable process may be utilized for quantifying or otherwise determining an amount of energy (e.g., absorbed dose) to be delivered to cause an end effect on any suitable target invasive entity (e.g., fungus, bacteria, virus, etc.) of any suitable target (e.g., internal organ, skin, canal, etc.) that may be in any suitable host (e.g., in any suitable region of a human, animal, plant patient (e.g., exterior surface or in any suitable cavity or vessel or the like)). At one operation of the process, the target invasive entity may be determined (e.g., using any suitable detection tools, such as determining genetic sequence of a virus, etc.). At another operation of the process, the sensitivity of the determined target invasive entity to a particular energy-based therapy (e.g., UVR, UVB, etc.) may be estimated (e.g., using Sagripanti and Lytle's SnS model to calculate virus sensitivity). At another operation of the process, the waveband specific "dose" required to result in 10% remaining invasive entity that is a 1-log reduction that is a $D_{10}$ value may be estimated based on the estimated sensitivity. At another operation of the process, the treatment volume may be defined (e.g., using any suitable techniques (e.g., a clinical decision) to determine where the invasive entity is having an active effect (e.g., via CT scan, simulation, noninvasive imaging of target, etc. (e.g., in parallel to ionizing radiation treatment planning))). At another operation of the process, the maximal multiple of $D_{10}$ value (e.g., $D_{10}\times0.8$, $D_{10}\times0.9$, $D_{10}\times1$, $D_{10}\times2$, $D_{10}\times3$, $D_{10}\times4$, etc.) of the target invasive entity (e.g., a virus, bacteria, fungi, and/or the like) that overlaps within the shoulder (e.g., perhaps down to a cellular $D_{90}$-dose resulting in a 10% reduction of cells) of the cellular survival curve pertaining to the treatment volume may be determined. The maximal multiple of $D_{10}$ value that can be administered to result in no more than a cellular D90 that is dose to result in a 10% reduction of cells may determine the permissible dose per fraction. Fractions may be spaced by 2-6 hours to allow for cellular recovery (e.g., timing may ultimately be determined by the disease being treated). At another operation of the process, the percent depth-dose or depth dose characterizations (i.e., to identify the isodose distribution) of the particular energy-based therapy in a particular treatment volume density (e.g., optical density, electron density) may be determined with any suitable mathematical algorithmic simulators (e.g., MonteCarlo simulation). At another operation of the process, the volume of the defined treatment volume that will receive 100% of the maximal permissible dose per fraction may be optimized (e.g., by evaluating simulated isodose distribution (e.g., via histogram analysis)). No region of the defined treatment volume should be simulated to receive greater than 100% of the maximal permissible dose per fraction. If there is a region of the defined treatment volume simulated to receive greater than 100% of the maximal permissible dose per fraction (i.e., a "hot spot"), then the dose output parameters (e.g., power, time, energy) of the energy emitter should be adjusted so that no region of the defined treatment volume simulated may receive greater than 100% of the maximal permissible dose per fraction. The total or cumulative prescribed dose may ultimately be determined by the host toxicity profile and symptomatology profile and quantitative or semi-quantitative, direct or indirect measurements of the invasive entity over time. The ultimate goal is to optimize the therapeutic ratio in managing the defined disease caused by the target's invasive entity. At another operation of the process, the prescribed dose may be delivered as energy (e.g., as a defined waveband and quantity of energy) to the target of the host in any suitable manner (e.g., using any suitable apparatus (see, e.g., system 1700 of FIG. 17, system 1800 of FIG. 18, and/or the like)). Therefore, the process may provide for waveband selection, and a dose and fractionation scheme that may be modified based on the invasive entity type and the area and/or volume of the treatment target.

As shown in FIG. 1, any suitable system 100 may be used by the processes of this disclosure. System 100 may include any suitable host 102, which may include any suitable target 104, which may include any suitable target invasive entity 106. System 100 may also include any suitable emitter(s) 110 for emitting any suitable phenomena (e.g., energy, light, magnetism, etc.) at host 102, any suitable sensor(s) 112 for sensing any suitable phenomena (e.g., energy, light, magnetism, etc.) from host 102 or elsewhere in the environment (e.g., the sun), and any suitable computing device(s) 114 that may be communicatively coupled to emmiter(s) 110 and/or sensor(s) 112 and may be configured to include any suitable input components, output components, communication components, processing components, memory components, and/or the like for carrying out any suitable algorithms or processes or functionalities described herein (e.g., models, simulators, calculations, etc.).

There are various ways in which the services offered by the therapy platform to reduce the viral load may be commercialized. Evidence now confirms that COVID-19 can remain airborne for longer times and further distances than originally thought. In addition to close contact with infected people and contaminated surfaces, spread of COVID-19 may also occur via airborne particles in indoor environments, in some circumstances beyond the 6 foot range encouraged by some social distancing recommendations. While inactivating virus in buildings themselves cannot solve the COVID-19 pandemic, it cannot be denied that they will play a crucial role in minimizing viral transmission. No matter a building's occupancy type, the therapy platform can provide many options to help a building's indoor air quality ("IAQ"). For example, ultraviolet germicidal irradiation ("UVGI") or UVR may be used to disinfect water, surfaces, and air, but, traditionally, it has not been used in air conditioning systems, especially ductless fan coils. UVC energy can "escape" fan coil return and/or supply air openings to potentially do harm to eyes and skin. The therapy platform may be designed to prevent this, making UVC use in ductless systems safe. UVC may kill or inactivate virus/microorganisms, and/or degrade most organic material to eliminate the mold, mildew, and slime along with their nutrients that accumulate on coils and in drain pans. Often times facilities like schools and hotels may not have central heating, ventilation, and air conditioning ("HVAC") systems delivering air through ducts and may contain individual packaged terminal air conditioner ("PTAC") units. Ultraviolet germicidal irradiation ("UVGI") lights can be installed in each unit, allowing a customer to realize all the benefits of germicidal lighting in PTACs and fan coil units. Installation may feature a low profile lamp with a metal shield and mounting bracket providing optimum exposure in tight spaces. Duct cleaning and sanitizing services may be provided by the therapy platform for removing contaminants from an HVAC system and applying EPA registered sanitizers that may be approved for HVAC systems. The Division of Occupational Health and Safety ("DOHS") may recommend the following for prevention of air duct contamination for preventing COVID-19 duct contamination: (1) perform routine preventive maintenance on HVAC systems, by complying with manufacturer schedules for changing HVAC filters, cleaning coils, and other components; (2) ensure that air intakes are located away from contaminant sources; (3) consider routine inspections of ductwork. The National Air Duct Cleaning Association ("NADCA")'s standard, "Assessment, Cleaning and Restoration of HVAC Systems ACR 2013," recommends that HVAC systems be visually inspected for cleanliness at regular intervals, depending on building use. For healthcare facilities, the standard recommends annual inspections of air handling units and supply/return ductwork.

The following may describe a portion of the therapy platform as a novel medical discipline dedicated to the management, treatment, and surveillance of invasive diseases (e.g., radiation virology, radiation bacteriology, radiation mycology, electromagnetic irradiation for the treatment of viral infections, etc.).

As mentioned, Severe Acute Respiratory Syndrome Coronavirus-2 ("SARS-CoV-2"), causes Coronavirus Disease 2019 ("COVID-19"), which originated in Wuhan, Hubei Province, China during December 2019 (see, e.g., reference REF079 of the list of references provided hereinbelow). COVID-19, which presents a clinical picture of the "respiratory tract infection" with exaggerated "ACE-inhibitor-like pharmacotoxicity" (e.g., pronounced inflammatory response andvasoconstriction of small vessels in multiple organ systems) was deemed a 'pandemic' in March 2020, with a force that has overwhelmed country-specific and global infectious disease protocols (see, e.g., reference REF287 of the list of references provided hereinbelow).

In the context of life-threatening invasive or parasitic diseases (e.g., viral/bacterial/fungal infections and cancer), the combination of medical knowledge from established separate medicalspecialties is required for the development and implementation of BioDefense protocols of the therapy platform. The current training in each of the separate disciplines of surgical oncology, radiation oncology, medical oncology, dermatology, and infectious disease does not significantly overlap. Consequently, it would be beneficial for the specialists in each of these disciplines to practice with awareness of the relevance of the other disciplines. Combined training, as is seen with the origins of Biophysics and Dermatopathology, would be useful towards national and global protection against life-threatening invasive diseases.

EMR within the ultraviolet ("UV") and ionizing radiation ("IR") wavebands also results in the inactivation of viruses and viral-induced inflammatory responses, respectively. Therefore, the creation of a novel medical discipline, BioDefense, may be provided by the therapy platform to train physicians on how to manage life-threatening invasive diseases with the arsenal of knowledge that has been developed by leading scientists throughout the past several decades (see, e.g., references REF080-REF082 of the list of references provided hereinbelow). For contemporaneous applicability to the COVID-19 pandemic, BioDefensive Medicine may be simultaneously inaugurated with sub-specialty, Radiation Virology, to direct intellectual resources towards the development of dosimetry and to optimize the therapeutic ratio of electro-magnetic radiation (EMR).

A therapeutic electromagnetic radiation spectrum for the COVID-19 pandemic is proposed. In 1896, Leopold Freund demonstrated the successful treatment of a tumor (i.e., hairy nevus) with x-rays; such demonstration marked the birth of Therapeutic Radiology that is now known as Radiation Oncology[5]. Since then, the therapeutic utility of electromagnetic irradiationin the x-ray and gamma-ray wavebands for solid tumors was developed through Radiobiology within the medical discipline of Radiation Oncology (see, e.g., reference REF083 of the list of references provided hereinbelow). In 1903, the Nobel Prize in Medicine was awarded to Niels Finsen for demonstrating the successful treatment of skin *Mycobacterium tuberculosis* ("TB") with EMR (see, e.g., reference REF084 of the list of references provided hereinbelow). Subsequent to this demonstration, external exposure to solar and EMR-emitting devices became the standard of care for TB until the invent of antibiotics. The therapeutic utility of UV radiation was developed through the field of Photobiology within the medical discipline of Dermatology. Bridging knowledge and applicability of Photobiology and Radiobiology is required in order to implement a concerted effort towards Global Viral Load Reduction ("GVLR") described herein.

For context, light can be visualized as an electro-magnetic wave corresponding to perpendicular oscillations of electric and magnetic fields. A wavelength ($\lambda$) is the distance between two successive points of the same phase along the wave. A wavelength is the distance per cycle of the wave. Light can also behave like a moving particle (e.g., analogous to a water molecule in an ocean wave) with each particle being quantized into discrete units or packets of energy, termed photons. The light energy (E $\lambda$) contained in a photon is defined as: E $\lambda$=hv=hc/$\lambda$, where h is termed the Planck's constant. A photon of light has an energy that is directly proportional to its frequency, and inversely proportional to its wavelength in a vacuum (i.e., ideal transmittance environment).

UV EMR may be emitted by the sun and/or UV emitters. IR EMR may be similarly emitted by radioactive substances (e.g., Radium-226, Cobalt-60, Iodine-125, Iridium-192, Gold-198, Lutetium-177) and IR emitters (e.g., superficial radiation devices, orthovoltage machines, linear accelerators, Gamma Knife). External exposures of phototherapy (i.e., UV EMR) or external beam radiotherapy (i.e., IR EMR) may utilize EMR-emitters to transfer energy from the patient exterior to the patient surface and/or interior, where this energy may be deposited in tissue as dose, whereas brachytherapy may involve EMR of short penetration distance (e.g., intracavitary, interstitial, catheter-based, antibody-mediated) (see, e.g., references REF085-REF087 of the list of references provided hereinbelow), using emitters that are placed within the body and near to the intended target.

The therapeutic EMR spectrum may be subdivided into 5 distinct wavebands (e.g., UV-A, UV-B, UV-C, X-Rays, Gamma-Rays). Each waveband may be characterized as EMR with a specific rangein wavelength, associated energies, penetration, and molecular/organismal interactions, as shown by the following Table 1, which may show the spectrum of electromagnetic radiation considering photons at UV energies and above, where the EMR electromagnetic spectrum of UV radiation may be defined most broadly as 10-400 nm, and, although, there is not universal agreement on distinct UV categories, the waveband can be subdivided into nominal photon energy ranges recommended by the ISO standard ISO-21348-(ISO 21348 Definitions of Solar Irradiance Spectral Categories).

TABLE 1

| Type | Wavelength (nm) | Nominal Photon Energy (eV) | Penetration Depth | Directly Ionizing | Indirectly Ionizing |
|---|---|---|---|---|---|
| UV-A | 400 to 315 | 3 to 4 | 50 μm (skin) [REF169] | No | Yes |
| UV-B | 315 to 280 | 4 to 5 | 20 μm (skin) [$^{REF169}$] | No | Yes |
| UV-C | 280 to 100 | 5 to 12 | <1 μm (skin) | No | Yes |
| Extreme UV | 100 to 10 | 10 to 100 | <1 μm (water) [$^{REF170}$] | Yes | Yes |
| X-rays | 10 nm to 6 pm | 100 eV to 200 keV | μm to < m (water) [$^{REF170, REF092}$] | Yes | Yes |
| Gamma | 10 pm and below | 100 keV and up | cm to > m (water) [$^{REF092}$] | Yes | Yes |

UV-A radiation may penetrate through the skin into the deeper dermal layers, whereas UV-B may only pass through the epidermis and into the superficial dermis (~50 μm) (see, e.g., reference REF088 of the list of references provided hereinbelow). Due to its strong absorbance in biological materials, far-UV-C (e.g., 207-222 nm) light cannot penetrate beyond the superficial epidermis (i.e., stratum corneum) (see, e.g., reference REF089 of the list of references provided hereinbelow). Generally, as UV-C, X-ray, and gamma-ray EMR wavelengths shorten and energies increase, EMR penetration into tissues increases to penetrate through the body (see, e.g., references REF090 and REF091 of the list of references provided hereinbelow). Additionally, at these higher energies, dose from secondary radiation can also become significant (see, e.g., reference REF092 of the list of references provided hereinbelow). It is important to note that depth dose in tissue for the UV waveband may not yet be defined as it has been for the IR waveband. A few studies report a very wide range of depth dose penetration. For example, induction of UV-induced 53BP1 focus formation occurred at a maximal depth of 40 μm in 3D-culture of MiaPaCa-2 cells (see, e.g., reference REF093 of the list of references provided hereinbelow). Studies on UV-B mortality of zooplankton in turbid creek water (e.g., analogous to cellular cytoplasm) show that inactivating intensities of UV-B can penetrate 2.2 to 13.5 m (see, e.g., reference REF094 of the list of references provided hereinbelow). Depth dose characterizations for energy deposition within the UV EMR waveband may be defined in near-future studies.

The first known efforts toward UV percent depth dose calculations in/on cells were performed by Coohill et al. in 1984 and were expanded upon in 1990 (see, e.g., reference REF295 of the list of references provided hereinbelow and FIG. 3). Evaluating the light penetration characteristics into skin or tissue using the Monte Carlo algorithm is possible (see, e.g., reference REF296 of the list of references provided hereinbelow). The penetration lines may be very similar to the isodose lines seen in treatment planning for electron beam ionizing radiation and brachytherapy with radioactive isotopes. The isodose penetration of decreasing UV wavelengths may parallel the shape of what one would expect with increasing beam energy. To determine what percent of UV is absorbed as it travels through different tissue-types (e.g., soft-tissue, bone, fat, skin, mucosa, etc.), including air cavities (e.g., lung), these tools may be utilized. Note, the epidermis used for the majority of available UV dosimetry studies may be filled with chromophores that are not found in non-skin tissues of the body and may therefore, aside from visualization of the overall radiation distribution, be irrelevant in the irradiation of other tissues.

The energy threshold to cause direct ionizing damage to biological molecules is around 10 eV; EMR of lower energies within the visual light spectrum, UV-A and UV-B wavebands may cause indirect damage (e.g., genetic damage and mutations) to biological molecules via water photolysis production of reactive oxygen species (e.g., hydroxyl radical, hydrogen peroxide, nitric oxide and nitrogen dioxide) and ions (e.g., oxygen ion) (see, e.g., Table 1) (see, e.g., references REF095 and REF096 of the list of references provided hereinbelow).

The lower quanta which may characterize the photons present in UV-A, relative to other UV frequencies, may be least efficient towards viral inactivation; as may be seen with solar disinfection systems that are predominantly based on UV-A irradiation, greater doses and exposure times to this waveband may be required to result in comparable damage to the viral genetic material (see, e.g., references REF097 and REF098 of the list of references provided hereinbelow). The greater energies associated to the UV-Band UV-C wavebands may result in more efficient viral inactivation by generating a larger density of reactive oxygen species and ions capable of indirect chemical and molecular alterations in RNA and DNA (e.g., formation of cyclobutane-pyrimidine dimers, 6-4 photoproducts (6-4PPs) and direct RNA and DNA strand breaks (see, e.g., reference REF096 of the list of references provided hereinbelow). The 200-300 nm UV-B and UV-C waveband cusp may be characterized as having peak absorption in DNA (see, e.g., reference REF099 of the list of references provided hereinbelow). Approximately one-third and two-thirds of ionizing EMR dose deposition may result in direct and indirect biological damage, respectively. The greater energies and absorbed dose characteristics of ionizing EMR may be associated with a more efficient production of single-stranded ("ss") and double-stranded ("ds") DNA breaks in mammalian cells, which may be ideal for inducing apoptosis of cytotoxic inflammatory infiltrates in tissues such as the lung.

Studies of bacteriophages (i.e., surrogates for investigation of mammalian viruses) have demonstrated that the UV-C ~(254 nm) dose required for 90% (i.e., 1-log) viral reduction may be 1.32-3.20 $mJ/cm^2$ for single stranded ("ss") RNA, 2.50-4.47 $mJ/cm^2$ for ssDNA, 3.80-5.36 $mJ/cm^2$ for double stranded ("ds") RNA, and 7.70-8.13 $mJ/cm^2$ for dsDNA (see, e.g., reference REF100 of the list of references provided hereinbelow). For all four viral genome constructs (e.g., ss versus ds, RNA vs DNA), ss is more sensitive than ds and RNA is more sensitive than DNA. Viral genome size also affects sensitivity to UV, where larger genomes are more sensitive (see, e.g., references REF080, REF081, and REF101 of the list of references provided hereinbelow). The viral survival reduction in environment and host(s) may be a biphasic process, so the UV dose for 99% (i.e., 2 log) viral reduction may be twice the dose compared to the dose required to achieve a 90% viral reduction until a certain turning point when a shallower survival curve develops out of the protective/attenuating effects of organic substances (see, e.g., references REF102 and REF103 of the list of references provided hereinbelow). For example, the first part of the viral reduction curve may be steep and log-linear (i.e., UV dose for 99% (i.e., 2 log) viral reduction may be twice the dose compared to the dose required to achieve a 90% viral reduction); the second part of the curve may be shallower, resulting from the protective/attenuating effects of organic substances on virions (i.e., organic material in the path of UV light will absorb part or all energy before reaching the viral particle). Applying the Sagripanti and Lytle model that includes adjustments for the biphasic viral inactivation curve, the UV-B ~(310 nm) D10 (dose required for 90% (e.g., 1-log) viral reduction) of SARS-CoV-2 may be 69 $mJ/cm^2$ (see, e.g., reference REF081 of the list of references provided hereinbelow). The direct action of electrons may result in double-strand breaks in DNA that when un-repaired may cause mitotic (e.g., reproductive) death of cells within the treatment tissue volume. The effect of ionizing irradiation may be the reproductive death of cells within the treatment tissue volume. The inflammatory infiltrate similar to that seen during an infectious process or during wound healing may be radiosensitive and may be largely eliminated via interphase death (e.g., apoptosis) after approximately 2 Gy (see, e.g., reference REF003 of the list of references provided hereinbelow). While UV is capable of resulting in direct damage (e.g., particularly in the UV-C waveband), the effect of UV results via indirect damage.

Historically, airborne-mediated microbial diseases such as influenza (see, e.g., reference REF104 of the list of references provided hereinbelow) and TB have presented a similar major public health challenge as do coronaviruses now. Both are well-understood airborne infections that are also effectively inactivated with UV EMR of air, surfaces, and skin from which the platform can extrapolate some predictive disease dynamics for this COVID-19 pandemic.

In Great Britain, epidemiological data on the distribution of influenza mortality during the past 300 years could not be accounted for by direct person-to-person transmission or account for seasonal predilection of outbreaks. Sagripanti and Lytle defined the susceptibility of influenza to solar radiation in a manner that describes virus survival in the shadows via seasonal oscillation between the hemispheres (see, e.g., reference REF101 of the list of references provided hereinbelow). Similar behavior is expected and is already being demonstrated for SARS-CoV-2 where low-latitude locations have experienced a steady SARS-CoV-2 death rate (e.g., Puerto Rico, USA; 18.2208° N) and higher-latitude locations have experienced a decreasing SARS-CoV-2 death rate during the summer solstice (e.g., New York, USA; 40.7128° N) followed by an increase in approach of the winter solstice. It has been calculated that SARS-CoV-2 is inactivated by 90% at solarnoon within 11-34 mins during the summer solstice and 11->300 mins during the winter-solstice, contingent on the latitude location (see, e.g., reference REF081 of the list of references provided hereinbelow). Therefore, in Puerto Rico one would expect a 1-log reduction within 11 mins of solar noon UV exposure throughout the year. However, in NewYork, one would expect a 1-log reduction of SARS-CoV-2 within >300 mins and 22 mins at solar noon during the winter and summer solstices, respectively. Based on the Sagripanti and Lytle model, SARS-CoV-2 may be 2-fold more sensitive to solar UV than influenza (see, e.g., reference REF101 of the list of references provided hereinbelow). Therefore, a greater oscillation of new infections may not be completely unexpected for SARS-CoV-2.

Similar to what has been observed with influenza, a deterministic model was developed to simulate TB transmission in highly endemic regions; the model could not be titrated to the endemic incidence rate without allowing for the occurrence of TB reinfection (see, e.g., reference REF105 of the list of references provided hereinbelow). These findings indicate that TB reinfection by a pathogen plays a critical role in transmission and in maintaining an endemic environment, which is likely also the case for SARS-CoV-2 (COVID-19) (see, e.g., reference REF105 of the list of references provided hereinbelow). Increased viral loads of airborne SARS-CoV-2 have been identified in areas prone to crowding; increased viral load in air is presumed to be associated with increased risk of transmission, cross-infection and perhaps reinfection (see, e.g., reference REF106 of the list of references provided hereinbelow). It is important to note that cross-infection with mutated strains may lead to a heterogeneous SARS-CoV-2 superinfection, characterized by a prolonged COVID-19 disease course.

Retrospective and prospective studies, in the context of fully recovered patients, have clearly shown that exogenous reinfection contributes to a significant proportion of the recurrent TB cases (see, e.g., references REF105-REF109 of the list of references provided hereinbelow). A population-based cohort study of the United States National Tuberculosis Surveillance System found that 15% of patients were classified as having reinfections with differing genotypes (i.e., mutated strains) (see, e.g., reference REF107 of the list of references provided hereinbelow). A retrospective cohort study in Shanghai, China, found that 41.8% were reinfected with a different strain of TB (see, e.g., reference REF109 of the list of references provided hereinbelow). A prospective cohort study from Milan, Italy, diagnosed exogenous TB reinfection in 23% of the cohort patients (see, e.g., reference REF108 of the list of references provided hereinbelow). Cases of SARS-CoV-2 viral reactivation or reinfection have already started to surface in multiple countries (see, e.g., references REF110 and REF111 of the list of references provided hereinbelow).

The highly mutable nature of coronaviruses, compounded with limited viral targeted therapies, will likely make the risk of reinfection and development of drug-resistant strains a clinical concern (as is, and has been, seen with influenza and TB). Inhibiting viral replication improves time to recovery by only ~30% (see, e.g., references REF112 and REF113 of the list of references provided hereinbelow); the inhibiting drug(s) may not actually inactivate the virus that has infected the person, but may only reduce its growth rate. EMR is an agent that can inactivate viruses irrespective of the mutational status, with UV having a greater inactivation efficiency and therapeutic gain compared to ionizing radiation (i.e., the dose required for ionizing EMR viral inactivation is in the kGy dose range that may be incompatible with life). A direct approach to implement GVLR towards prevention of viral transmission and reinfection may be the inactivation of virions that are airborne, on high-touch surfaces, in water sources, food sources, and within hosts (see, e.g., reference REF089 of the list of references provided hereinbelow).

Solar EMR may be attenuated by ozone, oxygen, and water so that about 5% of the photon's reaching the surface of the Earth are in the UV (e.g., below 400 nm), 28% in the visible and 67% in the infrared (e.g., beyond 740 nm) wavebands. UV-A and UV-B comprise 95% and ~5% of the UVEMR reaching the Earth's surface (see, e.g., reference REF114 of the list of references provided hereinbelow). Because most UV-C wavelengths are filtered by the atmosphere, analogously to the effect of a flattening filter in linear accelerators, natural solar disinfection may be primarily mediated by UV-A and UV-B wavelengths, with some biological impact caused by the visible and infrared wavebands. It is possible to extrapolate the required dosage of UV-A and/or UV-B from a solar disinfection system required to result in significant (e.g., 1-log) viral reductions; and the presumed dosage can be calculated from the viral UV-C sensitivity and the effective solar flux (see, e.g., reference REF080 of the list of references provided hereinbelow). This method of calculating the 254-nm-equivalent solar flux and solar exposure time needed to inactivate viruses may allow for optimization of solar disinfection systems for biodefense (see, e.g., reference REF080 of the list of references provided hereinbelow).

The viral nucleic acid may be the target for virus inactivation by UV radiation. When the viruses are grouped by nucleic acid type and standedness, the size of the DNA or RNA may be the major determinate of UV sensitivity. A term designated "inactivation quantum yield" ($\varphi$), defined as the ratio of the inactivation cross section ($\sigma$) to the absorption cross section (s), represents the probability that an absorbed photon will lead to an inactivated virus. This value should be relatively constant for a given type of nucleic acid regardless of size but will differ among nucleic acid types. The product of quantum yield and absorption cross section gives the inactivation cross section (i.e., the UV sensitivity), and may be used to predict the UV sensitivity of untested viruses. The quantum yield and/or the absorption cross sections may potentially be determined for such viruses.

On the other hand, a quantity proportional to the quantum yield can be estimated from similar viruses, and together with the size of the untested virus, a UV sensitivity can be estimated. Since the inactivation cross section is proportional to the inactivation constant, k, and the absorption cross section is proportional to the genome size, $\Phi=\sigma/s=\alpha k/GS=\alpha(D_{37}\times GS)^{-1}$, where a is a proportionality constant. Thus, the quantum yield is proportional to the inverse of the product of the $D_{37}$ and the genome size. This product, which is hereby designate "size-normalized sensitivity" ("SnS"), has the practical advantage of consisting of quantities already known for similar viruses (see, e.g., reference REF080 of the list of references provided hereinbelow). As with the quantum yield, the SnS should be relatively constant for each type of viral nucleic acid and is expected to be independent of nucleic acid size (i.e., it represents a means to normalize the UV sensitivity with regard to viral target size). Further, dividing the SnS by the genome size of an untested virus yields an estimate of the $D_{37}$ for that virus.

By convention, UV dose may be described as dose in an area, or a slice of the volume where dose is being deposited. Yet the "dose" from UV may be actually deposited in a very small volume (e.g., very little photon travel compared to external beam ionizing) on the order of micro-meters thick. UV may be thought of as short distance B-emission like 177-Lu (e.g., Lutetium-177 radionuclide, $^{177}$Lu, Lu177, 177Lu, 177Lu, etc.). Failure to identify depth dose distribution may be the source of 2-fold variation or error margin described by Lytle and Sagripanti in their SnS estimation model. Further, the aforementioned $D_{37}$ may be based on the assumption of a uniform dose distribution which may not be the case with UV because it has a very fast fall off with depth, consequently to improve upon the existent SnS model, it may be helpful to look at the distribution of virus by depth and to calculate the dose at different depth segments and fraction of remaining "active" virus at each depth. It might also help to understand the distribution of virus throughout the irradiated volume. Also whether or not the testing solution had "settled" or was "stationary" virus prior to irradiation or if the virus was in motion as is expected when within a cell versus an environmental surface. Additionally, it may be important to define how motion versus static shielding molecules affect the absorbed target dose.

Disinfection using UV radiation is used in wastewater treatment applications and is finding an increased usage in municipal drinking water treatment. Systematic solar disinfection is a low-cost means of biodefense and water treatment that can be readily implemented towards improving the water quality, particularly in tropical regions with high UV indices (see, e.g., references REF097 and REF098 of the list of references provided hereinbelow). Commercial companies of spring water may use UV disinfection equipment to sterilize their water. Solar water disinfection has been researched for cost-effectively treating contaminated water using natural sunlight as fast as in 6 hours. Effective >6-log inactivation of MS2 bacteriophage in Swiss tap water has been achieved by exposure to a total fluence of 1.34 kJ/cm$^2$ (see, e.g., reference REF0115 of the list of references provided hereinbelow). High temperatures significantly enhanced MS2 inactivation; specifically, at 40 degrees C., 3-log inactivation was achieved in Swiss tap water after exposure to a fluence of only 0.18 kJ/cm$^2$ (i.e., 3.7 times more effective) (see, e.g., reference REF115 of the list of references provided hereinbelow). Importantly, it has been demonstrated that solar disinfection systems significantly reduce the viral load of ssRNA viruses, such as SARS-CoV-2 (COVID-19).

The solar disinfection treatment process of water can be implemented in households and farms. Individuals can fill plastic water bottles with water and leave them out in the sun for a period of hours, however, solar UV depth dosimetry needs to be developed to define adequate exposure times required to disinfect certain water volumes in containers of different materials and thicknesses. The cited studies have investigated the solar disinfection capacity of water contained in polyethylene-terephthalate ("PET") bottles. At least six hours was required to disinfect water contained in PET bottles. Notably, the PET container material attenuates most of the UV-B wavelengths, therefore, optical inactivation mechanisms in operation during solar disinfection result from UV-A wavelengths and visible light (see, e.g., references REF097 and REF098 of the list of references provided hereinbelow). A larger scale use of solar disinfection on municipal wastewater used for crop irrigation could allow for crops that are safer to consume (see, e.g., reference REF116 of the list of references provided hereinbelow). Classical mechanical methods or typical filtration systems may remove, via filter entrapment, inactivated virus and other contaminants from water. Importantly, solar disinfection systems may be more effective in inactivating bacteria over viruses, due to the smaller genome of the latter.

Since UV-C wavelengths are attenuated by the Earth's atmosphere (i.e., do not reach earth due to the ozone layer), it may be necessary to use UV-C emitting devices in order to generate this bandwidth. UV-C emitting devices may be, for example, mercury lamps, pulsed xenon lamps, or LEDs. Low pressure mercury lamps emit mercury-vapor, UV lamps mercury-vapor, UV lamps emit about 86% of their radiation at 254 nm, with 265 nm being the peak germicidal effectiveness curve. Pulsed xenon lamps emit at a broader spectrum of UV-C (100-280 nm) with visible light (380-700 nm) (see, e.g., reference REF117 of the list of references provided hereinbelow). UV at these germicidal wavelengths may result in ss or ds breaks in a microorganism's DNA/RNA so that it cannot reproduce, making it either bacteri/vericidal or bacteri/veriostatic. EMR including pulsed xenon and continuous UV-C emitting devices may follow the inverse square law where the light intensity (fluence) decreases as the square of the distance from the light source. The lower UV-C output associated with pulsed xenon emitters, relative to continuous UV-C emitters, may amplify the behavior of intensity loss at increasing distances (see, e.g., references REF118 and REF119 of the list of references provided hereinbelow). In both cases, intensity fall with distance can be compensated by increasing the time of exposure (see, e.g., reference REF119 of the list of references provided hereinbelow).

UV-C LEDs may be as effective as mercury and pulsed xenon devices; LEDs are compact in size, which offers opportunity for smaller applications (e.g., UV waveband brachytherapy) and allows for greater flexibility in design of disinfection protocols. LEDs have the benefit of being void of mercury, alleviating any environmental health concerns associated with that element.

They have instant on/off, and have unlimited cycling throughout the day. More importantly, due to their monochromatic nature (e.g., ±5 nm), these LEDs can target a specific wavelength needed for disinfection (see, e.g., www.wateronline.com). This is especially important, knowing that pathogens vary in their sensitivity to specific UV wavelengths. Further, multiple UV wavebands can be delivered simultaneously with UV LEDs, optimizing targeting of viruses, bacteria, and fungi; specifically, this may be accomplished by combining LED emissions from the primary germicidal region (e.g., 250 nm-280 nm) with a wavelength from the polypeptide absorbance region below (e.g., 220-230 nm). The combination of both wavelengths can mimic the efficacy of UV emissions from a medium-pressure mercury UV-C lamp, which has been shown to be more effective at inactivating pathogens than low-pressure mercury UV-C lamps (see, e.g., reference REF120 of the list of references provided hereinbelow). Given that low-pressure mercury lamps are more predominantly used in UV-C emitting devices, UV LEDs may allow for the potential to achieve more efficient disinfection cycles.

The amount of pathogen inactivation may be directly related to the UV-C absorbed dose. UV-C dosage may be the product of the intensity and the duration of the exposure (see, e.g., reference REF119 of the list of references provided hereinbelow). Disinfection times for UV-C emitting devices may be typically very short (e.g., in the order of minutes). End of lamp life (intensity drops to 80% shortly before end of lamp life lamp life), lamp outage, or ballast failure could cause UV-C intensity to fall. In the case of partial lamp outage, in order to maintain therapeutic efficacy, adjustments in disinfection cycle may take place. Alterations in cycle can include an increased exposure time to achieve effective UV-C dosage. Other options include increasing intensity by shortening the distance of the light source to target surfaces, or by increasing the number of UV-C emitting devices in the space. Implementation of annually scheduled lamp replacement procedures may decrease work-flow interruptions related to lamp outages. Electrical and mechanical issues, such as ballast failure, may require professional repair in order to return to full functionality and efficiency.

A 1-log reduction in SARS-CoV-2 viral load may be achieved with 2-5 mJ/cm$^2$ of UV-C irradiation (see, e.g., reference REF121 of the list of references provided hereinbelow). The 1-log reduction dose for SARS-CoV-2 may overlap the required dose range for other ssRNA viruses, suggesting that SARS-CoV-2 is radiosensitive and no more resistant to UV EMR than other ssRNA viruses. In fact, Sagripanti and Lytle predicted the UV sensitivity of SARS-CoV-2 (see, e.g., reference REF081 of the list of references provided hereinbelow). Their above described SnS model had the advantage of having UV inactivation data from two viruses in the same Coronaviridae family, Murine Hepatitis Virus ("MHV") and Equine Torovirus ("EToV"), which had nearly identical genome sizes and $D_{37}$s. SARS-CoV-2, was predicted to be twice as sensitive to solar-UV inactivation as influenza virus, suggesting that, as with the 'flu,' the summer season should have been associated with a near complete remission of the disease. Said remission was not experienced in the northern hemisphere summer. It is anticipated that SARS-CoV-2 vaccination will reduce the COVID-19 disease burden to that of influenza, however, to reduce the COVID-19 disease burden to that of small pox (i.e., complete or near complete eradication), a GVLR regimen should be implemented. Far-UVC (e.g., 207-222 nm) may also efficiently inactivate aerosolized and surfaced viruses; specifically, 2 mJ/cm$^2$ of 222-nm UV-C may inactivate >95% of aerosolized H1N1 influenza virus (see, e.g., reference REF089 of the list of references provided hereinbelow). Ultraviolet lamps may be used to sterilize workspaces and tools used in biology laboratories and medical facilities. UV-C EMR in indoor public locations may provide a promising, safe, and cost-effective method towards GVLR; such could be achieved with the widespread addition of UV-emitting lamps (or LEDs) alongside light bulbs in places of major public transit (see, e.g., reference REF089 of the list of references provided hereinbelow). Scientists are increasingly proposing the use of UV to reduce SARS-CoV-2 pollution in air (see, e.g., reference REF122 of the list of references provided hereinbelow).

Unless poor penetrating wavebands of far-UVC are employed, UV-C sterilization may be used solely at times when the places are free of human presence or when humans are adequately shielded. Notably, the CDC has approved UV-C disinfection of N95 masks (without folds) for reuse and has publicly accepted that COVID-19 is an airborne disease.

While external UV EMR treatment is important to reduce aerosolized and surfaced viral load, internal UV-B EMR is likely the safest and most efficient mechanism to inactivate patient or host viral load. It is estimated that just 69 mJ/cm$^2$ UV-B dose (e.g., 310 nm) may be needed to result in 1-log viral reduction of SARS-CoV-2 at a certain cell layer depth dose. The $LD_{50}$ of human oral mucosa cells irradiated with 310 nm UVB is 401.8 mJ/cm$^2$ (see, e.g., reference REF123 of the list of references provided hereinbelow). Mucosal cell survival curves for UV-B irradiation may be not readily available/accessible, however it has been reported that no acute damage or cytotoxicity to human oral mucosa cells occurred with doses up to 105 mJ/cm$^2$ with UV-B (e.g., 310 nm). These data indicate that 105 mJ/cm$^2$ falls within the shoulder of the human mucosa cellular survival curve. Fraction sizes of 69-138 mJ/cm$^2$ (e.g., dose within and perhaps on the brink of the exponential linear survival slope) may be ideal to achieve a therapeutic gain of 1-log (90%) to 2-log (99%) viral inactivation to a presumable depth of ~50 μm in tissues of primary virus inoculation sites (e.g., nasopharynx, oropharynx, hypopharynx, oral cavity). The UV isodose lines and/or dose distribution may be simulated. For example, isodose lines can be calculated for UV therapy by applying UV specifications (e.g., percent depth dose characterizations, UV photon movement characteristics, etc.) into a mathematical algorithm (e.g., montecarlo simulation) (see, e.g., reference REF296 of the list of references provided hereinbelow). Allowing for a 2-6 hour inter-fraction period may permit redistribution of virus and shielding organic materials within cells and cellular repair of mammalian DNA damage (if any). Interfraction redistribution may reduce the influence of the biphasic viral survival curve.

Multiple studies have already demonstrated the clinical efficacy and safety of UV EMR (with or without photo sensitizers and antimicrobial drugs) in treating a variety of skin and mucosal microbial infections (e.g., bacteria, parasites, fungi, yeast and viruses) (see, e.g., references REF124-REF129 of the list of references provided hereinbelow). In addition to genome inactivation, one group identified that UV EMR of skin results in activation of humanmacrophages via toll-like receptors that in turn, upregulate the vitamin D receptor gene resulting in induction of the antimicrobial peptide, cathelicidin (see, e.g., reference REF084 of the list of references provided hereinbelow). A study of narrow band (NB) UVB irradiation with 1170 mJ/cm$^2$ of inflammatory facial acne vulgaris lesions (i.e., active micro-infection) demonstrated significant therapeutic synergism ($P=0.002$) with systemic azithromycin (see, e.g., reference REF130 of the list of references provided hereinbelow). A recent case report demonstrated the cure of a skin human papillomavirus infection with nbUVB alone (see, e.g., references REF131 and REF132 of the list of references provided hereinbelow).

Standard of care techniques for brachytherapy and intraoperative radiotherapy (see, e.g., references REF133-REF135 of the list of references provided hereinbelow) may be modified to deliver internal UV EMR waveband photons (see, e.g., references REF136-REF143 of the list of references provided hereinbelow) to directly inactivate replicating and shedding virus that contribute to active infection, increasing viral load, and infectivity to others (see, e.g., reference REF144 of the list of references provided hereinbelow). The analogy of SARS-CoV-2 hotspots in ACE2-rich tissues to bacterial accumulation in abscesses enables an understanding of the clinical purpose of locoregional therapy. Similarly, there is some evidentiary support that the resection or Radiotherapy (locoregional therapy) of primary tumors in the setting of metastatic disease is associated with overall survival improvements (see, e.g., reference REF145 of the list of references provided hereinbelow). These findings suggest that locoregional EMR therapy of primary sites of infectious virion shedding could also lead to overall survival benefits in patients with systemic COVID-19 disease by reducing the viral load.

Extracorporeal photopheresis (ECP) may be a safe and effective therapeutic regimen to reduce systemic viral load in patients with SARS-CoV-2 infection (see, e.g., reference REF146 of the list of references provided hereinbelow). ECP is a leukapheresis-based therapy that is approved for the treatment of certain subtypes of cutaneous T-cell lymphoma, particularly the erythrodermic and leukemic variant Sézary syndrome for which it has received FDA approval in 1988 (see, e.g., reference REF147 of the list of references provided hereinbelow). Moreover, it is utilized in the context of Graft-versus-Host Disease, and in the context of rejection of solid organ transplantation, and hematopoietic stem cell transplantation (see, e.g., references REF148-REF150 of the list of references provided hereinbelow). During traditional ECP, patient whole blood may be collected, leukocytes may be separated (buffy coat) and then exposed to UV-A in the presence of the photosensitizer 8-methoxypsoralen (see, e.g., reference REF151 of the list of references provided hereinbelow). In the context of SARS-CoV-2-disinfection, UV-B and/or UV-C wavelengths (e.g., without a cellular photosensitizer) may be used on whole blood (e.g., as is) for efficiency; EMR may be incorporated into technologies for extracorporeal membrane oxygenation in order to have the additional effect of blood oxygenation to disinfection (see, e.g., reference REF152 of the list of references provided hereinbelow).

EMR can be modulated so that UV EMR is utilized for the purpose of anti-viral activityand IR EMR is optimized to cause irreparable DNA damage and cellular apoptosis of viral-induced inflammatory infiltrate in critical organs (i.e., the target of IR EMR is cellular DNA versus the viral genetic material target of UV EMR) (see, e.g., reference REF153 of the list of references provided hereinbelow). In the context of mitigating critical COVID-19 symptomatology, low-dose external beam IR to whole organs can be employed to induce apoptosis of inflammatory infiltrate thereby inhibiting the production of selected cytokines that produce irreparable tissue damage in the lungs and brain or other organs (see, e.g., references REF154-REF156 of the list of references provided hereinbelow). Mitigation of secondary viral reactivation may be an important point of safety when utilizing IR EMR (see, e.g., references REF091 and REF157-REF159 of the list of references provided hereinbelow).

Safety-tissue reactions and stochastic effects may be considered. While the antimicrobial potential of external and/or internal EMR has long been established, a concern remains because EMR can cause inflammatory reactions (e.g., sunburns, mucositis, etc.) and carcinogenesis. Tissue reactions may be defined as EMR damage that result in cell death and cell removal from a tissue or organ by the immune system (e.g., sunburn, herpetic reactivation, etc.) (see, e.g., reference REF091 of the list of references provided hereinbelow). The severity of tissue reactions may increase in direct correlation to exposure dose. Stochastic effects (e.g., cancer) may be the result of mutations in a cell's genetic material. The severity of stochastic effects may not be correlated with dose, but the probability of their occurrence increases with dose.

While tissue reactions and stochastic effects are a concern, particularly with the proposed implementation of internal UV EMR, it is important to note that larger doses per fraction and larger cumulative doses are already used clinically for benign conditions. Specifically, the calculated dose of 69 mJ/cm$^2$ UV-B required to cause a 1-log reduction of SARS-CoV-2 is 2 to 3 fold less than the doses currently used to treat benign conditions such as allergic rhinitis, gingivitis, periodontal infections, and oral graft-versus-host-disease (see, e.g., references REF136 and REF138-143 of the list of references provided hereinbelow). Further, mucosal doses of more than 200 mJ/cm$^2$ irradiation with 310 nm NB-UVB may be needed to induce apoptosis, and therefore, tissue reactions (see, e.g., reference REF160 of the list of references provided hereinbelow). These data support the likelihood of a therapeutic gain with the use of internal UV EMR in the context of a systemic viral infection.

Cancer induction is one of the most important somatic effects and risks of EMR exposure, and has limited its widespread use in public settings. This is clinically evident with the increased skin cancer incidence in people with excessive sun or IR exposure of the skin (see, e.g., references REF161-165 of the list of references provided hereinbelow).

Further, chronic inflammation resulting from longstanding environmental exposures (e.g., UV, background radiation), alone or in synergy, has also been associated with the development of cancer (see, e.g., reference REF166 of the list of references provided hereinbelow). Additive stochastic effects can occur with EMR exposure of tissues infected with carcinogenic viruses (e.g., human papillomavirus) (see, e.g., references REF131, REF167, and REF168 of the list of references provided hereinbelow). EMR-induced cellular damage that does not result in apoptosis or interphase death, can cause major mutagenic changes in the nucleotide sequence of the cellular genome (e.g., versus the viral genome), which, if unrepaired before DNA synthesis and/or cell division, may lead to permanent defects in the cell's genome. These defects, when transcribed and translated, can lead to the development of cancer and other stochastic effects.

The relative risk model defining how radiation-induced cancers are expressed, assumes that radiation causes a multiplicative increase in the natural cancer incidence, meaning that most of the radiation-induced cancers will manifest in the same time window as spontaneous ones, that is, in older age. As an environmental carcinogen, the stochastic events (e.g., as opposed to cancers related to genetic susceptibility) are expected to occur around the same time that spontaneous cancers are expected to appear (e.g., one would expect adults to express the UVR-induced cancers starting at ages of 50-70 years). The relative risk model, adopted from solid-tumor data for ionizing radiations, can be extrapolated and applied to longer EMR wavelengths of lower energy (e.g., UV waveband) in order to understand the risk of carcinogenesis. It is important to note that UV is more mutagenic than IR because there is a larger fraction of surviving mutated cells upon exposure (see, e.g., references REF161-REF165 of the list of references provided hereinbelow). However, doses of UV EMR that are below the threshold required for apoptosis (e.g., within the shoulder region of the cellular survival curve) may be less carcinogenic due to inherent and efficient cellular repair mechanisms (i.e., within the shoulder region, the cells repair mechanisms are not overwhelmed and are capable of repairing any cellular UV damage). Nevertheless, the risk of stochastic effects may remain. Enhancing the early detection (e.g., theragnostic PET/CT imaging (see, e.g., reference REF085 of the list of references provided hereinbelow)) and treatment of secondary malignancies may reduce their severity.

The science behind UV inactivation of viruses, bacteria, and fungi is well established. However, for clinical implementation, a dedicated medical specialty to the use of EMR in the above described context should be developed. The therapy platform may be configured such that the field of Biodefense commence as a certificate program for internationally licensed physicians (e.g., in parallel to the beginnings of therapeutic radiology) with scalability to create a residency training program dedicated to Biodefensive medicine.

To date, the number of structured clinical trials that have evaluated the utility of antimicrobial EMR is low and the protocols used by different groups are heterogeneous. Further, there is a dearth of published literature on radiotherapy "dose" in the context of UV and soft X ray energies. While intracavitary LED-mediated UV EMR may be possible with available endoscopic devices or thoracentesis procedures, the following problems need to be resolved before widespread clinical implementation: (1) dosimetry, (2) efficacy, (3) toxicity, and (4) therapeutic gain. The therapy platform investigates and is configured to determine effective or optimal therapeutic waveband(s), dose rate, percent depth dose, EMR intensity/exposure time per fraction, number of fractions, tissue/fluid volume to be treated, cumulative dose required to achieve the maximal therapeutic effect (e.g., SARS-CoV-2 inactivation), minimal toxicities (e.g., mucositis, secondary cancers), and/or methods for defining dose itself for low energy EMR.

Ultimately, the development of tissue reactions and stochastic effects may be related to which wavelengths are used, the photon energy, the dose rate, the exposure time, and/or the cumulative dose delivered. These features may be taken into account in the risk-benefit analyses associated to standard of care IR EMR treatment planning. Therefore, UV EMR treatment planning may be optimized to the standards utilized for IR EMR treatment planning before implementing widespread non-investigational clinical use.

UVC may be best used for irradiation of air and surfaces, while narrow band UVB (e.g., 310 nm) may be used internally in a way that mimics brachytherapy with ionizing radioactive isotopes. In other words, instead of iodine-125, lutetium-177, yittrium-90, or iridium-192, the therapy platform may use an LED or other bulb or emitter operative to emit UVB at a particular wavelength and/or waveband with a defined output and exposure time to deliver a calculated therapeutic dose to target tissue (e.g., SARS-CoV-2 rich tissue). Other wavelengths in the infrared band could be added to minimize tissue fibrosis (e.g., via downregulating "TGF-B") that may be caused by the massive virus induced inflammatory reaction (e.g., like in the lung that may actually be what is killing people). Reducing the viral load with UVB would lower that burden of end tissue damage caused by COVID-19.

In some embodiments, the therapy platform does not need to reach sterilization levels, as it may just need to achieve a meaningful viral reduction. It has been calculated that a 69 mj/cm$^2$ absorbed dose may be sufficient for a 1 log reduction (90%). That dose can be doubled and still be mostly within the shoulder of the cell survival curve. While a drug may be provided that inhibits viral replication, such a drug may do nothing to reduce the viral load that is already in the tissues. With provided data on percent transmission to the center of a cell and center of tissue (e.g., 100 um), montecarlo simulator, and methods for linear accelerator MU calculations, the percent depth dose ("PDD") of UVB in tissues may be calculated, for example, as may be provided by the table 300 shown in FIG. 3. When the PDD can be estimated by the therapy platform, then the therapy platform may be configured to determine what output may be needed (e.g., within a certain confidence) to ensure that the target tissue receives the required or calculated therapeutic dose and/or to ensure that surrounding tissues do not receive toxic doses. There is some wiggle room to be able to double the prescription dose so that some part of the target tissue could safely see a 2 (or greater) log reduction dose.

There may not be too much toxicity, as long as the therapy platform does not operate to come off the shoulder of the cell survival curve for nbUVB and allows ample time (e.g., 2-6 hours) for cell repair in between fractions. nbUVB has significant clinical data for irradiation of oral and nasal mucosa and skin for doses much higher than 69 mj/cm$^2$ because, in current clinical uses, the target is inflammatory infiltrate (i.e., cell death versus virus inactivation), which requires a much higher UVB dose than would be required to inactivate viruses. Further, UVB absorption may be more nucleic acids and less proteins as compared to UVC. As mentioned, isodose lines can be calculated for UV therapy by applying UV specifications (e.g., percent depth dose characterizations, UV photon movement characteristics, etc.) into a mathematical algorithm (e.g., montecarlo simulation) (see, e.g., reference REF296 of the list of references provided hereinbelow). Evaluating the light penetration characteristics into skin or tissue using the Monte Carlo algorithm is possible (see, e.g., reference REF296 of the list of references provided hereinbelow). The montecarlo simulator may be used to determine the dose differences based on tissue heterogeneity (see, e.g., reference REF300 of the list of references provided hereinbelow). Therefore, dose differences may be determined with available mathematical algorithms for photons of any waveband on the electromagnetic spectrum.

One exemplary GVLR regimen that may be implemented by the therapy platform may include the following operations. A first operation may include identifying a threat or diagnosing a disease. A second operation may include determining a Modis Operendis of the identified threat or determining a patho-physiology or mechanism of the identified disease. A third operation may include identifying the individual(s) best suited to lead defense efforts (e.g., military, physicians, attorneys, scientists, etc.). A fourth operation may include identifying a power source (e.g., the sun, any suitable emitters, etc.) and collecting supplies (e.g., medications, etc.). A fifth operation may include debilitating the threat or disease (e.g., by addressing and/or blunting the symptoms that weaken the host). A sixth operation may include dividing the threat into macro- and micro-components or decreasing the overall burden of the disease. A seventh operation may include intoxicating or attacking to induce lethal injury or sublethal injury to the invasive entity (not to the host). An eighth operation may include blocking the threat's survival mechanisms including ability to repopulate and/or depriving the threat from supplies needed to recover from sublethal injury. A ninth operation may include repeating one or more of the fourth through eight operations until the threat is contained. A tenth operation may include annexing, territorializing, and/or destroying the threat or living with, sterilizing, or eradicating the disease. An eleventh operation may include surveilling for recurrence(s). A twelfth operation may include implementing preventive or security measures.

Figure 2:
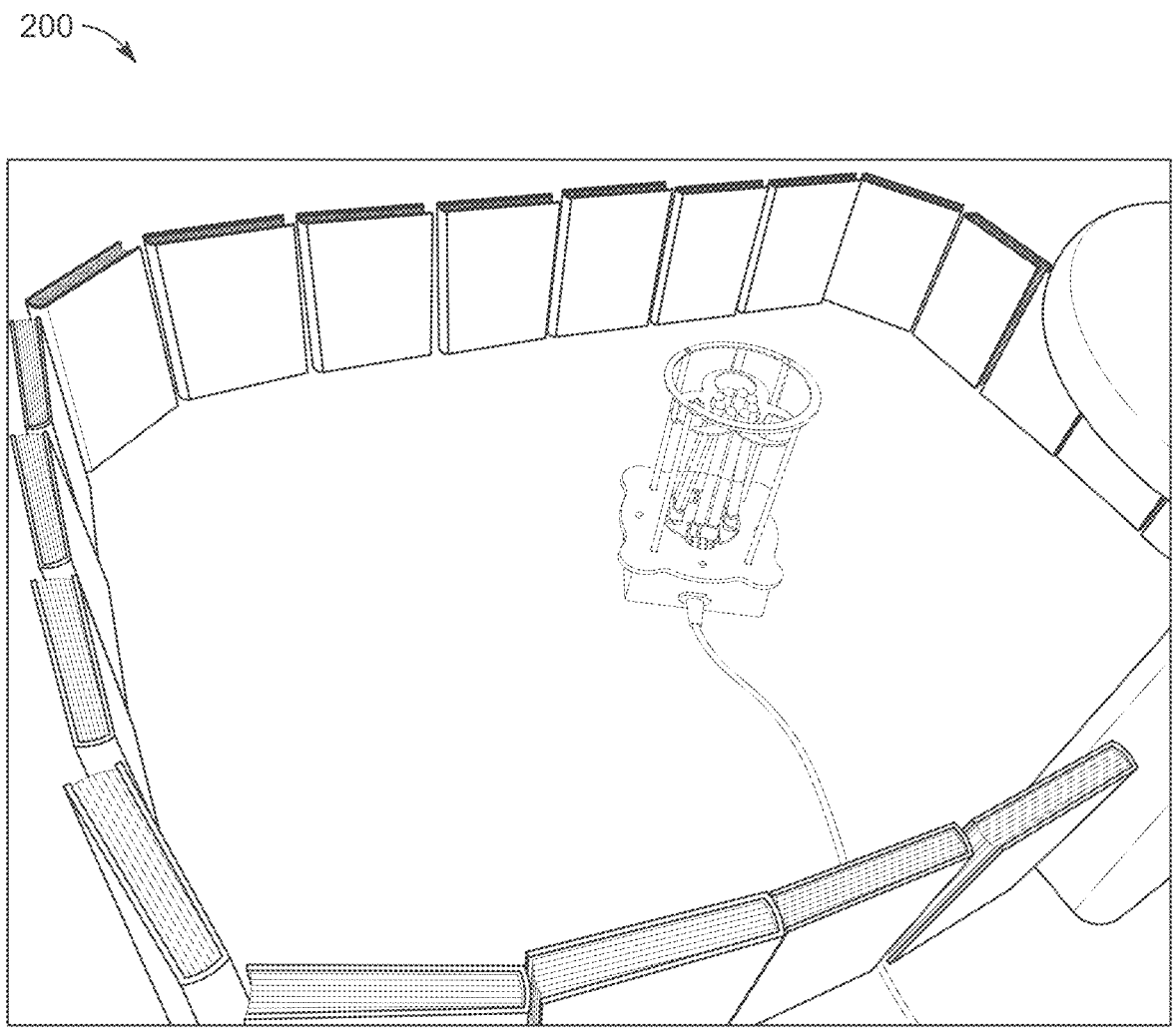
FIG. 2 is a schematic view of an illustrative system.

One particular example of a system that may be used for implementing a load reduction process may be shown by system 200 of FIG. 2, where, for example, mycotic (e.g., fungal) load reduction of an encyclopedia Britannica set as a target may be carried out by the system that includes a UV lamp positioned in the middle of an arrangement of the target and provide outward radial emission of the prescribed energy to the target treatment area (e.g., book surfaces).

A cost effective and sustainable home and/or commercial clean water solution is provided. This may include the creation of a water farm.

Figure 4:
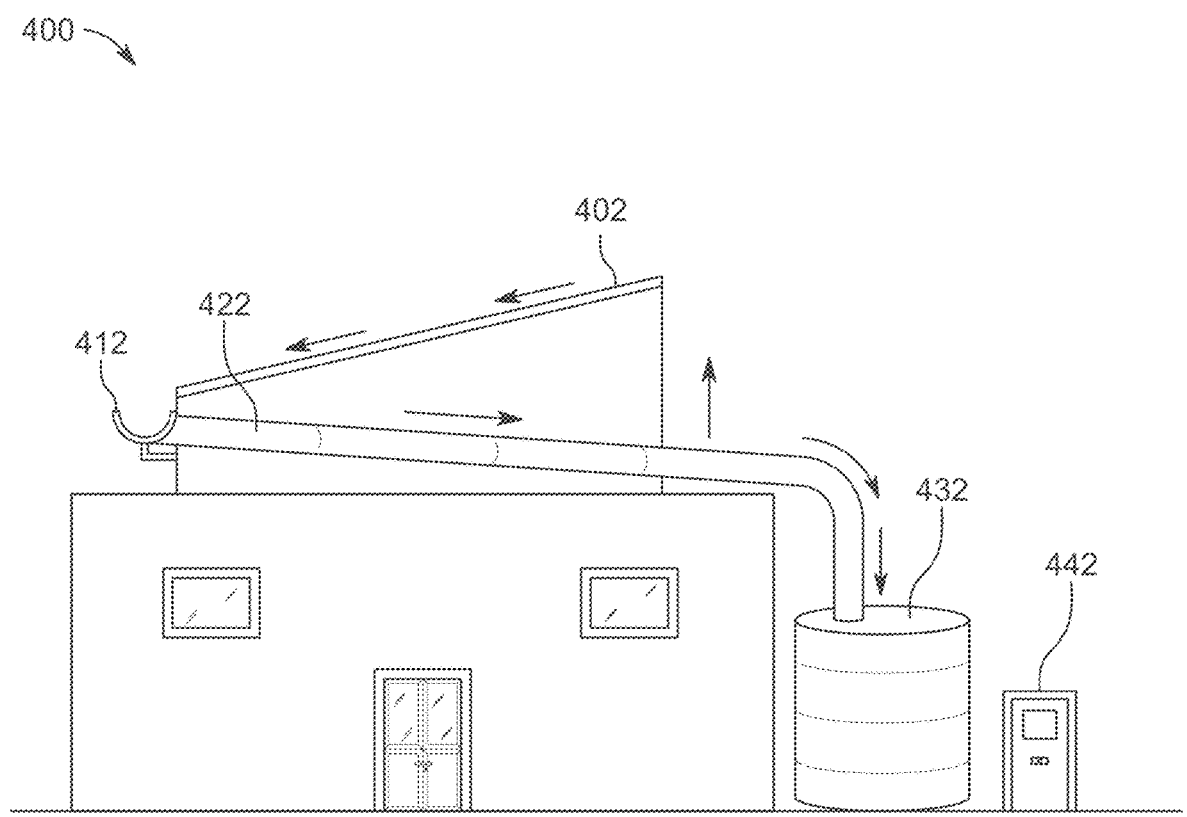
FIG. 4 is a diagram of a system for collecting rainwater.
Figure 5:
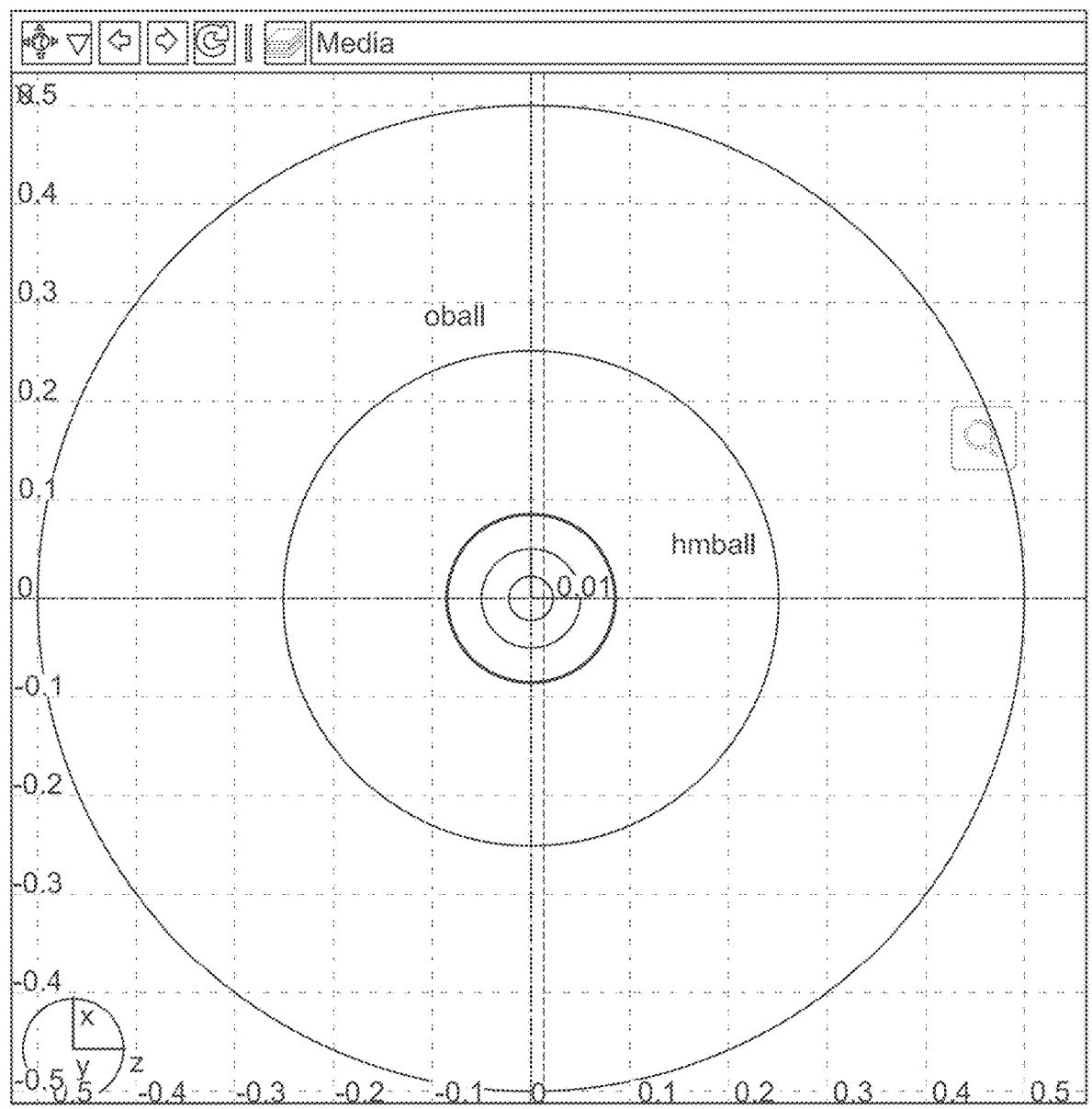
FIG. 5 is a graph of geometry for simulation.

As shown by FIG. 4, a structure 400 (e.g., a home or commercial building, etc.) may include a slanted roof 402 (e.g., with or without solar panels) at or near a bottom of which may be provided a water collector 412 that may collect water (e.g., rainwater) that flows down slanted roof 402. An aqueduct 422, which may be made of quartz glass or any other suitable UV transparent material, may extend from collector 412 to a tank 432, which may be provided with a filter and/or pump and/or UV (e.g., UV-C) irradiator 442. As rainwater falls on roof 402, gravity causes water to drain from roof 402 into collector 412, and gravity causes water from collector 412 to travel down aqueduct 422, which may be covered with material that allows UV penetration and sterilization of water. Water flow rate may be modulated so as to maximize solar disinfection prior to being stored in tank 432, which may contain filters, and/or pumps, and/or UV-C irradiator 442 for further sterilization of rainwater for household and/or commercial consumption. Solar panels and gravity may power this solar disinfection system. This system or system series can exist above a man-made structure or above vegetation.

Additional disinfection applications that could be incorporated may include, but are not limited to, osmotic filter, ion exchange, UV-C lamp, carbon filter, HEPA filter, and/or the like. Procedures may be adjusted according to the type of contaminants present in the original water source (e.g., rainwater, river water, pond/lake water, glacier water, etc.).

FOLH1 targeted agents may be used to revive boron neutron capture therapy ("BNCT"). BNCT is a noninvasive tumoricidal (e.g., killing of tumor cells) technique that has been historically underutilized. In other words, BNCT has been underutilized because prior targets used to deliver Boron-10 ($^{10}$B) have had a poor therapeutic ratio because binding to the tumor has not been sufficiently specific. As a result, although promising results may be demonstrated in the treatment of primary aggressive brain tumors and malignant melanoma ("MM"), many programs with neutron accelerators have closed down due to the failure to identify optimal and/or safe and/or non-invasive methods with which to deliver $^{10}$B, specifically to tumor sites (e.g., $^{10}$B was being absorbed by non-target tissue). BNCT may be initiated when $^{10}$B nuclei adsorb thermal neutrons. The resultant nuclear fission may create helium-4 ($^4$He), an alpha ("α") emitter, and high-energy lithium-7 ($^7$Li) nuclei, capable of high local linear energy transfer in a ~5-9 μm radius. Therefore, the therapy platform may be configured to deliver $^{10}$B to cellular targets by binding to folate hydrolase-1 (FOLH1; also known as prostate-specific membrane antigen ("PSMA")) followed by endocytosis. This will result in specific alpha particle radiation of target tissue.

The theragnostic agent J591 has demonstrated excellent tumor specificity in both primary and metastatic prostate cancer and most solid tumor neovessels via targeting of membrane-expressed folate hydrolase-1 (FOLH1; prostate-specific membrane antigen ("PSMA")) (see, e.g., references REF171-REF182 of the list of references provided hereinbelow). J591 conjugates may be administered intravenously, specifically bind to FOLH1, and undergo antigenic modulation upon binding with subsequent cell entry (see, e.g., references REF183 and REF184 of the list of references provided hereinbelow). Thereby, J591 may provide a platform for potential effective $^{10}$B delivery within FOLH1-expressing cells (e.g., neoendothelium of solid tumors). In vitro targeting of FOLH1, by conjugating auristatin (e.g., alpha-emitter) to J591, increased the therapeutic index of auristatin by 700-fold and improved the median survival by 9-fold in prostate cancer xenografts (see, e.g., reference REF185 of the list of references provided hereinbelow).

J591 may be produced from NSO cells by Lonza Biologics (Slough, UK). The molecular weight of J591 is approximately 147,000 daltons as determined by Matrix Assisted Laser Desorption Mass Spectrometry (MALDI-TOF). J591 has been effectively conjugated to chelator, 1,4,7,10-Tetraazacyclododecane-1,4,7,10-tetraacetic acid (DOTA), with a maximum of 2-5 DOTA per J591 molecule to retain FOLH1 binding immunoreactivity of 80% (Immunomedics, Inc.). Lutitium-177 ($^{177}$Lu) has been strongly attached to DOTA-J591 by the Weill Cornell Radiochemistry Laboratories, resulting in improved in vivo stability and greater tumor uptake of the radionuclide metal atoms.

The conjugation of $^{10}$B to J591 may increase the therapeutic index of BNCT by increased $^{10}$B localization and specificity to sites of disease. Targeting of $^{10}$B to FOLH1 expressing tumor associated cells or tumor cells via J591 has the potential to provide excellent spatial and temporal resolution of cell kill by BNCT, and there is the potential for a greater therapeutic gain compared to standard external beam radiotherapy. Conjugation of $^{10}$B to an agent or embodiment (e.g., FOLH1-targeting monoclonal antibodies, small molecules, and antibody fragments) with FOLH1 binding capacity may increase the therapeutic index of BNCT by increasing $^{10}$B localization and specificity to tumor sites. Specific delivery of $^{10}$B to FOLH1 expressing tumor associated cells or tumor cells via monoclonal antibodies, small molecules, and antibody fragments can provide excellent spatial and temporal resolution of cell kill by BNCT. Thus, there is the potential for a greater therapeutic gain compared to standardly available ionizing radiotherapy modalities.

A goal is the synthesis of a stable $^{10}$B-DOTA-Albumin construct. First, the feasibility of $^{10}$B coupling to J591 or other FOLH1 targeting agent will be evaluated by creating a $^{10}$B-J591 (or other agent) construct. Methods will be adapted from established procedures (see, e.g., references REF186-REF188 of the list of references provided hereinbelow). Conjugation will be confirmed by mass spectroscopy.

Another goal is to demonstrate internalization of $^{10}$B-J591 in LNCaP cells. $^{10}$B-DOTA-J591 will be incubated with LNCaP cells at 4 C. The temperature can be elevated to 37 C for three hours to allow for maximal conjugate internalization. LNCaP cells in permeabilized and unpermeabilized conditions may be incubated with Alexa Fluor 488 goat anti-mouse IgG (Invitrogen). Internalization may be evaluated by immunofluorescence (e.g., as done in Merkel cell carcinoma tissue).

Any suitable process may be utilized for Boron neutron capture therapy ("BNCT") targeting FOLH1 (e.g., PSMA). For example, the process may provide a method for adaptively treating a volume of cells (e.g., tumor) with electromagnetic irradiation. One operation of the process may include conjugation of a chemical nuclei (e.g., $^{10}$B) or molecule to an agent or embodiment (e.g., monoclonal antibodies, small molecules and antibody fragments, etc.) with FOLH1 binding capacity (e.g., as may be carried out in a lab using well known equipment). Another operation of the process may include administration of the nuclei-agent construct into a body of cells (e.g., as may be administered intravenously in a patient or poured onto skin or any other target of the patient (e.g., portion of stomach during surgery)). Another operation of the process may include exposing a volume of cells to the nuclei-agent construct (e.g., as a result of the administration operation). Another operation of the process may include waiting for a period of time after the administration/exposing (e.g., in order to allow binding and/or internalization to occur). Another operation of the process may include exposing the volume of cells to electromagnetic irradiation (e.g., photons, particles, neutrons (e.g., thermal neutrons), etc.) to result in modification of the chemical nuclei (e.g., $^{10}$B) or molecule within the volume of cells. For example, the volume of cells could be tissue or tumor. For example, the cells can be animal or plant. For example, the chemical or molecule may be anything from a single element to a drug. For example, the agent or embodiment may be anything that can bind to both the chemical or molecule and FOLH1. For example, the waiting period may be 40 minutes to 7 days for binding and internalization. A process may also provide a method of increasing the therapeutic ratio of BNCT by conjugation of $^{10}$B to an agent or embodiment (e.g., FOLH1-targeting monoclonal antibodies, small molecules and antibody fragments, etc.) with FOLH1 binding capacity. The invented agent or embodiment will increase the therapeutic index of BNCT by increasing $^{10}$B specific, localization to tumor sites. A process may also provide a method to specifically deliver $^{10}$B to FOLH1 expressing tumor associated cells or tumor cells via monoclonal antibodies, small molecules and antibody fragments to provide optimal spatial and temporal resolution of cell kill by BNCT. Such methods may result in greater therapeutic gain compared to standard ionizing radiotherapy modalities (e.g., linear accelerators, particle accelerators, brachytherapy, etc.). A process may also provide a method for exposure of FOLH1-expressing cells to an agent or embodiment (e.g., FOLH1-targeting monoclonal antibodies, small molecules and antibody fragments, etc.) with dual capacity for $^{10}$B and FOLH1 binding to specifically deliver $^{10}$B constructs inside of tumor cells and/or cells within a tumor.

Microdosimetry for antibody-based or small molecule-based brachytherapy may be provided by the therapy platform (see, e.g., reference REF289 of the list of references provided hereinbelow). Development of treatment planning software that includes absorbed dose calculations for antibody-based or small molecule-based brachytherapy may require quantification or semi-quantification of the target molecule per tumor volume (e.g., tumor cell FOLH1) or unit length of blood vessel (e.g., neovessel FOLH1).

Radiation treatment planning for antibody-based brachytherapy may be provided by the therapy platform using reflectance confocal microscopy ("RCM") 2D and/or 3D images and histological 2D and/or 3D images with the MonteCarlo Algorithm.

A target and delivery mechanism may be provided by the therapy platform. Folate hydrolase-1 (FOLH1; also known as prostate-specific membrane antigen) is a trans-membrane cell surface receptor, which may be expressed on the luminal surface of the endothelial cells lining the neovasculature of most solid tumors (see, e.g., reference REF001 of the list of references provided hereinbelow). J591 is a monoclonal antibody ("mAB") that may be specific to the extracellular domain of FOLH1. Upon J591 binding to FOLH1, the cell may be triggered to endocytose the FOLH1 protein, J591, and anything that may be conjugated to J591 (e.g., radioisotopes, cytotoxic agents, nanospheres, etc.). One of the linkers used to conjugate radioisotopes to J591 may be DOTA. Approximately 5 DOTA molecules may be conjugated to each J591 mAB and each DOTA molecule can carry a single radioisotope (e.g., 5 radioactive atoms per J591 mAB). Upon cell surface binding, the FOLH1-J591 complex may be then translocated to lysosomes and degraded. In the case of radioisotopes, the radioisotope may be then trapped within the cell until it completes its radioactive decay. Of note, small peptides and antibody fragments can be similarly used as a vehicle to deliver radioisotopes to solid tumor neovessels. For simplicity, various ones of these methods may focus on J591 as the delivery method.

Neovasculature imaging with reflectance confocal microscopy ("RCM") may be provided by the therapy platform. In vivo reflectance confocal microscopy may allow for intraoperative imaging of solid tumors or the direct visualization of skin tumors at a quasi-histopathologic resolution. The quasi-histopathologic resolution may permit visualization of most histological manifestations, such as epidermal architecture, cell size, shape, and microvasculature. The unique ability to measure reflectance also provides RCM with a pseudo FDG-PET scan quality for imaging metabolically active cells (e.g., immune and neoplastic cells) that may have an inherently high interface refraction.

A confocal microscope of the therapy platform may utilize a laser as its source of monochromatic and coherent light to focus on a microscopic target. The path of light may travel along optically conjugated focal planes: the point source of light; the illuminated tissue segment; and a pinhole-sized aperture of the spatial filter. A near-infrared reflectance microscope (e.g., Vivascope 1500, Lucid Inc, Rochester, N.Y.) of the platform may be equipped with a diode laser with peak emission at 830 nm and a maximum power of 25 mW. Each microscope image may have an effective 500×500-μm field of view and a spatial resolution in the lateral dimension of 0.5-1.0 μm (e.g., permits imaging of cells, nuclei, microvasculature and on occasion, subcellular structures such as nucleoli). The imaging depth may be 200 to 300 μm.

When the light beam is scanned horizontally in two orthogonal directions (y and x axis) parallel to the plane of focus, a series of vertically (z axis), stacked en-face sections of the tissue may be acquired. The resolution of these virtual sections on the z axis may be 2 to 5 μm and therefore their thickness may correlate closely with the axial thickness of standard histologic sections. The captured optical signals may be processed by the detector interface software, to reconstruct a thin horizontal microscopic image that can be displayed on a screen and/or be recorded in real-time. The final image may be displayed on and/or by a display component of the platform (e.g., a screen with a resolution of 1000×1000 pixels and 255 shades of gray) and can be stored in a database or transferred telemetrically to facilitate a personalized brachytherapy radiation treatment planning process.

Histopathological mapping of neovessels may be provided by the therapy platform. Total neovessel unit length within different tumor volume ranges can be measured directly and histopathologically. FOLH1 expression can be quantified by flow cytometry and/or artificial intelligence. Once the target in the tissue volume is quantified as an actual number, then that number may be utilized in an algorithm to determine a most accurate dose. Otherwise, semi-quantified measurements may be used as may be done in cancer staging and diagnosis. Quantified FOLH1 expression can be compared to semi-quantitative parameters by immunohistochemistry ("IHC") (e.g., +1, +2, +3, +4).

Target density on neovessels within a given tumor volume may be provided by the therapy platform. LNCaP (e.g., prostate cancer) cells are approximately 18 μm in spherical diameter (see, e.g., reference REF301 of the list of references provided hereinbelow). There are approximately 1,000,000 FOLH1 proteins on the surface of LNCaP cells; 1,000,000 FOLH1 proteins correspond to +4 immunohistochemistry (IHC) staining intensity (i.e., maximal or 100% FOLH1 expression). Solving for the surface area of a sphere, the surface area of a LNCaP cell may be 1,017.88 μm². The density of FOLH1 molecule/μm² on a LNCaP cell may be 982.43 FOLH1/μm². For simplicity, the density of FOLH1 molecule/μm² on a LNCaP cell (e.g., a gold standard for FOLH1 expression) may be defined as 982.43 FOLH1/μm².

The blood vessel could be thought of as analogous to a brachytherapy catheter. The tumor between the blood vessels may be treated by the therapy platform. Therefore, the spacing between blood vessels could be thought of as the spacing between catheters. To calculate the dose to the tumor, the therapy platform may be configured to calculate the dose being emitted by the blood vessels, which may be directly related to the FOLH1 expression density (e.g., quantity of targets available for radioisotope delivery via antibody or small molecule). To determine the total FOLH1 luminal binding capacity within a given non-prostate solid tumor volume, the binding density per the total unit length of a neovessel may be measured (e.g., in μm), multiplied by the defined FOLH1 expression density, and then squared.

The density of FOLH1 molecule/μm² on a LNCaP cell (+4 staining intensity) may be calculated as 982 FOLH1/μm². If it is assumed that FOLH1 IHC semi-quantitative staining intensity follows a linear scale with FOLH1 expression density, then the following may be approximated: +4 (100% expression)=982 FOLH1/μm²; +3 (75% expression)=737 FOLH1/μm²; +2 (50% expression)=491 FOLH1/μm², and +1 (25% expression)=246 FOLH1/μm². The neoendothelium in non-prostatic solid tumors generally has a +1, +2, +3 IHC staining intensity (see, e.g., reference REF289 of the list of references provided hereinbelow).

To determine the FOLH1 bound radioisotope density per unit length of the neovessel, the platform may be configured to calculate the internal surface area of the length of a cylinder (e.g., excluding the ends; A=2πrl). If it is assumed that the diameter of Merkel cell carcinoma neovessels varies from ~2.8 (small) to 5.5 (medium) to 8.3 (large)μm (see, e.g., reference REF289 of the list of references provided hereinbelow), that the length to be considered for calculation is 100 μm, and that the formula can be applied for the surface area (A) of a cylinder to calculate the luminal surface area of a neovessel, then the platform can calculate the estimated available FOLH1 targets for antibody or small molecule binding.

Solving for the surface area of a cylinder, the surface areas of the luminal surface area per 10 μm of small, medium and large neovessels may be A=(2)(3.14)(1.4 μm)(10 μm)=87.92 μm², A=(2)(3.14)(2.75 μm)(10 μm)=172.7 μm², and A=(2)(3.14)(4.15 μm)(10 μm)=260.6 μm², respectively. Utilizing both the known density of FOLH1 molecule/μm² on LNCaP cells and the luminal surface area of a neovessel, the platform may be configured to solve for the following FOLH1 densities on a linear scale based on IHC staining intensity per every 10 μm length of small vessels: (88)(982)=86,416 FOLH1 molecules (+4; 100% expression), (88)(737)=64,856 FOLH1 molecules (+3; 75% expression);

(88)(491)=43,208 FOLH1 molecules (+2; 50% expression), and (88)(246)=21,648 FOLH1 molecules (+1; 25% expression). The total number of FOLH1 molecules within a given tumor volume can be calculated: (1) Measure total neovessel length in tumor (in μm), (2) Divide total length by 10 μm, and (3) multiply that value by the approximate number of FOLH1 molecules based on the IHC staining intensity. For example: A tumor with +3 staining neovessels of 30,000 μm in total unit length may be divided by 10 μm and multiplied 64,856 FOLH1 molecules (i.e., # of FOLH1/10 μm length of +3 staining neovessel) has a total of 194,568,000 FOLH1 molecules.

As stated above, approximately 5 DOTA molecules may be conjugated to each J591 mAB and each DOTA molecule can carry a single radioisotope (i.e., 5 radioactive atoms per J591 mAB). Generally, small molecules carry fewer radioisotopes and one would expect a lower deliver of radioisotope atoms if a small molecule is used. Therefore, once the total number of FOLH1 targets within a given tumor volume is calculated, it can then be assumed that with 100% J591 binding, 5-fold more radioisotopes will enter the endothelial cell (i.e., 5 $^{177}$Lu atoms/J591) as compared to the number of FOLH1 targets (e.g., +3 IHC staining intensity indicates that there are 194,568,000 FOLH1/μm of neovessel length, meaning that 2,501,326.8 J591 antibodies×5 $^{177}$Lu atoms/J591 will deliver 972,840,000 $^{177}$Lu atoms to the tumor). Greater electron track visualization can be made by viewing every 10 μm of a neovessel as a "dwell point" (e.g., such as that used in high dose rate brachytherapy methods) to simulate the dose distribution of electrons emitted from that dwell point based on the number of FOLH1 molecules and the specific activity of the radioisotope delivered to the FOLH1 molecules.

For prostate cancer cells, total number of FOLH1 molecules in a tumor is a function of cell size and IHC staining intensity.

Source of ionizing radiation may be considered by the platform. 177-Lutetium may be the most commonly used radioconjugate in J591-brachytherapy clinical trials, however a variety of different isotopes can be conjugated to J591 (e.g., for simplicity, the remainder of these methods will be based on the use of $^{177}$Lu) (see, e.g., references REF004, REF290, and REF291 of the list of references provided hereinbelow). $^{177}$Lu emits β particles (0.497 MeV; t½=6.74 days). There are four groups of β emissions; the dominating group is 0.497 MeV, contributing about 90% of relative intensity. Accounting for all β particles, Auger and conversion electrons, the mean energy of the emitted electrons is 0.147 MeV. Low energy electrons are the signature advantage of $^{177}$Lu, with maximum range of about 2.2 mm and mean range about 0.67 mm in water (i.e., tumor equivalent). Note that other radioisotopes can be used and/or pharmaceutical agents and/or gene modifying agents (e.g., CRISPR Cas-9).

Microdosimetry for brachytherapy based on tumor neovasculature may be provided by the platform. Based on the known radioactive properties of $^{177}$Lu atoms, a Monte Carlo simulation with FLUKA may be performed by the platform to calculate the tracks of emitted electrons (or photons, protons or neutrons) in water media to demonstrate the penetration characteristics of $^{177}$Lu electrons (or other source). The full β particles spectrum may be used for simulation. A full radiation dose computation can be achieved by incorporating the calculated number of $^{177}$Lu atoms for a particular total unit length of neoendothelium within a given volume of tissue into Monte Carlo simulation.

Optimal mCi/infusion and timing of infusions may be controlled by the platform. Dose per fraction, fractionation scheme can be determined via standard radiotherapy inverse treatment planning methods such that therapeutic levels of ionizing radiation may be delivered to and absorbed by the target volume with an acceptable toxicity profile.

Conventional treatment with external beam radiotherapy of widely metastatic disease is limited by the normal tissue tolerance of tissues surrounding tumor deposits within the treatment field. Brachytherapy of tumor neovasculature may be the only current form of radiation therapy that can effectively deliver ionizing radiation to disseminated metastatic disease (see, e.g., references REF140 and REF289 of the list of references provided hereinbelow).

$^{177}$Lu-J591 may provide a highly localized dose distribution, enabling local tumor and micrometastatic disease irradiation, while limiting irradiation beyond the tumor boundaries. Combining the physical and biological half-lives and the 3D density distribution of $^{177}$Lu, volumetric dose distribution obtained through the Monte Carlo simulation can calculate deposited dose and serve to guide administration of $^{17}$Lu-J591 to achieve therapeutic radiation doses at sites of disseminated disease.

Figure 6:
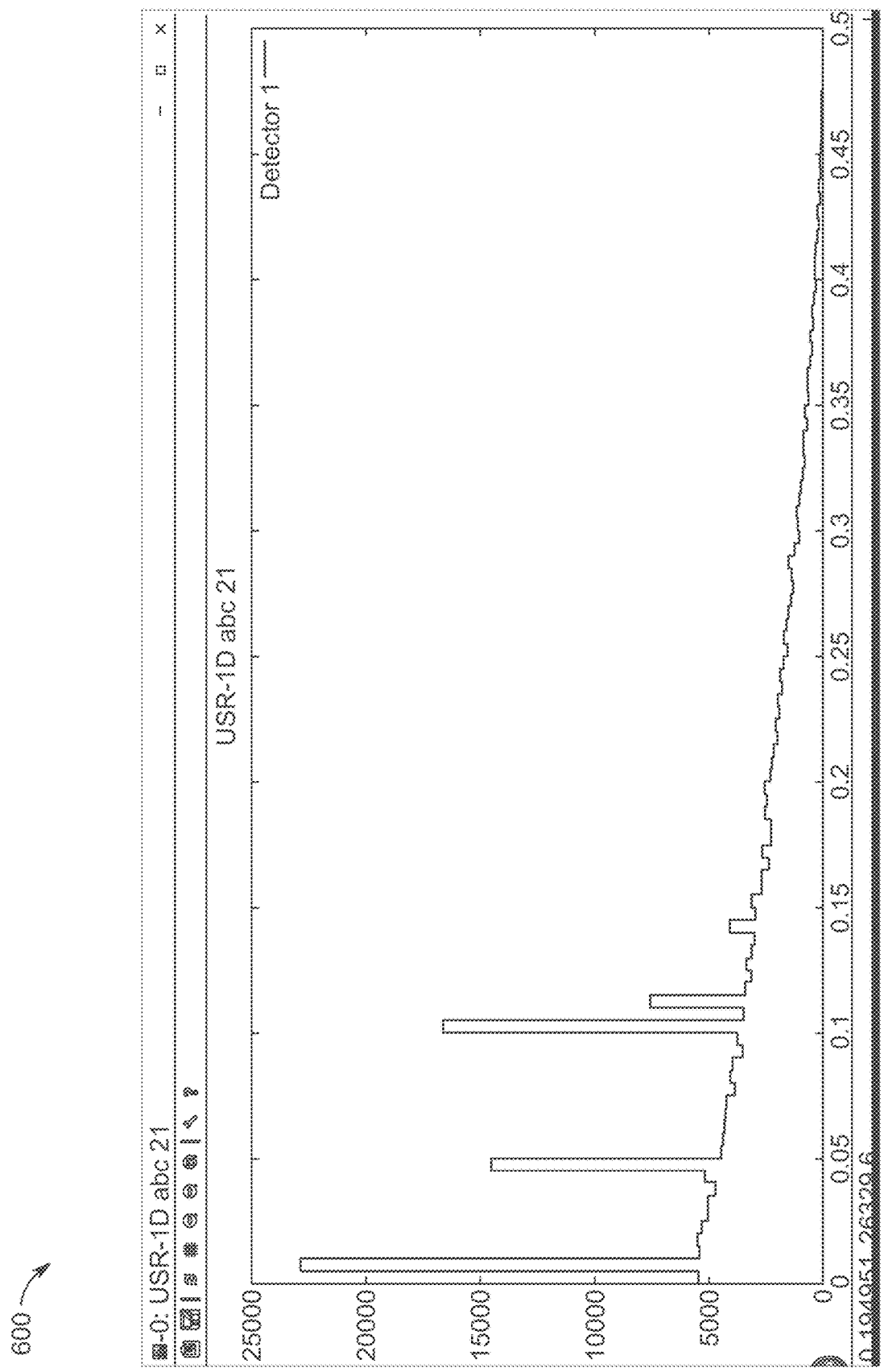
FIG. 6 is a graph of energy spectrum used in simulation.

Example preliminary simulation performed by Drs. Wu and Sheng: Monte Carlo simulation tool, FLUKA version: 2011-2X.6 was used to simulate the dose deposition of electrons emitted from $^{177}$Lu in water based on Reflectance Confocal Microscope viva-stack 3D images (see, e.g., reference REF289 of the list of references provided hereinbelow). Geometry for simulation is shown by graph 500 in FIG. 5. FIG. 6 shows graph 600 of energy spectrum of β ray emitted from $^{177}$Lu and has been used in this simulation.

For the simulation of absorbed dose and dose distribution, a semi-analogue mode may be used in FLUKA. Each single radioactive nucleus may be treated according to Monte Carlo simulation protocol in time-independent fashion: random decay time, random daughters, and random radiation. Media for particle transport in this simulation may be liquid water.

2D dose distribution in different layers may be provided by the platform. FIGS. 8A-8F show graphs 800A-800F of dose distribution averaged in each voxel (x=5 um, y=5 um, z=4.5 um) in respective layers 17, 20, 30, 40, 50, 52 (e.g., based on Viva-stack images). The estimation of Lu$^{177}$ atom distribution may be based on the following assumptions: (a) the endothelial cell dimension is 17 μm long and 1.5 μm thick; (b) the cross-section of micro neo-vasculature has an average diameter of 10 μm and has 20 circumferential endothelial cells; (c) each endothelial cell has 200,000 FOLH1 molecules that are targeted by J591 antibodies; (d) each J591 molecule is conjugated by 5 Lu177 atoms; I linear density of Lu177 atoms along neo-vessel can be approximated to: 111,170.09 FOLH1/μm$^2$ (+4; 100% expression), 83,377.56 FOLH1/μm$^2$ (+3; 75% expression), 55,585.04 FOLH1/μm$^2$ (+2; 50% expression), and 27,792.52 FOLH1/μm$^2$ (+1; 25% expression).

Figure 7A:
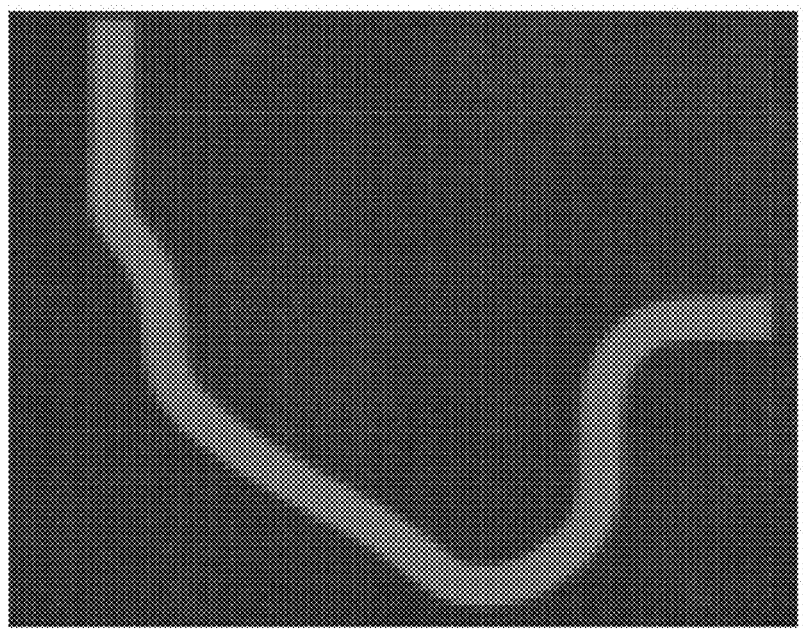
FIG. 7A shows a contoured blood vessel.
Figure 7B:
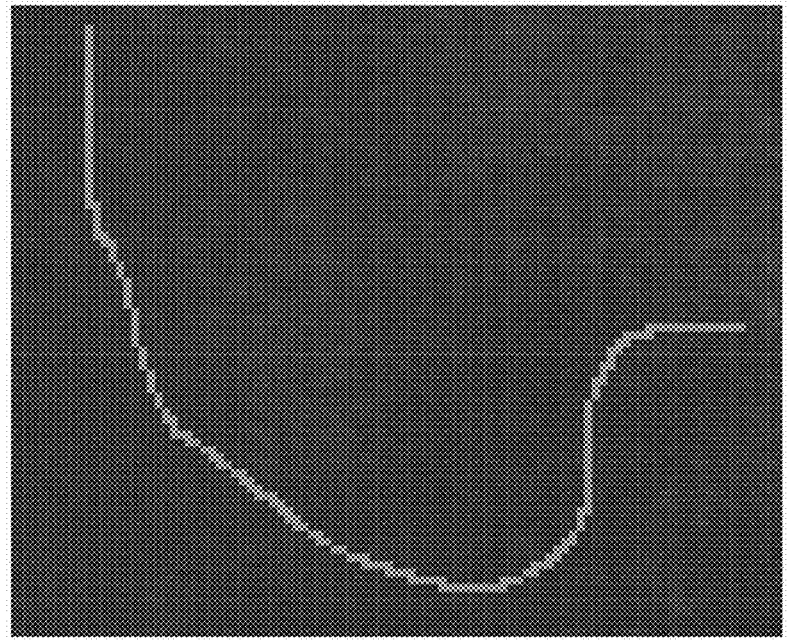
FIG. 7B shows a corresponding location of a source with respect to the vessel of FIG. 7A.
Figure 8A:
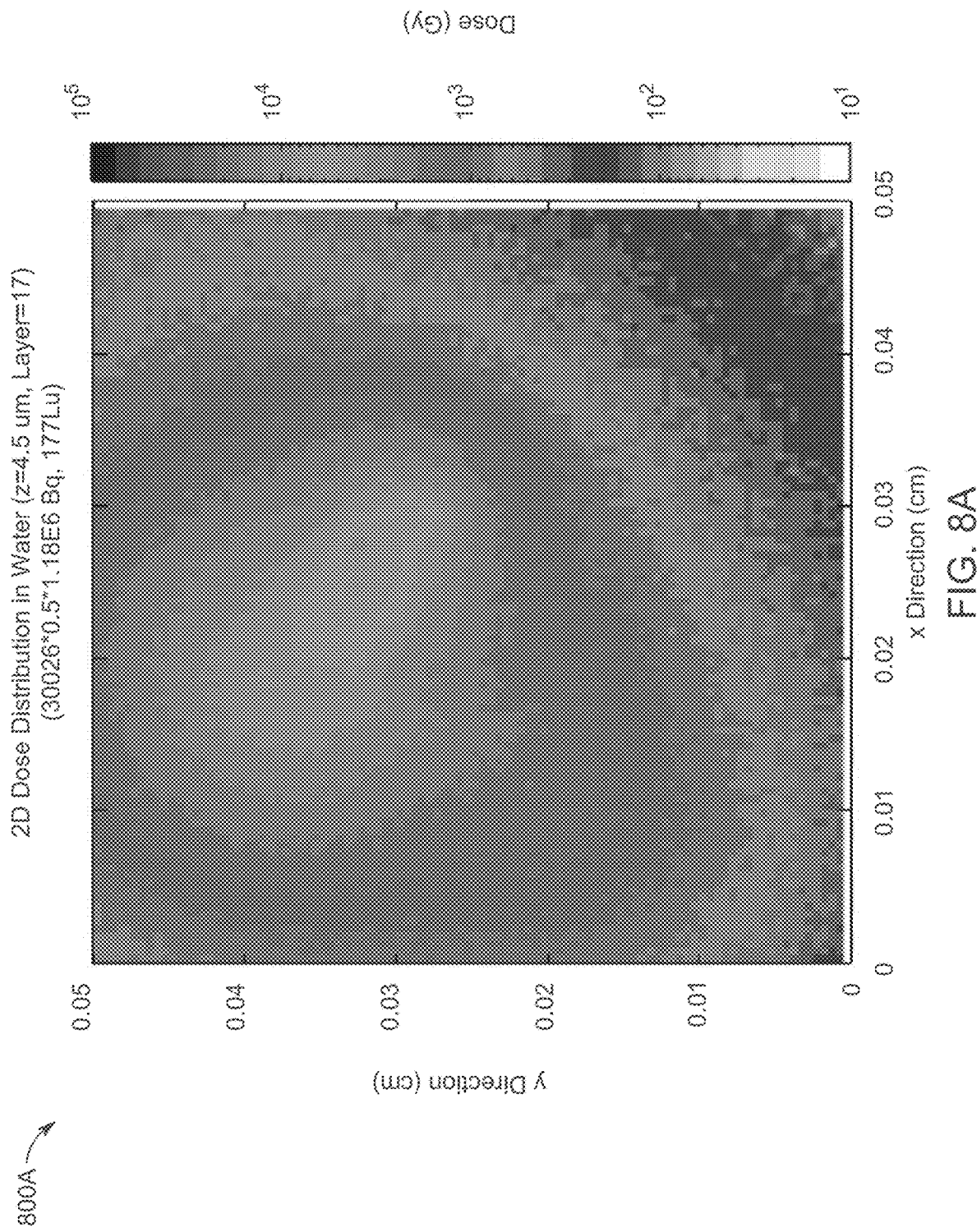
Figure 8B:
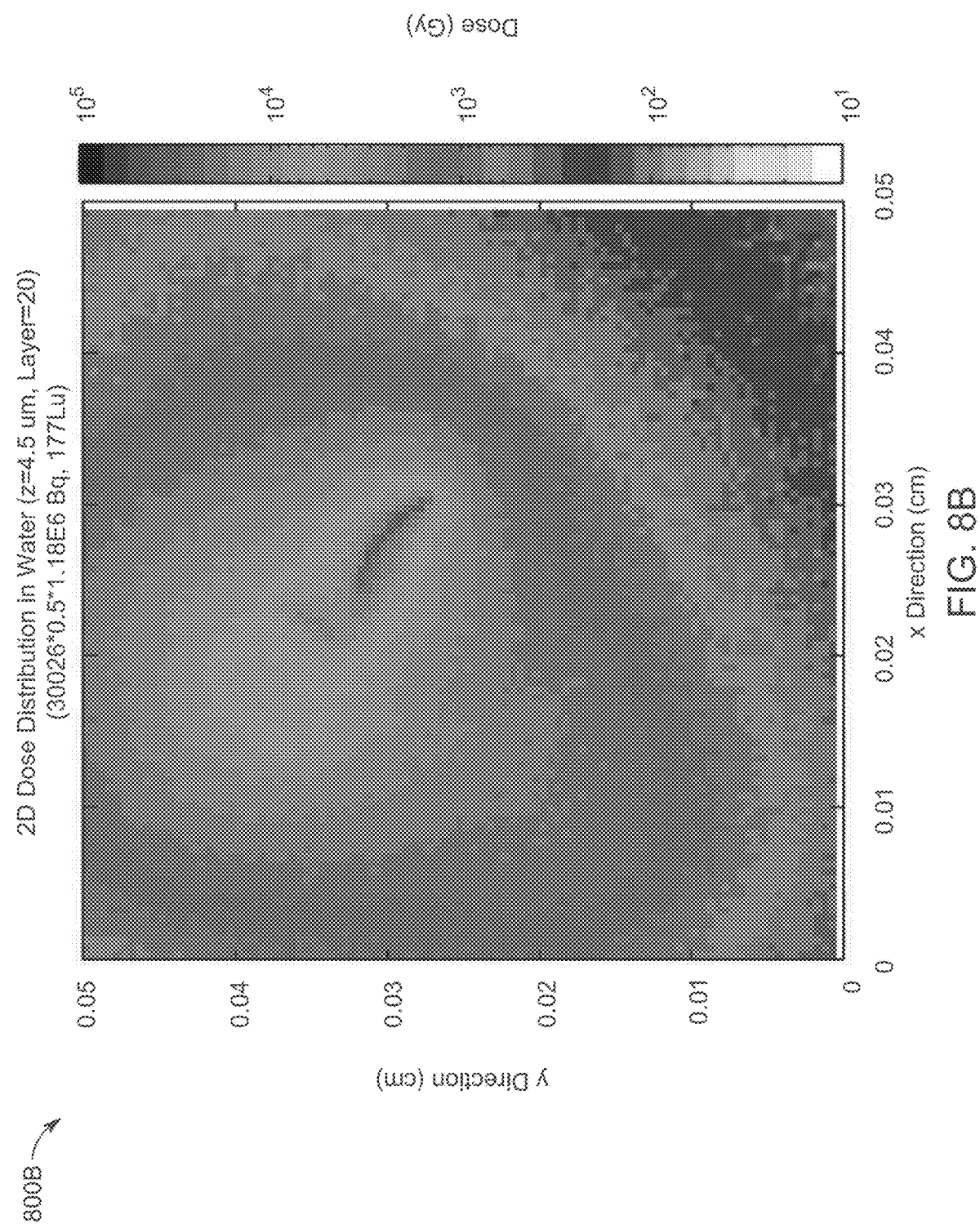
Figure 8D:
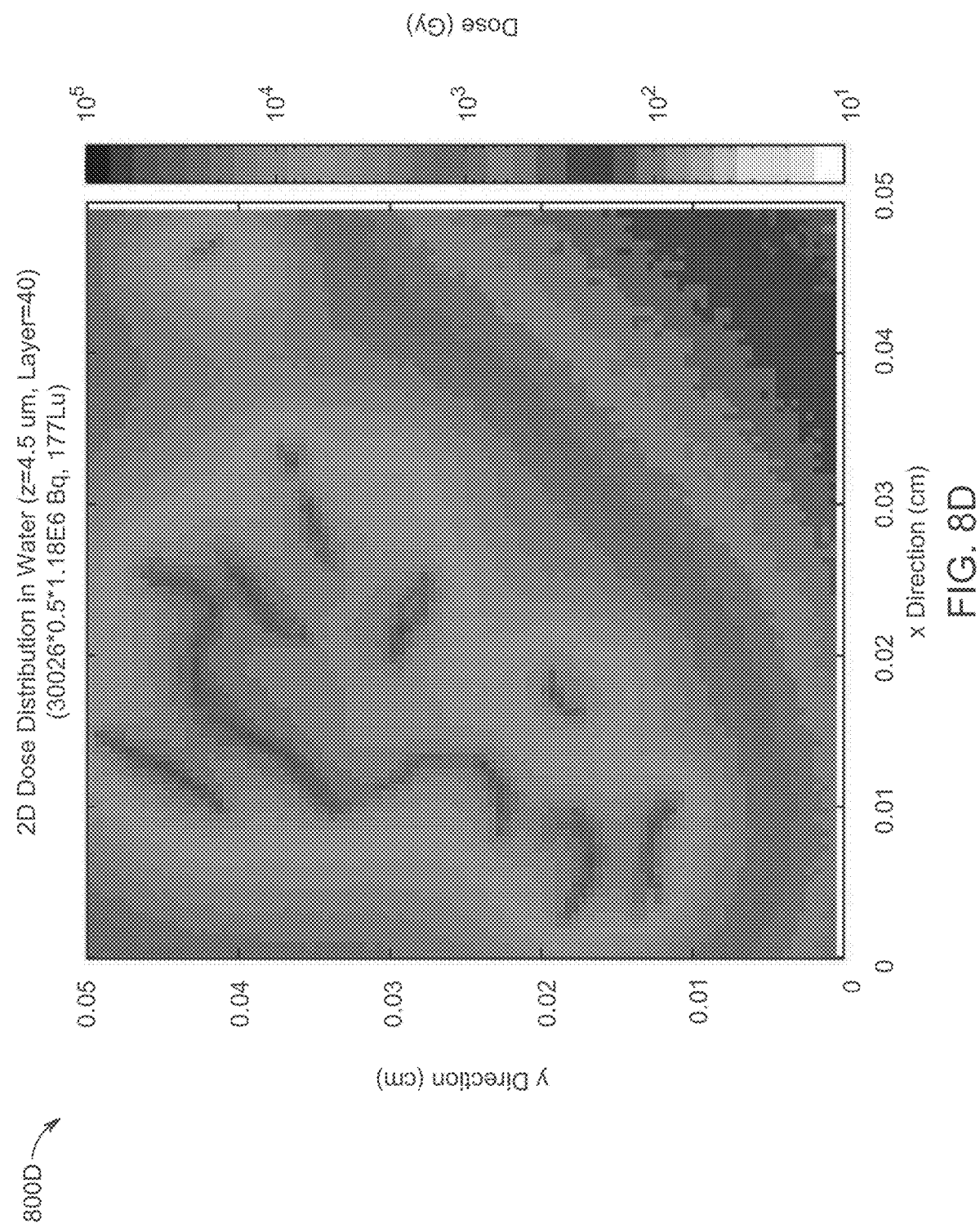
Figure 8E:
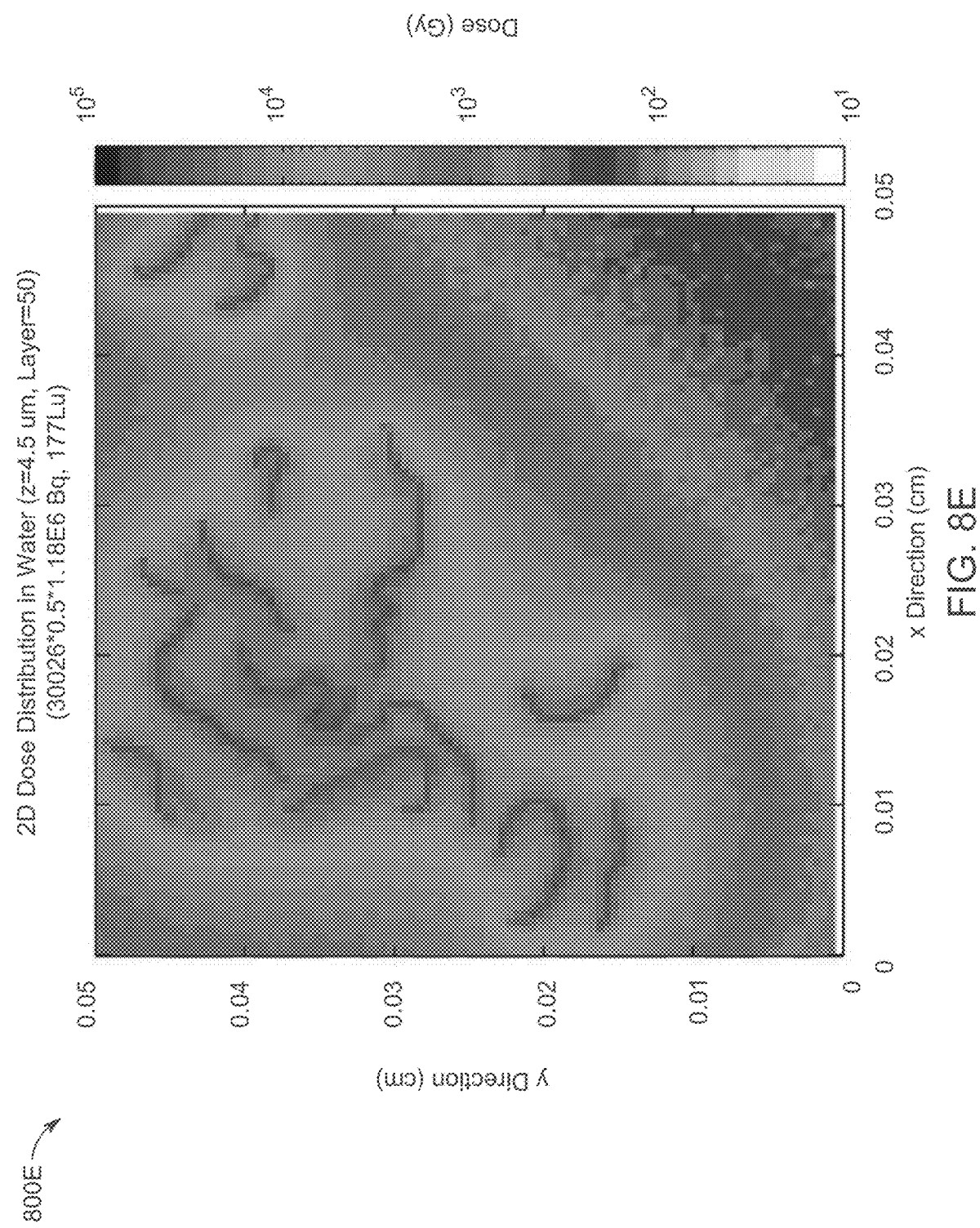
Figure 9A:
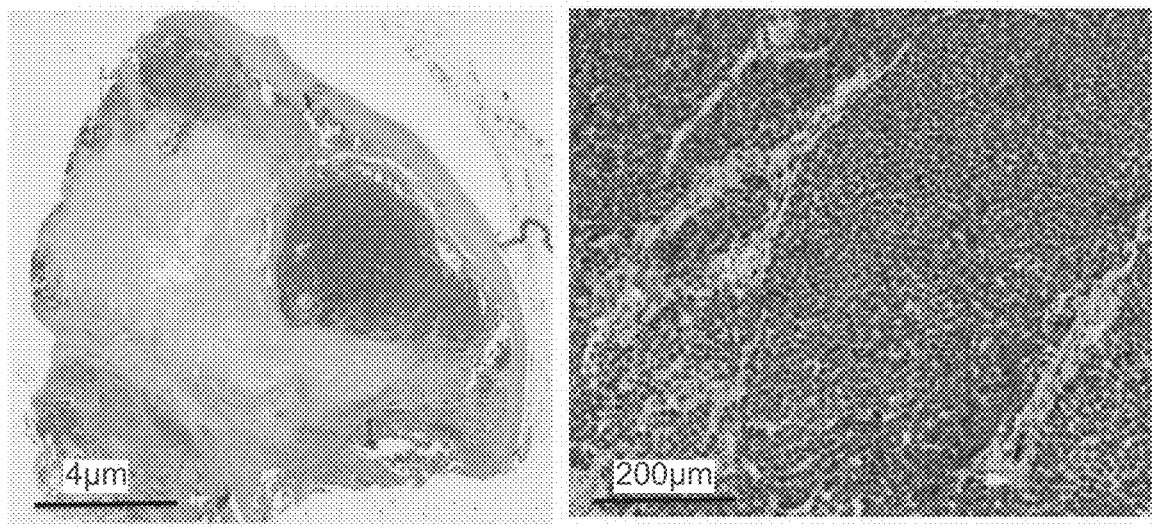
FIGS. 9A and 9B are images showing FOLH1 is expressed in the neo-vasculature.
Figure 9B:
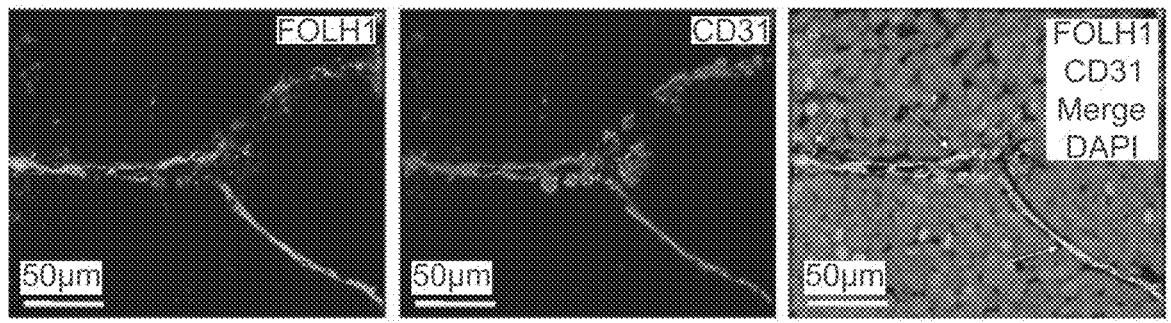
Figure 10:
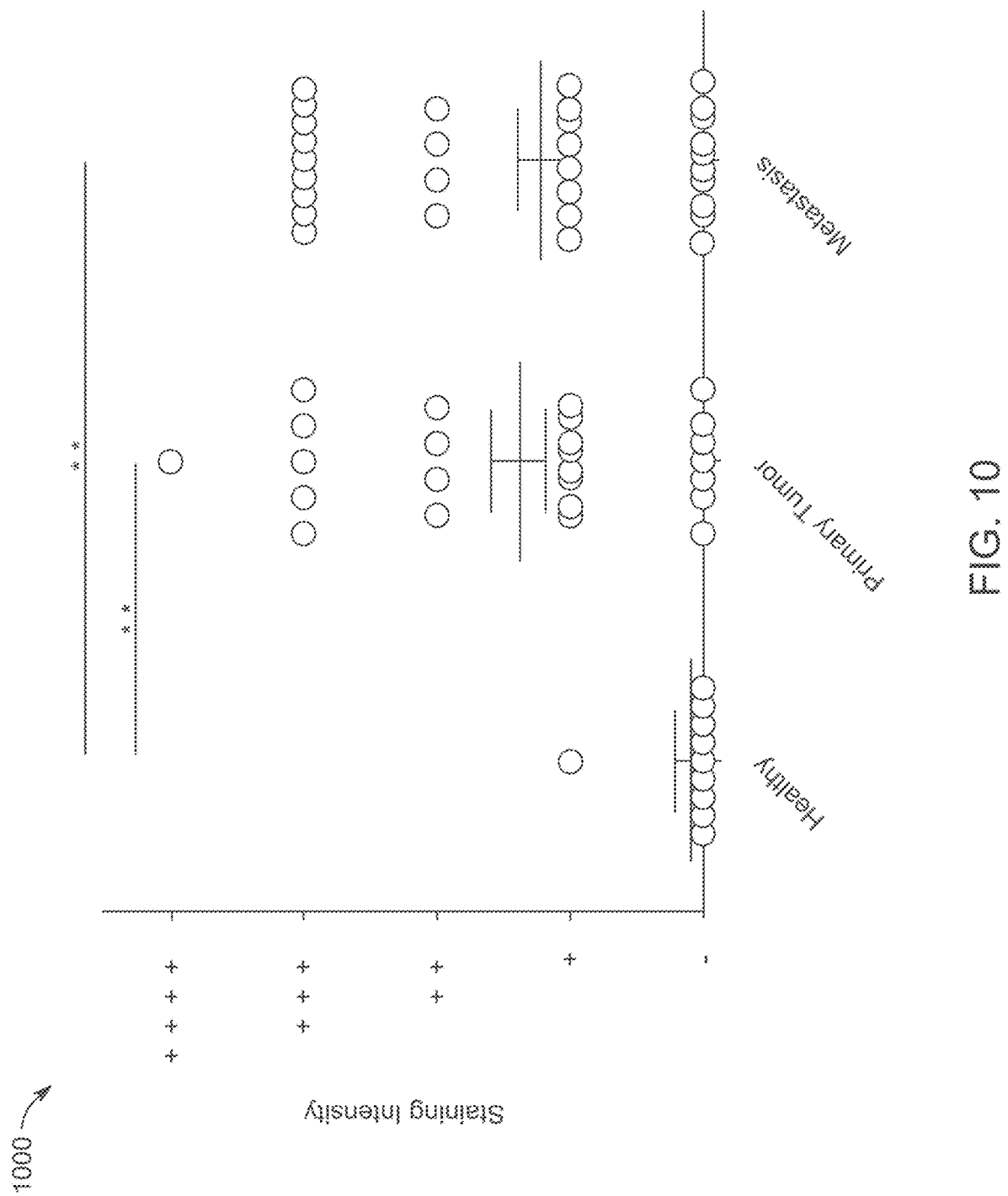
FIG. 10 is a chart of semi-quantification of FOLH1 staining intensity.

There may be in total 90080 pixels contoured as blood vessel, and assuming the average contour width as 3 pixels, then length of blood vessel may be estimated to be 30026*0.5 μm. The 177Lu atom can be estimated to be 30026*0.5*1.18E6. In this simulation, those atoms were distributed uniformly in the center of blood vessel contoured in Viva-stack images. FIGS. 7A and 7B may show an example of a contoured blood vessel in image 700A and the corresponding location of $^{177}$Lu source in image 700B, respectively.

Absorbed dose in Sphere balls may be provided by the platform. Four sphere balls may be constructed to simulate absorbed dose, with the same quantity of $^{177}$Lu in water. Center of the spheres may be located at x=0.025, y=0.025, z=0.017 with radius being 0.01 cm, 0.05 cm, 0.25 cm, and 0.5 cm respectively. The absorbed dose (Gy) may be determined to be 4726 Gy for the 0.01 cm radius, 656.8 Gy for the 0.05 cm radius, 6.42 Gy for the 0.25 cm radius, and 0.80 Gy for the 0.5 cm radius.

It would be important to list the initial activity of $^{177}$Lu used for the calculation (e.g., 25 mCi), describe the dose rate and then the absorbed dose after full decay. FOLH1 targets may replenish themselves within a week for a second infusion. Therefore, weekly infusions could be feasible. If the absorbed dose is assumed to be 50%-100% of available targets at each infusion, the cumulative absorbed dose may be calculated. Infusions can be administered with supportive care until the cumulative absorbed dose reaches the prescribed radiation dose.

Any suitable process may be utilized for enabling microdosimetry. For example, the process may provide a method for measuring the absorbed dose of energy (e.g., electromagnetic irradiation) or molecule (e.g., drug) delivered via a target(s) within a volume of cells (e.g., tumor). One operation of the process may include measuring the specific activity and initial activity of a chemical nuclei (e.g., $^{10}$B, $^{177}$Lu, $^{90}$Y, etc.) that is attached to an agent or embodiment (e.g., monoclonal antibodies, small molecules and antibody fragments, etc.) with target binding capacity, or measuring the initial molecule quantity that is attached to an agent or embodiment (e.g., monoclonal antibodies, small molecules and antibody fragments, etc.) with target binding capacity (e.g., as may be accomplished in a radiochemistry lab using known techniques). Another operation of the process may include quantification or semi-quantification of target molecule(s) (e.g., FOLH1) per a given volume of cells, where the target may be directly measured (e.g., by flow cytometry) or indirectly measure (e.g., by immunohistochemistry staining intensity), where the target may be located on all or some of the cells or other structure(s) within the defined volume of cells. Another operation of the process may include inputting the value(s) defined in the measuring operation and in the quantification operation into any suitable mathematical algorithm (e.g., a Monte Carlo simulation) that may be capable of conducting a multiple probability simulation or a mathematical technique, that may be able to estimate the possible outcomes of an uncertain event. The delivered and absorbed dose may be estimated via the mathematical algorithm. Another operation of the process may include prescribing a dose to the volume of cells based on the simulation.

Folate Hydrolase-1 (FOLH1; PSMA) is a type II transmembrane protein, luminally expressed by solid tumor neovasculature. Monoclonal antibody (mAb), J591, is a vehicle for mAb-based brachytherapy in FOLH1$^+$ cancers. Brachytherapy is a form of radiotherapy that involves placing a radioactive material a short distance from the target tissue (e.g., on the skin or internally); brachytherapy is commonly accomplished with the use of catheters, needles, metal seeds and antibody or small peptide conjugates. Herein, FOLH1 expression in primary (p) and metastatic (m) MCC is characterized to determine its targeting potential for J591-brachytherapy.

Paraffin sections from pMCC and mMCC were evaluated by immunohistochemistry for FOLH1. Monte Carlo simulation was performed using the physical properties of conjugated radioisotope lutetium-177 ($^{177}$Lu). Kaplan-Meier survival curves were calculated based on patient outcome data and FOLH1 expression.

81 MCC tumors were evaluated. 67% ($^{54}/_{81}$) of all cases, 77% ($^{24}/_{31}$) pMCC and 60% ($^{30}/_{50}$) mMCC tumors were FOLH1+. Monte Carlo simulation showed highly localized ionizing tracks of electrons emitted from the targeted neovessel. 42% ($^{34}/_{81}$) of patients with FOLH1+/−MCC had available survival data for analysis. No significant differences in our limited data set were detected based on FOLH1 status (p=0.4718; p=0.6470), staining intensity score (p=0.6966; p=0.9841), or by grouping staining intensity scores (− and + versus ++, +++, +++) (p=0.8022; p=0.8496) for MCC specific survival or recurrence free survival, respectively.

The first evidence of prevalent FOLH1 expression within MCC-associated neovessels, in 60-77% of patients in a large MCC cohort, may be reported by the platform. Given this data, and the need for alternatives to immune therapies it is appropriate to explore the safety and efficacy of FOLH1-targeted brachytherapy for MCC.

The incidence rates of Merkel cell carcinoma ("MCC"), an aggressive cutaneous malignancy, have tripled from 0.15 cases per 100,000 individuals in 1986 to 0.7 per 100,000 in 2013, corresponding to 2,488 cases/year (see, e.g., references REF189-REF191 of the list of references provided hereinbelow). MCC is three times more lethal than melanoma, with a 46% disease-associated mortality rate, and 5-year disease-specific survival rates of 66% and 11-30% for local and metastatic disease, respectively (see, e.g., references REF190 and REF192 of the list of references provided hereinbelow). These concerning survival rates reflect MCC's propensity for local recurrence and regional nodal involvement (see, e.g., reference REF193 of the list of references provided hereinbelow), where 30-50% of locally staged patients eventually develop a distant metastasis (see, e.g., references REF192 and REF194 of the list of references provided hereinbelow).

MCC is often diagnosed late in its pathogenesis, thereby requiring systemic approaches early in management. Systemic therapy using standard chemotherapeutic agents such as etoposide, epirubicin, doxorubicin, cyclophosphamide and cisplatin-based chemotherapeutic regimens as radiosensitizers or as definitive treatment remains disappointing. These systemic agents are associated with high toxicity rates, transient responses, resistance and no overall survival benefits (see, e.g., references REF195-REF198 of the list of references provided hereinbelow). MCC's poor prognosis, high recurrence and mortality rates, in parallel with disappointing outcomes with conventional treatments warrant evaluating alternative therapeutic modalities. The need for novel strategies to treat rare diseases like MCC is recognized by the U.S. Food and Drug Administration (FDA), assisting in drug development for diseases affecting fewer than 200,000 people by providing financial and logistical incentives.

Recent studies showing PD-L1 expression in the tumor microenvironment of MCCs, and PD-1 expression by MCC-specific tumor infiltrating and circulating T cells, supported investigating the utility of immune checkpoint inhibitors (see, e.g., references REF199 and REF200 of the list of references provided hereinbelow). A phase 2 trial of avelumab (a human anti-PD-L1 IgG1 monoclonal antibody (mAb)) in patients with metastatic MCC refractory to chemotherapy demonstrated a 31.8% durable objective response rate according to Response Evaluation Criteria in Solid Tumors version 1.1 (see, e.g., references REF201 and REF202 of the list of references provided hereinbelow), culminating in avelumab being the first FDA-approved immunotherapy for MCC in March 2017.

Despite these promising results with use of targeted immunotherapy, approximately half of patients do not respond to PD-1/PD-L1 axis targeting, necessitating development of alternative therapeutic strategies. Merkel cell carcinoma (MCC) tumors and metastatic deposits have large mitotic fractions that are susceptible to ionizing radiation damage. They are highly vascularized, leading to intrinsic sensitivity to photon and electron external beam radiation therapy (EBRT) via an increased oxygen enhancement ratio. Several studies and the NCCN guidelines promote definitive or adjuvant external beam radiation therapy ("EBRT") to optimize localized tumor control in pMCC that are surgically inoperable, resections with borderline or positive margin status, tumors greater than 1 cm in the context of a positive lymph node biopsy, presence of lymphovascular invasion, and history of immunodeficiency (see, e.g., references REF203-REF209 of the list of references provided hereinbelow).

Although MCC is intrinsically radiosensitive, the field size of conventional treatment with EBRT is limited by the radiation tolerance of normal tissues or organs at risk surrounding tumor deposits (e.g., optic nerve, spinal cord, lung).

Brachytherapy is a form of radiotherapy that involves placing a radioactive material a short distance from the target tissue (e.g., on the skin or internally); brachytherapy is commonly accomplished with the use of catheters, needles, metal seeds and antibody or small peptide conjugates. Antibody-based brachytherapy is a clinically validated form of radiation therapy that uses a monoclonal antibody ("mAb") to deliver radioactive isotopes directly to sites of local and metastasized cancer (see, e.g., references REF210-REF217 of the list of references provided hereinbelow). The intrinsic properties of $^{177}$Lu, make it an ideal candidate for antibody-based brachytherapy; $^{177}$Lu decays by β particle (i.e., electrons) emission (0.497 MeV; $t_{1/2}$=6.74 days) of relatively short-range (0.2-0.3 mm). The calculated optimal tumor size for treatment with $^{177}$Lu is 1.2-3 mm (see, e.g., reference REF218 of the list of references provided hereinbelow); for larger tumors, the clinical efficacy of longer range β emitters has been demonstrated (e.g., $^{90}$Y) (see, e.g., reference REF219 of the list of references provided hereinbelow). Clinical data on FOLH1-targeting with α-emitters (e.g., two protons and two neutrons) in prostate cancer (Pca) is promising and suggests that α-emitters could be considered for hypoxic tumors (see, e.g., reference REF220 of the list of references provided hereinbelow). The mAb J591 has demonstrated excellent tumor theragnostic specificity in Pca, and in the neovasculature of several solid tumors, via targeting of membrane-expressed folate hydrolase-1 (FOLH1; also known as prostate-specific membrane antigen) (see, e.g., references REF210, REF212, REF213, REF215, and REF221 of the list of references provided hereinbelow). FOLH1 is a transmembrane enzyme receptor that is upregulated on the cell membrane of prostate cancer, intracellularly in melanoma and neovascular lumen (e.g., inside of tumor-associated blood vessel) of virtually all solid tumors (see, e.g., references REF210 and REF222 of the list of references provided hereinbelow). Importantly, there has not been a single patient reported to have toxicity to non-tumor-related vessels. As mentioned, the monoclonal antibody to the extracellular domain of FOLH1, J591, has demonstrated excellent tumor theragnostic specificity in prostate cancer, and in the neovasculature of several solid tumors, via targeting of cell membrane-expressed FOLH1 (see, e.g., references REF001, REF212, REF213, REF215, and REF221 of the list of references provided hereinbelow). Numerous other small molecules and antibody fragments have demonstrated comparable binding specificity to FOLH1 and cellular endocytosis or internalization (see, e.g., reference REF001 of the list of references provided hereinbelow). These FOLH1-targeting agents or embodiments may be administered intravenously, bind to FOLH1, and subsequently enter the cell (see, e.g., reference REF001 of the list of references provided hereinbelow). Time for maximal internalizations may vary from approximately 40 minutes with small molecules to 7 days with monoclonal antibodies. FOLH1-targeting monoclonal antibodies, small molecules, and antibody fragments may provide effective platforms for $^{10}$B or LU177 delivery specifically within FOLH1-expressing cells (e.g., prostate cancer cells, blood vessel cells of solid tumors, etc.).

In vivo targeting of FOLH1 by conjugating auristatin (a cytotoxic agent) to J591 (monoclonal antibody) increased the therapeutic index of auristatin by 700-fold, and improved the median survival of Pca xenografts by 9 months (see, e.g., reference REF223 of the list of references provided hereinbelow). Use of J591 to deliver a chemotherapy drug to a tumor site, may increase the therapeutic ratio by 700 times. Clinically, $^{177}$Lu-J591 is well-tolerated, non-immunogenic, and can be fractionated. Studies with unconjugated J591 report no dose-limiting toxicities in patients with solid tumors (see, e.g., reference REF224 of the list of references provided hereinbelow). An ongoing trial is investigating in vivo localization of metastasized solid tumors with FOLH1 PET/CT imaging using positron emitting $^{89}$Zr-J591, and the effects on tumor perfusion and cellularity with a cumulative dose of 70 mCi of $^{177}$Lu-J591 (see, e.g., reference REF302 of the list of references provided hereinbelow) (NCT00967577).

Herein the expression of FOLH1 may be validated in primary (p) and metastatic (m) MCC. Paraffin sections of pMCC and mMCC were provided by academic medical centers in Switzerland, Czech Republic, Germany and the United States. A total of 81 MCC tumors were evaluated for FOLH1 expression by standard immunohistochemistry. One primary and one metastatic tumor was obtained from the same patient. Primary antibodies used were 3E6 (DAKO) mouse IgG1 monoclonal anti-human FOLH1, mouse IgG1 isotype antibody (Abcam) and anti-CD31 (IgG1, Abcam). Mouse IgG1 isotype antibody (Abcam) at corresponding concentrations was used as a negative control. Anti-CD31 (IgG1) was used as a positive control to stain vasculature. Biotinylated goat-anti-mouse (Southern Biotech, Birmingham, USA) was used as a secondary antibody. Sections were imaged with Aperio ScanScope (Leica Biosystems, Wetzlar, Germany). The MCC cases were classified as (−), (+), (++), (+++) and (++++) staining intensities; (++++) was characterized as maximal staining as seen in Pca. Three dermatopathologists in New York, United States reviewed all slides for FOLH1 immunostaining and intensity. The slides were reviewed independently and together; in the setting of inter-observer measurement difference, the measurement with majority agreement was used.

Overall, 67% ($^{54}/_{81}$) of cases showed FOLH1$^+$ neovessels. 77% ($^{24}/_{31}$) of pMCC cases and 60% ($^{30}/_{50}$) of mMCC cases demonstrated FOLH1-positivity, FOLH1$^+$ was restricted to MCC neovessels (as confirmed by co-labeling with anti-CD31). For example, as shown by images 900A and 900B in FIGS. 9A and 9B, respectively, FOLH1 is expressed in the neo-vasculature of primary and meta-stastic Merkel cell carcinoma: (a) Immunohistochemistry staining of metastatic MCC paraffin sections with a mouse IgG1 monoclonal anti-human FOLH1; and (b) Immunofluorescent co-labelling of FOLH1 (green) with the endothelial marker CD31 (red) in a case of meta-static MCC, where arrows may indicate co-labelling of FOLH1 and CD31 (yellow), folate hydrolase-1; MCC, Merkel cell carcinoma. The majority of FOLH1$^+$ vessels were identified in the periphery of infiltrating tumor cells. No FOLH1 tumor cell staining was identified. One FOLH1$^+$ paraffin section contained both p- and mMCC tumors, suggesting that biopsy of pMCC can predict some degree of FOLH1$^+$ homogeneity in metastasis. Semi-quantification of FOLH1 staining intensity showed that both pMCC and mMCC expressed significantly more FOLH1 as compared to healthy skin. For example, as shown by chart 1000 of FIG. 10, semi-quantification of FOLH1 staining intensity may be charted. The MCC cases were classified as (−), (+), (++), (+++), and (++++) staining intensities: (++++) was characterized as maximal staining as seen in prostate cancer where there is both cellular and neovascular staining. Both primary and metastatic MCC expressed significantly more FOLH1 as compared to healthy skin. **p<0.01. FOLH1, folate hydrolase-1; MCC, Merkel cell carcinoma. Therefore, the number of FOLH1 targets in a given MCC tumor for antibody-based brachytherapy microdosimetry may be semi-quantitatively estimated.

Figure 11:
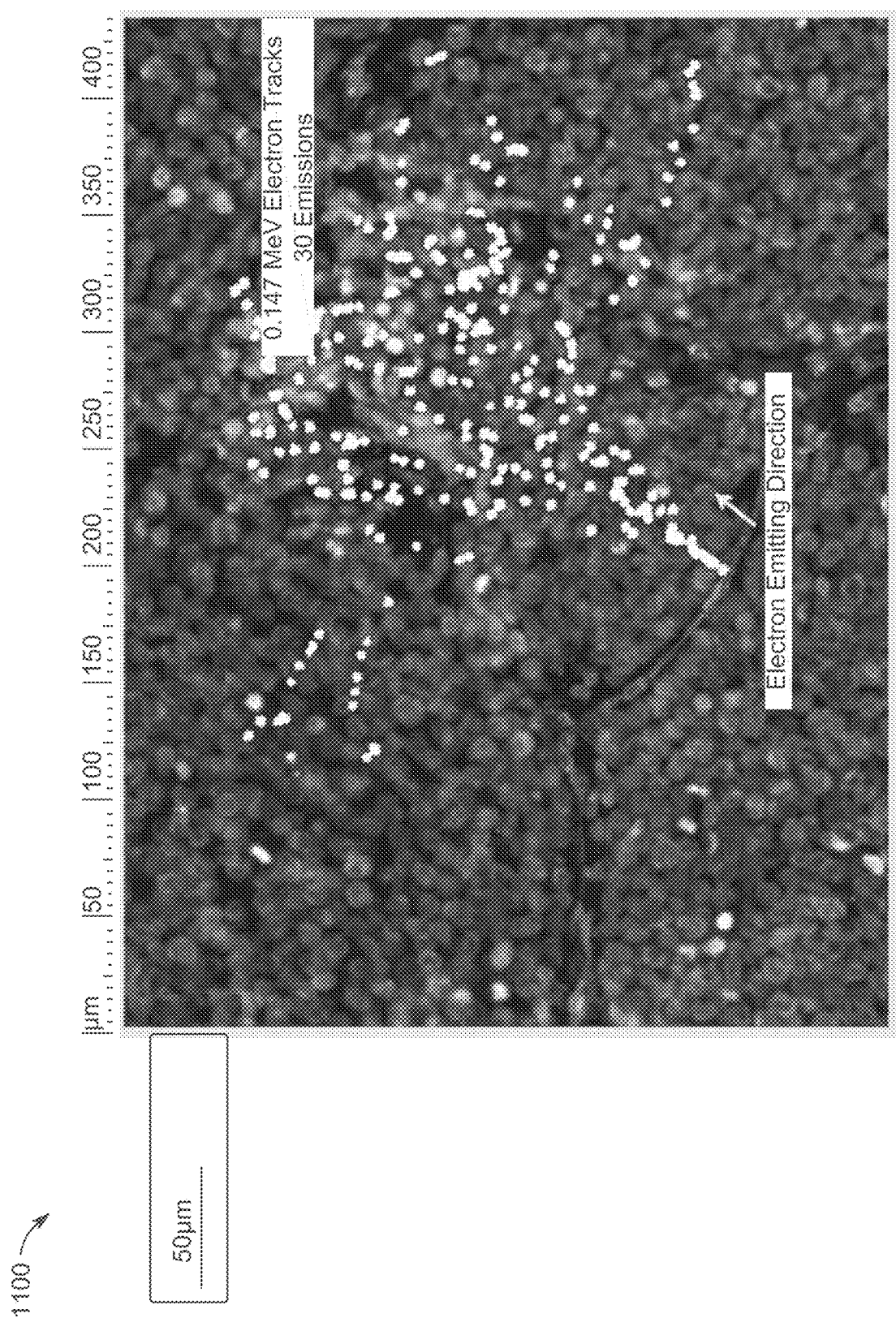
FIG. 11 is a demonstration of a track structure of 30 electrons emitted from $^{177}$Lu.

Monte Carlo simulation with MCNPX (V2.5.0) was used to calculate the tracks of 30 emitted electrons and ionization points in water media to show the penetration characteristics of $^{177}$Lu electrons (0.147 MeV mean energy) (see, e.g., reference REF225 of the list of references provided hereinbelow) from a single point in direction perpendicular to blood flow. The total range of the electrons at such energy level is in the order of 200 μm. The electron ionization tracks originating from the neovessel were then superimposed onto the histopathological image of a FOLH1$^+$ MCC neovessel. As supported by our Monte Carlo simulation, $^{177}$Lu-J591 provides a highly localized dose distribution, which permits specific, systemic targeting of disseminated disease with ionizing irradiation while limiting irradiation beyond the tumor boundaries. For example, FIG. 11 provides a demonstration 1100 of the track structure of 30 electrons emitted from $^{177}$Lu. The natural decay of $^{177}$Lu occurs spherically from its point source; for clarity, only electrons emitted in a single direction and visible in a single plane that is perpendicular to neo-vessel blood flow were depicted. A mean energy of 0.147 MeV was chosen to best depict the electron tracks. The figure demonstrates 30 electrons with the same energy of 0.147 MeV emitted from the same point on a neo-vessel within a MCC tumor, in the same 2-D direction. Sites of overlapping ionization points and tumor cell nuclei (DAPI; Blue) are sites of potential DNA damage and subsequent cell death. Note, that the apparent discontinuity of the tracks are due to the fact that electrons travel in and out of the 2-D plane depicted in this figure (i.e., the tracks scatter above and below the plane).

Figure 12A:
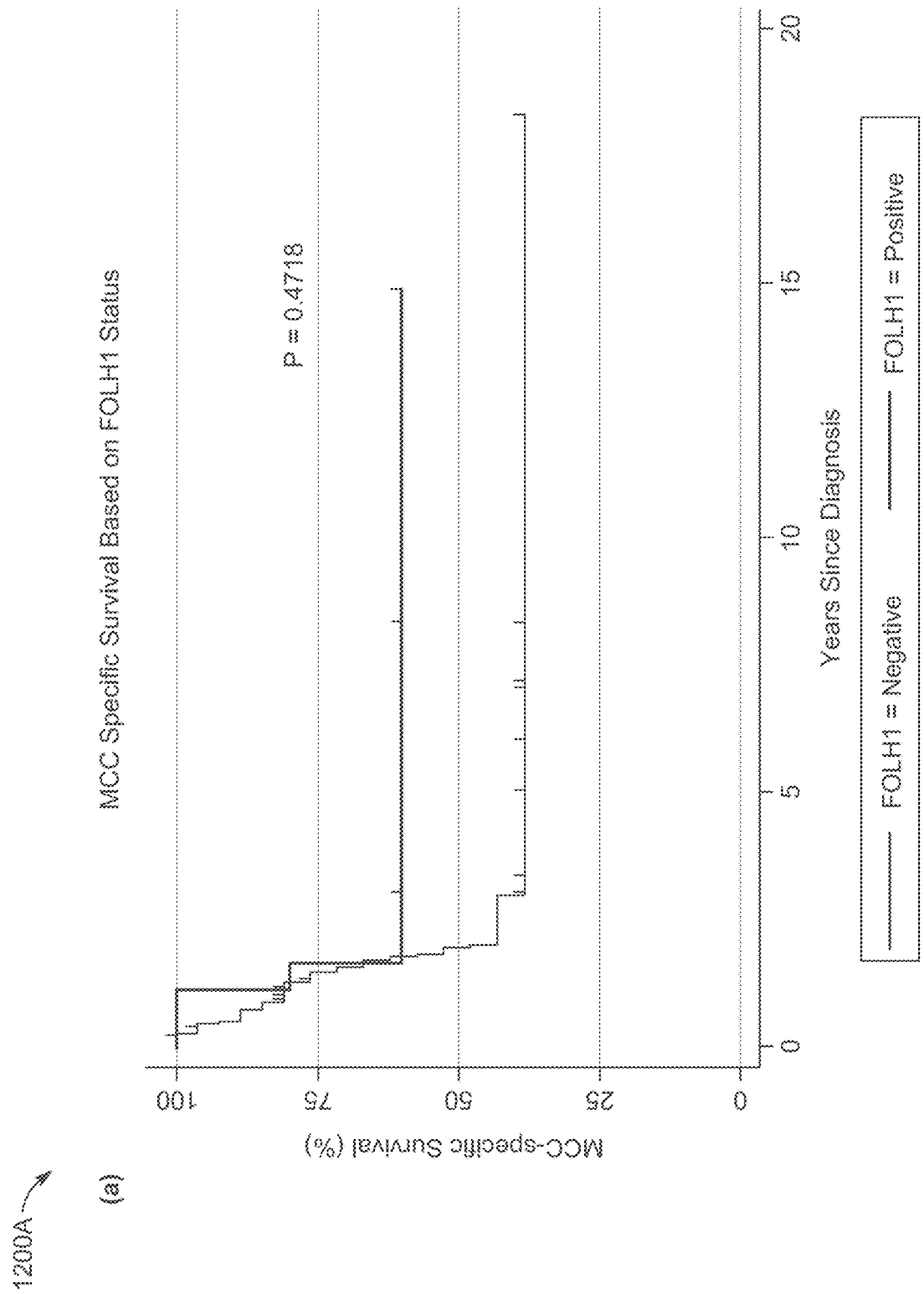
FIGS. 12A-12F are exemplary Kaplan-Meier curves for MCC-specific survival and recurrence free survival.
Figure 12B:
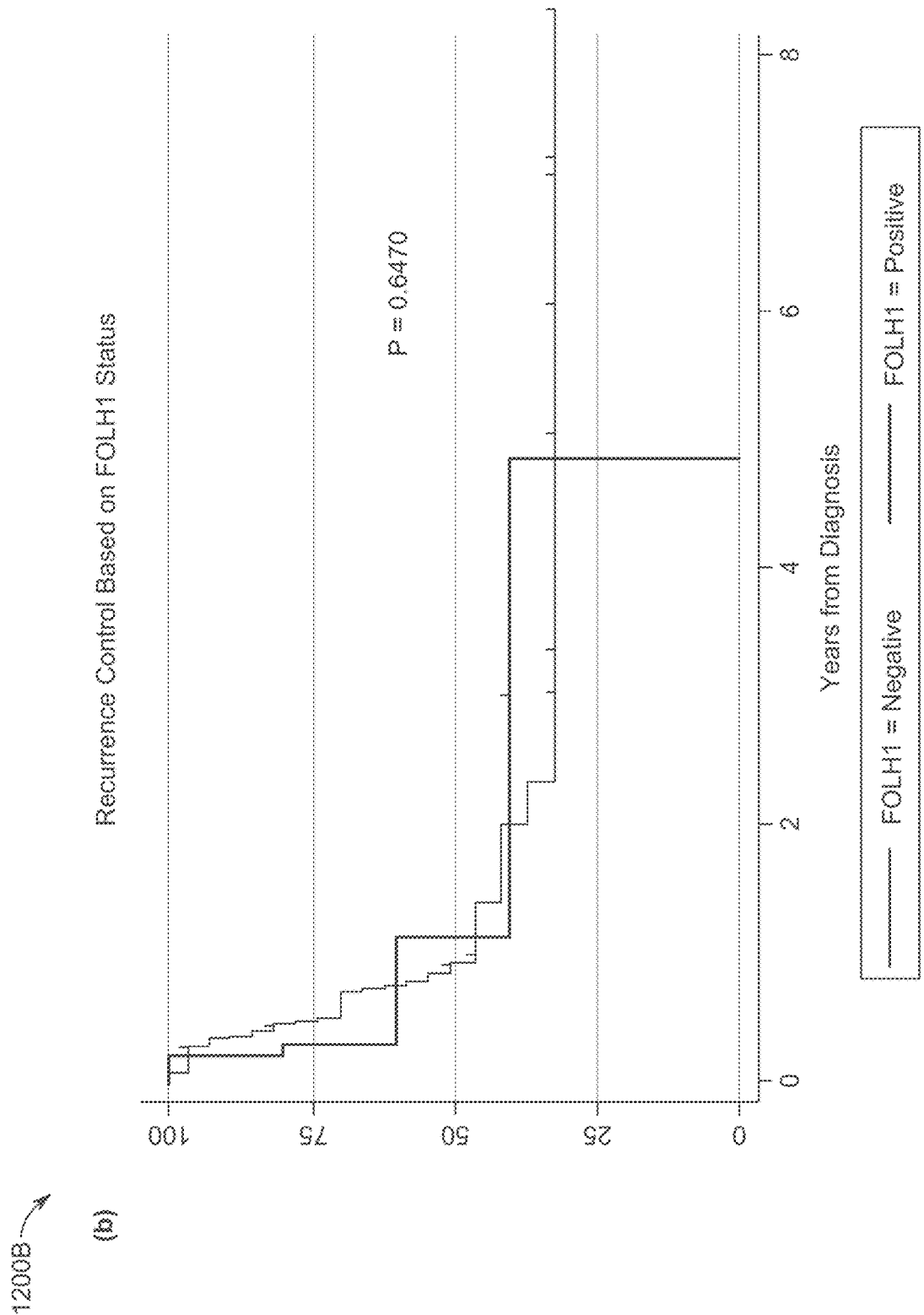
Figure 12C:
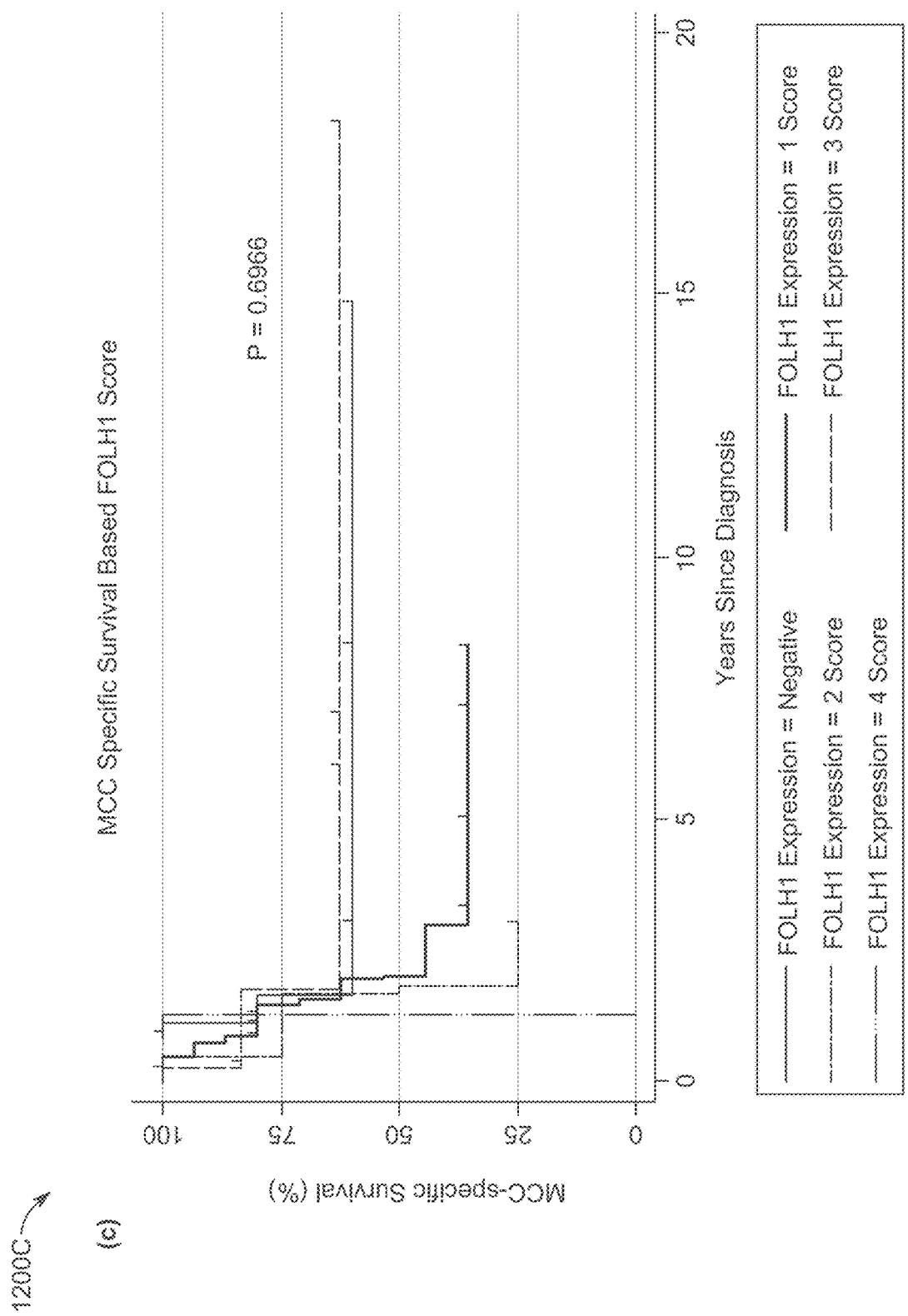
Figure 12D:
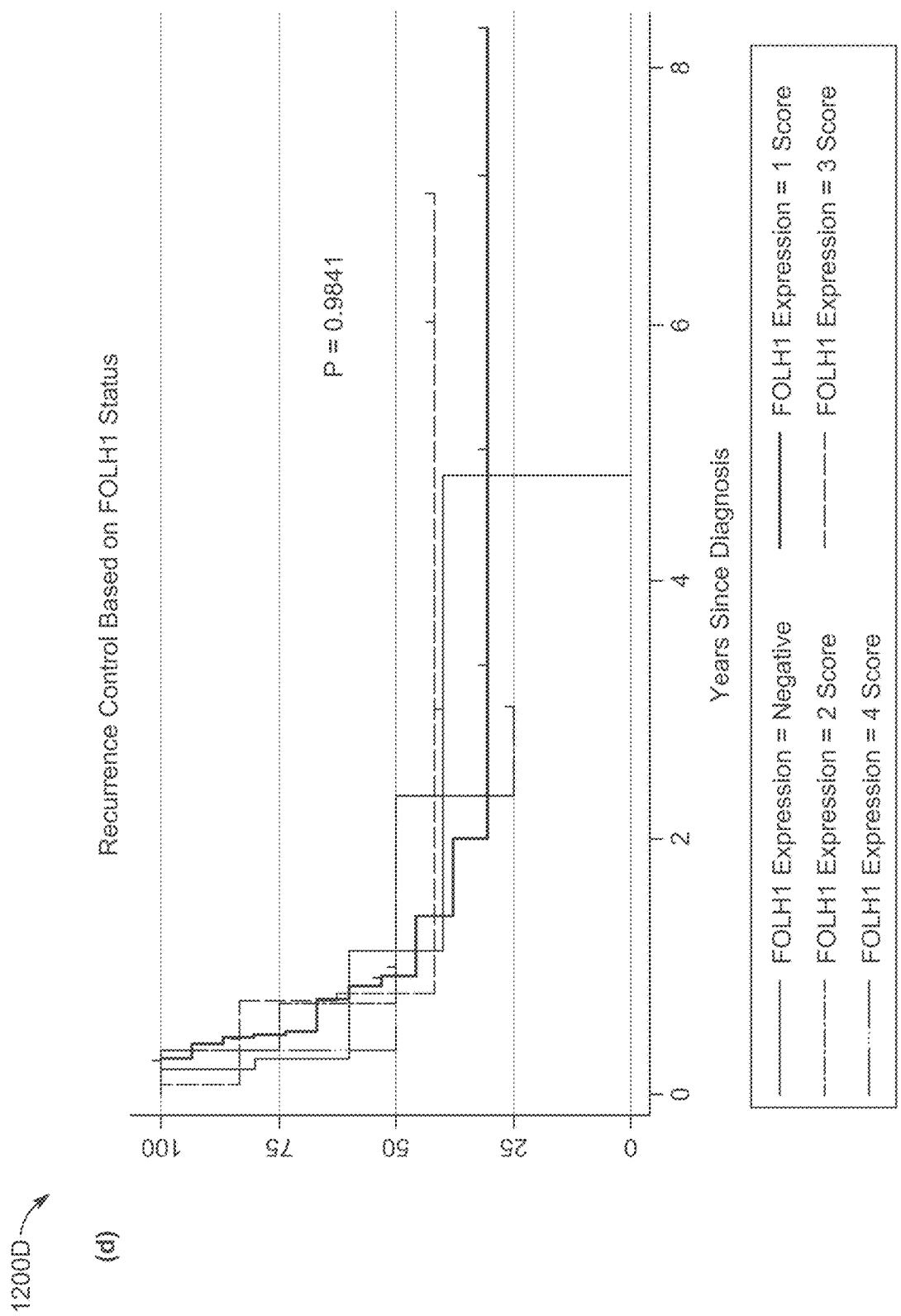
Figure 12E:
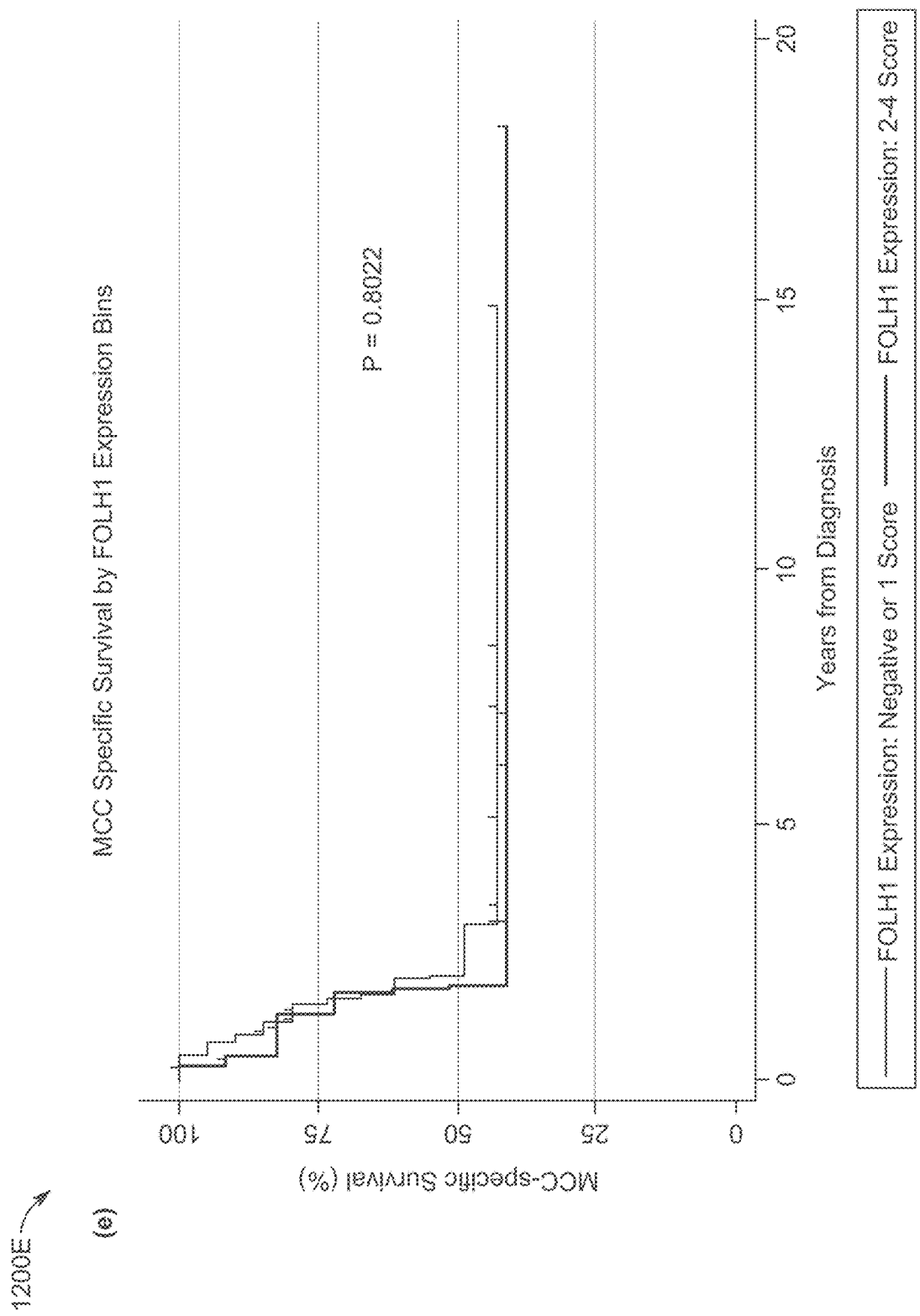
Figure 12F:
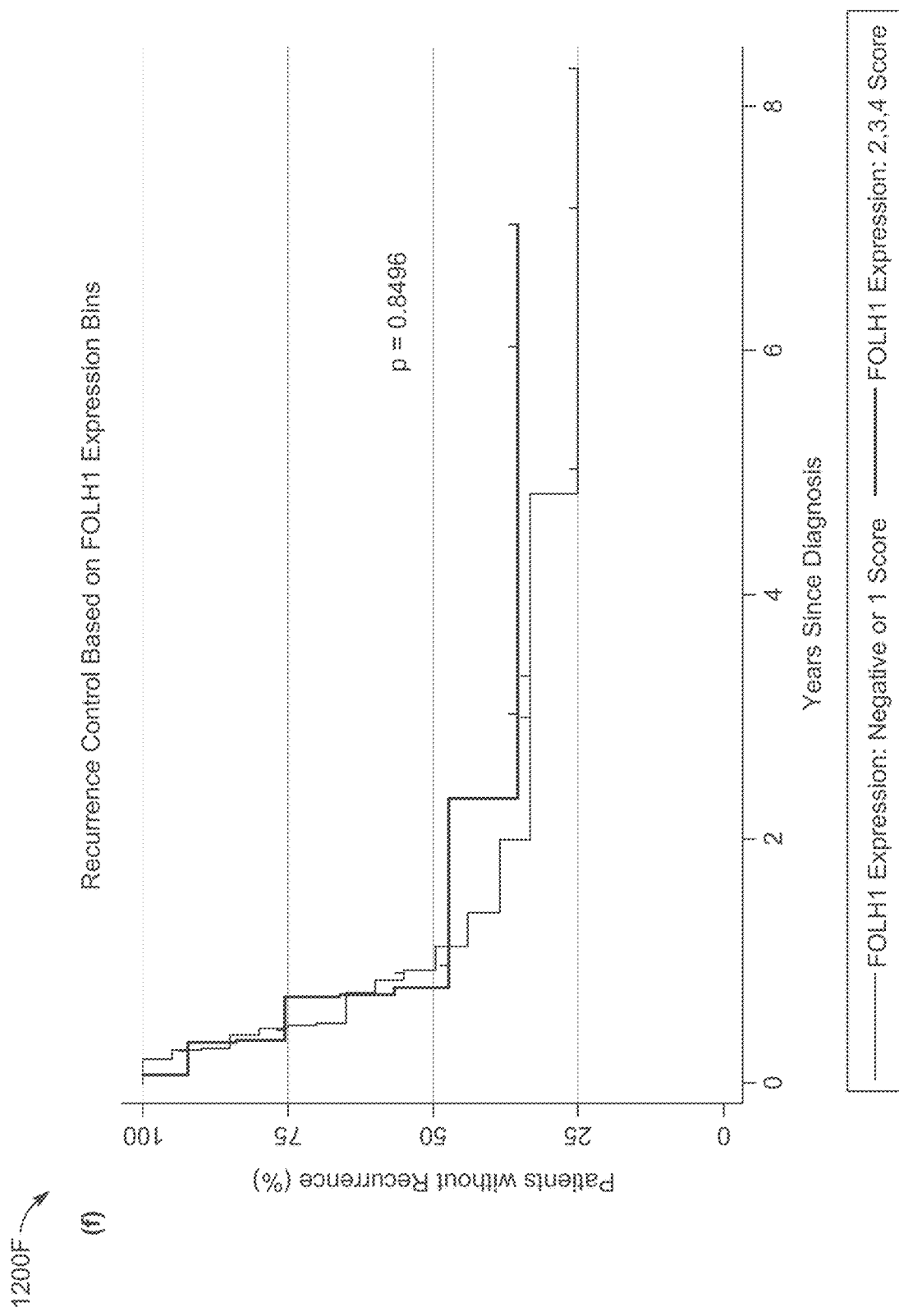

Statistical analyses on patient survival were performed using Stata software version 14.0 (StataCorp). Survival analyses were calculated from time of diagnosis to the outcome event. For MCC-specific survival, an event was defined as death by MCC. Recurrence-free survival's event was either a MCC recurrence or death by MCC. Patients that were lost to follow-up were censored in all analyses. Kaplan-Meier survival curves were created to visualize patient survival outcome based on FOLH1 tumor expression. For example, as shown in FIGS. 12A-12F, exemplary Kaplan-Meier curves are provided for MCC-specific survival and recurrence free survival, where curve 1200A of FIG. 12A is for MCC-specific survival based on FOLH1 status (curves a), curve 1200B of FIG. 12B is for recurrence control based on FOLH1 status (curves b), curve 1200C of FIG. 12C is for MCC-specific survival based on FOLH1 score (curves c), curve 1200D of FIG. 12D is for recurrence control based on FOLH1 score (curves d), curve 1200E of FIG. 12E is for MCC-specific survival based on FOLH1 expression bins (curves e), and curve 1200F of FIG. 12F is for recurrence control based on FOLH1 expression bins (curves f). No significant differences were detected based on (curves a and h) FOLH1 status (p=0.4718; p=0.6470), (curves c and d) staining intensity score (p=0.6966; p=0.9841), or by (curves e and f) grouping staining intensity scores (− and + vs. ++, +++, +++)(p=0.8022; p=0.8496) for MCC specific survival or recurrence free survival, respectively. FOLH1, folate hydrolase-1; MCC. Merkel cell carcinoma. The log-rank test was performed to determine if there were differences between FOLH1 status groups and a P value less than 0.05 was considered statistically significant.

Patient demographics, survival outcome, and FOLH1 neovessel expression data was available and evaluated in a cohort of 35/81 MCC patients, as shown by the table 1300 of FIG. 13. Patients with FOLH1$^+$ (in each group of staining intensity) and FOLH1$^−$MCC were demographically homogeneous with regards to sex, age at diagnosis, immunosuppression status, prior therapies, stage at diagnosis, and local or distant recurrences. No significant differences in our limited data set were detected based on FOLH1 status (p=0.4718; p=0.6470), staining intensity score (p=0.6966; p=0.9841), or by grouping staining intensity scores (− and + versus ++, +++, +++)(p=0.8022; p=0.8496) for MCC specific survival or recurrence free survival, respectively. Given the rarity of MCC, the results may not be powered to show that there is no significant difference.

Other studies have shown FOLH1 expression is not prognostic in RCC (see, e.g., reference REF226 of the list of references provided hereinbelow), but has prognostic implications in other solid tumors (see, e.g., references REF227-REF230 of the list of references provided hereinbelow). Nevertheless, MCC expression of FOLH1 is significantly more common than the observed expression of human epidermal growth factor receptor-2 (HER-2) in breast cancer (16%; 95% CI, 12%, 21%) (see, e.g., reference REF231 of the list of references provided hereinbelow) than the reported ~49% PD-L1 and ~55% PD-1 expression on MCC tumor cells and infiltrating lymphocytes, respectively (see, e.g., reference REF200 of the list of references provided hereinbelow). Comparison of FOLH1 target expression to HER-2, PD-L1 and PD-1 expression, suggests that FOLH1 may be a viable therapeutic target for MCC patients, particularly for treatment with antibody-based brachytherapy.

Need for novel strategies to treat rare diseases like MCC is recognized by the U.S. Food and Drug Administration (FDA), assisting in drug development for diseases affecting fewer than 200,000 people by providing financial and logistical incentives. Targeted molecular and mAb-based therapies for MCC are promising strategies that depend on our evolving understanding of tumor biology and disease pathogenesis (see, e.g., reference REF232 of the list of references provided hereinbelow). To this end, the platform may be configured to report the first evidence of prevalent FOLH1 expression within MCC-associated neovessels, in 60-77% of patients in a large MCC cohort. Given this data, and the need for alternatives to immune therapies, it is appropriate to explore the safety and efficacy of FOLH1-targeted brachytherapy for MCC.

Puerto Ricans are a trihybrid population created in the late 15$^{th}$ century from peoples of three (3) continents: 1) Asia (aboriginal Taino/Arawakan), 2) Europe (largely Spanish/Hispanic), and 3) Africa (via the slave trade) (see, e.g., references REF233 and REF234 of the list of references provided hereinbelow). Hence, nearly all Puerto Ricans represent the Hispanic Ethnicity, Native American and African American races, see Plessey v. Ferguson 163 U.S. 537 (1896). Presently, healthcare, including cancer care, in Puerto Rico, is decentralized. Therefore, in a single cancer care team, there will be multiple private practice healthcare providers that may or may not be working in collaboration. Further, the floods related to Hurricane Maria, also left Puerto Rico with a heavy burden of black mold—a major public health hazard/concern. Mold produces allergens, irritants; certain molds produce toxic substances known as mycotoxins (i.e., known carcinogen). Allergens and irritants produced by mold can result in allergic reactions in sensitive individuals via IgE-mediated mechanisms. Individuals with chronic exposures to mold, frequently experience the following symptoms: sneezing, cough (52%), runny nose (i.e., rhinitis)(62%), red eyes, skin rashes, respiratory symptoms/asthmatic attacks (34%), fatigue (23%), central nervous system symptoms (25%), headaches/migraines (34%) and cancer (see, e.g., references REF235-REF237 of the list of references provided hereinbelow).

The pathogenesis of mycotoxin-induced cancers is well-documented within the medical literature (see, e.g., reference REF236 of the list of references provided hereinbelow). Specifically, the patho-mechanism involves the absorption of liposoluble mycotoxins via mucous membranes (e.g., gastrointestinal, respiratory tract) into the blood stream and subsequent dissemination throughout the body. Mycotoxins are then able to penetrate human cells and modify the cellular genome, resulting in mutations that may lead to the development of cancer (see, e.g., reference REF236 of the list of references provided hereinbelow). Chronic inflammation resulting from longstanding environmental exposures (e.g., mold) has also been associated with the development of cancer, in addition to diabetes mellitus, cardiovascular disease and autoimmune disorders (see, e.g., reference REF238 of the list of references provided hereinbelow). Chronic inflammation may be an additional mechanism by which mold exposure leads to cancer (see, e.g., reference REF238 of the list of references provided hereinbelow). Presently, it may be unknown what the absolute and relative risks of mold exposure and development of cancer are.

Underrepresented minorities comprise less than 10% of participation in clinicals trials and less than 5% in clinical trials related to cancer, which is far less than their representation the U.S. Census (i.e., 13% African-American, 12.5% Hispanic-American) (see, e.g., reference REF239 of the list of references provided hereinbelow). Consequently, guidelines developed from said investigative efforts may not be reflective of minority health needs. As a commonwealth of the U.S., Puerto Rico represents fertile soil for increasing participation of underrepresented minorities in clinical trials. Therefore, the project and investigations proposed herein, represents an opportunity to increase the proportion of underrepresented minorities involved in trials to guide evidence-based clinical practice, to a level commensurate with the representation of these groups by the U.S. Census.

Prostate cancer radiotherapy and sexual toxicities may be handled by the platform. Prostate cancer (Pca) is the number one cancer diagnosed in men with 183,529 new cases diagnosed in 2015 alone; it is the second leading cause of cancer-related deaths in men with 28,848 men dying as result of prostate cancer in 2015. Prostate cancer trailed only lung and bronchial cancer in this regard (see, e.g., reference REF240 of the list of references provided hereinbelow). After prostate radiotherapy, patients often report impaired sexual function; including erectile dysfunction ("ED"), increased time until orgasm, decreased intensity of orgasm and/or dry ejaculation. Tactile sensation of the penis, scrotum, perineum, and anal regions generally remains intact (see, e.g., reference REF241 of the list of references provided hereinbelow). Sexual toxicities are common regardless of RT modality and increase during each year of follow-up. For example, reported ED rates increase with time from treatment, with 4% ED rates at one month, increasing to 47% at 60 months post-therapy (see, e.g., reference REF242 of the list of references provided hereinbelow). Another study by Donovan et al. reviewing patient-reported outcomes among 1,643 men participating in the Prostate Testing for Cancer and Treatment ("ProtecT") randomized controlled trial revealed that radiotherapy negatively effects sexual function peaking at 6 months, followed by some recovery, then stability of a newly established sexual functional status (while maintaining superior preservation of sexual function compared with radical prostatectomy at all time points) (see, e.g., reference REF243 of the list of references provided hereinbelow).

Innovations in screening and treatment (whether radiation or surgical therapy) of Pca are translating into a steadily increasing population of survivors. However, this survivor population must contend with the long-term side effects of their treatment (e.g., urinary and/or sexual problems), necessitating development of methods to mitigate these toxicities and maintain their quality of life (QOL) (see, e.g., references REF244-REF246 of the list of references provided hereinbelow). Patients with Pca report significantly decreased QOL owing to decreased sexual function and/or sexual toxicities related to definitive treatment (see, e.g., references REF247 and REF248 of the list of references provided hereinbelow). The Pca patient's experience can extend to impairing the QOL of the partner as well (see, e.g., reference REF249 of the list of references provided hereinbelow), ultimately leading to relationship difficulties and increased regret after Pca treatment. To this end, it has been reported that men are willing to accept a 10% decrease in overall survival if the inferior treatment regimen would optimize preservation of their erectile function (see, e.g., reference REF250 of the list of references provided hereinbelow).

Medical devices are prescribed to men with refractory ED following prostaglandin esterase 5 inhibitor ("PDE-5i") monotherapy, or to enhance the erection produced with PDE-5i. Vacuum erection devices ("VED") mechanically engorge the corpora and glans with venous blood to produce an erection that is independent of autonomic or sensory neuronal control (that may be compromised to varying degrees with irradiation) (see, e.g., reference REF246 of the list of references provided hereinbelow). The device may include a clear plastic cylinder with a vacuum seal that is placed around the penile base. A manual or electric pump then produces a negative pressure within the cylinder to pull blood into the phallus (see, e.g., reference REF251 of the list of references provided hereinbelow). If the patient is unable to maintain the erection after VED-induced erection, an elastic constriction ring may be placed at the base of the penis for up to 30 minutes to maintain the erection throughout sexual intercourse. Erectile efficacy rates (intercourse) using VEDs are as high as 90%, but reported satisfaction ranges from 30-70% (see, e.g., references REF252 and REF253 of the list of references provided hereinbelow).

VEDs have been used for penile rehabilitation after radical prostatectomy, where patients are more likely to develop immediate ED following treatment (see, e.g., references REF254 and REF255 of the list of references provided hereinbelow). There are few studies examining VED use during or following radiation therapy. One report indicated that radiotherapy patients were less likely to use a VED compared to patients who had undergone prostatectomy (see, e.g., reference REF256 of the list of references provided hereinbelow). It is unclear whether this finding is related to decreased need for device usage following radiotherapy in comparison to prostatectomy or decreased knowledge of the device by radiation oncologists.

A recent meta-analysis demonstrated some potential benefit of VEDs during prostatic irradiation (see, e.g., reference REF257 of the list of references provided hereinbelow). Maintenance of erection requires neurovascular cavernosal reactivity and venous occlusion. Given the inhibition of the 69 ethici-cavernosal reflex loop following radiotherapy, VEDs may be a good option to achieve vascular engorgement and to maintain ejaculatory ductal patency (see, e.g., references REF244 and REF246 of the list of references provided hereinbelow). Regular erections, even in the absence of intercourse, can help to preserve vascular patency in the cavernosa during periods of psychogenic or iatrogenic impotency (see, e.g., references REF244-REF246 of the list of references provided hereinbelow). VEDs can enhance the efficacy of PDE-5i by bypassing the need for internal/external stimuli during states of acute neurotoxicity when the neuronal action potentials along autonomic and sensory nerves innervating the penis are diminished (see, e.g., references REF258 and REF259 of the list of references provided hereinbelow). VED can lead to reduced radiation sexual toxicities if utilized during and after prostate radiotherapy (see, e.g., references REF244 and REF246 of the list of references provided hereinbelow).

Sexual toxicities associated with prostate cancer radiotherapy has been examined. An open label trial may address important questions for optimizing and standardizing the management of commonly encountered prostate radiation toxicities. This trial is needed to advance scientific understanding/knowledge and clinical practice in this area of oncology, as no similar trial has been conducted to date. Further, the trial may demonstrate the utility of the project platform system. Hypothesis: VED use during and after prostate radiotherapy can lead to reduced radiation sexual toxicities (see, e.g., references REF244 and REF246 of the list of references provided hereinbelow). Significance: If this hypothesis is shown to be true, the use of VED could tremendously impact QoL measures for prostate cancer survivors. Study Design: Prospective open label trial. Masking: None (Open Label).

The following statistical analyses may be performed: ANOVA, Kaplan-Meir, Incidence ratio with Cox Proportional Hazard regression, Odds ratio with Logistic regression, Stratified analysis of incidence ratio or difference, Life table analysis of cumulative probabilities, or Stratified analysis proportion difference or ratio or odds ratio, depending on the data type (Continuous and/or Nominal independent variables, vs. Normal independent variables (see, e.g., reference REF303 of the list of references provided hereinbelow). All standard deviations (for comparisons of data points with means (detection of outliers) and standard errors of the mean (for comparisons of means) will be determined using equipartition of variance. For this particular study, patients that have enrolled in the project platform who have been diagnosed with prostate cancer with plans to undergo prostate radiotherapy will be identified. The patients will be stratified by their prescribed fractionation (e.g., standard fractionation, hypofractionation, and stereotactic body irradiation) and randomly assigned to two study groups: control (no intervention) and VED use (intervention). Each patient in the intervention group will be asked to achieve a maximal erection with a VED, three times a week to begin on day 1 of their prostate radiotherapy and continued for an 8 month period. The patients in both study groups will be asked to complete a SHIM questionnaire at baseline, month 1, month 2, month 3, month 4, month 5, month 6, month 7, and month 8. Rigiscan measurements of penis blood pressure will be obtained at baseline, month 2, month 6 and month 8. QoL questionnaires will be completed by each patient for close out at month 8.

Primary Outcome Measures: 1. SHIM Score (as a proxy for erectile function) [Time Frame: 8 months]. Secondary Outcome Measures: 1. Rigiscan reported penile blood pressure change from baseline to 8 months; 2. Patient reported outcomes related to QoL; 3. The effect of fractionation (e.g., standard fractionation, hypofractionation, and stereotactic body irradiation) on the development of erectile, ejaculatory and orgasmic dysfunction with or without VED use.

Data Management and Statistical Analysis (see, e.g., references REF260 and REF261 of the list of references provided hereinbelow): Multi-variate analysis will be performed using ANOVA. Kaplan-Meir plots will be made for analysis of time to endpoint (cumulative loss of function (or survival) for each treatment group and tested for significance of difference between groups using Cox Proportional Hazard regression. If Odds ratios need to be used, Logistic regression will be used. Statistical differences will be tested using Chi Square. For Time dependent nominally independent variables, Stratified analysis will be applied to incidence ratio or difference data. Cumulative probabilities will be analyzed using Life Table Analysis. Statistical differences will be tested using the Mantel-Haenszel test. For time-independent nominally independent variables, Stratified analysis will be used with statistical differences tested by Mantel-Haenszel test. All standard deviations (for comparisons of data points with means (detection of outliers) and standard errors of the mean (for comparisons of means)) will be determined using equipartition of variance.

Figure 17:
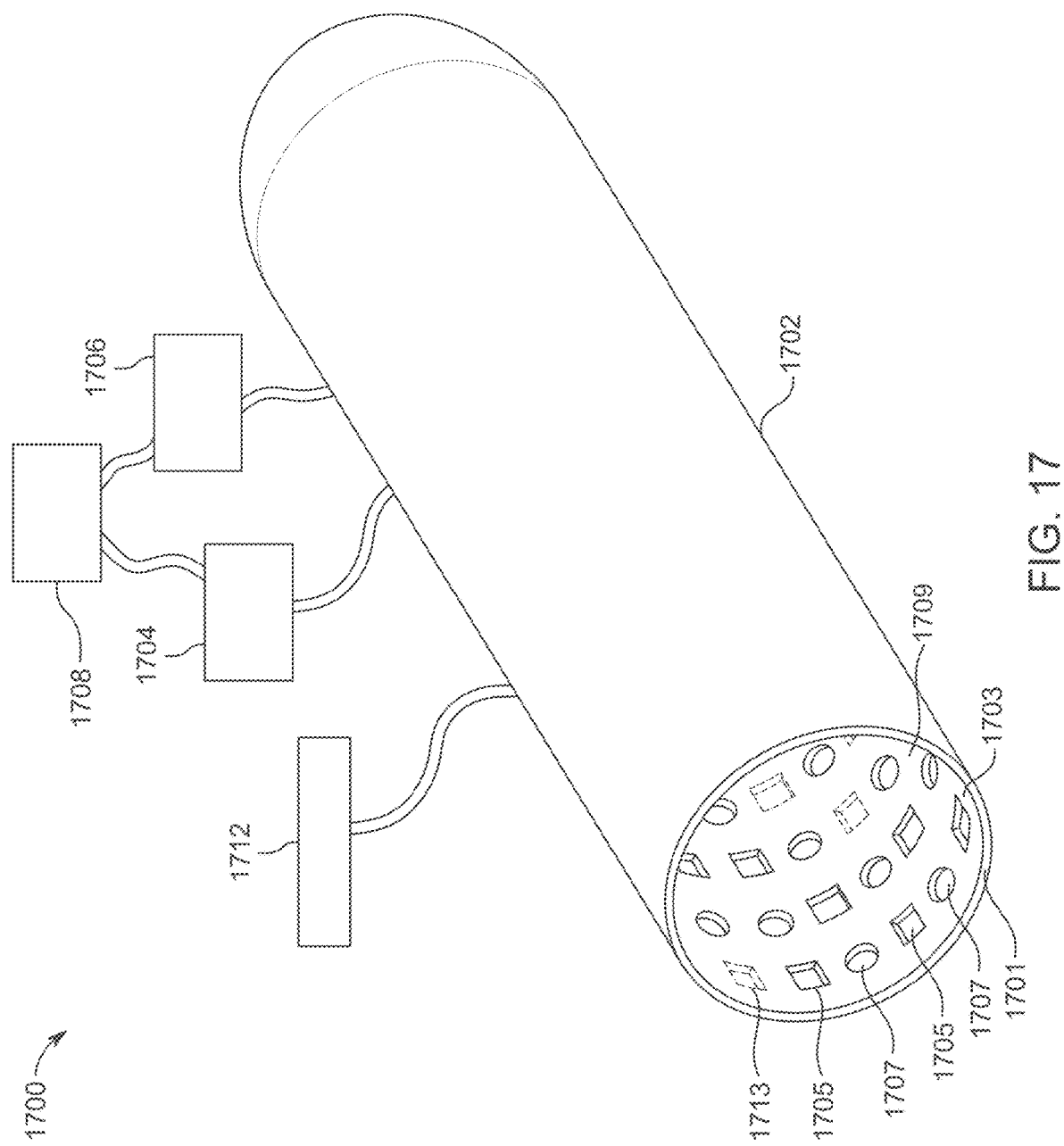
FIG. 17 is a perspective view of a therapy system for a patient appendage.

For example, as shown in FIG. 17, an appendage radiotherapy system 1700 may be provided with a hollow (e.g., cylindrical) body 1702 that may be configured with any suitable geometry to enable receiving within hollow 1709 through an open end 1701 an entire or part of any suitable patient body appendage (e.g., penis, arm, finger, nose, etc.) prior to and/or during radiotherapy, and/or for at least six months after completion of radiotherapy. Hollow cylindrical body 1702 may be coupled to any suitable suctioning apparatus 1704 that may provide a suctioning capacity along an interior surface 1703 of hollow 1709 of body 1702 (e.g., when the body appendage is positioned within the hollow of body 1702), such as for suctioning any suitable fluid in hollow 1709 through one or more suction passageway openings 1705 provided through surface 1703. Moreover, system 1700 may include any suitable radiotherapy or light apparatus 1706 that may provide any suitable light on the body appendage when it is positioned within hollow 1709 of body 1702. For example one or more light emitters (e.g., infrared light emitters) may be operative to shine light from apparatus 1706 through one or more light passageway openings 1707 provided through surface 1703 and onto the mucosal lining of the body appendage (e.g., to shoot light radially inward when the body appendage is positioned within hollow 1709 of body 1702). Additionally or alternatively, system 1700 may include any suitable magnet apparatus 1712 that may provide any suitable magnetic energy on the body appendage when it is positioned within hollow 1709 of body 1702. For example one or more magnetic coils may be operative to provide magnetic energy from apparatus 1712 through one or more magnetic energy passageway openings 1713 provided through surface 1703 and onto the mucosal lining of the body appendage (e.g., to magnetically stimulating radially inward when the body appendage is positioned within hollow 1709 of body 1702). Any suitable number of openings 1705, 1707, and/or 1713 may be arranged in any suitable pattern along the length of interior surface 1703 of hollow 1709 of body 1702 (e.g., evenly distributed, mesh pattern, randomly, etc. (e.g., along the entirety, or the same or different specific portions of surface 1703, etc.)). Any suitable controller 1708 may be coupled to apparatus 1704, 1706, and 1712 for simultaneously controlling (e.g., electronically) the suctioning, light (e.g., energy) emitting, and/or magnetic stimulation in an intelligent manner commensurate with the needs of the patient. As just one example, system 1700 may provide a VED that may be used for suctioning a penis during and/or before and/or after IR light may be emitted onto the penis, which may decrease scarring, and/or during and/or before and/or after magnetic stimulation may be provided onto the penis, which may increase nerve conduction.

Figure 18:
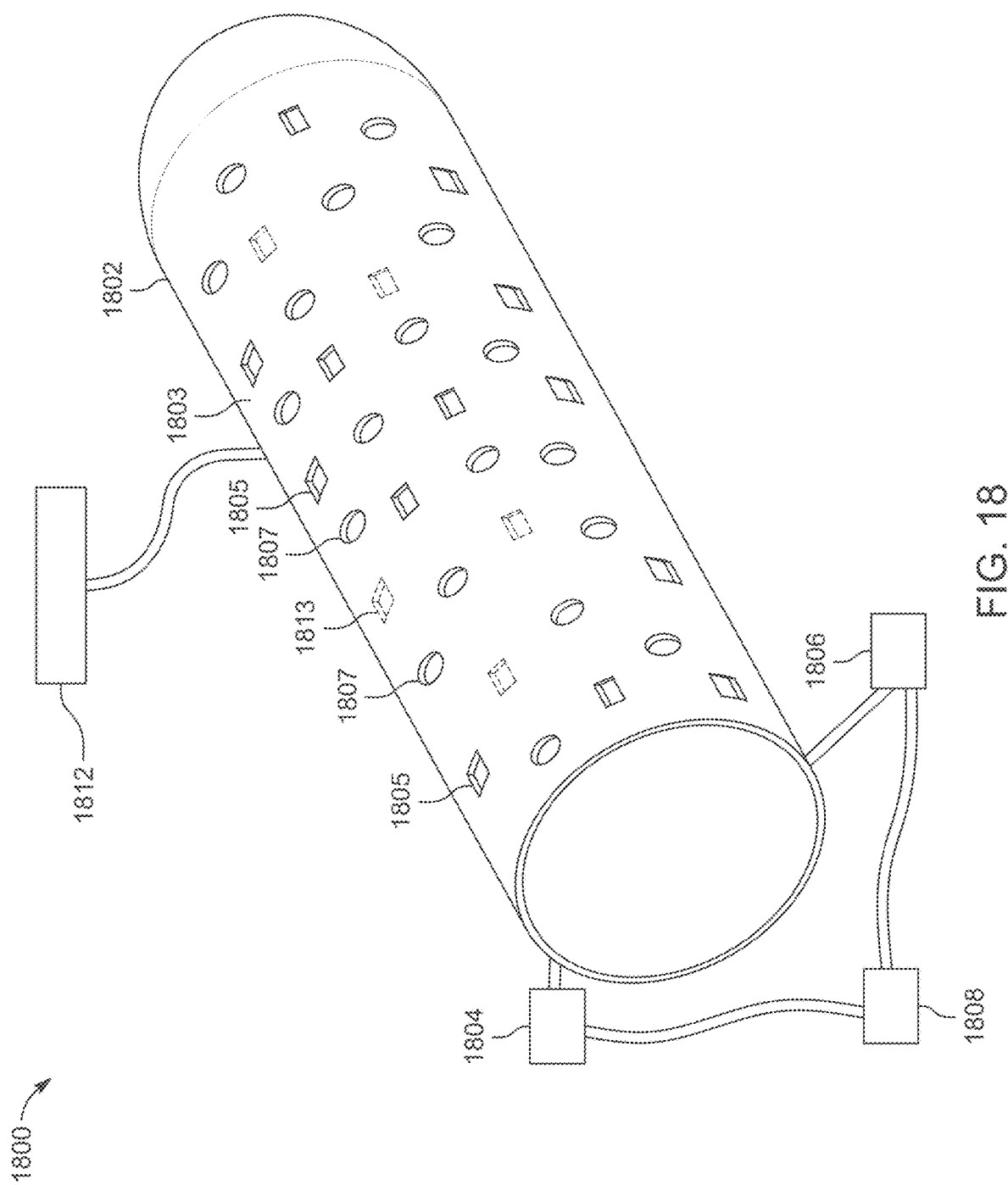
FIG. 18 is a perspective view of a therapy system for a patient cavity.

As another example, as shown in FIG. 18, a cavity radiotherapy system 1800 may be provided with a body 1802 that may be configured with any suitable geometry to enable any suitable portion or the entirety thereof being receiving within a hollow of any suitable patient body cavity (e.g., vagina, ear canal, etc.) prior to and/or during radiotherapy, and/or for at least six months after completion of radiotherapy. Body 1802 may be coupled to any suitable suctioning apparatus 1804 that may provide a suctioning capacity along an exterior surface 1803 of body 1802 (e.g., when the body 1802 is at least partially positioned within the patient body cavity), such as for suctioning any suitable fluid in the environment through one or more suction passageway openings 1805 provided through surface 1803. Moreover, system 1800 may include any suitable radiotherapy or light apparatus 1806 that may provide any suitable light on the patient body cavity when body 1802 is positioned at least partially within the patient body cavity. For example one or more light emitters (e.g., infrared light emitters) may be operative to shine light from apparatus 1806 through one or more light passageway openings 1807 provided through surface 1803 and onto the mucosal lining of the patient body cavity (e.g., to shoot light radially outward when body 1802 is at least partially positioned within the patient body cavity). Additionally or alternatively, system 1800 may include any suitable magnet apparatus 1812 that may provide any suitable magnetic energy on the patient body cavity when body 1802 is positioned at least partially within the patient body cavity. For example one or more magnetic coils may be operative to provide magnetic energy from apparatus 1812 through one or more magnetic energy passageway openings 1813 provided through surface 1803 and onto the mucosal lining of the patient body cavity (e.g., to offer magnetic field coverage radially outward when body 1802 is at least partially positioned within the patient body cavity). Any suitable number of openings 1805, 1807, and/or 1813 may be arranged in any suitable pattern along the length of surface 1803 of body 1802 (e.g., evenly distributed, mesh pattern, randomly, etc. (e.g., along the entirety, or the same or different specific portions of surface 1803, etc.)). Any suitable controller 1808 may be coupled to apparatus 1804, 1806, and 1812 for simultaneously controlling (e.g., electronically) the suctioning and light (e.g., energy) emitting, and/or magnetic stimulation in an intelligent manner commensurate with the needs of the patient. As just one example, system 1800 may be used for suctioning the patient body cavity during and/or before and/or after IR light may be emitted onto the patient body cavity, which may decrease scarring, and/or during and/or before and/or after magnetic stimulation may be provided onto the patient body cavity.

System 1700, system 1800, and/or the like (e.g., catheters, needles, endoscopes, and/or the like) may be provided with such light passageway openings or surface holes to allow any suitable light, such as UV, blue light (e.g., for bacteria), infrared light (e.g., for scar reduction/inhibition), and/or the like, to pass through and penetrate target tissue, where the holes can be covered with quartz glass or any suitable light transparent material for sterilization ability for subsequent treatment of other patients.

Magnetic stimulation of peripheral neuropathy may be provided by the platform. The concept may involve adoption of transcrainial magnetic stimulation technology (e.g., BrainsWay) and applying to any appendage of a patient (e.g., hands, feet, penis, and/or limb stumps) with peripheral neuropathy. The magnetic coils may be distributed in an arrangement that would offer magnetic field coverage to the entire appendage. The magnetic stimulation can result in re-myelination of nerves, which may translate into small-nerve repair in the hands and feet of patients with conditions such as diabetic neuropathy or smokers neuropathy. Terminal nerve recovery or some other mechanism induced by magnetic stimulation may ameliorate the re-charge pain associated with limb amputation. Decreased nerve conduction in men with erectile disfunction may be provided therapy for recovering nerve conduction through such magnetic stimulation.

EMR-induced de novo expression or upregulation of FOLH1 for FOLH1 targeted drug, radioisotope or gene therapy (e.g., CRISPR Cas9) delivery may be provided by the platform. Tumor necrosis factor ("TNF")-alpha upregulates FOLH1 expression in tumor cells and neovessels has been identified (see, e.g., reference REF072 of the list of references provided hereinbelow). Since IR EMR induces secretion of TNF-alpha, that irradiation of cells may also induce or upregulate expression of FOLH1. Eternal beam ionizing radiation EMR upregulated FOLH1 expression in prostate cancer cell lines may be demonstrated. Ionizing radiation EMR or other stimulation of FOLH1 expression for the purpose of FOLH1 targeted drug, radioisotope or gene therapy (e.g., CRISPR Cas9) delivery is possible.

External beam irradiation and androgen deprivation upregulate FOLH1 target expression for antibody-based brachytherapy and antibody-drug conjugates in prostate cancer may be provided by the platform (e.g., external beam irradiation upregulates FOLH1 expression).

Prostate cancer is the most prevalent solid tumor in men. J591 is a monoclonal antibody (mAB) to folate hydrolase-1 (FOLH1), also known as prostate-specific membrane antigen (PSMA), that possesses the ability to sensitively and specifically target disseminated prostate tumor cells, thereby increasing the therapeutic index of any conjugated cytotoxic agent or the therapeutic ratio of conjugated radioisotopes. The effects of fractionated or single-fraction irradiation on FOLH1 biomarker expression in LNCaP (androgen sensitive cells) and in CWR22Rv1 (androgen resistant cells) with and without androgen deprivation therapy ("ADT") may be characterized by the platform. The in vitro results show that FOLH1 expression increases with ADT and 2 Gray (Gy) fractionated irradiation, but not with single-fraction ablative doses of 7.5 Gy. These results suggest that standard-of-care treatment with ionizing radiation and ADT alters the biomarker landscape, in which increased FOLH1 target expression would increase the therapeutic-index or -ratio of J591 conjugates by way of increased drug/radioisotope endocytosis. When validated in a clinical trial setting (see, e.g., reference REF304 of the list of references provided hereinbelow), these findings impact the current prostate cancer treatment paradigm.

Prostate cancer (Pca) remains the most prevalent solid tumor in men (see, e.g., reference REF262 of the list of references provided hereinbelow). It is estimated that in 2018, there were 1,26,106 new Pca cases worldwide and 358,989 deaths associated with Pca (Globocan 2018, www.Gco.iarc.fr). Pca is usually a slow-growth disease, with a 95% relative survival among all diagnosed cases over a 15-year period (American Cancer Society) External beam radiotherapy (EBRT) and interstitial brachytherapy are the most common forms of radiotherapy used to treat Pca. The folate hydrolase-1 (FOLH1; also known as prostate-specific membrane antigen ("PSMA"); glutamate carboxypeptidase II (GCPII); N-acetyl-L-aspartyl-L-glutamate peptidase I ("NAALADase I")) enzyme encoded by the FOLH1 gene is garnering considerable interest as a highly specific theragnostic target for Pca and several other solid tumors (see, e.g., reference REF263 of the list of references provided hereinbelow). In Pca, the degree of FOLH1 up-regulation directly correlates with Pca histopathological grade, stage, and androgen resistance, (e.g., castrate-resistant prostate cancer; CR-Pca) (see, e.g., references REF264-REF267 of the list of references provided hereinbelow). Of particular therapeutic interest, J591, a monoclonal antibody (mAB) to FOLH1, is specific to, and is effectively endocytosed after binding to the extracellular domain of FOLH1 (see, e.g., references REF268 and REF269 of the list of references provided hereinbelow). Thus, J591 provides a platform for antibody-based cytotoxic agent or radionuclide (i.e., brachytherapy) delivery selectively within FOLH1-expressing Pca cells. PSMA, also known as folate hydrolase 1 ("FOLH1"), is a highly specific biomarker and therapeutic target for Pca. J591, a monoclonal antibody specific to PSMA, may be a primary method used to detect PSMA expression, and may be a vehicle to deliver targeted therapies to Pca cells. ADT may upregulate PSMA. Preclinical models of androgen resistant ("AR") xenografts demonstrate PSMA upregulation by ADT increases the therapeutic index of J591-drug conjugates, suggestive of enhanced drug uptake. The effect of external beam radiation (EBRT) on PSMA expression in PC cells±ADT has been evaluated.

The mechanism underlying increased FOLH1 expression on Pca cells or neovessels may be further investigated. FOLH1 upregulation in Pca may be partially mediated through nitric oxide (see, e.g., reference REF270 of the list of references provided hereinbelow). Within blood vessels, nitric oxide (NO) is produced by endothelial nitric oxide synthase (NOS; eNOS/NOS1) and is modulated by calcium/calmodulin (see, e.g., reference REF271 of the list of references provided hereinbelow). NO further generates cyclic guanosine monophosphate (cGMP), leading to cellular membrane permeabilization and the passage of cells (see, e.g., reference REF272 of the list of references provided hereinbelow). Previous studies demonstrate that the eNOS inhibitor cavtratin decreases microvasculature permeability, blocking tumor growth (see, e.g., references REF273 and REF274 of the list of references provided hereinbelow).

A tumor-secreting FOLH1-induction factor in the 50-100 kDa molecular weight range has been characterized (see, e.g., reference REF275 of the list of references provided hereinbelow). Increased neovascular FOLH1 expression has been demonstrated in androgen-resistant (AR)-Pca xenografts that constitutively express less cellular FOLH1 than androgen-sensitive (AS) lines, such as LNCaP, suggesting there is a balance to the ratio of neovascular to cellular expression of FOLH1 in Pca (see, e.g., reference REF275 of the list of references provided hereinbelow). Proteomic data presented at the American Association for Cancer Research annual meeting in 2017 (poster #1905) demonstrated that TNF-$\alpha$ (predicted molecular weight of 25.6 kDa) is responsible for partial FOLH1 upregulation in melanoma. As ionizing radiation increases regional TNF-$\alpha$ expression, it may be hypothesized and demonstrated that irradiation of melanoma cell lines could upregulate FOLH1 expression (see, e.g., reference REF276 of the list of references provided hereinbelow).

FOLH1 targeting has been shown to increase the therapeutic index of cytotoxic agents both in vitro and in preclinical models. In vitro studies have demonstrated a 700-fold increase in the cytotoxic activity of J591-auristatin conjugate compared to unconjugated J591 and free auristatin in Pca (see, e.g., reference REF277 of the list of references provided hereinbelow). Induced FOLH1 upregulation may further increase the therapeutic-index or -ratio of other J591 conjugates.

The objective of a study of the platform is to characterize the effects of fractionated and single-fraction irradiation on FOLH1 expression in androgen-sensitive (AS; LNCaP) and androgen-resistant (AR; CWR22Rv1) cell lines, with and without androgen deprivation therapy.

Androgen deprivation and EBRT may be used. LNCaP and CWR22Rv1 cell lines were gifted by Dr. Neil H. Bander (Weill Cornell Medicine). LNCaP cells are AS human prostate adenocarcinoma cells derived from the left supraclavicular lymph node metastasis from a 50-year-old Caucasian male. They are adherent epithelial cells growing in aggregates and as single cells (see, e.g., reference REF284 of the list of references provided hereinbelow). CWR22Rv1 cells are AR human prostate carcinoma epithelial cell line derived from a xenograft that was serially propagated in mice after castration-induced regression and relapse of the parental, androgen-dependent CWR22 xenograft (ATCC CRL-2505).

Each cell line (e.g., Androgen sensitive LNCaP and androgen resistant CWR22Rv1 PC cell lines) was cultured in standard media (see, e.g., reference REF269 of the list of references provided hereinbelow) and charcoal-stripped media (i.e., removal of androgens; androgen deprivation therapy ("ADT")) for two weeks. Approximately $3 \times 10^6$ cells were plated using 15 T-75 flasks for each media growth group. Both cell lines in each growth media were grown in a standard cell culture growth chamber and had a subgroup of un-irradiated cells to serve as a control. Those un-irradiated cells were grown to confluence and tumor-released parameters for each fraction cohort.

Both cell lines were grown in both media conditions, and received either no external beam radiation therapy ("EBRT"), EBRT in 2 Gray (Gy; XRAD 225 Precision X-Ray INC. N Branford, Conn.) daily fractions to a cumulative maximum of 10 Gy, or 7.5 Gy in 1 fraction. Specifically, the 2 Gy irradiation proceeded as follows: on day 1, 10 T-75 flasks were irradiated at the defined dose. On day 2, 8 T-75 flasks were re-irradiated at the defined dose. On day 3, 6 T-75 flasks were re-irradiated at the defined dose. On day 4, 4 T-75 flasks were re-irradiated at the defined dose. On day 5, 2 T-75 flasks were re-irradiated at the defined dose. 24 hr after each delivered fraction (on days 1-5), a cohort of 2 irradiated and 1 un-irradiated T-75 flasks were trypsinized and prepared for flow cytometry. Similarly, cohorts of flasks at various times after the single 7.5 Gy dose were trypsinized and prepared for flow cytometry.

FOLH1 cell surface expression—Cell surface FOLH1 expression was measured by flow cytometry (DxP, Cytek) as mean fluorescence intensity 24 hr after each 2 Gy fraction, or on days 1, 3, 5, 7, and 9 after a single 7.5 Gy fraction. Briefly, all cells were treated with DNAse and fixed with 4% paraformaldehyde for 30 min. at room temperature. J591 and goat/mouse monoclonal antibody (mAB) conjugated to Alexa-488 (1:50 dilution) were used as primary and secondary mABs, respectively. Primary mAB incubation time was 1 hr; secondary mAB incubation time was 30 min at room temperature.

Results: Androgen deprivation and EBRT may be provided by the platform. LNCaP in standard media upregulated FOLH1 by 2.97-fold (SEM±0.72) with fractionated EBRT to a cumulative dose of 4 Gy, peaking on days 2 and 3 after receiving cumulative doses of 4 Gy and 6 Gy, respectively. For example, as shown by graph 1400 of FIG. 14, fractionated EBRT upregulated FOLH1 in LNCaP cells to a cumulative dose of 4 Gy, LNCaP in standard media upregulated PSMA by 2.97-fold (SEM±0.72) with fractionated EBRT to a cumulative dose of 4 Gy, peaking on days 2 and 3 after 4 Gy and 6 Gy cumulative doses, respectively. CWR22Rv1 in standard medium, upregulated FOLH1 (PSMA) expression by 3.21-fold (SEM±0.44) after a cumulative dose of 8 Gy, peaking on day 4. For example, as shown by graph 1500 of FIG. 15, fractionated EBRT upregulated FOLH1 in CWR22Rv1 cells to a cumulative dose of 8 Gy but may not have the same effects in combination with ADT alone, with CWR22Rv1 in standard medium, upregulated PSMA expression by 3.21-fold (SEM±0.44) after a cumulative dose of 8 Gy, peaking on day 4.

Figure 14:
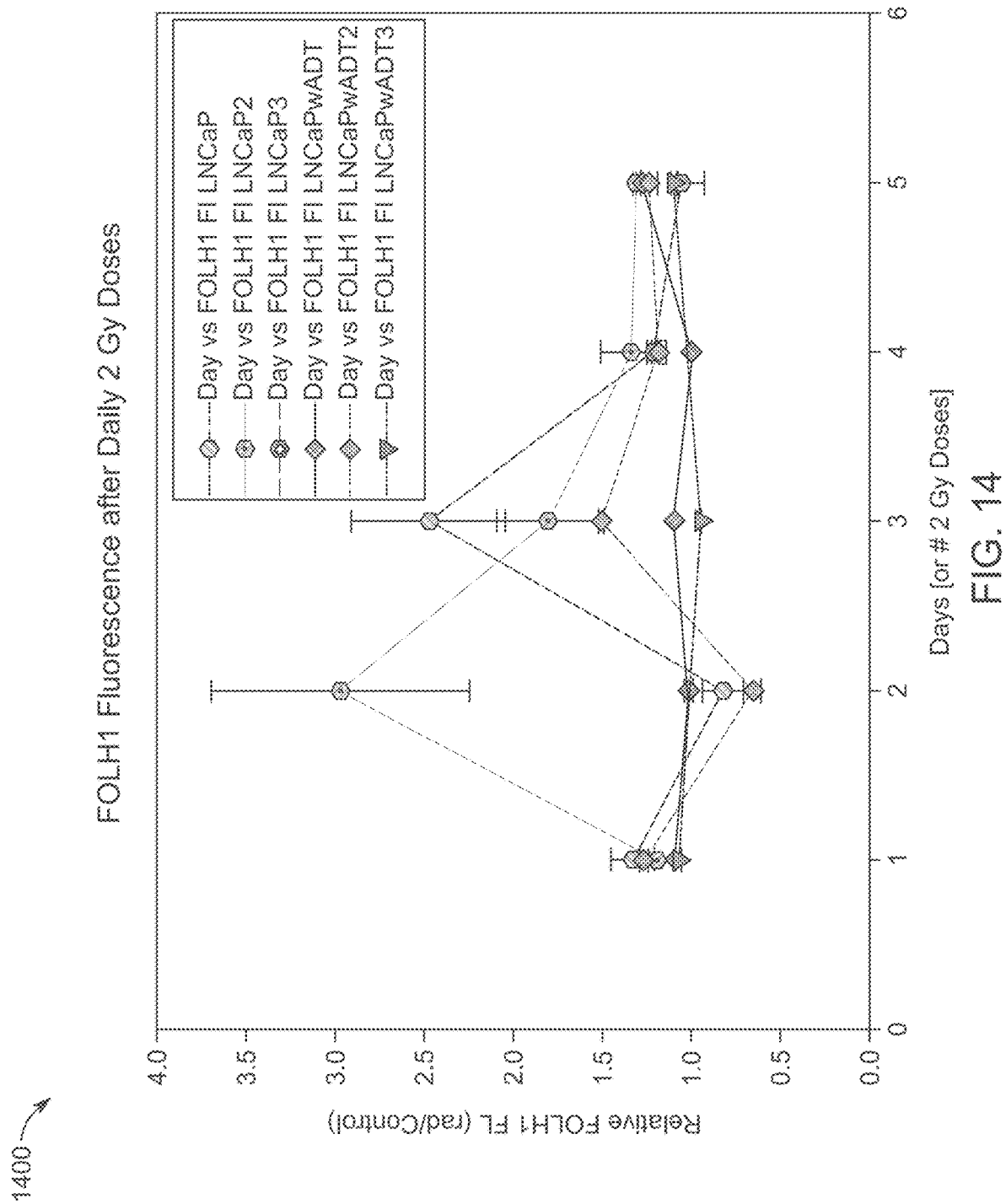
FIG. 14 is a graph of fractionated EBRT upregulated FOLH1 in LNCaP cells.
Figure 15:
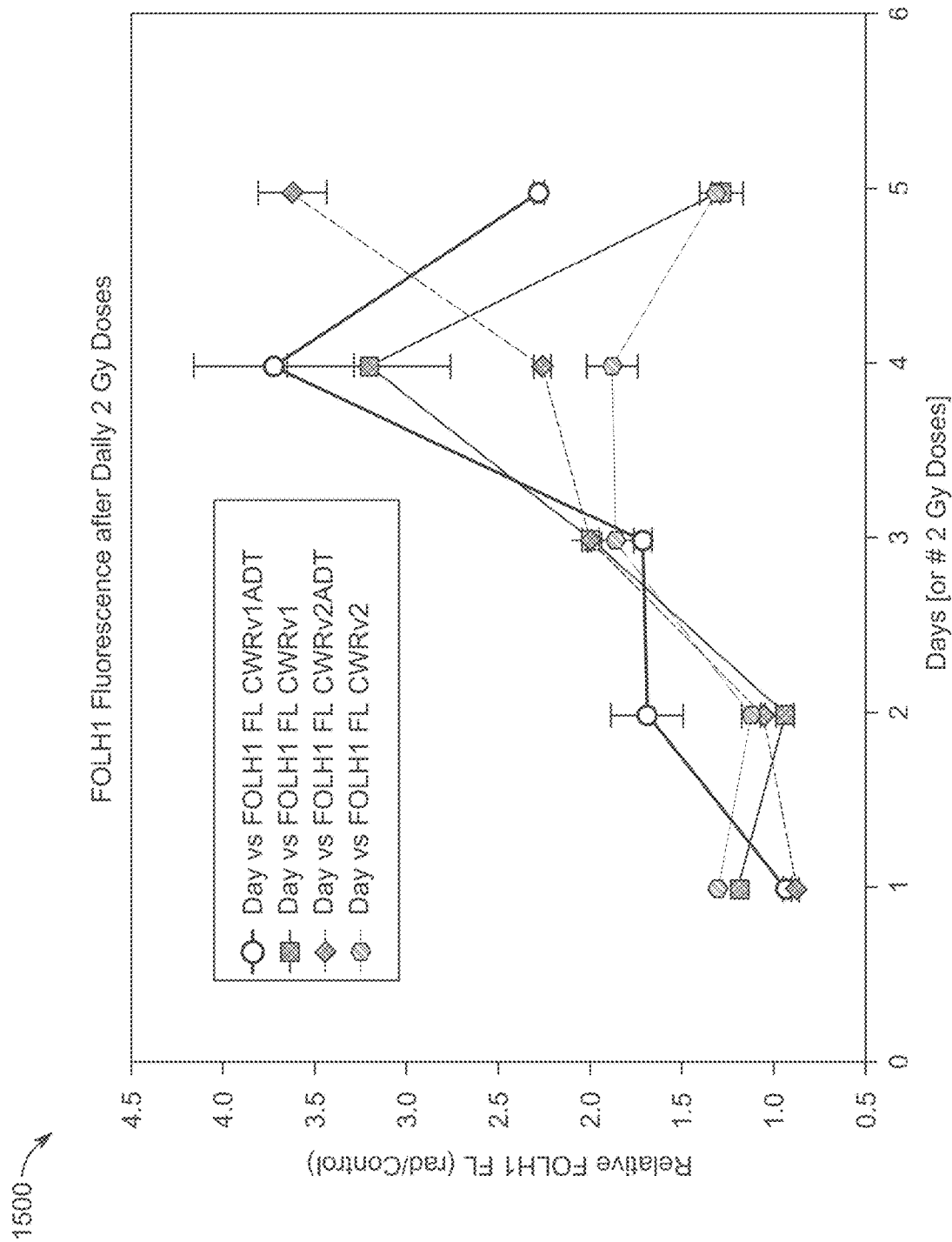
FIG. 15 is a graph of fractionated EBRT upregulated FOLH1 in CWR22Rv1 cells.
Figure 16:
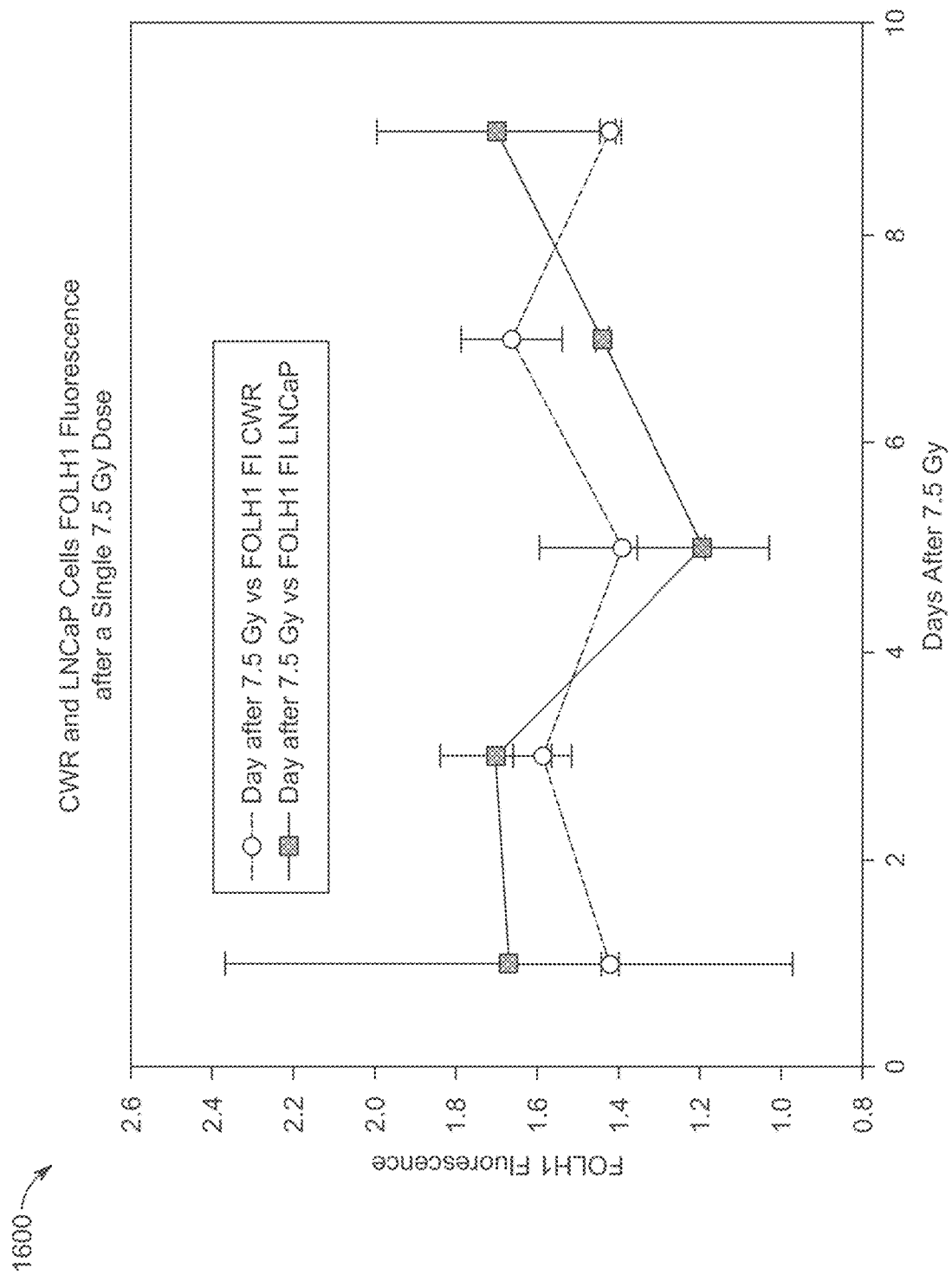
FIG. 16 is a graph of fractionated EBRT upregulated FOLH1.

In the presence of ADT (charcoal-stripped media), EBRT did not further increase LNCaP cell FOLH1 expression (maximal fold-change of 1.01 (SEM±0.02) relative to ADT alone (see, e.g., FIG. 14). Compared to CWR22Rv1 with ADT alone, ADT plus EBRT upregulated FOLH1 by 3.73-fold (SEM±0.44) after a cumulative fractionated dose of 8 Gy, peaking on days 4 and 5 (see, e.g., FIG. 15). However, 7.5 Gy in one fraction did not significantly increase FOLH1 (PSMA) expression of LNCaP or CWR22Rv1 in standard media. LNCaP showed a maximal fold-change of 1.14 (SEM±0.29) on day 9. CWR22Rv1 showed a maximal fold-change of 1.27 (SEM±0.02) on day 1. For example, as shown by graph 1600 of FIG. 16, one fraction 7.5 Gy did not increase FOLH1 expression in either LNCAp nor CWR22Rv1 cells. However, 7.5 Gy in one fraction did not significantly increase FOLH1 expression of LNCaP or CWR22Rv1 in standard media. LNCaP showed a maximal fold-change of 1.14 (SEM±0.29) on day 9. CWR22Rv1 showed a maximal fold-change of 1.27 (SEM±0.02) on day 1.

The data gathered in the above-described study demonstrates that FOLH1 expression is both independently and synergistically enhanced by ADT and by low-dose fractionated EBRT, but not with single-fraction ablative EBRT. These observations warrant additional studies using in vitro and in vivo Pca models to validate these findings. There appears to be an optimal EBRT dose range to effectively upregulate FOLH1 expression. Validation of FOLH1 upregulation by ADT and EBRT supports use of J591-drug conjugates or brachytherapy as an adjunct treatment to these standard therapies for Pca. Furthermore, if fractionated EBRT upregulates FOLH1, then targeted brachytherapy using appropriately selected J591-radionuclide conjugates may increase their own therapeutic index in a time-dependent manner via regional low-dose rate $\beta$- or Auger electron emission. The clinical implications of these results are currently under investigation in the setting of post-prostatectomy or post-EBRT patients with biochemical failure (see, e.g., reference REF304 of the list of references provided hereinbelow).

EBRT and ADT are well-established standard-of-care therapies for Pca. In the clinical setting, ADT is standardly utilized as an adjunct to radiation therapy for intermediate to high-risk localized Pca, for patients with biochemical failure status-post radiation therapy or radical prostatectomy, and in metastatic disease. Conventionally-fractionated EBRT may optimize J591 targeting of microscopic disease with an acceptable therapeutic ratio, resulting in improved local control, time to biochemical failure, and time to recurrence in patients post prostatic irradiation, or prostatectomy or with metastatic disease (see, e.g., reference REF278 of the list of references provided hereinbelow). Preclinical work has demonstrated that certain enantiomers of duocarmycin analogues are effective radiosensitizers of hypoxic cells when combined with EBRT, indicating that there may be a therapeutic benefit in combining infusions of J591-drug and -radioisotope conjugates (see, e.g., reference REF279 of the list of references provided hereinbelow). Further, J591-brachytherapy permits sensitive and specific targeting of disseminated tumor cells with ionizing radiation (a feat that is not possible with EBRT due to the tissue tolerance of surrounding tissues within the treatment field), thereby providing a unique opportunity for systemic neoantigen release that could enable development of an in situ cancer vaccine or abscopal responses when used in combination with immune check-point inhibition or CD3 T-cell stimulators.

A number of closed and ongoing clinical trials have correlated PSA response to treatment with survival benefits in the metastatic setting (see, e.g., references REF280-REF283 of the list of references provided hereinbelow) (NCT00538668, NCT02552394). While efforts underway to elucidate mechanisms of resistance to ADT, the enhanced tumor sensitivity via FOLH1 upregulation that is provided by ADT may provide a new therapeutic avenue in this setting. The biological features of FOLH1 provide a significant therapeutic opportunity to leverage and build upon both ADT and EBRT for Pca. More clinical studies are needed to validate J591-brachytherapy or drug conjugates in combination with ADT, EBRT, immune check-point inhibition or CD3 T-cell stimulators. PSMA upregulation may aid in optimizing J591 targeting for treatment of local and disseminated or micrometastatic disease. Validation of PSMA upregulation by ADT and EBRT supports use of J591-drug conjugates as an adjunct treatment to these standard therapies for PC. Furthermore, if fractionated EBRT upregulates PSMA, then targeted brachytherapy using appropriately selected J591-radionucleotide conjugates may increase its own therapeutic index in a time-dependent manner as a result of regional low-dose rate beta ("$\beta$") or alpha ("$\alpha$") emission. ADT and/or EBRT can be used to deliberately increase target expression and therefore increase the absorbed dose of ionizing radiation (or drug) delivered with antibody or small molecule-based brachytherapy.

Any suitable process may be utilized for enabling FOLH1 upregulation or androgen induced upregulation of FOLH1. One operation of the process may include applying energy to a volume of cells. Another operation of the process may include waiting some time after the energy application for FOLH1 target to upregulate or to appear de novo. Another operation of the process may include exposing the volume of cells to an embodiment (e.g., monoclonal antibodies, small molecules and antibody fragments, etc.) with target binding capacity.

Any suitable process may be utilized for increasing absorbed dose. For example, the process may provide a method for optimizing the absorbed dose of electromagnetic irradiation delivered via a target(s) within in a volume of cells (e.g., tumor). One operation of the process may include identifying the initial activity of the chemical nuclei or initial molecule quantity that is attached to an agent or embodiment (e.g., monoclonal antibodies, small molecules and antibody fragments, etc.) with target binding capacity, and/or identifying the dose rate or absorption rate of the chemical nuclei or molecule into cells within the volume; and then identifying the absorbed dose based on any suitable microdosimetry method (e.g., as described herein). Another operation of the process may include identifying the time required for target replenishment after complete or partial target depletion and/or identifying the time required for target replenishment so that 50-100% of the initial dose of chemical nuclei or molecule attached to an agent or embodiment with target binding capacity could be absorbed as a subsequent dose. Another operation of the process may include waiting a period of time, based on the first identifying operation and based on the second identifying operation, between doses of or exposures to the embodiment with target binding capacity (e.g., determining that FOLH1 targets replenish within a week). For example, the volume of cells could be tissue or tumor. For example, the cells can be animal or plant. For example, the chemical or molecule could be anything from a single element atom to a drug. For example, the agent or embodiment can be anything that can bind to both the chemical or molecule and cell target.

Figure 19:
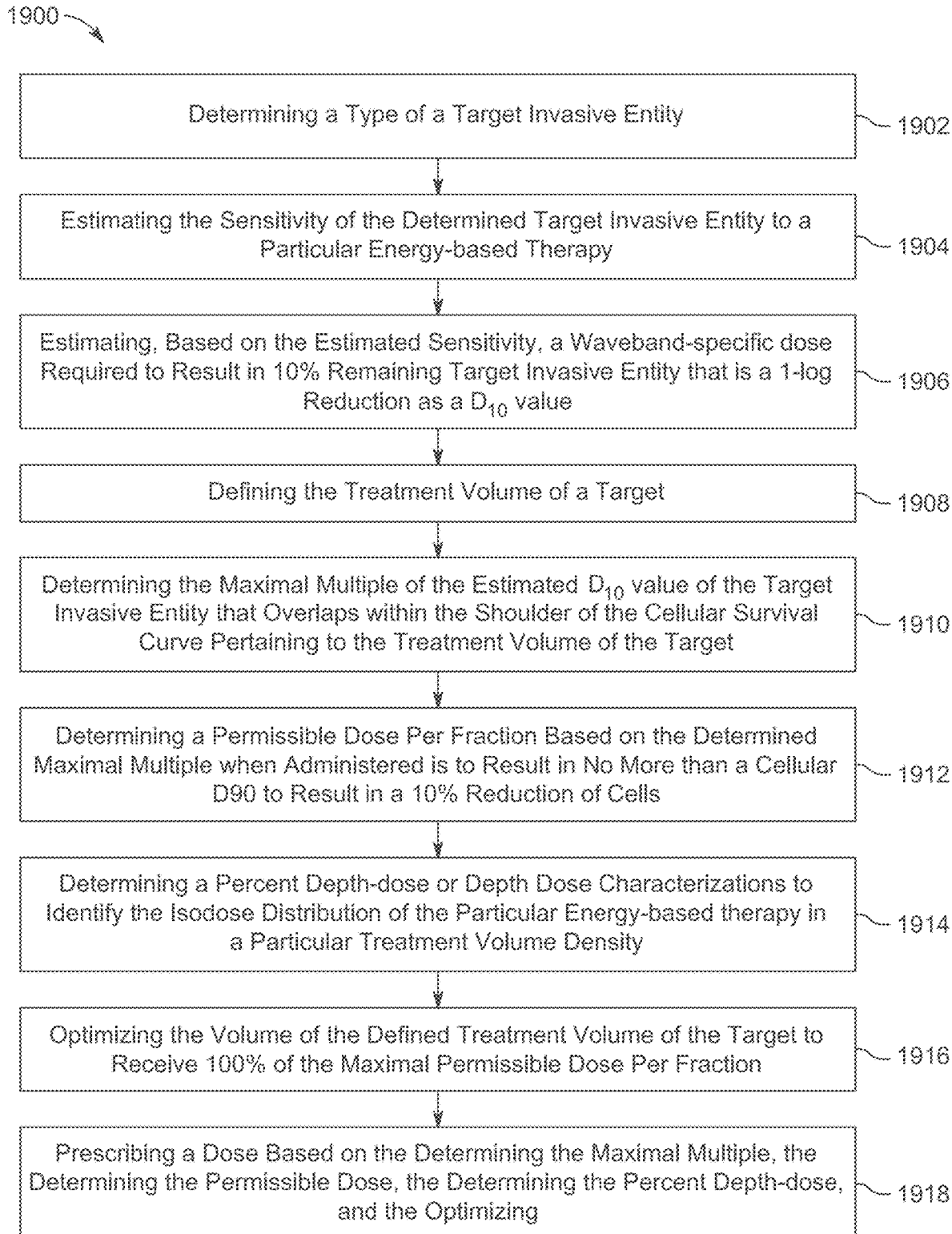
FIGS. 19-25 are flowcharts of illustrative processes.

FIG. 19 is a flowchart of an illustrative process 1900 for determining an amount of energy to be delivered to cause an end effect on a target invasive entity of a target in a host. Operation 1902 of process 1900 includes determining the type of the target invasive entity. Operation 1904 of process 1900 includes estimating the sensitivity of the determined target invasive entity to a particular energy-based therapy. Operation 1906 of process 1900 includes estimating, based on the estimated sensitivity, a waveband-specific dose required to result in 10% remaining target invasive entity that is a 1-log reduction as a $D_{10}$ value. Operation 1908 of process 1900 includes defining the treatment volume of the target. Operation 1910 of process 1900 includes determining the maximal multiple of the estimated $D_{10}$ value of the target invasive entity that overlaps within the shoulder of the cellular survival curve pertaining to the treatment volume of the target. Operation 1912 of process 1900 includes determining a permissible dose per fraction based on the determined maximal multiple when administered is to result in no more than a cellular D90 to result in a 10% reduction of cells. Operation 1914 of process 1900 includes determining a percent depth-dose or depth dose characterizations to identify the isodose distribution of the particular energy-based therapy in a particular treatment volume density. Operation 1916 of process 1900 includes optimizing the volume of the defined treatment volume of the target to receive 100% of the maximal permissible dose per fraction. Operation 1918 of process 1900 includes prescribing a dose based on the determining the maximal multiple, the determining the permissible dose, the determining the percent depth-dose, and the optimizing.

It is understood that the operations shown in process 1900 of FIG. 19 are only illustrative and that existing operations may be modified or omitted, additional operations may be added, and the order of certain operations may be altered.

Figure 20:
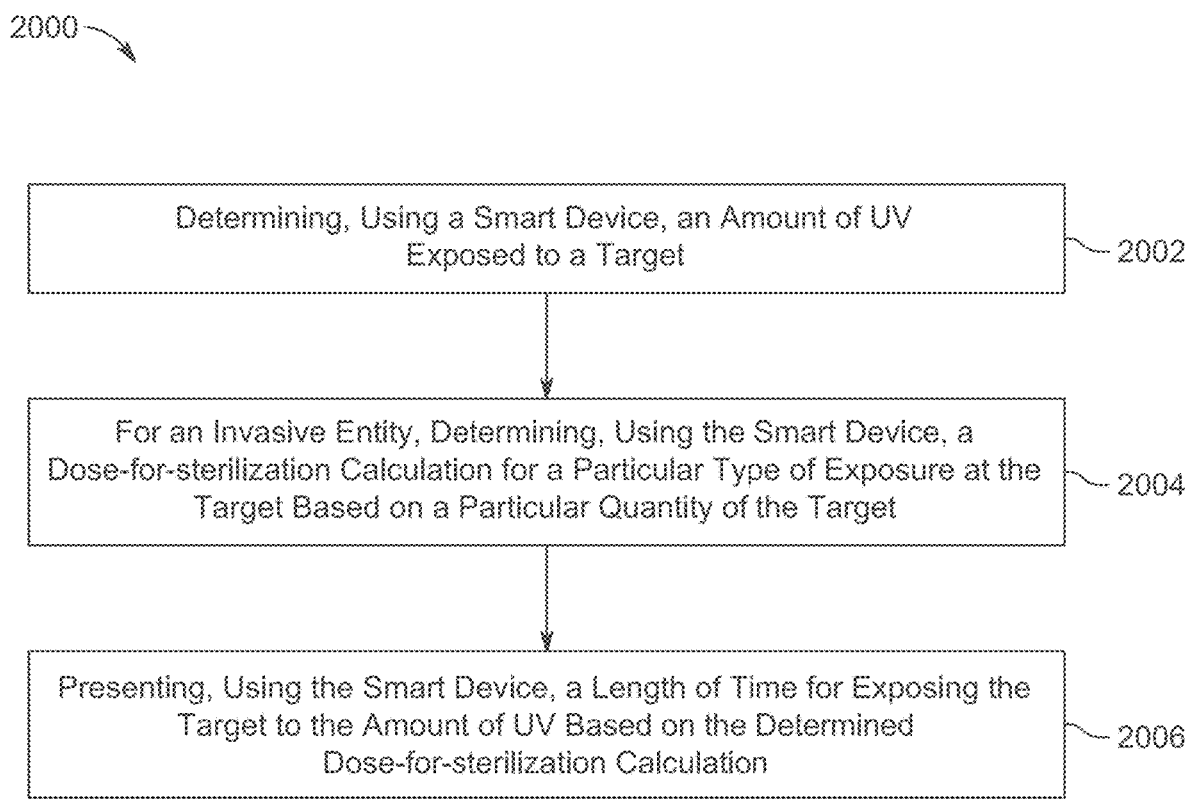

FIG. 20 is a flowchart of an illustrative process 2000 for providing therapy to a target using a smart device. Operation 2002 of process 2000 includes determining, using the smart device, an amount of UV exposed to the target. Operation 2004 of process 2000 includes for an invasive entity, determining, using the smart device, a dose-for-sterilization calculation for a particular type of exposure at the target based on a particular quantity of the target. Operation 2002 of process 2006 includes presenting, using the smart device, a length of time for exposing the target to the amount of UV based on the determined dose-for-sterilization calculation.

It is understood that the operations shown in process 2000 of FIG. 20 are only illustrative and that existing operations may be modified or omitted, additional operations may be added, and the order of certain operations may be altered.

Figure 21:
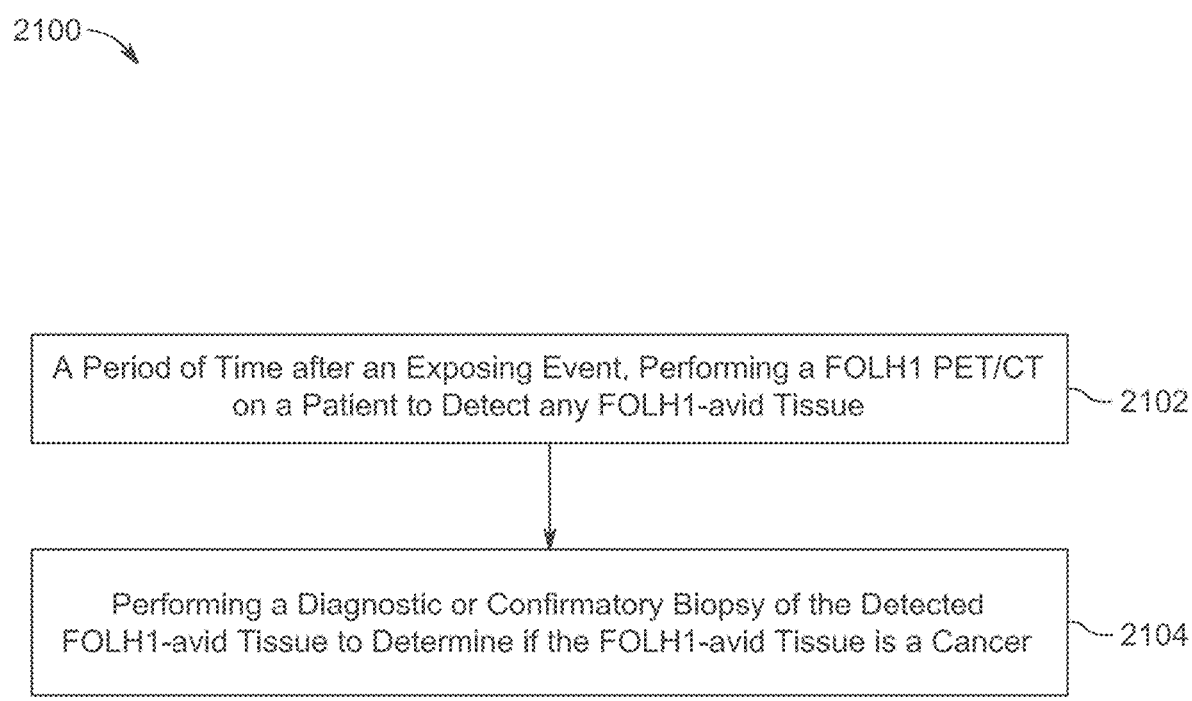

FIG. 21 is a flowchart of an illustrative process 2100 for monitoring a patient exposed to a known carcinogen at an exposing event. Operation 2102 of process 2100 includes, a period of time after the exposing event, performing a FOLH1 PET/CT on the patient to detect any FOLH1-avid tissue. Operation 2104 of process 2100 includes performing a diagnostic or confirmatory biopsy of the detected FOLH1-avid tissue to determine if the FOLH1-avid tissue is a cancer.

It is understood that the operations shown in process 2100 of FIG. 21 are only illustrative and that existing operations may be modified or omitted, additional operations may be added, and the order of certain operations may be altered.

Figure 22:
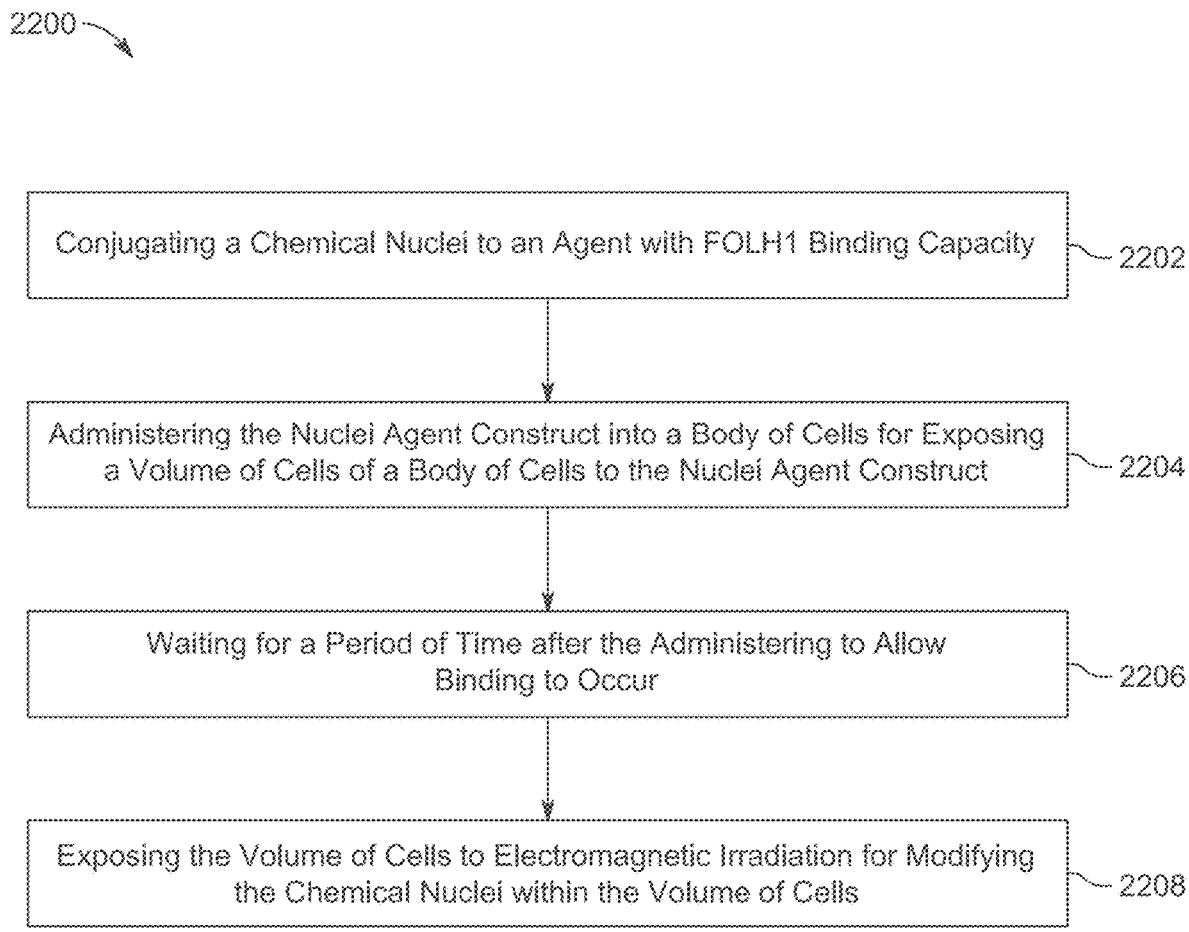

FIG. 22 is a flowchart of an illustrative process 2200 for adaptively treating a volume of cells with electromagnetic irradiation. Operation 2202 of process 2200 includes conjugating a chemical nuclei to an agent with FOLH1 binding capacity. Operation 2204 of process 2200 includes administering the nuclei-agent construct into a body of cells for exposing a volume of cells of the body of cells to the nuclei-agent construct. Operation 2206 of process 2200 includes waiting for a period of time after the administering to allow binding to occur. Operation 2208 of process 2200 includes exposing the volume of cells to electromagnetic irradiation for modifying the chemical nuclei within the volume of cells.

It is understood that the operations shown in process 2200 of FIG. 22 are only illustrative and that existing operations may be modified or omitted, additional operations may be added, and the order of certain operations may be altered.

Figure 23:
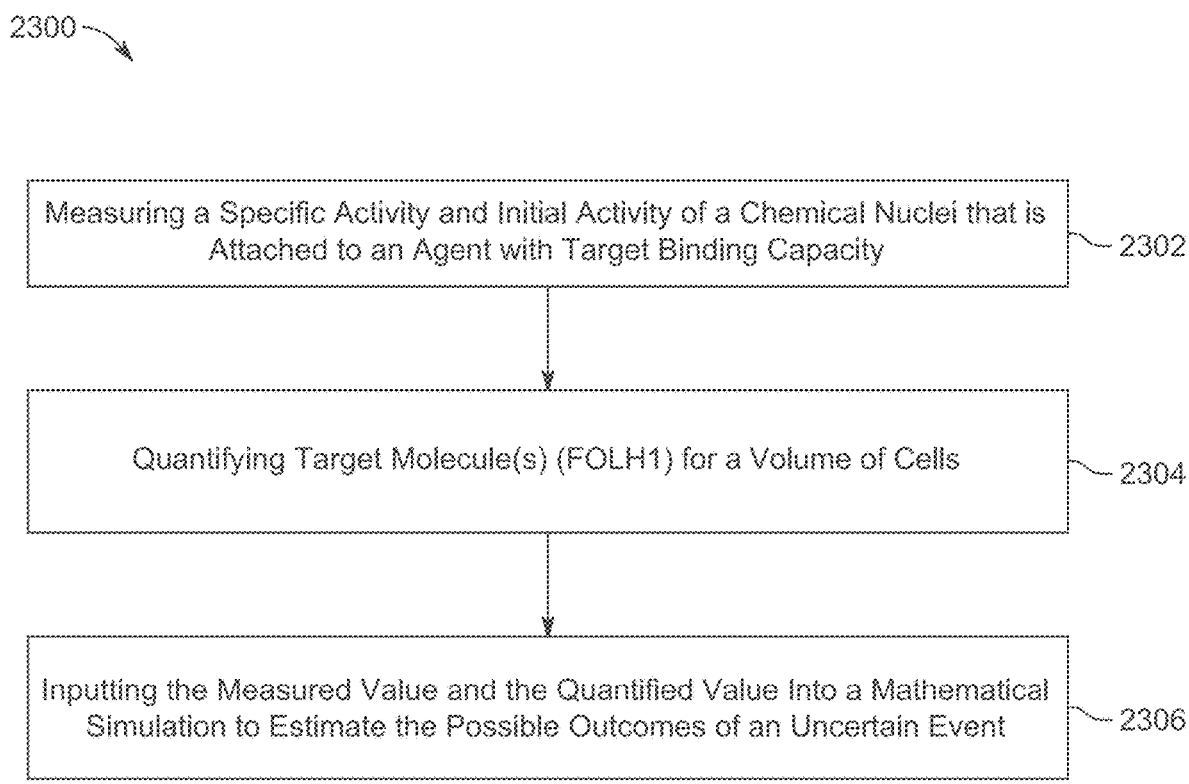

FIG. 23 is a flowchart of an illustrative process 2300 for measuring the absorbed dose of energy delivered via a target within a volume of cells. Operation 2302 of process 2300 includes measuring a specific activity and initial activity of a chemical nuclei that is attached to an agent with target binding capacity. Operation 2304 of process 2300 includes quantifying target molecule(s) (FOLH1) for the volume of cells. Operation 2306 of process 2300 includes inputting the measured value and the quantified value into a mathematical simulation to estimate the possible outcomes of an uncertain event.

It is understood that the operations shown in process 2300 of FIG. 23 are only illustrative and that existing operations may be modified or omitted, additional operations may be added, and the order of certain operations may be altered.

Figure 24:
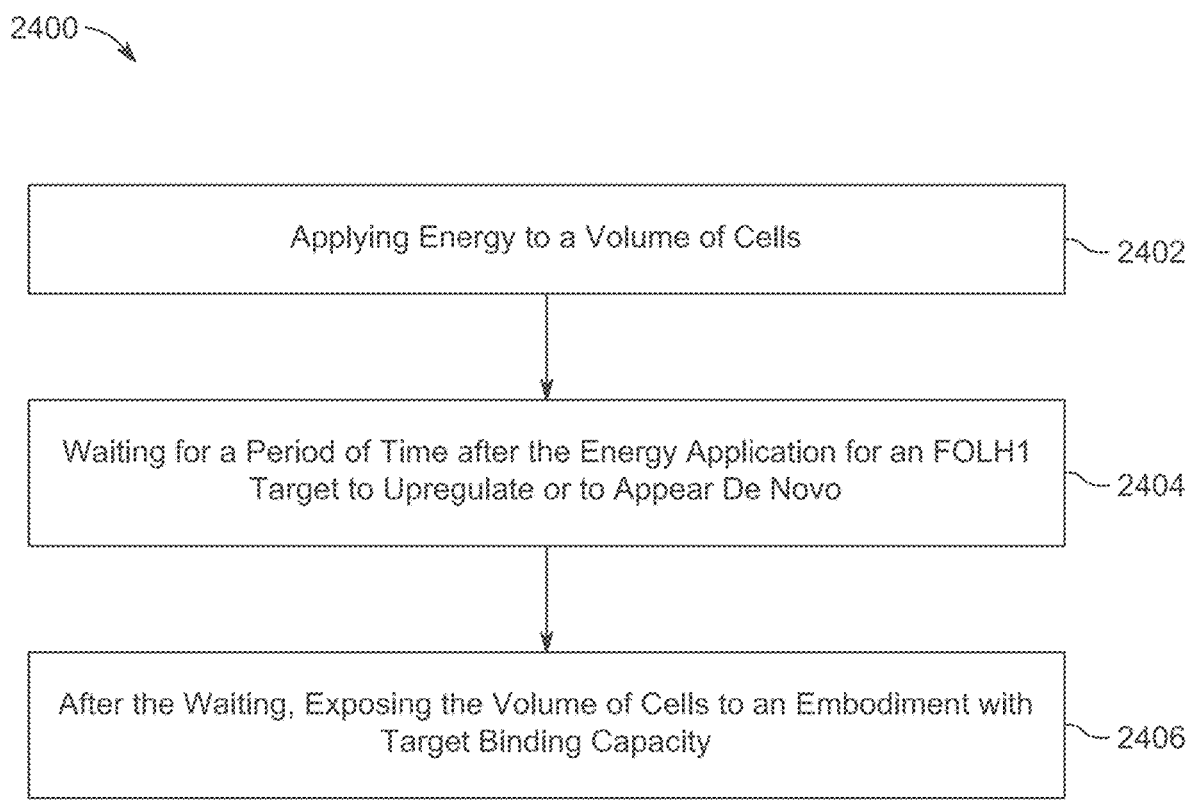

FIG. 24 is a flowchart of an illustrative process 2400 for enabling androgen deprivation upregulation. Operation 2402 of process 2400 includes applying energy to a volume of cells. Operation 2404 of process 2400 includes waiting for a period of time after the energy application for an FOLH1 target to upregulate or to appear de novo. Operation 2406 of process 2400 includes, after the waiting, exposing the volume of cells to an embodiment with target binding capacity.

It is understood that the operations shown in process 2400 of FIG. 24 are only illustrative and that existing operations may be modified or omitted, additional operations may be added, and the order of certain operations may be altered.

Figure 25:
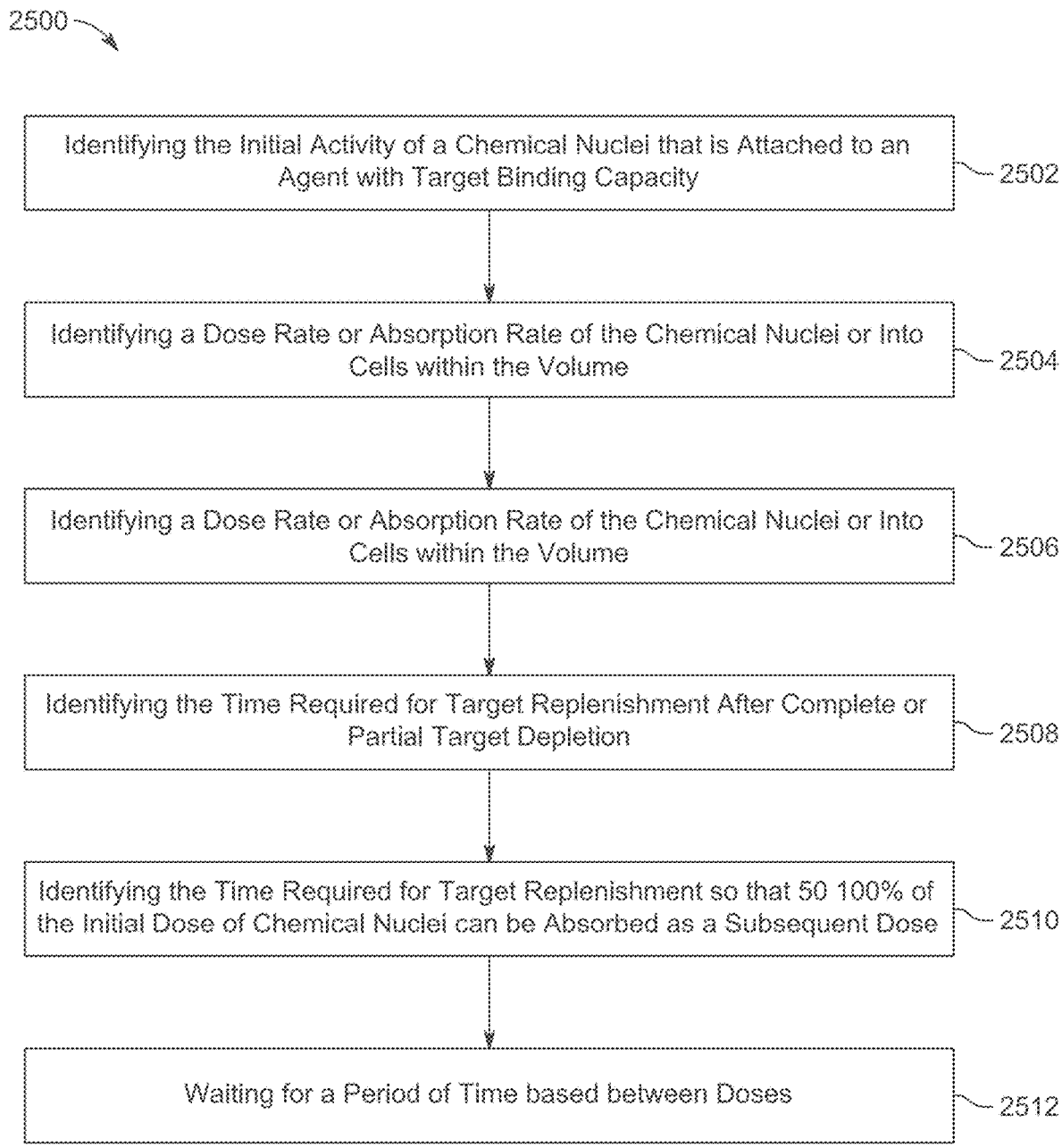

FIG. 25 is a flowchart of an illustrative process 2500 for optimizing the absorbed dose of electromagnetic irradiation delivered via a target within in a volume of cells. Operation 2502 of process 2500 includes identifying the initial activity of a chemical nuclei that is attached to an agent with target binding capacity. Operation 2504 of process 2500 includes identifying a dose rate or absorption rate of the chemical nuclei or into cells within the volume. Operation 2506 of process 2500 includes identifying the absorbed dose. Operation 2508 of process 2500 includes identifying the time required for target replenishment after complete or partial target depletion. Operation 2510 of process 2500 includes identifying the time required for target replenishment so that 50-100% of the initial dose of chemical nuclei can be absorbed as a subsequent dose. Operation 2512 of process 2500 includes waiting for a period of time based between doses.

It is understood that the operations shown in process 2500 of FIG. 25 are only illustrative and that existing operations may be modified or omitted, additional operations may be added, and the order of certain operations may be altered.

The following is a list of references mentioned elsewhere in this disclosure, and each reference is hereby incorporated by reference herein in its entirety:

| | |
|---|---|
| REF001 | Ramirez-Fort MK, Mahase SS, Osborne JR, Lange CS. Theragnostic Target, Prostate-Specific Membrane Antigen-Also Specific for Nonprostatic Malignancies. *Int J Radiat Oncol Biol Phys.* 2018; 101(3):646-649. |
| REF002 | Ramirez-Fort MK, Zeng J, Feily A, et al. Radiotherapy-induced reactivation of neurotrophic human herpes viruses: Overview and management. *J Clin Virol.* 2018; 98:18-27. |
| REF003 | Ramirez-Fort MK, Meier B, Feily A, Cooper SL, Lange CS. Adjuvant irradiation to prevent keloidal fibroproliferative growth should be standard of care. *Br J Dermatol.* 2017; 177(6):e327-e328. |
| REF004 | Niaz MJ, Batra JS, Walsh RD, et al. Pilot Study of Hyperfractionated Dosing of Lutetium-177-Labeled Antiprostate-Specific Membrane Antigen Monoclonal Antibody J591 ((177) Lu-J591) for Metastatic Castration-Resistant Prostate Cancer. *Oncologist.* 2020 Jan 30. Doi:10.1634/theoncologist.2020-0028. [Epub ahead of print] PubMed PMID: 31999003 |
| REF005 | Feily A, Seifi V, Ramirez-Fort MK. Fractional CO2 Laser Pretreatment to Autologous Hair Transplantation and Phototherapy Improves Perifollicular Repigmentation in Refractory Vitiligo: A Randomized, Prospective, Half-Lesion, Comparative Study. *Dermatol Surg.* 2016; 42(9): 1082-1088. |
| REF006 | Rassai S, Rafeie E, Ramirez-Fort MK, Feily A. Adjuvant Narrow Band UVB Improves the Efficacy of Oral Azithromycin for the Treatment of Moderate to Severe Inflammatory Facial Acne Vulgaris. *J Cutan Aesthet Surg.* 2014; 7(3):151-154. |
| REF007 | Au SC, Ramirez-Fort MK, Gottlieb AB. Analysis of trial data for infliximab and golimumab: baseline C-reactive protein level and prediction of therapeutic response in patients with psoriatic arthritis. *Arthritis Care Res (Hoboken).* 2014; 66(7):1114-1118. |
| REF008 | Doan HQ, Ung B, Ramirez-Fort MK, Khan F, Tyring SK. Zostavax : a subcutaneous vaccine for the prevention of herpes zoster. *Expert Opin Biol Ther.* 2013; 13(10):1467-1477. |
| REF009 | Feily A, Lotti T, Lange CS, Gianfaldoni S, Ramirez-Fort MK. Is HPV vaccination of pregnant women really safe? *Dermatol Ther.* 2018; 31(3):e12593. |
| REF010 | Kim SR, Khan F, Ramirez-Fort MK, Downing C, Tyring SK. Varicella zoster: an update on current treatment options and future perspectives. *Expert Opin Pharmacother.* 2014; 15(1):61-71. |
| REF011 | Mays R, Curry J, Kim K, et al. Eruptive squamous cell carcinomas after vemurafenib therapy. *J Cutan Med Surg.* 2013; 17(6):419-422. |
| REF012 | Nguyen DP, Xiong PL, Liu H, et al. Induction of PSMA and Internalization of an Anti-PSMA mAb in the Vascular Compartment. *Mol Cancer Res.* 2016; 14(1 1):1045-1053. |
| REF013 | Ramirez-Fort MK, Au SC, Javed SA, Loo DS. Management of cutaneous human papillomavirus infection: pharmacotherapies. *Curr Probl Dermatol.* 2014; 45:175-185. |
| REF014 | Ramirez-Fort MK, Case EC, Rosen AC, Cerci FB, Wu S, Lacouture ME. Rash to the mTOR inhibitor everolimus: systematic review and meta-analysis. *Am J Clin Oncol.* 2014; 37(3):266-271. |
| REF015 | Ramirez-Fort MK, Levin AA, Au SC, Gottlieb AB. Continuous versus intermittent therapy for moderate-to-severe psoriasis. *Clin Exp Rheumatol.* 2013; 31(4 Suppl 78):S63-70. |
| REF016 | Schlichte MJ, Downing CP, Ramirez-Fort M, Gordon R, Tyring S. Bloodroot associated eschar. *Dermatol Online J.* 2014; 20(7). |
| REF017 | Shelton M, Ramirez-Fort MK, Lee KC, Ladizinski B. Krokodil: from Russia with love. *JAMA Dermatol.* 2015; 151(1):32. |
| REF018 | Rasaii S, Sohrabian N, Gianfaldoni S, et al. Intralesional triamcinolone alone or in combination with botulinium toxin A is ineffective for the treatment of formed keloid scar: A double blind controlled pilot study. *Dermatol Ther.* 2019; 32(2):e12781. |

-continued

| | |
|---|---|
| REF019 | Varada S, Ramirez-Fort MK, Argobi Y, Simkin AD. Remission of refractory benign familial chronic pemphigus (hailey-hailey disease) with the addition of systemic cyclosporine. *J Cutan Med Surg.* 2015; 19(2): 163-166. |
| REF020 | Ladizinski B, Ramirez-Fort MK, Cohen YK, Rosendahl C, Elpern DJ. Pseudofolliculitis barbae: a dermatoscopic correlate. *Dermatol Pract Concept.* 2013; 3(2):53-54. |
| REF021 | Ladizinski B, Ramirez-Forte MK, Elpern DJ. Dermoscopy: What is your diagnosis? *Dermatol Pract Concept.* 2013; 3(3):23. |
| REF022 | Ramirez-Fort MK. Human papillomavirus-induced periungual pigmented Bowen's disease. *Dermatol Pract Concept.* 2012; 2(1):57-59. |
| REF023 | Ramirez-Fort MK, Al Jalbout S, Kittier H, Pellacani G. Lichenoid keratosis: non-invasive imaging in the setting of diagnostic uncertainty. *Dermatol Pract Concept.* 2013; 3(2):63-65. |
| REF024 | Javed S, Khan F, Ramirez-Fort M, Tyring SK. Bites and mites: prevention and protection of vector-borne disease. *Curr Opin Pediatr.* 2013; 25(4):488-491. |
| REF025 | Doan HQ, Ramirez-Fort MK, Rady PL. Viral oncogenesis. *Curr Probl Dermatol.* 2014; 45:33-46. |
| REF026 | Nguyen HP, Ramirez-Fort MK, Rady PL. The biology of human papillomaviruses. *Curr Probl Dermatol.* 2014; 45:19-32. |
| REF027 | Ramirez-Fort MK, Downing C, Doan HQ, et al. Coxsackievirus A6 associated hand, foot and mouth disease in adults: clinical presentation and review of the literature. *J Clin Virol.* 2014; 60(4):381-386. |
| REF028 | Ramirez-Fort MK, Sam H, Manders EK. Management of cutaneous human papillomavirus infection: surgery. *Curr Probl Dermatol.* 2014; 45:186-196. |
| REF029 | Varada S, Posnick M, Alessa D, Ramirez-Fort MK. Management of cutaneous human papillomavirus infection in immunocompromised patients. *Curr Probl Dermatol.* 2014; 45:197-215. |
| REF030 | Kleker BM, Ramirez-Fort MK, Puchalsky D, Longley BJ, Swanson A, Zone J. A generalized annular eruption with occasional vesicles. *Arch Dermatol.* 2012; 148(4):531-536. |
| REF031 | Khan F, Ramirez-Fort MK, Chan CS, Rosen T. Hyperkeratotic necrobiosis lipoidica. *Dermatol Pract Concept.* 2013; 3(1): 13-15. |
| REF032 | McClelland S, 3rd, Brown SA, Ramirez-Fort MK, Jaboin JJ, Zellars RC. The surgical nature of radiation oncology should be better reflected in pre-residency training. *Rep Pract Oncol Radiother.* 2019; 24(5):507-508. |
| REF033 | Bicknell LM, Ladizinski B, Tintle SJ, Ramirez-Fort MK. Lips as red as blood: areca nut lip staining. *JAMA Dermatol.* 2013; 149(11):1288. |
| REF034 | Ramirez-Fort MK, Doan HQ, Nguyen HP, Khan F, Kauffman J, Campbell LS. Chronic unilateral eruption of painful, erythematous papules and nodules. Piloleiomyoma. *JAMA Dermatol.* 2013; 149(7):865-866. |
| REF035 | Ramirez-Fort MK, Khan F, Rosendahl CO, Mercer SE, Shim-Chang H, Levitt JO. Acquired perforating dermatosis: a clinical and dermatoscopic correlation. *Dermatol Online J.* 2013; 19(7):18958. |
| REF036 | Ramirez-Fort MK, Lastra-Vicente R, Levitt JO, Sanchez JL, Reizner GT. Organizing a dermatology service mission. *Int J Dermatol.* 2013; 52(3):342-349. |
| REF037 | Schmidtberger L, Ladizinski B, Ramirez-Fort MK. Wax on, wax off: pubic hair grooming and potential complications. *JAMA Dermatol.* 2014; 150(2):122. |
| REF038 | Feily A, Hosseinpoor M, Bakhti A, et al. Digit-Length Ratios (2D:4D) as a Phenotypic Indicator of in Utero Androgen Exposure is Not Prognostic for Androgenic Alopecia: a Descriptive-Analytic Study of 1200 Iranian Men. *Dermatol Reports.* 2016; 8(1):6386. |
| REF039 | Mohebipour A, Gianfaldoni S, Lotti T, et al. Recycling of Previously Transplanted Hair: A Novel Indication for Follicular Unit Extraction. *Open Access Maced J Med Sci.* 2018; 6(6):1095-1097. |
| REF040 | Lu H, Stratton CW, Tang YW. Outbreak of pneumonia of unknown etiology in Wuhan, China: The mystery and the miracle. *J Med Virol.* 2020; 92(4):401-402. |
| REF041 | Xu X, Chen P, Wang J, et al. Evolution of the novel coronavirus from the ongoing Wuhan outbreak and modeling of its spike protein for risk of human transmission. *Sci China Life Sci.* 2020; 63(3):457-460. |
| REF042 | Yan R, Zhang Y, Li Y, Xia L, Guo Y, Zhou Q. Structural basis for the recognition of the SARS-CoV-2 by full-length human ACE2. *Science.* 2020. |
| REF043 | Rice GI, Jones AL, Grant PJ, Carter AM, Turner AJ, Hooper NM. Circulating activities of angiotensin-converting enzyme, its homolog, angiotensin-converting enzyme 2, and neprilysin in a family study. *Hypertension.* 2006; 48(5):914-920. |
| REF044 | Lai CC, Shih TP, Ko WC, Tang HJ, Hsueh PR. Severe acute respiratory syndrome coronavirus 2 (SARS-CoV-2) and coronavirus disease-2019 (COVID-19): The epidemic and the challenges. *Int J Antimicrob Agents.* 2020; 55(3):105924. |
| REF045 | Paules CI, Marston HD, Fauci AS. Coronavirus Infections-More Than Just the Common Cold. *JAMA.* 2020. |
| REF046 | Chan JF, Yuan S, Kok KH, et al. A familial cluster of pneumonia associated with the 2019 novel coronavirus indicating person-to-person transmission: a study of a family cluster. *Lancet.* 2020; 395(10223):514-523. |
| REF047 | Ong SWX, Tan YK, Chia PY, et al. Air, Surface Environmental, and Personal Protective Equipment Contamination by Severe Acute Respiratory Syndrome Coronavirus 2 (SARS-CoV-2) From a Symptomatic Patient. *JAMA.* 2020. |
| REF048 | Szeto W, Yam WC, Huang H, Leung DYC. The efficacy of vacuum-ultraviolet light disinfection of some common environmental pathogens. *BMC Infect Dis.* 2020; 20(1):127. |

-continued

| | |
|---|---|
| REF049 | Bedell K, Buchaklian AH, Perlman S. Efficacy of an Automated Multiple Emitter Whole-Room Ultraviolet-C Disinfection System Against Coronaviruses MHV and MERS-CoV. *Infect Control Hosp Epidemiol.* 2016; 37(5):598-599. |
| REF050 | Hoshino Y, Dalai SK, Wang K, et al. Comparative efficacy and immunogenicity of replication-defective, recombinant glycoprotein, and DNA vaccines for herpes simplex virus 2 infections in mice and guinea pigs. *Journal of virology.* 2005; 79(1):410-418. |
| REF051 | Wakim LM, Jones CM, Gebhardt T, Preston CM, Carbone FR. CD8(+) T-cell attenuation of cutaneous herpes simplex virus infection reduces the average viral copy number of the ensuing latent infection. *Immunology and cell biology.* 2008; 86(8):666-675. |
| REF052 | Koelle DM, Chen HB, Gavin MA, Wald A, Kwok WW, Corey L. CD8 CTL from genital herpes simplex lesions: recognition of viral tegument and immediate early proteins and lysis of infected cutaneous cells. *Journal of immunology.* 2001; 166(6):4049-4058. |
| REF053 | Koelle DM, Posavad CM, Barnum GR, Johnson ML, Frank JM, Corey L. Clearance of HSV-2 from recurrent genital lesions correlates with infdtration of HSV-specific cytotoxic T lymphocytes. *The Journal of clinical investigation.* 1998; 101(7):1500-1508. |
| REF054 | Cadnum JL, Jencson AL, Gestrich SA, et al. A comparison of the efficacy of multiple ultraviolet light room decontamination devices in a radiology procedure room. *Infect Control Hosp Epidemiol.* 2019; 40(2):158-163. |
| REF055 | Fisher EM, Shaffer RE. A method to determine the available UV-C dose for the decontamination of filtering facepiece respirators. *J Appl Microbiol.* 2011; 110(1):287-295. |
| REF056 | Lindblad M, Tano E, Lindahl C, Huss F. Ultraviolet-C decontamination of a hospital room: Amount of UV light needed. *Burns.* 2019. |
| REF057 | Mbonimpa EG, Blatchley ER, 3$^{rd}$, Applegate B, Harper WF, Jr. Ultraviolet A and B wavelength-dependent inactivation of viruses and bacteria in the water. *J Water Health.* 2018; 16(5):796-806. |
| REF058 | Nakashima H, Koyanagi Y, Harada S, Yamamoto N. Quantitative evaluations of the effect of UV irradiation on the infectivity of HTLV-III (AIDS virus) with HTLV-I-carrying cell line, MT-4. *J Invest Dermatol.* 1986; 87(2):239-243. |
| REF059 | Pichon M, Lebail-Carval K, Billaud G, Lina B, Gaucherand P, Mekki Y. Decontamination of Intravaginal Probes Infected by Human Papillomavirus (HPV) Using UV-C Decontamination System. *J Clin Med.* 2019; 8(11). |
| REF060 | Sagripanti JL, Lytle CD. Inactivation of influenza virus by solar radiation. *Photochem Photobiol.* 2007; 83(5):1278-1282. |
| REF061 | Silva AA. The Shadow Rule, the UV Index, and the 5S Steps in the Tropics. *Health Phys.* 2020. |
| REF062 | Song L, Li W, He J, et al. Development of a Pulsed Xenon Ultraviolet Disinfection Device for Real-Time Air Disinfection in Ambulances. *J Healthc Eng.* 2020; 2020:6053065. |
| REF063 | Urban M, Motteram J, Jing HC, et al. Inactivation of plant infecting fungal and viral pathogens to achieve biological containment in drainage water using UV treatment. *J Appl Microbiol.* 2011; 110(3):675-687. |
| REF064 | Jacobson CC, Kumar S, Kimball AB. Latitude and psoriasis prevalence. *J Am Acad Dermatol.* 2011; 65(4):870-873. |
| REF065 | Schweitzer AD, Howell RC, Jiang Z, et al. Physico-chemical evaluation of rationally designed melanins as novel nature-inspired radioprotectors. *PloS One.* 2009; 4(9):e7229. |
| REF066 | Ramirez-Fort MK, Gottlieb AB, Au SC, Lebwohl MG. A cross-sectional study of Fitzpatrick's skin type and psoriasis in Puerto Rico. Journal of the American Academy of Dermatology, 2014 May; 70(5); suppl 1; Page AB79 |
| REF067 | Chauhan PS, Kaur 1, Dogra S, De D, Kanwar AJ. Narrowband ultraviolet B versus psoralen plus ultraviolet A therapy for severe plaque psoriasis: an Indian perspective. *Clin Exp Dermatol.* 2011; 36(2):169-173. |
| REF068 | Kwon IH, Woo SM, Choi JW, Youn JI. A retrospective review of 20% vs. 10% incremental narrowband UVB regimens to treat psoriasis in skin phototypes III-V Koreans. *Photodermatol Photoimmunol Photomed.* 2009; 25(3):124-127. |
| REF069 | Sugiyama H, Misumi M, Kishikawa M, et al. Skin cancer incidence among atomic bomb survivors from 1958 to 1996. *Radiat Res.* 2014; 181(5):531-539. |
| REF070 | Ramirez-Fort MK, Kauffman JA, Khan F, Nguyen H, Rapini RP, Rady P, Tyring SK. [Observation]: A case of Merkel cell carcinoma infected by Merkel cell polyomavirus DNA. Journal of the American Academy of Dermatology. 2013 Apr; 68(4): suppl 1; Page AB131 |
| REF071 | Ramirez-Fort MK, Meier B, Lachance KS, Chruch CD, Lange CS, French LE, Nghiem P, Bander NH. (2017, September). Folate hydrolase-1 is a novel target for J591-brachytherapy in Merkel cell carcinoma. Poster presented at: European Society for Dermatological Research; Salzburg, Austria. |
| REF072 | Ramirez-Fort MK, Navarro V, Meier B, Liu H, Levesque M, Paulitschke V, Vissicchio JR, Moy J, Contassot E, Kim S, Robinson B, Christos P, Tagawa ST, Bander NH, French LE, Lange CS. (2017, April). Possible cancer stem cells: Folate hydrolase-1 is expressed in a subset of Oct4-positive melanoma cells. Poster presented at: American Association for Cancer Research; Washington, DC. |
| REF073 | Ramirez-Fort MK, Meier B, Vissicchio JR, Moy J, Liu H, Contassot E, Robinson BD, Navarro V, Kim S, Leconet W, Nguyen D, Nwokedi EC, Lange CS, Tagawa ST, Bander NH, French LE. Melanoma induces endothelial folate hydrolase-1 (FOLH1) expression and facilitated internalization of immunotheragnostic agent, |

-continued

| | |
|---|---|
| | J591. Int J Radiat Oncol Biol Phys. 2016 Oct 1 ; 96(2S): E703-E704. PubMed PMID: 27675409. |
| REF074 | Feily, A., et al., Follicular Transplantation, Microneedling, and Adjuvant Narrow-band Ultraviolet-B Irradiation as Cost-Effective Regimens for Palmar-Plantar Vitiligo: A Pilot Study. Cureus, 2020. 12(4): p. e7878. |
| REF075 | Feily, A., V. Seifi, and M.K. Ramirez-Fort, Fractional CO2 Laser Pretreatment to Autologous Hair Transplantation and Phototherapy Improves Perifollicular Repigmentation in Refractory Vitiligo: A Randomized, Prospective, Half-Lesion, Comparative Study. Dermatol Surg, 2016. 42(9): p. 1082-8. |
| REF076 | Takada, A., et al., Bactericidal effects of 310 nm ultraviolet light-emitting diode irradiation on oral bacteria. BMC Oral Health, 2017. 17(1): p. 96. |
| REF077 | Miwa, S., et al., Imaging UVC-induced DNA damage response in models of minimal cancer. J Cell Biochem, 2013. 114(11): p. 2493-9. |
| REF078 | Al-Aidaroos, A.M., et al., High mortality of Red Sea zooplankton under ambient solar radiation. PloS One, 2014. 9(10): p. e108778. |
| REF079 | Lu H, Stratton CW, Tang YW. Outbreak of pneumonia of unknown etiology in Wuhan, China: Themystery and the miracle. *J Med Virol.* 2020; 92(4):401-402. |
| REF080 | Lytle CD, Sagripanti JL. Predicted inactivation of viruses of relevance to biodefense by solar radiation. *J Virol.* 2005; 79(22):14244-14252. |
| REF081 | Sagripanti JL, Lytle CD. Estimated Inactivation of Coronaviruses by Solar Radiation With SpecialReference to COVID-19. *Photochem Photobiol.* 2020. |
| REF082 | Lange CS, Gilbert CW. Studies on the cellular basis of radiation lethality. 3. The measurement ofstem-cell repopulation probability. *Int J Radiat Biol Relat Stud Phys Chem Med.* 1968; 14(4):373-388. |
| REF083 | Kogelnik HD. [100 years radiotherapy. On the birth of a new specialty]. *Wien Klin Wochenschr.* 1998; 110(9):313-320. |
| REF084 | Jarrett P, Scragg R. A short history of phototherapy, vitamin D and skin disease. *Photochem Photohiol Sci.* 2017; 16(3):283-290. |
| REF085 | Ramirez-Fort MK, Mahase SS, Osborne JR, Lange CS. Theragnostic Target, Prostate-Specific Membrane Antigen-Also Specific for Nonprostatic Malignancies. *Int J Radiat Oncol Biol Phys.* 2018; 101(3):646-649. |
| REF086 | Niaz MJ, Batra JS, Walsh RD, et al. Pilot Study of Hyperfractionated Dosing of Lutetium-177- Labeled Antiprostate-Specific Membrane Antigen Monoclonal Antibody J591 ((177) Lu-J591) forMetastatic Castration-Resistant Prostate Cancer. *Oncologist.* 2020. |
| REF087 | Niaz MO, Sun M, Ramirez-Fort MK, Niaz MJ. Review of Lutetium-177-labeled Anti-prostate-specific Membrane Antigen Monoclonal Antibody J591 for the Treatment of Metastatic Castration-resistant Prostate Cancer. *Cureus.* 2020; 12(2):e7107. |
| REF088 | Singer S, Berneburg M. Phototherapy. *J Dtsch Dermatol Ges.* 2018; 16(9):1120-1129. |
| REF089 | Welch D, Buonanno M, Grilj V, et al. Far-UVC light: A new tool to control the spread of airborne-mediated microbial diseases. *Sci Rep.* 2018; 8(1):2752. |
| REF090 | Ramirez-Fort MK, Rogers MJ, Santiago R, et al. Prostatic irradiation-induced sexual dysfunction: a review and multidisciplinary guide to management in the radical radiotherapy era (Part I defining the organ at risk for sexual toxicities). *Rep Pract Oncol Radiother.* 2020; 25(3):367-375. |
| REF091 | Ramirez-Fort MK, Zeng J, Feily A, et al. Radiotherapy-induced reactivation of neurotrophichuman herpes viruses: Overview and management. *J Clin Virol.* 2018; 98:18-27. |
| REF092 | "Introduction to health physics." Cember, Herman, Johnson TE, and Alaei P eds. Medical Physics 35.12 (2008): 5959. |
| REF093 | Miwa S, Yano S, Hiroshima Y, et al. Imaging UVC-induced DNA damage response in models ofminimal cancer. *J Cell Biochem.* 2013; 114(11):2493-2499. |
| REF094 | Al-Aidaroos AM, El-Sherbiny MM, Satheesh S, et al. High mortality of Red Sea zooplankton underambient solar radiation. *PloS One.* 2014; 9(10):e108778. |
| REF095 | Takeda K, Fujisawa K, Nojima H, Kato R, Ueki R, Sakugawa H. Hydroxyl radical generation with ahigh power ultraviolet light emitting diode (UV-LED) and application for determination of hydroxyl radical reaction rate constants. J Photochem. 2017; 340:8-14. |
| REF096 | Rastogi RP, Richa, Kumar A, Tyagi MB, Sinha RP. Molecular mechanisms of ultraviolet radiation-induced DNA damage and repair. *J Nucleic Acids.* 2010; 2010:592980. |
| REF097 | McGuigan KG, Joyce TM, Conroy RM, Gillespie JB, Elmore-Meegan M. Solar disinfection of drinking water contained in transparent plastic bottles: characterizing the bacterial inactivation process. *J Appl Microbiol.* 1998; 84(6):1138-1148. |
| REF098 | Dessie A, Alemayehu E, Mekonen S, Legesse W, Kloos H, Ambelu A. Solar disinfection: an approach for low-cost household water treatment technology in Southwestern Ethiopia. *JEnviron Health Sci Eng.* 2014; 12(1):25. |
| REF099 | Amichai B, Grunwald MH, Davidovici B, Shemer A. "Sunlight is said to be the best of disinfectants"*: the efficacy of sun exposure for reducing fungal contamination in used clothes. *Isr Med Assoc J.* 2014; 16(7):431-433. |
| REF100 | Tseng CC, Li CS. Inactivation of viruses on surfaces by ultraviolet germicidal irradiation. *J OccupEnviron Hyg.* 2007; 4(6):400-405. |
| REF101 | Sagripanti JL, Lytle CD. Inactivation of influenza virus by solar radiation. *Photochem Photobiol.* 2007; 83(5):1278-1282. |
| REF102 | Sagripanti JL, Lytle CD. Sensitivity to ultraviolet radiation of Lassa, vaccinia, and Ebola viruses dried on surfaces. *Arch Virol.* 2011; 156(3):489-494. |

-continued

| | |
|---|---|
| REF103 | Sagripanti JL, Voss L, Marschall HJ, Lytle CD. Inactivation of vaccinia virus by natural sunlight andby artificial UVB radiation. *Photochem Photobiol.* 2013; 89(1): 132-138. |
| REF104 | Ianevski A, Zusinaite E, ShtaidaN, et al. Low Temperature and Low UV Indexes Correlated with Peaks of Influenza Virus Activity in Northern Europe during 2010(-)2018. *Viruses.* 2019; 11(3). |
| REF105 | Trauer JM, Denholm JT, McBryde ES. Construction of a mathematical model for tuberculosistransmission in highly endemic regions of the Asia-Pacific. *J Theor Biol.* 2014; 358:74-84. |
| REF106 | Liu Y, Ning Z, Chen Y, et al. Aerodynamic analysis of SARS-CoV-2 in two Wuhan hospitals. *Nature.* 2020. |
| REF107 | Interrante JD, Haddad MB, Kim L, Gandhi NR. Exogenous Reinfection as a Cause of Late Recurrent Tuberculosis in the United States. *Ann Am Thorac Soc.* 2015; 12(11):1619-1626. |
| REF108 | Schiroli C, Carugati M, Zanini F, et al. Exogenous reinfection of tuberculosis in a low-burden area. *Infection.* 2015; 43(6):647-653. |
| REF109 | Shen X, Yang C, Wu J, et al. Recurrent tuberculosis in an urban area in China: Relapse orexogenous reinfection? *Tuberculosis (Edinb).* 2017; 103:97-104. |
| REF110 | Smith J. South Korea reports more recovered coronavirus patients testing positive again. https://www.reuters.com/article/us-health-coronavirus-southkorea/south-korea-reports-more-recovered-coronavirus-patients-testing-positive-again-idUSKCN21V0JQ. |
| REF111 | Ye G, Pan Z, Pan Y, et al. Clinical characteristics of severe acute respiratory syndrome coronavirus 2 reactivation. *J Infect.* 2020; 80(5):el4-el7. |
| REF112 | Gordon CJ, Tchesnokov EP, Woolner E, et al. Remdesivir is a direct-acting antiviral that inhibits RNA-dependent RNA polymerase from severe acute respiratory syndrome coronavirus 2 with high potency. *J Biol Chem.* 2020. |
| REF113 | Ledford H. Hopes rise for coronavirus drug remdesivir. *Nature.* 2020. |
| REF114 | Maverakis E, Miyamura Y, Bowen MP, Correa G, Ono Y, Goodarzi H. Light, including ultraviolet. *JAutoimmun.* 2010; 34(3):J247-257. |
| REF115 | Carratala A, Dionisio Calado A, Mattle MJ, Meierhofer R, Luzi S, Kohn T. Solar Disinfection of Viruses in Polyethylene Terephthalate Bottles. *Appl Environ Microbiol.* 2016; 82(1):279-288. |
| REF116 | Bichai F, Polo-Lopez MI, Fernandez Ibanez P. Solar disinfection of wastewater to reduce contamination of lettuce crops by *Escherichia coli* in reclaimed water irrigation. *Water Res.* 2012; 46(18):6040-6050. |
| REF117 | Casini B, Tuvo B, Cristina ML, et al. Evaluation of an Ultraviolet C (UVC) Light-Emitting Device forDisinfection of High Touch Surfaces in Hospital Critical Areas. *Int J Environ Res Public Health.* 2019; 16(19). |
| REF118 | Nerandzic MM, Thota P, Sankar CT, et al. Evaluation of a pulsed xenon ultraviolet disinfection system for reduction of healthcare-associated pathogens in hospital rooms. *Infect Control HospEpidemiol.* 2015; 36(2):192-197. |
| REF119 | Lindblad M, Tano E, Lindahl C, Huss F. Ultraviolet-C decontamination of a hospital room: Amount of UV light needed. *Burns.* 2019. |
| REF120 | Beck SE, Ryu H, Boczek LA, et al. Evaluating UV-C LED disinfection performance and investigating potential dual-wavelength synergy. *Water Res.* 2017; 109:207-216. |
| REF121 | Lowe J.J., Paladino, K.D., Farke, J.D., et al. N95 Filtering Facepiece Respirator UltravioletGermicidal Irradiation (UVGI) Process for Decontamination and Reuse 2020; https://www.nebraskamed.com/sites/default/files/documents/covid-19/n-25-decon-process.pdt. Accessed 16 March 2020. |
| REF122 | Chang, Kenneth. "Scientists Consider Indoor Ultraviolet Light to Zap Coronavirus in the Air". The New York Times. 9 May 2020 (accessed May 25, 2020) |
| REF123 | Takada A, Matsushita K, Horioka S, Furuichi Y, Sumi Y. Bactericidal effects of 310 nm ultraviolet light-emitting diode irradiation on oral bacteria. *BMC Oral Health.* 2017; 17(1):96. |
| REF124 | Perez-Laguna V, Gilaberte Y, Millan-Lou MI, et al. A combination of photodynamic therapy and antimicrobial compounds to treat skin and mucosal infections: a systematic review. *PhotochemPhotobiol Sci.* 2019; 18(5):1020-1029. |
| REF125 | Perez-Laguna V, Garcia-Malinis AJ, Aspiroz C, Rezusta A, Gilaberte Y. Antimicrobial effects of photodynamic therapy. *G Ital Dermatol Venereal.* 2018; 153(6):833-846. |
| REF126 | Schreiner M, Baumler W, Ecki DB, Spath A, Konig B, Eichner A. Photodynamic inactivation ofbacteria to decolonize 95ethicillin-resistant *Staphylococcus aureus* from human skin. *Br J Dermatol.* 2018; 179(6):1358-1367. |
| REF127 | Khaskhely NM, Maruno M, Uezato H, et al. Low-dose UVB contributes to host resistance against Leishmania amazonensis infection in mice through induction of gamma interferon and tumor necrosis factor alpha cytokines. *Clin Diagn Lab Immunol.* 2002; 9(3):677-686. |
| REF128 | Mashayekhi Goyonlo V, Karrabi M, Kiafar B. Efficacy of erbium glass laser in the treatment of OldWorld cutaneous leishmaniasis: A case series. *Australas J Dermatol.* 2019; 60(1):e29-e32. |
| REF129 | Balevi A, Ustuner P, Kaksi SA, Ozdemir M. Narrow-band UV-B phototherapy: an effective andreliable treatment alternative for extensive and recurrent pityriasis versicolor. *J Dermatolog Treat.* 2018; 29(3):252-255. |
| REF130 | Rassai S, Rafeie E, Ramirez-Fort MK, Feily A. Adjuvant Narrow Band UVB Improves the Efficacy of Oral Azithromycin for the Treatment of Moderate to Severe Inflammatory Facial Acne Vulgaris. *JCutan Aesthet Surg.* 2014; 7(3):151-154. |

| | |
|---|---|
| REF131 | Nguyen HP, Ramirez-Fort MK, Rady PL. The biology of human papillomaviruses. *Curr ProblDermatol.* 2014; 45:19-32. |
| REF132 | Zhang K, Ren J, Ren JX, Liu C, Sun L. Successful treatment of verruca plana with NB-UVB:A casereport. *Dermatol Ther.* 2020; 33(2):e13207. |
| REF133 | Cantero-Munoz P, Urien MA, Ruano-Ravina A. Efficacy and safety of intraoperative radiotherapyin colorectal cancer: a systematic review. *Cancer Lett.* 2011; 306(2):121-133. |
| REF134 | Ruano-Ravina A, Cantero-Munoz P, Eraso Urien A. Efficacy and safety of intraoperative radiotherapy in breast cancer: a systematic review. *Cancer Lett.* 2011; 313(1):15-25. |
| REF135 | Nishioka A, Ogawa Y, Miyatake K, et al. Safety and efficacy of image-guided enzyme-targeting radiosensitization and intraoperative radiotherapy for locally advanced unresectable pancreatic cancer. *Oncol Lett.* 2014; 8(1):404-408. |
| REF136 | Treister N, Li S, Lerman MA, Lee S, Soiffer R. Narrow-band UVB phototherapy for managementof oral chronic graft-versus-host disease. *Photodermatol Photoimmunol Photomed.* 2015; 31(2):75-82. |
| REF137 | Morita A, Weiss M, Maeda A. Recent developments in phototherapy: treatment methods anddevices. *Recent Pat Inflamm Allergy Drug Discov.* 2008; 2(2):105-108. |
| REF138 | Koreck AI, Csoma Z, Bodai L, et al. Rhinophototherapy: a new therapeutic tool for themanagement of allergic rhinitis. *J Allergy Clin Immunol.* 2005; 115(3):541-547. |
| REF139 | Kemeny L, Koreck A. Ultraviolet light phototherapy for allergic rhinitis. *J Photochem Photohiol B.* 2007; 87(1):58-65. |
| REF140 | Csoma Z, Ignacz F, Bor Z, et al. Intranasal irradiation with the xenon chloride ultraviolet B laser improves allergic rhinitis. *J Photochem Photohiol B.* 2004; 75(3):137-144. |
| REF141 | Kovalenko EL. [The results of treating periapical periodontitis with ultraviolet irradiation of the root canal and the use of gentamycin]. *Lik Sprava.* 1998(5):136-139. |
| REF142 | Alyasin S, Nabavizadeh SH, Houshmand H, Esmaeilzadeh H, Jelodar S, Amin R. Short Time Efficiency of Rhinophototherapy in Management of Patients with Allergic Rhinitis Resistant to Medical Therapy. *Iran J Allergy Asthma Immunol.* 2016; 15(4):317-327. |
| REF143 | Koreck A, Szechenyi A, Morocz M, et al. Effects of intranasal phototherapy on nasal mucosa inpatients with allergic rhinitis. *J Photochem Photobiol B.* 2007; 89(2-3):163-169. |
| REF144 | Wolfel R, Corman VM, Guggemos W, et al. Virological assessment of hospitalized patients withCOVID-2019. *Nature.* 2020. |
| REF145 | Gera R, Chehade H, Wazir U, Tayeh S, Kasem A, Mokbel K. Locoregional therapy of the primarytumour in de novo stage IV breast cancer in 216 066 patients: A meta-analysis. *Sci Rep.* 2020; 10(1):2952. |
| REF146 | Barr ML, Meiser BM, Eisen HJ, et al. Photopheresis for the prevention of rejection in cardiac transplantation. Photopheresis Transplantation Study Group. *N Engl J Med.* 1998; 339(24):1744-1751. |
| REF147 | Edelson R, Berger C, Gasparro F, et al. Treatment of cutaneous T-cell lymphoma by extracorporeal photochemotherapy. Preliminary results. *N Engl J Med.* 1987; 316(6):297-303. |
| REF148 | McKenna KE, Whittaker S, Rhodes LE, et al. Evidence-based practice of photopheresis 1987-2001: a report of a workshop of the British Photodermatology Group and the U.K. Skin Lymphoma Group. *Br J Dermatol.* 2006; 154(1):7-20. |
| REF149 | Marshall SR. Technology insight: ECP for the treatment of GvHD-can we offer selective immune control without generalized immunosuppression? *Nat Clin Pract Oncol.* 2006; 3(6):302-314. |
| REF150 | Hivelin M, Siemionow M, Grimbert P, Lantieri L. Extracorporeal photopheresis: from solid organs to face transplantation. *Transpl Immunol.* 2009; 21(3):117-128. |
| REF151 | Cho A, Jantschitsch C, Knobler R. Extracorporeal Photopheresis-An Overview. *FrontMed(Lausanne).* 2018; 5:236. |
| REF152 | Rajagopal K, Keller SP, Akkanti B, et al. Advanced Pulmonary and Cardiac Support of COVID-19 Patients: Emerging Recommendations From ASAIO-a Living Working Document. *Circ Heart Fail.* 2020; 13(5):e007175 . |
| REF153 | Li JJ. Mitigating Coronavirus-Induced Acute Respiratory Distress Syndrome by Radiotherapy. *iScience.* 2020; 23(6):101215. |
| REF154 | Kefayat A, Ghahremani F. Low dose radiation therapy for COVID-19 pneumonia: a double-edgedsword. *Radiother Oncol.* 2020. |
| REF155 | Kirkby C, Mackenzie M. Is low dose radiation therapy a potential treatment for COVID-19pneumonia? *Radiother Oncol.* 2020. |
| REF156 | Ramirez-Fort MK, Meier B, Feily A, Cooper SL, Lange CS. Adjuvant irradiation to prevent keloidalfibroproliferative growth should be standard of care. *Br J Dermatol.* 2017; 177(6):e327-e328. |
| REF157 | Doan HQ, Ung B, Ramirez-Fort MK, Khan F, Tyring SK. Zostavax : a subcutaneous vaccine for the prevention of herpes zoster. *Expert Opin Biol Ther.* 2013; 13(10):1467-1477. |
| REF158 | Shimizuguchi T, Sekiya N, Hara K, et al. Radiation therapy and the risk of herpes zoster inpatients with cancer. *Cancer.* 2020. |
| REF159 | Lai YL, Su YC, Kao CH, Liang JA. Increased risk of varicella-zoster virus infection in patients withbreast cancer after adjuvant radiotherapy: A population-based cohort study. *PloS One.* 2019; 14(1):e0209365. |
| REF160 | Fujii T, Kitamura Y, Mizuguchi H, et al. Effects of irradiation with narrowband-ultraviolet B on up-regulation of histamine H1 receptor mRNA and |

| | |
|---|---|
| | induction of apoptosis in HeLa cells and nasal mucosa of rats. *J Pharmacol Sci.* 2018; 138(1):54-62. |
| REF161 | Preston DL, Ron E, Tokuoka S, et al. Solid cancer incidence in atomic bomb survivors: 1958-1998. *Radiat Res.* 2007; 168(1):1-64. |
| REF162 | Dennis LK, Vanbeek MJ, Beane Freeman LE, Smith BJ, Dawson DV, Coughlin JA. Sunburns and risk of cutaneous melanoma: does age matter? A comprehensive meta-analysis. *Ann Epidemiol.* 2008; 18(8):614-627. |
| REF163 | Amano S. Characterization and mechanisms of photoageing-related changes in skin. Damages of basement membrane and dermal structures. *Exp Dermatol.* 2016; 25 Suppl 3:14-19. |
| REF164 | Rivas M, Rojas E, Araya MC, Calaf GM. Ultraviolet light exposure, skin cancer risk and vitamin Dproduction. *Oncol Lett.* 2015; 10(4):2259-2264. |
| REF165 | Armstrong BK, Kricker A, English DR. Sun exposure and skin cancer. *Australas J Dermatol.* 1997; 38 Suppl 1:S1-6. |
| REF166 | Furman D, Campisi J, Verdin E, et al. Chronic inflammation in the etiology of disease across thelife span. *Nat Med.* 2019; 25(12):1822-1832. |
| REF167 | Doan HQ, Ramirez-Fort MK, Rady PL. Viral oncogenesis. *Curr Probl Dermatol.* 2014; 45:33-46. |
| REF168 | Hasche D, Stephan S, Braspenning-Wesch I, et al. The interplay of UV and cutaneous papillomavirus infection in skin cancer development. *PloS Pathog.* 2017; 13(11):e1006723. |
| REF169 | UV Penetration depths in skin Meinhardt, Merve, et al. "Wavelength-dependent penetration depths of ultraviolet radiation in human skin." *Journal of biomedical optics* 13.4 (2008):044030. |
| REF170 | Kirz, Janos, Chris Jacobsen, and Malcolm Howells. "Soft X-ray microscopes and their biological applications." *Quarterly reviews of biophysics* 28.1 (1995): 33-130. |
| REF171 | Bander, N.H., et al., Phase I trial of 177lutetium-labeled J591, a monoclonal antibody to prostate-specific membrane antigen, in patients with androgen-independent prostate cancer. J Clin Oncol, 2005. 23(21): p. 4591-601. |
| REF172 | Milowsky, ML, et al., Phase 1/2 multiple ascending dose trial of the prostate-specific membrane antigen-targeted antibody drug conjugate MLN2704 in metastatic castration-resistant prostate cancer. Urol Oncol, 2016. 34(12): p. 530 el5-530e21. |
| REF173 | Tagawa, S.T., et al., Phase II study of Lutetium-177-labeled anti-prostate-specific membrane antigen monoclonal antibody J591 for metastatic castration-resistant prostate cancer. Clin Cancer Res, 2013. 19(18): p. 5182-91. |
| REF174 | Holland, J.P., et al., 89Zr-DFO-J591 for immunoPET of prostate-specific membrane antigen expression in vivo. J Nucl Med, 2010. 51(8): p. 1293-300. |
| REF175 | Osborne, J.R., et al., A prospective pilot study of (89)Zr-J591/prostate specific membrane antigen positron emission tomography in men with localized prostate cancer undergoing radical prostatectomy. J Urol, 2014. 191(5): p. 1439-45. |
| REF176 | Pandit-Taskar, N., et al., (8)(9)Zr-huJ591 immuno-PET imaging in patients with advanced metastatic prostate cancer. Eur J Nucl Med Mol Imaging, 2014.41(11):p. 2093-105. |
| REF177 | Pandit-Taskar, N., et al., Indium 111-labeled J591 anti-PSMA antibody for vascular targeted imaging in progressive solid tumors. EJNMMI Res, 2015. 5: p. 28. |
| REF178 | Vallabhajosula, S., et al., Radioimmunotherapy of Metastatic Prostate Cancer with (1)(7)(7)Lu-DOTAhuJ591 Anti Prostate Specific Membrane Antigen Specific Monoclonal Antibody. Curr Radiopharm, 2016. 9(1): p. 44-53. |
| REF179 | Ramirez-Fort, M.K., et al., Theragnostic Target, Prostate-Specific Membrane Antigen-Also Specific for Nonprostatic Malignancies. Int J Radiat Oncol Biol Phys, 2018. 101(3): p. 646-649. |
| REF180 | Niaz, M.J., et al., Pilot Study of Hyperfractionated Dosing ofLutetium-177-Labeled Antiprostate-Specific Membrane Antigen Monoclonal Antibody J591 ((177) Lu-J591) for Metastatic Castration-Resistant Prostate Cancer. Oncologist, 2020. |
| REF181 | Niaz, M.J., et al., Pilot Study of Hyperfractionated Dosing ofLutetium-177-Labeled Antiprostate-Specific Membrane Antigen Monoclonal Antibody J591 ((177) Lu-J591) for Metastatic Castration-Resistant Prostate Cancer. Oncologist, 2020. |
| REF182 | Niaz, M.O., et al., Review of Lutetium-177-labeled Anti-prostate-specific Membrane Antigen Monoclonal Antibody J591 for the Treatment of Metastatic Castration-resistant Prostate Cancer. Cureus, 2020. 12(2): p. e7107. |
| REF183 | Liu, H., et al., Constitutive and antibody-induced internalization of prostate-specific membrane antigen. Cancer Res, 1998. 58(18): p. 4055-60. |
| REF184 | Rajasekaran, S.A., et al., A novel cytoplasmic tail MXXXL motif mediates the internalization of prostate-specific membrane antigen. Mol Biol Cell, 2003. 14(12): p. 4835-45. |
| REF185 | Ma, D., et al., Potent antitumor activity of an auristatin-conjugated, fully human monoclonal antibody to prostate-specific membrane antigen. Clin Cancer Res, 2006. 12(8): p. 2591-6. |
| REF186 | Wu, G., et al., Site-specific conjugation of b or on-containing dendrimers to anti-EGF receptor monoclonal antibody cetuximab (IMC-C225) and its evaluation as a potential delivery agent for neutron capture therapy. Bioconjug Chem, 2004. 15(1): p. 185-94. |
| REF187 | Wu, G., et al., Boron containing macromolecules and nanovehicles as delivery agents for neutron capture therapy. Anticancer Agents Med Chem, 2006. 6(2): p. 167-84. |
| REF188 | Barth, R.F., et al., Design, synthesis, and evaluation of cisplatin-containing EGFR targeting bioconjugates as potential therapeutic agents for brain tumors. Onco Targets Ther, 2016. 9: p. 2769-81. |

| | |
|---|---|
| REF189 | Hodgson NC. Merkel cell carcinoma: changing incidence trends. Journal of surgical oncology. 2005; 89(1): 1-4. |
| REF190 | Lemos B, Nghiem P. Merkel cell carcinoma: more deaths but still no pathway to blame. The Journal of investigative dermatology. 2007; 127(9):2100-3. |
| REF191 | Paulson KG, Park SY, Vandeven NA, Lachance K, Thomas H, Chapuis AG, et al. Merkel cell carcinoma: Current US incidence and projected increases based on changing demographics. J Am Acad Dermatol. 2018; 78(3):457-63 e2. |
| REF192 | Allen PJ, Bowne WB, Jaques DP, Brennan MF, Busam K, Coit DG. Merkel cell carcinoma: prognosis and treatment of patients from a single institution. J Clin Oncol. 2005; 23(10):2300-9. |
| REF193 | Tothill R, Estall V, Rischin D. Merkel cell carcinoma: emerging biology, current approaches, and future directions. American Society of Clinical Oncology educational book/ASCO American Society of Clinical Oncology Meeting. 2015; 35:e519-26. |
| REF194 | Tai PT, Yu E, Tonita J, Gilchrist J. Merkel cell carcinoma of the skin. Journal of cutaneous medicine and surgery. 2000; 4(4):186-95. |
| REF195 | Garneski KM, Nghiem P. Merkel cell carcinoma adjuvant therapy: current data support radiation but not chemotherapy. Journal of the American Academy of Dermatology. 2007; 57(1):166-9. |
| REF196 | Poulsen M, Rischin D, Walpole E, Harvey J, Mackintosh J, Ainslie J, et al. High-risk Merkel cell carcinoma of the skin treated with synchronous carboplatin/etoposide and radiation: a Trans-Tasman Radiation Oncology Group Study-TROG 96:07. Journal of clinical oncology : official journal of the American Society of Clinical Oncology. 2003; 21(23):4371-6. |
| REF197 | Poulsen MG, Rischin D, Porter 1, Walpole E, Harvey J, Hamilton C, et al. Does chemotherapy improve survival in high-risk stage I and II Merkel cell carcinoma of the skin? International journal of radiation oncology, biology, physics. 2006; 64(1):114-9. |
| REF198 | Sharma D, Flora G, Grunberg SM. Chemotherapy of metastatic Merkel cell carcinoma: case report and review of the literature. American journal of clinical oncology. 1991; 14(2):166-9. |
| REF199 | Afanasiev OK, Yelistratova L, Miller N, Nagase K, Paulson K, Iyer JG, et al. Merkel polyomavirus-specific T cells fluctuate with merkel cell carcinoma burden and express therapeutically targetable PD-1 and Tim-3 exhaustion markers. Clin Cancer Res. 2013; 19(19):5351-60. |
| REF200 | Lipson EJ, Vincent JG, Loyo M, Kagohara LT, Luber BS, Wang H, et al. PD-L1 expression in the Merkel cell carcinoma microenvironment: association with inflammation, Merkel cell polyomavirus and overall survival. Cancer Immunol Res. 2013; 1(1):54-63. |
| REF201 | Kaufman HL, Russell J, Hamid 0, Bhatia S, Terheyden P, D'Angelo SP, et al. Avelumab in patients with chemotherapy-refractory metastatic Merkel cell carcinoma: a multicentre, single-group, open-label, phase 2 trial. Lancet Oncol. 2016; 17(10):1374-85. |
| REF202 | Kaufman HL, Russell JS, Hamid O, Bhatia S, Terheyden P, D'Angelo SP, et al. Updated efficacy of avelumab in patients with previously treated metastatic Merkel cell carcinoma after >/= 1 year of follow-up: JAVELIN Merkel 200, a phase 2 clinical trial. J Immunother Cancer. 2018; 6(1):7. |
| REF203 | Gunaratne DA, Howle JR, Veness MJ. Definitive radiotherapy for Merkel cell carcinoma confers clinically meaningful in-field locoregional control: A review and analysis of the literature. J Am Acad Dermatol. 2017; 77(1):142-8 el. |
| REF204 | Balakrishnan V, Berry S, Stew B, Sizeland A. Benefits of combined modality treatment of Merkel cell carcinoma of the head and neck: single institution experience. The Journal of laryngology and otology. 2013; 127(9):908-16. |
| REF205 | Bichakjian CK, Olencki T, Alam M, Andersen JS, Berg D, Bowen GM, et al. Merkel cell carcinoma, version 1.2014. Journal of the National Comprehensive Cancer Network : JNCCN. 2014; 12(3):410-24. |
| REF206 | Kang SH, Haydu LE, Goh RY, Fogarty GB. Radiotherapy is associated with significant improvement in local and regional control in Merkel cell carcinoma. Radiation oncology. 2012; 7:171. |
| REF207 | Kang SH, Haydu LE, Goh RY, Fogarty GB. Radiotherapy is associated with significant improvement in local and regional control in Merkel cell carcinoma. Radiation oncology. 2012; 7:171. |
| REF208 | Sexton KW, Poteet SP, Hill JB, Schmidt A, Patel A, Del Corral GA, et al. Adjuvant radiation therapy increases disease-free survival in stage IB Merkel cell carcinoma. Annals of plastic surgery. 2014; 73(5):531-4. |
| REF209 | Network NCC. NCCN Clinical Practice Guidelines in Oncology. Merkel Cell Carcinoma (Version 1.2016). 2016 (accessed April 2016). |
| REF210 | Ramirez-Fort MK, Mahase SS, Osborne JR, Lange CS. Theragnostic Target, Prostate-Specific Membrane Antigen-Also Specific for Nonprostatic Malignancies. Int J Radiat Oncol Biol Phys. 2018; 101(3):646-9. |
| REF211 | Tagawa ST, Vallabhajosula S, Christos PJ, Jhanwar YS, Batra JS, Lam L, et al. Phase 1/2 study of fractionated dose lutetium-177-labeled anti-prostate-specific membrane antigen monoclonal antibody J591 ((177) Lu-J591) for metastatic castration-resistant prostate cancer. Cancer. 2019; 125(15):2561-9. |
| REF212 | Niaz MJ, Batra JS, Walsh RD, Ramirez-Fort MK, Vallabhajosula S, Jhanwar YS, et al. Pilot Study of Hyperfractionated Dosing of Lutetium-177-Labeled Antiprostate-Specific Membrane Antigen Monoclonal Antibody J591 ((177) Lu-J591) for Metastatic Castration-Resistant Prostate Cancer. Oncologist. 2020; 25(6):477-e895. |

-continued

| | |
|---|---|
| REF213 | Niaz MO, Sun M, Ramirez-Fort MK, Niaz MJ. Review of Lutetium-177-labeled Anti-prostate-specific Membrane Antigen Monoclonal Antibody J591 for the Treatment of Metastatic Castration-resistant Prostate Cancer. Cureus. 2020; 12(2):e7107. |
| REF214 | Batra JS, Niaz MJ, Whang YE, Sheikh A, Thomas C, Christos P, et al. Phase I trial of docetaxel plus lutetium-177-labeled anti-prostate-specific membrane antigen monoclonal antibody J591 ((177)Lu-J591) for metastatic castration-resistant prostate cancer. Urol Oncol. 2020. |
| REF215 | Nguyen DP, Xiong PL, Liu H, Pan S, Leconet W, Navarro V, et al. Induction of PSMA and Internalization of an Anti-PSMA mAb in the Vascular Compartment. Mol Cancer Res. 2016; 14(11):1045-53. |
| REF216 | Tagawa ST, Akhtar NH, Nikolopoulou A, Kaur G, Robinson B, Kahn R, et al. Bone marrow recovery and subsequent chemotherapy following radiolabeled anti-prostate-specific membrane antigen monoclonal antibody j591 in men with metastatic castration-resistant prostate cancer. Front Oncol. 2013; 3:214. |
| REF217 | Tagawa ST, Milowsky MI, Morris M, Vallabhajosula S, Christos P, Akhtar NH, et al. Phase II study of Lutetium-177-labeled anti-prostate-specific membrane antigen monoclonal antibody J591 for metastatic castration-resistant prostate cancer. Clin Cancer Res. 2013; 19(18):5182-91. |
| REF218 | O'Donoghue JA, Bardies M, Wheldon TE. Relationships between tumor size and curability for uniformly targeted therapy with beta-emitting radionuclides. J Nucl Med. 1995; 36(10):1902-9. |
| REF219 | Milowsky MI, Nanus DM, Kostakoglu L, Vallabhajosula S, Goldsmith SJ, Bander NH. Phase I trial of yttrium-90-labeled anti-prostate-specific membrane antigen monoclonal antibody J591 for androgen-independent prostate cancer. J Clin Oncol. 2004; 22(13):2522-31. |
| REF220 | Kratochwil C, Bruchertseifer F, Rathke H, Hohenfellner M, Giesel FL, Haberkorn U, et al. Targeted alpha-Therapy of Metastatic Castration-Resistant Prostate Cancer with (225)Ac-PSMA-617: Swimmer-Plot Analysis Suggests Efficacy Regarding Duration of Tumor Control. J Nucl Med. 2018; 59(5):795-802. |
| REF221 | Niaz MO, Sun M, Ramirez-Fort MK, Niaz MJ. Prostate-specific Membrane Antigen Based Antibody-drug Conjugates for Metastatic Castration-resistance Prostate Cancer. Cureus. 2020; 12(2):e7147. |
| REF222 | Ramirez-Fort MK, Meier B, Liu H, et al. Possible cancer stem cells: Folate hydrolase-1 is expressed in a subset of Oct4-positive melanoma cells. Poster presented at: American Association for Cancer Research; 1-5 April 2017; Washington, DC. |
| REF223 | Ma D, Hopf CE, Malewicz AD, Donovan GP, Senter PD, Goeckeler WF, et al. Potent antitumor activity of an auristatin-conjugated, fully human monoclonal antibody to prostate-specific membrane antigen. Clin Cancer Res. 2006; 12(8):2591-6. |
| REF224 | Morris MJ, Pandit-Taskar N, Divgi CR, Bender S, O'Donoghue JA, Nacca A, et al. Phase I evaluation of J591 as a vascular targeting agent in progressive solid tumors. Clin Cancer Res. 2007; 13(9):2707-13. |
| REF225 | National Nuclear Data Center ENSDF Decay Data in the MIRD (Medical Internal Radiation Dose). Format for 177Lu. 2012 |
| REF226 | Kim SH, Park WS, Park EY, Park B, Joo J, Joung JY, et al. The prognostic value of BAP1, PBRM1, pS6, PTEN, Tgase2, PD-L1, CA9, PSMA, and Ki-67 tissue markers in localized renal cell carcinoma: A retrospective study of tissue microarrays using immunohistochemistry. PloS One. 2017; 12(6):e0179610. |
| REF227 | Haffner MC, Laimer J, Chaux A, Schafer G, Obrist P, Brunner A, et al. High expression of prostate-specific membrane antigen in the tumor-associated neo-vasculature is associated with worse prognosis in squamous cell carcinoma of the oral cavity. Mod Pathol. 2012; 25(8):1079-85. |
| REF228 | Mhawech-Fauceglia P, Smiraglia DJ, Bshara W, Andrews C, Schwaller J, South S, et al. Prostate-specific membrane antigen expression is a potential prognostic marker in endometrial adenocarcinoma. Cancer Epidemiol Biomarkers Prev. 2008; 17(3):571-7. |
| REF229 | Zeng C, Ke ZF, Yang Z, Wang Z, Yang SC, Luo CQ, et al. Prostate-specific membrane antigen: a new potential prognostic marker of osteosarcoma. Med Oncol. 2012; 29(3):2234-9. |
| REF230 | Perner S, Hofer MD, Kim R, Shah RB, Li H, Moller P, et al. Prostate-specific membrane antigen expression as a predictor of prostate cancer progression. Hum Pathol. 2007; 38(5):696-701. |
| REF231 | Cronin KA, Harlan LC, Dodd KW, Abrams JS, Ballard-Barbash R. Population-based estimate of the prevalence of HER-2 positive breast cancer tumors for early stage patients in the US. Cancer Invest. 2010; 28(9):963-8. |
| REF232 | Donepudi S, DeConti RC, Samlowski WE. Recent advances in the understanding of the genetics, etiology, and treatment of Merkel cell carcinoma. Semin Oncol. 2012; 39(2):163-72. |
| REF233 | Fernandez-Cobo M, Jobes DV, Yanagihara R, et al. Reconstructing population history using JC virus: Amerinds, Spanish, and Africans in the ancestry of modem Puerto Ricans. *Hum Biol.* 2001; 73(3):385-402. |
| REF234 | Gravel S, Zakharia F, Moreno-Estrada A, et al. Reconstructing Native American migrations from whole-genome and whole-exome data. *PloS Genet.* 2013; 9(12):e1004023. |
| REF235 | Edmondson DA, Nordness ME, Zacharisen MC, Kump VP, Fink JN. Allergy and "toxic mold syndrome". *Ann Allergy Asthma Immunol.* 2005; 94(2):234-239. |

-continued

| | |
|---|---|
| REF236 | Ahmed Adam MA, Tabana YM, Musa KB, Sandai DA. Effects of different mycotoxins on humans, cell genome and their involvement in cancer (Review). *Oncol Rep.* 2017; 37(3):1321-1336. |
| REF237 | Zhang X, Norback D, Fan Q, et al. Dampness and mold in homes across China: Associations with rhinitis, ocular, throat and dermal symptoms, headache and fatigue among adults. *Indoor Air.* 2019; 29(1):30-42. |
| REF238 | Furman D, Campisi J, Verdin E, et al. Chronic inflammation in the etiology of disease across the life span. *Nat Med.* 2019; 25(12):1822-1832. |
| REF239 | McClelland S, 3$^{rd}$, Xanthopoulos EP, Mitin T. The Sin of Exclusion: Applicability of Trials Encouraging Omission of Radiation Therapy to Nonwhite Patients With Breast Cancer. *J Oncol Pract.* 2018; 14(11):635-638. |
| REF240 | https://gis.cdc.gov/Cancer/USCS/DataViz.html obtained 9/29/2018 |
| REF241 | Teloken C. Management of erectile dysfunction secondary to treatment for localized prostate cancer. *Cancer Control.* 2001; 8(6):540-545. |
| REF242 | Mantz CA, Nautiyal J, Awan A, et al. Potency preservation following conformal radiotherapy for localized prostate cancer: impact of neoadjuvant androgen blockade, treatment technique, and patient-related factors. *The cancer journal from Scientific American.* 1999; 5(4):230-236. |
| REF243 | Donovan JL, Hamdy FC, Lane JA, et al. Patient-Reported Outcomes after Monitoring, Surgery, or Radiotherapy for Prostate Cancer. *N Engl J Med.* 2016; 375(15):1425-1437. |
| REF244 | Ramirez-Fort MK, Rogers MJ, Santiago R, et al. Prostatic irradiation-induced sexual dysfunction: a review and multidisciplinary guide to management in the radical radiotherapy era (Part I defining the organ at risk for sexual toxicities). *Rep Pract Oncol Radiother.* 2020; 25(3):367-375 |
| REF245 | Ramirez-Fort MK, Suarez P, Carrion M, et al. Prostatic irradiation-induced sexual dysfunction: A review and multidisciplinary guide to management in the radical radiotherapy era (Part III on Psychosexual Therapy and the Masculine Self-Esteem). *Rep Pract Oncol Radiother.* 2020; 25(4):625-631. |
| REF246 | Rogers MJ, Ramirez-Fort MK, Kashanian JA, et al. Prostatic irradiation-induced sexual dysfunction: A review and multidisciplinary guide to management in the radical radiotherapy era (Part II on Urological Management). *Rep Pract Oncol Radiother.* 2020; 25(4):619-624. |
| REF247 | Forbat L, White I, Marshall-Lucette S, Kelly D. Discussing the sexual consequences of treatment in radiotherapy and urology consultations with couples affected by prostate cancer. *BJU Int.* 2012; 109(1):98-103. |
| REF248 | Korfage IJ, Hak T, de Koning HJ, Essink-Bot ML. Patients' perceptions of the side-effects of prostate cancer treatment-a qualitative interview study. *Soc Sci Med.* 2006; 63(4):911-919. |
| REF249 | O'Brien R, Rose P, Campbell C, et al. "I wish I'd told them": a qualitative study examining the unmet psychosexual needs of prostate cancer patients during follow-up after treatment. *Patient Educ Couns.* 2011; 84(2):200-207. |
| REF250 | Singer PA, Tasch ES, Stocking C, Rubin S, Siegler M, Weichselbaum R. Sex or survival: trade-offs between quality and quantity of life. *Journal of clinical oncology: official journal of the American Society of Clinical Oncology.* 1991 ; 9(2):328-334. |
| REF251 | McMahon CG. Nonsurgical treatment of cavernosal venous leakage. *Urology.* 1997; 49(1):97-100. |
| REF252 | Hellstrom WJ, Montague DK, Moncada I, et al. Implants, mechanical devices, and vascular surgery for erectile dysfunction. *J Sex Med.* 2010; 7(1 Pt 2):501-523. |
| REF253 | Porst H, Burnett A, Brock G, et al. SOP conservative (medical and mechanical) treatment of erectile dysfunction. *J Sex Med.* 2013; 10(1):130-171. |
| REF254 | Brison D, Seftel A, Sadeghi-Nejad H. The resurgence of the vacuum erection device (VED) for treatment of erectile dysfunction. *J Sex Med.* 2013; 10(4):1124-1135. |
| REF255 | Kimura M, Caso JR, Banez LL, et al. Predicting participation in and successful outcome of a penile rehabilitation programme using a phosphodiesterase type 5 inhibitor with a vacuum erection device after radical prostatectomy. *BJU Int.* 2012; 110(11 PtC):E931-938. |
| REF256 | Bergman J, Gore JL, Penson DF, Kwan L, Litwin MS. Erectile aid use by men treated for localized prostate cancer. *J Urol.* 2009; 182(2):649-654. |
| REF257 | Liu C, Lopez DS, Chen M, Wang R. Penile Rehabilitation Therapy Following Radical Prostatectomy: A Meta-Analysis. *J Sex Med.* 2017; 14(12):1496-1503. |
| REF258 | Nolan MW, Marolf AJ, Ehrhart EJ, et al. Pudendal nerve and internal pudendal artery damage may contribute to radiation-induced erectile dysfunction. *Int J Radiat Oncol Biol Phys.* 2015; 91(4):796-806. |
| REF259 | Mahmood J, Connors CQ, Alexander AA, et al. Cavernous Nerve Injury by Radiation Therapy May Potentiate Erectile Dysfunction in Rats. *Int J Radiat Oncol Biol Phys.* 2017; 99(3):680-688. |
| REF260 | Lange CS, Liberman DF, Clark RW, Ferguson P. The organization and repair of DNA in the mammaliam chromosome. I. Calibration procedures and errors in the determination of the molecular weight of native DNA. *Biopolymers.* 1977; 16(5):1063-1081. |
| REF261 | Lange CS, Liberman DF, Clark RW, Ferguson P, Sheck LE. The organization and repair of DNA in the mammalian chromosome. III. Determination of the molecular weight of a mammalian native DNA. *Biopolymers.* 1977; 16(5):1093-1014. |
| REF262 | Siegel RL, Miller KD, Jemal A. Cancer statistics, 2016. *CA Cancer J Clin.* 2016; 66(1):7-30. |
| REF263 | Ramirez-Fort MK, Mahase SS, Osborne JR, Lange CS. Theragnostic Target, Prostate-Specific Membrane Antigen-Also Specific for Nonprostatic Malignancies. *Int J Radiat Oncol Biol Phys.* 2018; 101(3):646-9. |

-continued

| | |
|---|---|
| REF264 | Silver DA, Pellicer I, Fair WR, Heston WD, Cordon-Cardo C. Prostate-specific membrane antigen expression in normal and malignant human tissues. Clinical cancer research : an official journal of the American Association for Cancer Research. 1997; 3(1):81-5. |
| REF265 | Troyer JK, Beckett ML, Wright GL, Jr. Detection and characterization of the prostate-specific membrane antigen (PSMA) in tissue extracts and body fluids. Int J Cancer. 1995; 62(5):552-8. |
| REF266 | Wright GL, Jr., Grob BM, Haley C, Grossman K, Newhall K, Petrylak D, et al. Upregulation of prostate-specific membrane antigen after androgen-deprivation therapy. Urology. 1996; 48(2):326-34. |
| REF267 | Wright GL, Jr., Haley C, Beckett ML, Schellhammer PF. Expression of prostate-specific membrane antigen in normal, benign, and malignant prostate tissues. Urol Oncol. 1995; 1(1):18-28. |
| REF268 | Liu H, Rajasekaran AK, Moy P, Xia Y, Kim S, Navarro V, et al. Constitutive and antibody-induced internalization of prostate-specific membrane antigen. Cancer research. 1998; 58(18):4055-60. |
| REF269 | Rajasekaran SA, Anilkumar G, Oshima E, Bowie JU, Liu H, Heston W, et al. A novel cytoplasmic tail MXXXL motif mediates the internalization of prostate-specific membrane antigen. Mol Biol Cell. 2003; 14(12):4835-45. |
| REF270 | Furchgott RF. The 1996 Albert Lasker Medical Research Awards. The discovery of endothelium-derived relaxing factor and its importance in the identification of nitric oxide. JAMA. 1996; 276(14):1186-8. |
| REF271 | Hemmens B, Mayer B. Enzymology of nitric oxide synthases. Methods Mol Biol. 1998; 100:1-32. |
| REF272 | Kraehling JR, Sessa WC. Contemporary Approaches to Modulating the Nitric Oxide-cGMP Pathway in Cardiovascular Disease. Circ Res. 2017; 120(7):1174-82. |
| REF273 | Gratton JP, Lin MI, Yu J, Weiss ED, Jiang ZL, Fairchild TA, et al. Selective inhibition of tumor microvascular permeability by cavtratin blocks tumor progression in mice. Cancer Cell. 2003; 4(1):31-9. |
| REF274 | Lin MI, Yu J, Murata T, Sessa WC. Caveolin-1-deficient mice have increased tumor microvascular permeability, angiogenesis, and growth. Cancer Res. 2007; 67(6):2849-56. |
| REF275 | Nguyen DP, Xiong PL, Liu H, Pan S, Leconet W, Navarro V, et al. Induction of PSMA and Internalization of an Anti-PSMA mAb in the Vascular Compartment. Mol Cancer Res. 2016; 14(11):1045-53. |
| REF276 | Ramirez-Fort MK, Meier B, Liu H, et al. Possible cancer stem cells: Folate hydrolase-1 is expressed in a subset of Oct4-positive melanoma cells. Poster presented at: American Association for Cancer Research; 1-5 April 2017; Washington, DC. |
| REF277 | Ma D, Hopf CE, Malewicz AD, Donovan GP, Senter PD, Goeckeler WF, et al. Potent antitumor activity of an auristatin-conjugated, fully human monoclonal antibody to prostate-specific membrane antigen. Clin Cancer Res. 2006; 12(8):2591-6. |
| REF278 | Kosuri S, Akhtar NH, Smith M, Osborne JR, Tagawa ST. Review of salvage therapy for biochemically recurrent prostate cancer: the role of imaging and rationale for systemic salvage targeted anti-prostate-specific membrane antigen radioimmunotherapy. Adv Urol. 2012; 2012:921674. |
| REF279 | Tercel M, Lee HH, Yang S, Liyanage HD, Mehta SY, Boyd PD, et al. Preparation and antitumour properties of the enantiomers of a hypoxia-selective nitro analogue of the duocarmycins. ChemMedChem. 2011; 6(10):1860-71. |
| REF280 | Tagawa ST, Milowsky MI, Morris M, Vallabhajosula S, Christos P, Akhtar NH, et al. Phase II study of Lutetium-177-labeled anti-prostate-specific membrane antigen monoclonal antibody J591 for metastatic castration-resistant prostate cancer. Clinical cancer research : an official journal of the American Association for Cancer Research. 2013; 19(18):5182-91. |
| REF281 | Bander NH, Milowsky MI, Nanus DM, Kostakoglu L, Vallabhajosula S, Goldsmith SJ. Phase I trial of 177lutetium-labeled J591, a monoclonal antibody to prostate-specific membrane antigen, in patients with androgen-independent prostate cancer. Journal of clinical oncology : official journal of the American Society of Clinical Oncology. 2005; 23(21):4591-601. |
| REF282 | Milowsky MI, Nanus DM, Kostakoglu L, Vallabhajosula S, Goldsmith SJ, Bander NH. Phase I trial of yttrium-90-labeled anti-prostate-specific membrane antigen monoclonal antibody J591 for androgen-independent prostate cancer. Journal of clinical oncology : official journal of the American Society of Clinical Oncology. 2004; 22(13):2522-31. |
| REF283 | Tagawa ST, Vallabhajosula S, Osborne J, Goldsmith SJ, Petrillo K, Tyrell L, Dhillon GS, Beltran H, Bander NH, Nanus DM. Phase I trial of fractionated-dose 177lutetium radiolabeled anti-prostate-specific membrane antigen (PSMA) monoclonal antibody J591 (177Lu-J591) in patients (pts) with metastatic castration-resistant prostate cancer (metCRPC). J Clin Oncol 28:7s, 2010 (suppl; abstr 4667) |
| REF284 | Horoszewicz JS, Leong SS, Kawinski E, Karr JP, Rosenthal H, Chu TM, Mirand EA, Murphy GP 1983. LNCaP model of human prostatic carcinoma. Cancer Res. 43 (4):1809-18. PMID 6831420. |
| REF285 | Ramirez-Fort MK, Rogers MJ, Santiago R, Mahase SS, Mendez M, Zheng Y, Kong X, Kashanian JA, Niaz MJ, McClelland S 3$^{rd}$, Wu X, Bander NH, Schlegel P, Mulhall JP, Lange CS. Prostatic irradiation-induced sexual dysfunction: a review and multidisciplinary guide to management in the radical radiotherapy era (Part I defining the organ at risk for sexual toxicities). Rep Pract Oncol Radiother. 2020 |

-continued

| | |
|---|---|
| | May-Jun; 25(3):367-375. Doi: 10.1016/j.rpor.2020.03.007. Epub 2020 Mar 19. PMID: 32322175; PMCID: PMC 7163290. |
| REF286 | Rogers MJ, Ramirez-Fort MK, Kashanian J, Broster SA, Matta J, Mahase SS, Fort DV, Niaz MJ, McClelland S 3$^{rd}$, Bander NH, Fort, M, Lange CS, Schlegel P, Mulhall J. Prostatic irradiation-induced sexual dysfunction: A review and multidisciplinary guide to management in the ablative RT era (Part II: On Uriological Management). Rep Pract Oncol and Radiother. 2020 May-Jun; 25(5):61 9-624. Doi: 10.1016/j.rpor.2020.03.0011 Epub 2020 May 6. |
| REF287 | Ramirez-Fort MK, Suarez P, Carrion M, Postle C, Weiner J, Lange CS, Arribas R, Fort M. Prostatic irradiation-induced sexual dysfunction: A review and multidisciplinary guide to management in the ablative RT era (Part III: Psychosexual Therapy). Rep Pract Oncol and Radiother. 2020 May-Jun; 25(5):625-631. Doi: 10.1016/j.rpor.2020.03.0014. Epub 2020 Apr 30. |
| REF288 | Ramirez-Fort MK, Meier-Schiesser B, Niaz MJ, Niaz MO, Feily A, Fort M, Lange CS, Caba D. Dermatofibrosarcoma Protuberans: The Current State of Multidisciplinary Management. Skinmed. 2020 Oct 1; 18(5):288-293. PMID: 33160438. https://pubmed.ncbi.nlm.nih.gov/33160438/ |
| REF289 | Ramirez-Fort MK, Meier-Schiesser B, Lachance K, Mahase SS, Church CD, Niaz MJ, Liu H, Navarro V, Nikolopoulou A, Kazakov DV, Contassot E, Nguyen DP, Sach J, Hadravsky L, Sheng Y, Tagawa ST, Wu X, Lange CS, French LE, Nghiem PT, Bander NH. Folate hydrolase-1 (FOLH1) is a novel target for antibody-based brachytherapy in Merkel cell carcinoma. Skin Health Dis. 2020; e9. https://doi.org/10.1002/ski2.9 |
| REF290 | Niaz MO, Sun M, Ramirez-Fort MK, Niaz MJ. Prostate-specific Membrane Antigen Based Antibody-drug Conjugates for Metastatic Castration-resistance Prostate Cancer. Cureus. 2020 Feb 29; 12(2):e7147. Doi: 10.7759/cureus.7147. Review. PubMed PMID: 32257692; PubMed Central PMCID: PMC7105266. |
| REF291 | Niaz MO, Sun M, Ramirez-Fort MK, Niaz MJ. Review of Lutetium-177-labeled Anti-prostate-specific Membrane Antigen Monoclonal Antibody J591 for the Treatment of Metastatic Castration-resistant Prostate Cancer. Cureus. 2020 Feb 26; 12(2):e7107. Doi: 10.7759/cureus.7107. Review. PubMed PMID: 32257655; PubMed Central PMCID: PMC7100619. |
| REF292 | Ramirez-Fort MK, Meier-Schiesser B, Niaz MJ, Niaz MO, Feily A, Fort M, Lange CS, Caba D. Dermatofibrosarcoma Protuberans: The Current State of Multidisciplinary Management. Skinmed. 2020 Oct 1; 18(5):288-293. PMID: 33160438. https://pubmed.ncbi.nlm.nih.gov/33160438/ |
| REF293 | Feily A, Feily A, Alexander JS, Niaz MJ, Gianfaldoni S, Lotti T, Ramirez-Fort MK*. Pseudo-dense Hair Transplantation: Strategy of "Less Inside, More Outside" and Central Bulking with Curled Chest Hairs as Treatment for Scalp Scars. J Cutan Aesthet Surg. 2020 Jul-Sep; 13(3):226-228. Doi: 10.4103/JCAS.JCAS_104_19. PMID: 33209000; PMCID: PMC7646433. |
| REF294 | Feily A, Firoozifard A, Sokhandani T, Elosegui-Rodriguez P, Perez-Rivera E, Lange CS, Hosseinpoor M, Ramirez-Fort MK*. Follicular Transplantation, Microneedling, and Adjuvant Narrow-band Ultraviolet-B Irradiation as Cost-Effective Regimen for Palmar-Plantar Vitiligo: A Pilot Study. Cureus. 2020 Apr 28; 12(4):e7878. Doi: 10.7759/cureus.7878. PMID: 32489732; PMCID: PMC7255558 |
| REF295 | T.P. Coohill, and F. Ghetti. 2012. Action Spectroscopy: Ultraviolet Radiation. CRC Handbook of Organic Photochemistry and Photobiology. 3$^{rd}$ edition, vol. 2. Pgs. 1093-1103, eds |
| REF296 | Ash C, Dubec M, Donne K, Bashford T. Effect of wavelength and beam width on penetration in light-tissue interaction using computational methods. Lasers Med Sci. 2017 Nov; 32(8):1909-1918. Doi: 10.1007/s 10103-017-2317-4. Epub 2017 Sep 12. PMID: 28900751; PMCID: PMC5653719 |
| REF297 | Haensch S, Bianucci R, Signoli M, Rajerison M, Schultz M, Kacki S, Vermunt M, Weston DA, Hurst D, Achtman M, Carniel E, Bramanti B. Distinct clones of Yersinia pestis caused the black death. PloS Pathog. 2010 Oct 7; 6(10):e1001134. Doi: 10.1371/journal.ppat.1001134. PMID: 20949072; PMCID: PMC2951374 |
| REF298 | Fajuyigbe D, Young AR. The impact of skin colour on human photobiological responses. Pigment Cell Melanoma Res. 2016 Nov; 29(6):607-618. Doi: 10.1111/pcmr. 12511. Epub 2016 Aug 16. PMID: 27454804; PMCID: PMC5132026 |
| REF299 | Burrell LM, Risvanis J, Kubota E, Dean RG, MacDonald PS, Lu S, Tikellis C, Grant SL, Lew RA, Smith AI, Cooper ME, Johnston CI. Myocardial infarction increases ACE2 expression in rat and humans. Eur Heart J. 2005 Feb; 26(4):369-75; discussion 322-4. Doi: 10.1093/eurheartj/ehil 14. Epub 2005 Jan 25. PMID: 15671045 |
| REF300 | Raj Verma T, Kumar Painuly N, Prasad Mishra S, Yoganathan SA, Singh N, Bhatt MLB, Jamal N. Evaluation of Lung Density and Its Dosimetric Impact on Lung Cancer Radiotherapy: A Simulation Study. J Biomed Phys Eng, 2019 Feb 1, 9(1):17-28. PMID: 30881931; PMCID: PMC6409377 |
| REF301 | Park S, Ang RR, Duffy SP, Bazov J, Chi KN, Black PC, Ma H. Morphological differences between circulating tumor cells from prostate cancer patients and cultured prostate cancer cells. PloS One. 2014 Jan 8; 9(1):e85264. Doi: 10.1371/journal.pone.0085264. PMID: 24416373; PMCID: PMC3885705 |
| REF302 | 177Lu Radiolabeled Monoclonal Antibody HuJ591-GS (177Lu-J591) in Patients With Nonprostate Metastatic Solid Tumors: A Pilot Study; ClinicalTrials.gov Identifier: NCT00967577; August 28, 2009 |
| REF303 | RK Riegelman & RP Hirsch, *Studying a Study and Testing a Test*, Little Brown & Co., 1996 |

| | |
|---|---|
| REF304 | 177Lu Radiolabeled Monoclonal Antibody HuJ591 (177Lu-J591) and Ketoconazole in Patients With Prostate Cancer; ClinicalTrials.gov Identifier: NCT00859781; March 11, 2009 |
| REF305 | Linkedin post by Ramirez-Fort MK on March 16, 2020 at https://www.linkedin.com/in/marigdalia/detail/recent-activity. |
| REF306 | Lea DE., Actions of Radiations on Livings Cells, 1st ed. 402 pp. Macmillan, New York, 1947 |
| REF307 | El Ghissassi, Fatiha, Robert Baan, Kurt Straif, Yann Grosse, Béatrice Secretan, Véronique Bouvard, Lamia Benbrahim-Tallaa, Neela Guha, Crystal Freeman, Laurent Galichet, and Vincent Cogliano. 'A review of human carcinogens— Part D: radiation', The Lancet Oncology, 10:751-52. |

Moreover, the processes described with respect to FIGS. 1-25 (e.g., any applications and/or algorithms), as well as any other aspects of the disclosure, may each be implemented by software, but may also be implemented in hardware, firmware, or any combination of software, hardware, and firmware. They each may also be embodied as computer-readable code recorded on a computer-readable medium. The computer-readable medium may be any data storage device that can store data or instructions which can thereafter be read by a computer system. Examples of the computer-readable medium may include, but are not limited to, read-only memory, random-access memory, flash memory, CD-ROMs, DVDs, magnetic tape, and optical data storage devices (e.g., memory/processor of device(s) 114 of FIG. 1). The computer-readable medium can also be distributed over network-coupled computer systems so that the computer readable code is stored and executed in a distributed fashion. For example, the computer-readable medium may be communicated from one electronic device to another electronic device using any suitable communications protocol. The computer-readable medium may embody computer-readable code, instructions, data structures, program modules, or other data in a modulated data signal, such as a carrier wave or other transport mechanism, and may include any information delivery media. A modulated data signal may be a signal that has one or more of its characteristics set or changed in such a manner as to encode information in the signal.

While the above embodiments may be described in the context of a human subject, they may also be used for other animals (e.g., dogs, horses, etc.) by making appropriate modifications, which will be apparent to persons skilled in the relevant arts. While the above embodiments may be described in the context of a mammalian, they may also be used for plant or protozoan, bacteria, and fungi cells by making appropriate modifications, which will be apparent to persons skilled in the relevant arts.

Many alterations and modifications of the preferred embodiments will no doubt become apparent to a person of ordinary skill in the art after having read the foregoing description, it is to be understood that the particular embodiments shown and described by way of illustration are in no way intended to be considered limiting. Thus, references to the details of the described embodiments are not intended to limit their scope.

What is claimed is:

1. A method for determining an amount of energy to be delivered to cause an end effect on a target invasive entity of a target in a host, the method comprising:
determining the type of the target invasive entity;
estimating the sensitivity of the determined target invasive entity to a particular energy-based therapy;
estimating, based on the estimated sensitivity, a waveband-specific dose required to result in 10% remaining target invasive entity that is a 1-log reduction as a $D_{10}$ value;
defining the treatment volume of the target;
determining the maximal multiple of the estimated $D_{10}$ value of the target invasive entity that overlaps within the shoulder of the cellular survival curve pertaining to the treatment volume of the target;
determining a permissible dose per fraction based on the determined maximal multiple when administered is to result in no more than a cellular D90 to result in a 10% reduction of cells;
determining a percent depth-dose or depth dose characterizations to identify the isodose distribution of the particular energy-based therapy in a particular treatment volume density;
optimizing the volume of the defined treatment volume of the target to receive 100% of the maximal permissible dose per fraction; and
prescribing a dose based on the determining the maximal multiple, the determining the permissible dose, the determining the percent depth-dose, and the optimizing.

2. The method of claim 1, further comprising delivering the prescribed dose as energy to the target in the host.

3. The method of claim 1, wherein the particular treatment volume density is optical density.

4. The method of claim 1, wherein the target invasive entity comprises one of a fungus, a bacteria, or a virus.

5. The method of claim 1, wherein the target comprises one of an internal organ, skin, canal, or cavity.

6. The method of claim 1, wherein the target comprises one of a lung, nostril, oral cavity, rectal cavity, vaginal cavity, stomach, esophagus, or vascular blood volume.

7. The method of claim 1, wherein the host is one of a human, animal, or plant.

8. The method of claim 1, wherein the particular energy-based therapy comprises UVR.

9. The method of claim 1, wherein the particular energy-based therapy comprises UVB.

10. A method for monitoring a patient, the method comprising:
performing a folate hydrolase-1 ("FOLH1") positron emission tomography-computed tomography ("PET/CT") on the patient to detect any FOLH1-avid neoendothelial cells; and
performing a diagnostic or confirmatory biopsy of tissue associated with the detected FOLH1-avid neoendothelial cells to determine if the tissue is cancerous.

11. A method for adaptively treating a volume of cells with electromagnetic irradiation, the method comprising:

conjugating a chemical nuclei to an agent with FOLH1 binding capacity;

administering the nuclei-agent construct into a body of cells for exposing a volume of cells of the body of cells to the nuclei-agent construct;

waiting for a period of time after the administering to allow binding to occur; and exposing the volume of cells to electromagnetic irradiation for modifying the chemical nuclei within the volume of cells.

12. The method of claim 11, wherein the volume of cells is a tissue or tumor.

13. The method of claim 11, wherein the body of cells is in an animal or plant.

14. The method of claim 11, wherein the chemical nuclei is $^{10}B$.

15. The method of claim 11, wherein the agent comprises monoclonal antibodies, small molecules or antibody fragments.

16. The method of claim 11, wherein the agent can bind to both the chemical nuclei and FOLH1.

17. A method for measuring the absorbed dose of energy delivered via a target within a volume of cells, the method comprising:

measuring a specific activity and initial activity of a chemical nuclei that is attached to an agent with target binding capacity;

quantifying target molecule(s) (FOLH1) for the volume of cells;

inputting the measured value and the quantified value into a mathematical simulation to estimate the possible outcomes of an uncertain event.

18. A method for enabling androgen deprivation upregulation, the method comprising:

applying energy to a volume of cells;

waiting for a period of time after the energy application for an FOLH1 target to upregulate or to appear de novo; and after the waiting, exposing the volume of cells to an embodiment with target binding capacity.

19. The method of claim 18, wherein the embodiment comprises monoclonal antibodies, small molecules or antibody fragments.

20. A method for optimizing the absorbed dose of electromagnetic irradiation delivered via a target within in a volume of cells, the method comprising:

identifying the initial activity of a chemical nuclei that is attached to an agent with target binding capacity;

identifying a dose rate or absorption rate of the chemical nuclei or into cells within the volume;

identifying the absorbed dose;

identifying the time required for target replenishment after complete or partial target depletion;

identifying the time required for target replenishment so that 50-100% of the initial dose of chemical nuclei can be absorbed as a subsequent dose; and waiting for a period of time based between doses.

* * * * *